US009751927B2

(12) United States Patent
Sensfuss et al.

(10) Patent No.: US 9,751,927 B2
(45) Date of Patent: *Sep. 5, 2017

(54) STABLE, PROTRACTED GLP-1/GLUCAGON RECEPTOR CO-AGONISTS FOR MEDICAL USE

(71) Applicant: Novo Nordisk A/S, Bagsvaerd (DK)

(72) Inventors: Ulrich Sensfuss, Vanloese (DK); Thomas Kruse, Herlev (DK); Jesper F. Lau, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,316

(22) Filed: Jun. 10, 2016

(65) Prior Publication Data
US 2016/0355562 A1 Dec. 8, 2016

Related U.S. Application Data

(63) Continuation of application No. 14/836,192, filed on Aug. 26, 2015, now Pat. No. 9,474,790, which is a continuation of application No. PCT/EP2014/058084, filed on Apr. 22, 2014.

(60) Provisional application No. 61/814,969, filed on Apr. 23, 2013.

(30) Foreign Application Priority Data

Apr. 18, 2013 (EP) .................................. 13164272
Dec. 11, 2013 (EP) .................................. 13196656

(51) Int. Cl.
C07K 14/605 (2006.01)
A61K 38/28 (2006.01)
A61K 31/26 (2006.01)
A61K 38/26 (2006.01)

(52) U.S. Cl.
CPC ............ C07K 14/605 (2013.01); A61K 38/26 (2013.01); A61K 38/28 (2013.01)

(58) Field of Classification Search
CPC ....... C07K 14/605; A61K 38/26; A61K 38/28
See application file for complete search history.

(56) References Cited

U.S. PATENT DOCUMENTS

| | | | |
|---|---|---|---|
| 4,356,170 A | 10/1982 | Jennings et al. | |
| 5,408,037 A | 4/1995 | Smith et al. | |
| 5,424,286 A | 6/1995 | Eng | |
| 5,932,462 A | 8/1999 | Harris et al. | |
| 6,953,787 B2 | 10/2005 | Smith et al. | |
| 7,157,277 B2 | 1/2007 | DeFrees et al. | |
| 7,314,859 B2 | 1/2008 | Green et al. | |
| 2002/0049153 A1 | 4/2002 | Bridon et al. | |
| 2005/0027978 A1 | 2/2005 | Neuman et al. | |
| 2007/0105755 A1 | 5/2007 | DeFrees et al. | |
| 2007/0203058 A1 | 8/2007 | Lau et al. | |
| 2009/0062192 A1 | 3/2009 | Christensen et al. | |
| 2009/0137456 A1 | 5/2009 | Dimarchi et al. | |
| 2013/0157953 A1 | 6/2013 | Petersen et al. | |
| 2013/0288958 A1 | 10/2013 | Lau et al. | |
| 2015/0182594 A1 | 7/2015 | Lau et al. | |
| 2015/0274801 A1 | 10/2015 | Lau et al. | |
| 2015/0374794 A1 | 12/2015 | Sensfuss et al. | |
| 2016/0002311 A1 | 1/2016 | Lau et al. | |
| 2016/0271263 A1 | 9/2016 | Lau et al. | |
| 2016/0347812 A1 | 12/2016 | Lau et al. | |
| 2017/0051034 A1 | 2/2017 | Lau et al. | |

FOREIGN PATENT DOCUMENTS

| | | |
|---|---|---|
| AU | 2011231503 A1 | 9/2012 |
| CN | 1867360 A | 11/2006 |
| EP | 1695983 A2 | 8/2006 |
| JP | H03254692 A | 11/1991 |
| JP | H09-510438 A | 10/1997 |
| JP | 2007-505840 A | 3/2007 |
| JP | 2011-524419 A | 9/2011 |
| JP | 2014-510739 A | 5/2014 |
| RU | 2401276 C2 | 10/2010 |
| WO | 96/29342 | 9/1996 |
| WO | 97/09040 A1 | 3/1997 |
| WO | 97/26265 A1 | 7/1997 |
| WO | 97/41097 A2 | 11/1997 |
| WO | 97/41119 A1 | 11/1997 |
| WO | 97/41120 A1 | 11/1997 |
| WO | 9808871 A1 | 3/1998 |
| WO | 98/45292 A1 | 10/1998 |
| WO | 99/01423 A1 | 1/1999 |
| WO | 99/03861 A1 | 1/1999 |
| WO | 99/19313 A1 | 4/1999 |
| WO | 00/23415 A1 | 4/2000 |
| WO | 00/23416 A1 | 4/2000 |
| WO | 00/23417 A1 | 4/2000 |
| WO | 00/23425 A1 | 4/2000 |

(Continued)

OTHER PUBLICATIONS

Moran TH, Gut peptides in the control of food intake, International Journal of Obesity, 2009, vol. 33, pp. S7-S10.
Dakin C. L. et al., Oxyntomodulin Inhibits Food Intake in the Rat, Endocrinology, 2001, vol. 142, No. 10, pp. 4244-4250.
Sherwin R. S. et al., Hyperglucagonemia and blood glucose regulation in normal, obese and diabetic subjects, The New England Journal of Medicine, 1976, vol. 294, No. 9, pp. 455-461.
Cho Min Y. et al., Targeting the glucagon receptor family for diabetes and obesity therapy, Pharmacology & Therapeutics, 2012, vol. 135, No. 3, pp. 247-278.
Dan Donnelly, The structure and function of the glucagon-like peptide-1 receptor and its ligands, British Journal of Pharmacology, 2012, vol. 166, No. 1, pp. 27-41.

(Continued)

Primary Examiner — Julie Ha
Assistant Examiner — Li Ni Komatsu
(74) Attorney, Agent, or Firm — Leon Y. Lum

(57) ABSTRACT

The invention relates to novel stable and protracted GLP-1/glucagon receptor co-agonists, to the use of said peptides in therapy, to methods of treatment comprising administration of said peptides to patients, and to the use of said peptides in the manufacture of medicaments.

3 Claims, 1 Drawing Sheet

(56) References Cited

FOREIGN PATENT DOCUMENTS

| | | |
|---|---|---|
| WO | 00/23445 A1 | 4/2000 |
| WO | 00/23451 A1 | 4/2000 |
| WO | 00/37474 A1 | 6/2000 |
| WO | 00/39088 A1 | 7/2000 |
| WO | 00/41121 A1 | 7/2000 |
| WO | 00/42023 A1 | 7/2000 |
| WO | 00/42026 A1 | 7/2000 |
| WO | 00/50414 A1 | 8/2000 |
| WO | 00/63153 A1 | 10/2000 |
| WO | 00/63189 A1 | 10/2000 |
| WO | 00/63190 A1 | 10/2000 |
| WO | 00/63191 A1 | 10/2000 |
| WO | 00/63192 A1 | 10/2000 |
| WO | 00/63193 A1 | 10/2000 |
| WO | 00/63196 A1 | 10/2000 |
| WO | 00/63208 A1 | 10/2000 |
| WO | 00/63209 A1 | 10/2000 |
| WO | 00/64884 A1 | 11/2000 |
| WO | 00/69900 A2 | 11/2000 |
| WO | 02/08209 | 1/2002 |
| WO | 03/022304 A1 | 3/2003 |
| WO | 03/031464 A2 | 4/2003 |
| WO | 03/062290 A1 | 7/2003 |
| WO | 2004/062685 A2 | 7/2004 |
| WO | 2005/012347 A2 | 2/2005 |
| WO | 2005/016974 A1 | 2/2005 |
| WO | 2005/027978 A2 | 3/2005 |
| WO | 2006/053299 A2 | 5/2006 |
| WO | 2006/090119 A1 | 8/2006 |
| WO | 2006/097537 A2 | 9/2006 |
| WO | 2006097536 A2 | 9/2006 |
| WO | 2006/103298 A2 | 10/2006 |
| WO | 2006/134148 A2 | 12/2006 |
| WO | 2006/134340 A2 | 12/2006 |
| WO | 2007056362 A2 | 5/2007 |
| WO | 2007/087711 A1 | 8/2007 |
| WO | 2007/100535 A2 | 9/2007 |
| WO | 2007/126808 A1 | 11/2007 |
| WO | 2008/011633 A2 | 1/2008 |
| WO | 2008/071972 A1 | 6/2008 |
| WO | 2008/074032 A1 | 6/2008 |
| WO | 2008086086 A2 | 7/2008 |
| WO | 2008101017 A2 | 8/2008 |
| WO | 2008/151258 | 12/2008 |
| WO | 2008/151448 A1 | 12/2008 |
| WO | 2008152403 A1 | 12/2008 |
| WO | 2009/030771 A1 | 3/2009 |
| WO | 2009030738 A1 | 3/2009 |
| WO | 2009033738 A2 | 3/2009 |
| WO | 2009/062100 A1 | 5/2009 |
| WO | 2009/083549 A1 | 7/2009 |
| WO | 2009/089396 | 7/2009 |
| WO | 2009099763 A1 | 8/2009 |
| WO | 2009/108806 A1 | 9/2009 |
| WO | 2009155257 A1 | 12/2009 |
| WO | 2009155258 A2 | 12/2009 |
| WO | 2010011439 A1 | 1/2010 |
| WO | 2010/014708 A2 | 2/2010 |
| WO | 2010016940 A2 | 2/2010 |
| WO | 2010/045568 A1 | 4/2010 |
| WO | 2010070251 A1 | 6/2010 |
| WO | 2010070252 A1 | 6/2010 |
| WO | 2010070253 A1 | 6/2010 |
| WO | 2010070255 A1 | 6/2010 |
| WO | 2010/102886 A1 | 9/2010 |
| WO | 2010148089 A1 | 12/2010 |
| WO | 2011006497 A1 | 1/2011 |
| WO | 2011038900 A2 | 4/2011 |
| WO | 2011075393 A2 | 6/2011 |
| WO | 2011/117416 A1 | 9/2011 |
| WO | 2011117415 A1 | 9/2011 |
| WO | 2011117417 A1 | 9/2011 |
| WO | 2011119657 A1 | 9/2011 |
| WO | 2011160630 A2 | 12/2011 |
| WO | 2011160633 A1 | 12/2011 |
| WO | 2011163473 A1 | 12/2011 |
| WO | 2012088116 A2 | 6/2012 |
| WO | 2012088379 A2 | 6/2012 |
| WO | 2012098462 A1 | 7/2012 |
| WO | 2012130866 A1 | 10/2012 |
| WO | 2012138941 A1 | 10/2012 |
| WO | 2012150503 A2 | 11/2012 |
| WO | 2012158962 A2 | 11/2012 |
| WO | 2012158965 A2 | 11/2012 |
| WO | 2012169798 A2 | 12/2012 |
| WO | 2012177443 A2 | 12/2012 |
| WO | 2012177444 A2 | 12/2012 |
| WO | 2013041678 A1 | 3/2013 |
| WO | 2014170496 A1 | 10/2014 |
| WO | 2015086733 A1 | 6/2015 |

OTHER PUBLICATIONS

Hongxiang H. et al., Structure and function studies of glucagon-like peptide-1 (GLP-1): the designing of a novel pharmacological agent for the treatment of diabetes, Diabetes/Metabolism Research and Reviews, Wiley, London, GB, 2005, vol. 21, No. 4, pp. 313-331.

Groner et al., Journal of Thrombosis and Haemostasis, "Abstracts From XXII ISTH Congress", 2009, vol. 7, No. SUPPL2, pp. 508-517.

Angata et al., Journal of Biological Chemistry, "ST8SIA II and ST8SIA IV Polysialyltransferases Exhibit Marked Differences in Utilizing Various Acceptors Containing Oligosialic Acid and Short Polysialic Acid", 2002, vol. 277, No. 39, pp. 36808-36817.

Bonora et al., Post-translational Modification of Protein Biopharmaceuticals, "Engineering in a PTM: Pegylation.", 2009, pp. 341-357.

"Cho, Jw. et al., Proceedings of the National Academy of Sciences of the United Sta, ""Polysialic Acid Engineering: Synthesis of Polysialylated Neoglycosphingolipids by Using the Polysialyltransferase From Neuroinvasive *Escherichia coli* K1"", 1994, vol. 91, No. 24, pp. 11427-11431".

Eckhardt et al., Nature, "Molecular Characterization of Eukaryotic Polysialyltransferase-1", 1995, vol. 373, pp. 715-718.

"Fernandes et al., Biochimica ET Biophysica ACTA, ""Synthesis, Characterization and Properties of Sialylated Catalase Synthesis, Characterization and Properties of Sialylated Catalase""", 1996, vol. 1293, pp. 90-96".

Fontana et al., Advanced Drug Delivery Reviews, "Site-Specific Modification and Pegylation of Pharmaceutical Proteins Mediated by Transglutaminase", 2008, vol. 60, No. 1, pp. 13-28.

Gilbert et al., Journal of Biological Chemistry, "The Genetic Bases for the Variation in the Lipo-Oligosaccharide of the Mucosal Pathogen, Campylobacter Jejuni", 2002, vol. 277, No. 1, pp. 327-337.

Glabe et al., Journal of Biological Chemistry, "Glycosylation of Ovalbumin Nascent Chains", 1980, vol. 255, No. 19, pp. 9236-9242.

Graham et al, Journal of General Virology, "Characteristics of a Human Cell Line Transformed by DNA From Human Adenovirus Type 5", 1977, vol. 36, pp. 59-72.

Gregoriadis et al., S.T.P. Pharma Sciences, "Polysialylated Proteins: An Approach to Improve Enzyme Stability and Half-Life in the Blood Circulation", 1999, vol. 9, No. 1, pp. 61-66.

Higuchi et al., Genomics, "Characterization of Mutations in the Factor VIII Gene by Direct Sequencing of Amplified Genomic DNA", 1990, vol. 6, No. 1, pp. 65-71.

Jain S et al, BBA—General Subjects, Elsevier Science Publishers, NL, "Polysialylated Insulin: Synthesis, Characterization and Biological Activity In Vivo", 2003, vol. 1622, No. 1, pp. 42-49.

Jennings and Lugowski, Journal of Immunology, "Immunochemistry of Groups A, B, and C Meningococcal Polysaccharide—Tetanus Toxoid Conjugates", 1981, vol. 127, No. 3, pp. 1011-1018.

Julenius, K. et al., Bioinformatics for Glycobiology and Glycomics:, "Prediction of Glycosylation Sites in Proteins", 2009, pp. 163-185.

(56) References Cited

OTHER PUBLICATIONS

Karin Julenius et al., Glycobiology, "Prediction, Conservation Analysis, and Structural Characterization of Mammalian Mucin—Type O—Glycosylation Sites", 2004, vol. 15, No. 2, pp. 153-164.
Kiely et al., Journal of Biological Chemistry, "Studies on the Attachement of Carbohydrate to Ovalbumin Nascent Chains in HEN Oviduct", 1976, vol. 251, No. 18, pp. 5490-5495.
Kojima et al., FEBS Letters, "A Developmentally Regulated Member of the Sialyltransferase Family (ST8SIA II, STX) is a Polysialic Acid Synthase", 1995, vol. 373, No. 2, pp. 119-122.
"Kunou M. et al., Biomacromolecules., ""Synthesis of Sulfated Colominic Acids and Their Interaction With Fibroblast Growth Factors"", 2000, vol. 1, No. 3, pp. 451-458".
"Nakayama et al., Proceedings of the National Academy of Sciences of the USA, ""Expression Cloning of a Human Polysialyltransferase That Forms the Polysialylated Neural Cell Adhesion Molecule Present in Embryonic Brain"", 1995, vol. 92, No. 15, pp. 7031-7035".
P. J. Lenting et al., Haemophilia, "Factor VIII and Von Willebrand Factor—Too Sweet for Own Good", 2010, vol. 16, No. 5, pp. 194-199.
Saenko E L et al, Haemophilia, "Strategies Towards a Longer Acting Factor VIII", 2006, vol. 12, No. 3, pp. 42-51.
"Scheidegger et al., Journal of Biological Chemistry, ""A Human STX CDNA Confers Polysialic Acid Expression in Mammalian Cells"", 1995, vol. 270, No. 39, pp. 22685-22688".
Thim L, et al., Haemophilia, "Purification and Characterization of a New Recombinant Factor VIII(N8)", 2010, vol. 16, No. 2, pp. 349-359.
Urlaub G. et al, Somatic Cell and Molecular Genetics, "Effect of Gamma Rays at the Dihydrofolate Reductase Locus: Deletions and Inversions", 1986, vol. 12, No. 6, pp. 555-566.
Urlaub et al, Proceedings of the National Academy of Sciences of the USA, "Isolation of Chinese Hamster Cell Mutants Deficient in Dihydrofolate Reductase Activity", 1980, vol. 17, No. 7, pp. 4216-4220.
"Urlaub, Gail et al., Cell, ""Deletion of the Diploid Dihydrofolate Reductase Locus From Cultured Mammalian Cells"", 1983, vol. 33, No. 2, pp. 405-412".
Veronese et al, Journal of Bioactive and Compatible Polymers, "Branched and Linear Poly Ethylene Glycol): Influence of the Polymer Structure on Enzymological, Pharmacokinetic, and Immunological Properties of Protein Conjugates", 1997, vol. 12, No. 3, pp. 196-207.
Veronese et al., Advanced Drug Delivery Reviews, "I ntroduction and Overview of Peptide and Protein Pegylation", 2002, vol. 54, pp. 453-456.
Waechter et al, Proceedings of the National Academy of Sciences of the USA, "Effect of Methylation on Expression of Microinjected Genes", 1982, vol. 79, pp. 1106-1110.
Willis et al., Glycobiology, "Characterization of the ¿-2,8-Polysialyltransferase From Neisseria Meningitidis With Synthetic Acceptors, and the Development of a Self-Priming Polysialyltransferase Fusion Enzyme", 2008, vol. 18, No. 2, pp. 177-186.
Haack et al., "Analysis of Expression Kinetics and Activity of a New B-Domain Truncated and Full-Lenth FVIII Protein in Three Different Cell Lines," Ann Hematol, 1999, vol. 78, pp. 111-116.
Nakayama et al., "Expression Cloning of a Human Polysialyltransferase That Forms the Polysialylated Neural Cell Adhesion Molecule Present in Embryonic Brain," PNAS, 1995, vol. 32, No. 15, pp. 7031-7035.
Harduin-Lepers A et al. Biochemistry. "The Human Sialyltransferase Family" 2001. vol. 83(8) pp. 727-737.
Schulman et al., "Effect of Glucagon on Food Intake and Body Weight in Man", Journal of Applied Physiology, 1957, vol. 11, pp. 419-421.
Carpenter et al., "Modes of Stabilization of a Protein by Organic Solutes During Desiccation", Cryobiology, 1988, vol. 25, pp. 459-470.

Cohen et al., "Oxyntomodulin Suppresses Appetite and Reduces Food Intake in Humans", Journal of Clinical Endocrinology and Metabolism, 2003, vol. 88, No. 10, pp. 4696-4701.
Geary, "Effects of Glucagon, Insulin, Amylin and CGRP on Feeding", Neuropeptides, 1999, vol. 33, No. 5, pp. 400-405.
Hippen et al., "Alleviation of Fatty Liver in Dairy Cows With 14-Day Intravenous Infusions of Glucagon", Journal of Dairy Science, 1999, vol. 82, No. 6, pp. 1139-1152.
Mumenthaler et al, "Feasibility Study on Spray-Drying Protein Pharmaceuticals: Recombinant Human Growth Hormone and Tissue-Type Plasminogen Activator", Pharmaceutical Research, 1994, vol. 11, No. 1, pp. 12-20.
Pocai et al., "Glucagon-Like Peptide1/Glucagon Receptor Dual Agonism Reverses Obesity in Mice", Diabetes, 2009, vol. 58, pp. 2258-2266.
Roser, "Trehalose Drying: A Novel Replacement for Freeze Drying", Biopharmaceutical, 1991, vol. 4, pp. 47-53.
Williams et al., "The Lyophilization of Pharmaceuticals: A Literature Review", Journal of Parenteral Science and Technology, 1984, vol. 38, No. 2, pp. 48-59.
Wynne et al, "Subcutaneous Oxyntomodulin Reduces Body Weight in Overweight and Obese Subjects: A Double-Blind, Randomized, Controlled Trial", Diabetes, 2005, vol. 54, pp. 2390-2395.
Krstenansky, John L et al. J. Am. Chem. Soc. "Conformation considerations in the design of a glucagon analogue with increased receptor binding and adenylate cyclase potencies." 1986. vol. 108 p. 1696-1698.
Scrocchi et al., "Elimination of Glucgon-Like Peptide 1R Signaling Does Not Modify Weight Gain and ISLET Adaptation in Mice With Combined Disruption of Leptin and GLP-1 Action", Diabetes, 2000, vol. 49, No. 9, pp. 1552-1560.
Batterham et al., "Gut Hormone PYY3-36 Physiologically Inhibits Food Intake", Nature, 2002, vol. 418, pp. 650-654.
Broadhead et al., The Spray Dying of Pharmaceuticals, Drug Development and Industrial Pharmacy, 1992, vol. 18, No. 11-12, pp. 1169-1206.
Day et al., "A New Glucagon and GLP-1 Co-Agonists Eliminates Obesity in Rodents", Nature Chemical Biology, 2009, vol. 5, No. 10, pp. 749-757.
Druce and Ghatei, "Oxyntomodulin", Current Opinion in Endocrinology, 2006, vol. 13, No. 1, pp. 49-55.
Geary et al., "Individual, But Not Simultaneous Glucagon and Cholecystokinin Infusions Inhibit Feeding in Men", American Journal of Physiology, 1992, vol. 262, pp. R975-R980.
Zhang Et L., "Polyethylene Glycol Positioning Modification of Glucagon-Like Peptide", The Chinese Journal of Process Engineering, 2009, vol. 9, No. 6, pp. 1169-1173. Abstract only.
John Wilding. BMJ. "Science, Medecine and the Future Obesity Treatment." 1997. vol. 315. pp. 997-1000.
Bray et al. Nature. "Medicinal Strategies in the Treatment of Obesity." 2000. vol. 404. pp. 672-677.
Habegger et al. Natural Reviews of Endocrinology. "The Metabolic Actions of Glucagon Revisited." 2010. vol. 6. pp. 689-697.
Nielsen et al. Biochemistry. "Effect of Environmental Factors on the Kinetics of Insulin Fibril Formation: ¿ Elucidation of the Molecular Mechanism." 2001. vol. 40(20). pp. 6036-6046.
LeVine III, Harry. Methods in Enzymology. "Quantification of B-Sheet Amyloid Fibril Structures With Thioflavin T." 1999. vol. 309. pp. 274-284.
Naiki et al. Analytical Biochemistry. "Fluorometric Determination of Amyloid Fibrils in Vitro Using the Fluorescent Dye, Thioflavine T." 1989. vol. 177(2). pp. 244-249.
Remington's Pharmaceutical Sciences: The Science and Practice of Pharmacy, 19th Edition. 1995.
Berge et al. Journal of Pharmceutical Sciences. "Pharmaceutical Salts." 1977. vol. 66(1). pp. 1-19.
Beaven et al. European Journal of Biochemistry. "Formation and Structure of Gels and Fibrils From Glucagon." 1969. vol. 11(1). pp. 37-42.
Schade & Eaton. Acta Diabetologica. "Modulation of the Catabolic Activity of Glucagon by Endogenous Insulin Secretion in Obese Man." 1977. vol. 14. pp. 62-72.

(56) References Cited

OTHER PUBLICATIONS

Cegla J. et al., Energy intake following infusion of glucagon and GLP-1: a double-blind crossover study, Endocrine Abstracts, 2013, 1 page.
Day J. W. et al. Optimization of Co-Agonism at GLP-1 and Glucagon Receptors to Safely Maximize Weight Reduction in DIO-Rodents, PeptideScience, 2012, vol. 98, No. 5, pp. 443-450.
Jiang G. et al., Glucagon and regulation of glucose metabolism, American Journal of Physiology,Endocrinology and Metabolism, 2003, vol. 284, pp. E671-E678.
Moran T. H. et al., Gut peptides in the control of food intake, International Journal of Obesity, 2009, vol. 33, pp. S7-S10.
Pocai A., Unraveling oxyntomodulin, GLP1's enigmatic brother, Journal of Endocrinology, 2012, vol. 215, pp. 335-346.
Tan T. M. et al., Coadministration of Glucagon-Like Peptide-1 During Glucagon Infusion in Humans Results in Increased Energy Expenditure and Amelioration of Hyperglycemia, Diabetes, 2013, vol. 62, pp. 1131-1138.
Pedersen et al., "N- and C-Terminal Hydrophobic Patches Are Involved in Fibrillation of Glucagon +," Biochemistry, 2006, vol. 45, No. 48, pp. 14503-14512.

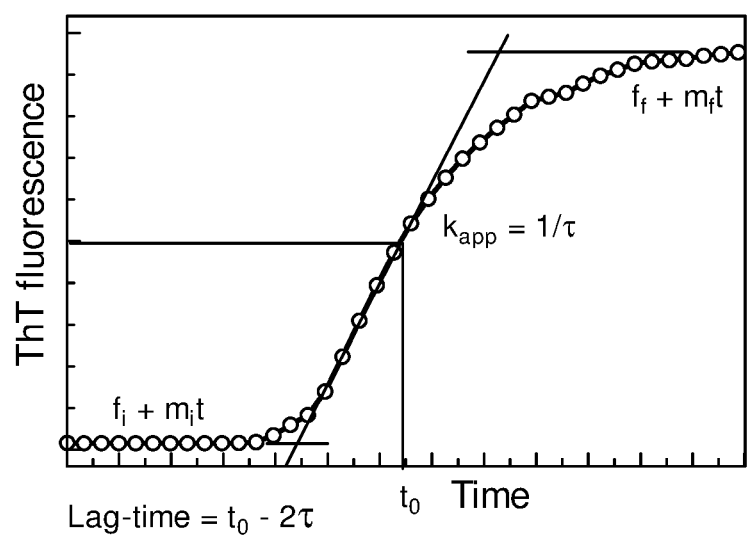

SEQUENCE LISTING

<160> NUMBER OF SEQ ID NOS: 5

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (2)..(2)
<223> OTHER INFORMATION: Xaa = Aib, Acb or Acpr
<220> FEATURE:
<221> NAME/KEY: MISC_FEATURE
<222> LOCATION: (3)..(3)
<223> OTHER INFORMATION: Xaa = Gln or His
<220> FEATURE:
<221> NAME/KEY: MISC_FEATURE
<222> LOCATION: (10)..(10)
<223> OTHER INFORMATION: Xaa = Leu, Ile or Val
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (16)..(16)
<223> OTHER INFORMATION: Xaa = Ser, Ala, Leu, Thr, Glu, Aib, Ile, Val or
      Lys
<220> FEATURE:
<221> NAME/KEY: MISC_FEATURE
<222> LOCATION: (17)..(17)
<223> OTHER INFORMATION: Xaa = Arg or Lys
<220> FEATURE:
<221> NAME/KEY: MISC_FEATURE
<222> LOCATION: (18)..(18)
<223> OTHER INFORMATION: Xaa = Arg, Ala or Lys
<220> FEATURE:
<221> NAME/KEY: MISC_FEATURE
<222> LOCATION: (20)..(20)
<223> OTHER INFORMATION: Xaa = Gln, Arg, Glu, Aib or Lys
<220> FEATURE:
<221> NAME/KEY: MISC_FEATURE
<222> LOCATION: (21)..(21)
<223> OTHER INFORMATION: Xaa = Asp, Glu or Lys
<220> FEATURE:
<221> NAME/KEY: MISC_FEATURE
<222> LOCATION: (24)..(24)
<223> OTHER INFORMATION: Xaa = Gln, Ala, Arg, Glu, Aib or Lys
<220> FEATURE:
<221> NAME/KEY: MISC_FEATURE
<222> LOCATION: (27)..(27)
<223> OTHER INFORMATION: Xaa = Met, Leu or Val
<220> FEATURE:
<221> NAME/KEY: MISC_FEATURE
<222> LOCATION: (28)..(28)
<223> OTHER INFORMATION: Xaa = Asn, Ser, Thr, Gln, Ala, Gly, Glu or Lys
<220> FEATURE:
<221> NAME/KEY: MISC_FEATURE
<222> LOCATION: (29)..(29)
<223> OTHER INFORMATION: Xaa = Thr, Gly, Ser, Gln, Ala, Glu or Lys

<400> SEQUENCE: 2

His Xaa Xaa Gly Thr Phe Thr Ser Asp Xaa Ser Xaa Tyr Leu Xaa Xaa
1               5                   10                  15

Xaa Xaa Ala Xaa Xaa Phe Val Xaa Trp Leu Xaa Xaa Xaa
            20                  25

<210> SEQ ID NO 3
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib, Acb or Acpr
<220> FEATURE:
<221> NAME/KEY: MISC_FEATURE
<222> LOCATION: (3)..(3)
```

```
<223> OTHER INFORMATION: Xaa = Gln or His
<220> FEATURE:
<221> NAME/KEY: MISC_FEATURE
<222> LOCATION: (10)..(10)
<223> OTHER INFORMATION: Xaa = Leu, Ile or Val
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (16)..(16)
<223> OTHER INFORMATION: Xaa = Ser, Ala, Leu, Thr, Glu, Aib, Ile, Val,
      or Lys
<220> FEATURE:
<221> NAME/KEY: MISC_FEATURE
<222> LOCATION: (17)..(17)
<223> OTHER INFORMATION: Xaa = Arg or Lys
<220> FEATURE:
<221> NAME/KEY: MISC_FEATURE
<222> LOCATION: (18)..(18)
<223> OTHER INFORMATION: Xaa = Arg, Ala or Lys
<220> FEATURE:
<221> NAME/KEY: MISC_FEATURE
<222> LOCATION: (20)..(20)
<223> OTHER INFORMATION: Xaa = Gln, Arg, Glu, Aib or Lys
<220> FEATURE:
<221> NAME/KEY: MISC_FEATURE
<222> LOCATION: (21)..(21)
<223> OTHER INFORMATION: Xaa = Asp, Glu or Lys
<220> FEATURE:
<221> NAME/KEY: MISC_FEATURE
<222> LOCATION: (24)..(24)
<223> OTHER INFORMATION: Xaa = Gln, Ala, Arg, Glu, Aib, or Lys
<220> FEATURE:
<221> NAME/KEY: MISC_FEATURE
<222> LOCATION: (27)..(27)
<223> OTHER INFORMATION: Xaa = Met, Leu or Val
<220> FEATURE:
<221> NAME/KEY: MISC_FEATURE
<222> LOCATION: (28)..(28)
<223> OTHER INFORMATION: Xaa = Asn, Ser, Thr, Gln, Ala, Gly, Glu, or Lys
<220> FEATURE:
<221> NAME/KEY: MISC_FEATURE
<222> LOCATION: (29)..(29)
<223> OTHER INFORMATION: Xaa = Thr, Gly, Ser, Gln, Ala, Glu or Lys
<220> FEATURE:
<221> NAME/KEY: MISC_FEATURE
<222> LOCATION: (30)..(30)
<223> OTHER INFORMATION: Xaa = Lys

<400> SEQUENCE: 3

His Xaa Xaa Gly Thr Phe Thr Ser Asp Xaa Ser Xaa Tyr Leu Xaa Xaa
1               5                   10                  15

Xaa Xaa Ala Xaa Xaa Phe Val Xaa Trp Leu Xaa Xaa Xaa Xaa
            20                  25                  30

<210> SEQ ID NO 4
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib, Acb, or Acpr
<220> FEATURE:
<221> NAME/KEY: MISC_FEATURE
<222> LOCATION: (3)..(3)
```

```
<223> OTHER INFORMATION: Xaa = Gln or His
<220> FEATURE:
<221> NAME/KEY: MISC_FEATURE
<222> LOCATION: (10)..(10)
<223> OTHER INFORMATION: Xaa = Leu, Ile, or Val
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (16)..(16)
<223> OTHER INFORMATION: Xaa = Ser, Ala, Leu, Thr, Glu, Aib, Ile, Val or
      Lys
<220> FEATURE:
<221> NAME/KEY: MISC_FEATURE
<222> LOCATION: (17)..(17)
<223> OTHER INFORMATION: Xaa = Arg or Lys
<220> FEATURE:
<221> NAME/KEY: MISC_FEATURE
<222> LOCATION: (18)..(18)
<223> OTHER INFORMATION: Xaa = Arg, Ala or Lys
<220> FEATURE:
<221> NAME/KEY: MISC_FEATURE
<222> LOCATION: (20)..(20)
<223> OTHER INFORMATION: Xaa = Gln, Arg, Glu, Aib or Lys
<220> FEATURE:
<221> NAME/KEY: MISC_FEATURE
<222> LOCATION: (21)..(21)
<223> OTHER INFORMATION: Xaa = Asp, Glu, Ser, or Lys
<220> FEATURE:
<221> NAME/KEY: MISC_FEATURE
<222> LOCATION: (24)..(24)
<223> OTHER INFORMATION: Xaa = Gln, Ala, Arg, Glu, Aib or Lys
<220> FEATURE:
<221> NAME/KEY: MISC_FEATURE
<222> LOCATION: (27)..(27)
<223> OTHER INFORMATION: Xaa = Met, Leu, or Val
<220> FEATURE:
<221> NAME/KEY: MISC_FEATURE
<222> LOCATION: (28)..(28)
<223> OTHER INFORMATION: Xaa = Asn, Ser, Thr, Gln, Ala, Gly, Glu or Lys
<220> FEATURE:
<221> NAME/KEY: MISC_FEATURE
<222> LOCATION: (29)..(29)
<223> OTHER INFORMATION: Xaa = Thr, Gly, Ser, Gln, Ala, Glu, or Lys

<400> SEQUENCE: 4

His Xaa Xaa Gly Thr Phe Thr Ser Asp Xaa Ser Xaa Tyr Leu Xaa Xaa
1               5                   10                  15

Xaa Xaa Ala Xaa Xaa Phe Val Xaa Trp Leu Xaa Xaa Xaa
            20                  25

<210> SEQ ID NO 5
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = Aib, Acb or Acpr
<220> FEATURE:
<221> NAME/KEY: MISC_FEATURE
```

```
<222> LOCATION: (3)..(3)
<223> OTHER INFORMATION: Xaa = Gln or His
<220> FEATURE:
<221> NAME/KEY: MISC_FEATURE
<222> LOCATION: (10)..(10)
<223> OTHER INFORMATION: Xaa = Leu, Ile or Val
<220> FEATURE:
<221> NAME/KEY: MISC_FEATURE
<222> LOCATION: (12)..(12)
<223> OTHER INFORMATION: Xaa = Lys or Arg
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (16)..(16)
<223> OTHER INFORMATION: Xaa = Ser, Ala, Leu, Thr, Glu, Aib, Ile, Val
      or Lys
<220> FEATURE:
<221> NAME/KEY: MISC_FEATURE
<222> LOCATION: (17)..(17)
<223> OTHER INFORMATION: Xaa = Arg or Lys
<220> FEATURE:
<221> NAME/KEY: MISC_FEATURE
<222> LOCATION: (18)..(18)
<223> OTHER INFORMATION: Xaa = Arg, Ala or Lys
<220> FEATURE:
<221> NAME/KEY: MISC_FEATURE
<222> LOCATION: (20)..(20)
<223> OTHER INFORMATION: Xaa = Gln, Arg, Glu, Aib or Lys
<220> FEATURE:
<221> NAME/KEY: MISC_FEATURE
<222> LOCATION: (21)..(21)
<223> OTHER INFORMATION: Xaa = Asp, Glu, Ser or Lys
<220> FEATURE:
<221> NAME/KEY: MISC_FEATURE
<222> LOCATION: (24)..(24)
<223> OTHER INFORMATION: Xaa = Gln, Ala, Arg, Glu, Aib or Lys
<220> FEATURE:
<221> NAME/KEY: MISC_FEATURE
<222> LOCATION: (27)..(27)
<223> OTHER INFORMATION: Xaa = Met, Leu or Val
<220> FEATURE:
<221> NAME/KEY: MISC_FEATURE
<222> LOCATION: (28)..(28)
<223> OTHER INFORMATION: Xaa = Asn, Ser, Thr, Gln, Ala, Gly, Glu or Lys
<220> FEATURE:
<221> NAME/KEY: MISC_FEATURE
<222> LOCATION: (29)..(29)
<223> OTHER INFORMATION: Xaa = Thr, Gly, Ser, Gln, Ala, Glu or Lys
<220> FEATURE:
<221> NAME/KEY: MISC_FEATURE
<222> LOCATION: (30)..(30)
<223> OTHER INFORMATION: Xaa = Lys

<400> SEQUENCE: 5

His Xaa Xaa Gly Thr Phe Thr Ser Asp Xaa Ser Xaa Tyr Leu Xaa Xaa
1               5                   10                  15

Xaa Xaa Ala Xaa Xaa Phe Val Xaa Trp Leu Xaa Xaa Xaa Xaa
            20                  25                  30
```

STABLE, PROTRACTED GLP-1/GLUCAGON RECEPTOR CO-AGONISTS FOR MEDICAL USE

CROSS-REFERENCE TO RELATED APPLICATIONS

This application is a continuation of U.S. application Ser. No. 14/836,192 filed Aug. 26, 2015 (U.S. Pat. No. 9,474, 790, issued Dec. 31, 2015), which is a continuation of International Application PCT/EP2014/058084 (WO 2014/170496), filed Apr. 22, 2014, which claims priority to European Patent Application 13164272.0, filed Apr. 18, 2013 and European Patent Application 13196656.6, filed Dec. 11, 2013; this application claims priority under 35 U.S.C. §119 to U.S. Provisional Application 61/814,969; filed Apr. 23, 2013; the contents of which are incorporated herein by reference.

TECHNICAL FIELD

The invention relates to novel stable and protracted GLP-1/glucagon receptor co-agonists, to their use in therapy, to methods of treatment comprising administration hereof to patients, and to the use hereof in the manufacture of medicaments.

SEQUENCE LISTING

The instant application contains a Sequence Listing which has been submitted in ASCII format via EFS-Web and is hereby incorporated by reference in its entirety. Said ASCII copy, created on Jun. 10, 2016, is named 8676US03SeqList_ST25.txt and is 6,919 bytes in size.

BACKGROUND

The increase in obesity incidence has reached epidemic proportions in the western world and more recently also in developing countries. Obesity is associated with significant co-morbidities such as cardiovascular diseases and Type 2 diabetes. Presently, the only treatment that eliminates obesity with high efficacy is bariatric surgery, but this treatment is costly and risky. Pharmacological intervention is generally less efficacious and associated with side effects. There is therefore an obvious need for more efficacious pharmacological intervention with fewer side effects and convenient administration.

Numerous gastro-intestinal peptide hormones are allegedly involved in the regulation of food intake, being either anorexigenic (e.g. CCK, GLP-1, PYY, secretin) or orexigenic (e.g. ghrelin) [Moran T H: Gut peptides in the control of food intake; *Int. J. Obes.* (*Lond*). 2009 33 S7-10]. Recently, oxyntomodulin, a product from the proglucagon gene in intestinal L-cells was shown to induce satiety and reduce body weight in both rodents and humans [Cohen M A et al: Oxyntomodulin suppresses appetite and reduces food intake in humans; *J. Clin. Endocrinol. Metab.* 2003 88 4696-4701; Dakin C L et al: Oxyntomodulin inhibits food intake in the rat; Endocrinology 2001 142 4244-4250]. Oxyntomodulin is a dual agonist activating both GLP-1 and glucagon receptors, albeit with reduced potency compared to GLP-1 and glucagon, respectively. The anorexigenic effect of oxyntomodulin was previously speculated to be mediated by the GLP-1 receptor, although numerous older studies indicated the involvement of pancreatic glucagon in the control of bodyweight. Two recent papers allegedly show glucagon as an attractive target and demonstrated the power of simultaneous GLP-1/glucagon receptor-targeting by constructing dual agonists and comparing the weight lowering effect in knock-out models [Pocai et al; Glucagon-Like Peptide 1/Glucagon Receptor Dual Agonism Reverses Obesity in Mice; *Diabetes,* 2009, 58, 2258-2266; Day et al; A new GLP-1 co-agonist eliminates obesity in rodents; *Nat. Chem. Biol.*, 2009, 5, 749-757].

One physiological effect of glucagon is to increase blood glucose levels in hypoglycaemic conditions by stimulating glycogenolysis and gluconeogenesis. However, the acute effect of glucagon on blood glucose levels seems to be modest when glucagon is infused at near-physiological levels [Sherwin R S et al: Hyperglucagonemia and blood glucose regulation in normal, obese and diabetic subjects; *N. Engl. J. Med.* 1976, 294, 455-461]. Glucagon receptor activation has also been shown to increase energy expenditure and decrease food intake in both rodents and humans [Habegger K M et al: The metabolic actions of glucagon revisited; *Nat. Rev. Endocrinol.* 2010 6 689-697] and these effects are robust and sustained in rodents. The risk of increased blood glucose levels due to glucagon agonism may be counter-acted by appropriate levels of GLP-1 agonism. A GLP-1/glucR co-agonist with a balanced effect on the two receptors may give rise to an improved weight loss compared to a pure GLP-1 agonist without compromising the glucose tolerance. However, there are several obstacles in developing such a co-agonist to a pharmaceutical product, relating to half-life, stability, solubility and receptor activity. For example, if glucagon is used as a starting point for such a co-agonist, the GLP-1 receptor activity needs to be established without destroying the activity at the glucagon receptor. Furthermore, since glucagon is inherently insoluble at neutral pH, it is chemically and physically unstable and its half-life in vivo is only a few minutes.

Several patent applications disclosing different GLP-1/glucagon receptor co-agonists are known in the art, e.g. WO 2008/101017, WO 2010/070255, WO 2012/150503, and WO 2012/169798.

In summary, there are several obstacles in developing such a co-agonist into pharmaceutical products, in particular:
  i) Receptor activity—The glucagon and GLP-1 receptor potency and/or binding affinity ratio of the co-agonist should be balanced in order to favour a robust reduction in body weight, without compromising glucose balance;
  ii) A protracted profile of action, i.e. an in vivo half-life that allows dosing for example once a day or once a week; and
  iii) Acceptable solubility, chemical and physical stability.

When glucagon is used as a starting point for such a co-agonist, the GLP-1 receptor activity and/or affinity needs to be established without destroying the glucagon activity. Native glucagon is inherently insoluble at neutral pH, it is chemically and physically unstable and its half-life in vivo is only a few minutes.

SUMMARY OF THE INVENTION

The invention relates to novel stable and protracted GLP-1/glucagon receptor co-agonists (also referred to as "peptides" or "derivatives" herein, in particular referred to as "glucagon derivatives" herein), to the use of said peptides in therapy, to methods of treatment comprising administration of said peptides to patients, and to the use of said peptides in the manufacture of medicaments for use in medicine, including the treatment of diabetes, obesity and related diseases and conditions.

In a first embodiment, the invention relates to a glucagon derivative comprising the amino acid sequence of Formula I (corresponding to SEQ ID NO:4 and SEQ ID NO:5):

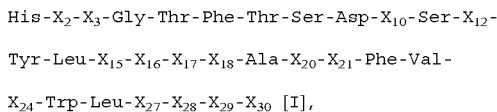

wherein,
$X_2$ represents Aib, Acb or Acpr;
$X_3$ represents Gln or His;
$X_{10}$ represents Leu, Ile or Val;
$X_{12}$ represents Lys or Arg;
$X_{15}$ represents Asp or Glu;
$X_{16}$ represents Ser, Ala, Leu, Thr, Glu, Aib, Ile, Val or Lys;
$X_{17}$ represents Arg or Lys;
$X_{18}$ represents Arg, Ala or Lys;
$X_{20}$ represents Gln, Arg, Glu, Aib or Lys;
$X_{21}$ represents Asp, Glu, Ser, or Lys;
$X_{24}$ represents Gln, Ala, Arg, Glu, Aib or Lys;
$X_{27}$ represents Met, Leu or Val;
$X_{28}$ represents Asn, Ser, Thr, Gln, Ala, Gly, Glu or Lys;
$X_{29}$ represents Thr, Gly, Ser, Gln, Ala, Glu or Lys;
$X_{30}$ represents Lys, or $X_{30}$ is absent;
which amino acid sequence comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of said lipophilic moiety, and wherein said substituent is attached at the epsilon position of a lysine residue in one of the amino acid positions 16, 17, 18, 20, 21, 24, 28, 29, or 30; and wherein said glucagon derivative is a C-terminal amide; or a pharmaceutically acceptable salt or prodrug thereof.

In one embodiment the invention relates to a pharmaceutical composition comprising a glucagon derivative according the invention and optionally one or more pharmaceutically acceptable excipients.

In one embodiment the invention relates to an intermediate product in the form of a glucagon peptide comprising a C-terminal amide and any one of the modifications a) to ppp) as defined herein as compared to glucagon (SEQ ID NO: 1), or a pharmaceutically acceptable salt, amide, or ester thereof.

In one embodiment the invention relates to a glucagon derivative of the invention, optionally in combination with one or more additional therapeutically active compounds, for use in medicine.

The invention may solve further problems that will be apparent from the disclosure of the exemplary embodiments.

BRIEF DESCRIPTION OF THE DRAWING

FIG. 1 depicts the ThT fibrillation assay results described in Example 76.

DETAILED DESCRIPTION OF THE INVENTION

The invention provides novel glucagon derivatives which are GLP-1/glucagon receptor co-agonists with a novel amino acid mutation, which in combination with other mutations and a substituent with negatively charged moieties, provide glucagon derivatives that activate both the GLP-1 and glucagon receptors. The inventors have found that, for example, the introduction of a leucine in position 10, in analogues with a substituent with at least three negative charges in addition to other substitutions gives rise to GLP-1/glucagon receptor co-agonists with improved physical stability, i.e. the analogues show none or delayed fibrillation in the assay used to assess physical stability and the recovery of the peptides were in general improved. Furthermore, the inventors have surprisingly found that the glucagon derivatives of the invention tend to reduce glucagon receptor binding and at the same time often improve the GLP-1 receptor binding. Therefore, the novel mutation(s) can be used as a tool for adjusting the ratio between glucagon and GLP-1 affinity which is pivotal for obtaining the desired effect on body weight and maintain blood glucose levels.

The inventors have found that the compounds of the invention have adequate aqueous solubility at neutral pH or slightly basic pH and with improved chemical stability i.e. the chemical degradation of the analogues are reduced. The inventors have found that the compounds of the invention have improved pharmacokinetic properties, i.e. they have prolonged half-life in vivo. Furthermore, the compounds of the invention induce a significant reduction in body weight after s.c. administration.

The glucagon derivatives of the invention may in particular be characterised as a glucagon derivative comprising the amino acid sequence of Formula I (corresponding to SEQ ID NO:4 and SEQ ID NO:5):

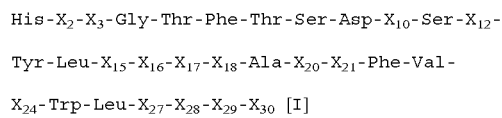

wherein
$X_2$ represents Aib, Acb or Acpr;
$X_3$ represents Gln or His;
$X_{10}$ represents Leu, Ile or Val;
$X_{12}$ represents Lys or Arg;
$X_{15}$ represents Asp or Glu;
$X_{16}$ represents Ser, Ala, Leu, Thr, Glu, Aib, Ile, Val or Lys;
$X_{17}$ represents Arg or Lys;
$X_{18}$ represents Arg, Ala or Lys;
$X_{20}$ represents Gln, Arg, Glu, Aib or Lys;
$X_{21}$ represents Asp, Glu, Ser or Lys;
$X_{24}$ represents Gln, Ala, Arg, Glu, Aib or Lys;
$X_{27}$ represents Met, Leu or Val;
$X_{28}$ represents Asn, Ser, Thr, Gln, Ala, Gly, Glu or Lys;
$X_{29}$ represents Thr, Gly, Ser, Gln, Ala, Glu or Lys;
$X_{30}$ represents Lys, or $X_{30}$ is absent;
which amino acid sequence comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, is attached at the epsilon position of a lysine residue in one of the amino acid positions 16, 17, 18, 20, 21, 24, 28, 29, or 30; and wherein said glucagon derivative is a C-terminal amide, or a pharmaceutically acceptable salt or prodrug thereof.

In one embodiment the glucagon derivative comprises the amino acid sequence of Formula I (corresponding to SEQ ID NO:2 and SEQ ID NO:3):

```
His-X2-X3-Gly-Thr-Phe-Thr-Ser-Asp-X10-Ser-X12-

Tyr-Leu-X15-X16-X17-X18-Ala-X20-X21-Phe-Val-

X24-Trp-Leu-X27-X28-X29-X30 [I]
``` wherein
$X_2$ represents Aib, Acb or Acpr;
$X_3$ represents Gln or His;
$X_{10}$ represents Leu, Ile or Val;
$X_{12}$ represents Lys or Arg;
$X_{15}$ represents Asp or Glu;
$X_{16}$ represents Ser, Ala, Leu, Thr, Glu, Aib, Ile, Val or Lys;
$X_{17}$ represents Arg or Lys;
$X_{18}$ represents Arg, Ala or Lys;
$X_{20}$ represents Gln, Arg, Glu, Aib or Lys;
$X_{21}$ represents Asp, Glu or Lys;
$X_{24}$ represents Gln, Ala, Arg, Glu, Aib or Lys;
$X_{27}$ represents Met, Leu or Val;
$X_{28}$ represents Asn, Ser, Thr, Gln, Ala, Gly, Glu or Lys;
$X_{29}$ represents Thr, Gly, Ser, Gln, Ala, Glu or Lys;
$X_{30}$ represents Lys, or $X_{30}$ is absent;
which amino acid sequence comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, is attached at the epsilon position of a lysine residue in one of the amino acid positions 16, 17, 18, 20, 21, 24, 28, 29, or 30; and wherein said glucagon derivative is a C-terminal amide, or a pharmaceutically acceptable salt or prodrug thereof.

In one embodiment the invention relates to glucagon derivative peptides, wherein said glucagon derivative peptides are GLP-1 and glucagon receptor co-agonists.

Glucagon Peptide

The peptide of the glucagon derivatives of the invention may be described by reference to i) the number of the amino acid residues in human glucagon (SEQ ID NO: 1) which corresponds to the amino acid residue which is modified (i.e. the corresponding position in glucagon (SEQ ID NO: 1)), and to ii) the actual modification. As regards position numbering in glucagon compounds: for the present purposes any amino acid substitution, deletion, and/or addition is indicated relative to the sequences of native human glucagon (1-29) (SEQ ID NO:1). Human glucagon amino acids positions 1-29 are herein to be the same as amino acid positions $X_1$ to $X_{29}$. The human glucagon (1-29) sequence is His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO:1). Glucagon (1-30) means human glucagon with an extension of one amino acid in the C-terminal, glucagon (1-31) means human glucagon with an extension of two amino acid in the C-terminal and glucagon (1-32) means human glucagon with an extension of three amino acid in the C-terminal.

In other words, the peptide of the glucagon derivative is a glucagon peptide which has a number of modifications of amino acid residues when compared to human glucagon (SEQ ID NO: 1). These modifications may represent, independently, one or more amino acid substitutions, additions, and/or deletions. For example, "[Aib2,Leu10,Lys16,Arg20, Leu27,Ser28]-Glucagon amide" designates glucagon (SEQ ID NO: 1), wherein the amino acid in position 2 has been substituted with Aib, the amino acid in position 10 has been substituted with Leu, the amino acid in position 16 has been substituted with Lys, the amino acid in position 20 has been substituted with Arg, the amino acid in position 27 has been substituted with Leu, the amino acid in position 28 has been substituted with Ser, and the C-terminal carboxylic acid has been replaced with a C-terminal amide.

Analogues "comprising" certain specified changes may comprise further changes, when compared to SEQ ID NO: 1. In a particular embodiment, the analogue "has" the specified changes.

In one embodiment, the terms "peptide" and "analogue" (including e.g. "glucagon peptide", "peptide analogue" and "glucagon analogue") are used interchangeably herein and refer to the amino acid sequence of the glucagon derivative of the invention.

The expressions "position" or "corresponding position" may be used to characterise the site of change in an amino acid sequence by reference to glucagon (SEQ ID NO: 1). The position, as well as the number of changes, are easily deduced, e.g. by simple handwriting and eyeballing.

The term "glucagon analogue" as used herein referring to the glucagon sequence wherein one or more amino acid residues of the native peptide have been substituted by other amino acid residues and/or wherein one or more amino acid residues have been deleted from the glucagon sequence and/or wherein one or more amino acid residues have been added to the peptide. Such addition or deletion of amino acid residues can take place at the N-terminal of the peptide and/or at the C-terminal of the peptide. A simple system is used to describe analogues. Formulae of peptide analogues and derivatives thereof are drawn using standard single letter or three letter abbreviations for amino acids used according to IUPAC-IUB nomenclature. The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been added to the peptide. Such addition or deletion of amino acid residues can take place at the N-terminal of the peptide and/or at the C-terminal of the peptide.

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Acb (1-Aminocyclobutanecarboxylic acid), Acpr (1-Aminocyclopropanecarboxylic acid), Abu (α-aminobutyric acid), Tle (tert-butylglycine), β-alanine, 3-aminomethyl benzoic acid, anthranilic acid.

As is apparent from the above examples, amino acid residues may be identified by their full name, their one-letter code, and/or their three-letter code. These three ways are fully equivalent. In one embodiment peptide analogues and derivatives thereof are drawn using standard one-letter or three-letter codes according to IUPAC-IUB nomenclature.

In the present context, common rules for peptide nomenclature based on the three or one letter amino acid code apply. Briefly, the central portion of the amino acid structure is represented by the three letter code (e.g. Ala, Lys) or one letter code (e.g. A, K) and L-configuration is assumed, unless D-configuration is specifically indicated by "D-" followed by the three letter code (e.g. D-Ala, D-Lys). A substituent at the amino group replaces one hydrogen atom and its name is placed before the three letter code, whereas a C-terminal substituent replaces the carboxylic hydroxy group and its name appears after the three letter code. For example, "acetyl-Gly-Gly-NH$_2$" represents CH$_3$—C(=O)—NH—CH$_2$—C(=O)—NH—CH$_2$—C(=O)—NH$_2$. Unless indicated otherwise, amino acids are connected to their neighbouring groups by amide bonds formed at the N-2 (α-nitrogen) atom and the C-1 (C=O) carbon atom.

The amino acid abbreviations used in the present context have the following meanings:

| Amino acid | Description |
|---|---|
| Acb | 1-Aminocyclobutancarboxylic acid |
| Acpr | 1-Aminocyclopropanecarboxylic acid |
| Ado | H$_2$N-CH$_2$CH$_2$-O-CH$_2$CH$_2$-O-CH$_2$-C(=O)OH |
| Aib | 2-Aminoisobutyric acid |
| Ala | Alanine |
| Asn | Asparagine |
| Asp | Aspartic acid |
| Arg | Arginine |
| Cit | Citrulline |
| Cys | Cysteine |
| Gln | Glutamine |
| Glu | Glutamic acid |
| γ-Glu | AND Enantiomer (alpha-nitrogen and gamma-carboxy group form the amide bonds to the two neighboring residues) |
| Gly | Glycine |
| His | Histidine |
| Hyp | 4-hydroxyproline |
| Ile | Isoleucine |
| Leu | Leucine |
| Lys | Lysine |
| Met | Methionine |
| Met(O) | (methionine sulfoxide structure) |
| Orn | Ornithine |
| Phe | Phenylalanine |
| Pro | Proline |
| Ser | Serine |
| Thr | Threonine |
| Tyr | Tyrosine |
| p(Tyr) | (phosphotyrosine structure) |
| Trp | Tryptophan |
| Val | Valine |

Amino acid abbreviations beginning with D-followed by a three letter code, such as D-Ser, D-His and so on, refer to the D-enantiomer of the corresponding amino acid, for example D-serine, D-histidine and so on.

The term "glucagon amide", means glucagon wherein the C-terminal carboxylic acid has been replaced with a C-terminal amide.

The glucagon derivative may comprise an amino acid sequence of Formula I having a total of up to 15 amino acid differences (also referred to herein as modifications) as compared to glucagon (SEQ ID NO: 1), for example one or more additions, one or more deletions and/or one or more substitutions. In one embodiment the amino acid sequence of Formula I comprises 3-15 amino acid residue modifications, such as substitutions or additions, as compared to glucagon (SEQ ID NO: 1). In one embodiment the amino acid sequence of Formula I comprises 4-15 or 5-15 amino acid residue modifications, such as substitutions or additions, as compared to glucagon (SEQ ID NO: 1). In one embodiment the amino acid sequence of Formula I comprises up to 14, such as up to 13 or up to 12, amino acid residue modifications, such as substitutions or additions, as compared to glucagon (SEQ ID NO: 1). In one embodiment the amino acid sequence of Formula I comprises up to 11, such as up to 10 or up to 9, amino acid residue modifications, such as substitutions or additions, as compared to glucagon (SEQ ID NO: 1). In one embodiment the amino acid sequence of Formula I comprises up to 8, such as up to 7 or up to 6, amino acid residue modifications, such as substitutions or additions, as compared to glucagon (SEQ ID NO: 1).

In one embodiment the glucagon derivative is of Formula I as described herein, wherein $X_2$ represents Aib, Acb or Acpr;
$X_3$ represents Gln or His;
$X_{10}$ represents Leu;
$X_{12}$ represents Lys or Arg;
$X_{15}$ represents Asp or Glu;
$X_{16}$ represents Ser, Ala, Leu, Thr, Glu, Aib, or Lys;
$X_{17}$ represents Arg or Lys;
$X_{18}$ represents Arg, or Ala;
$X_{20}$ represents Gln, Arg, Glu, or Lys;
$X_{21}$ represents Asp, Glu or Lys;
$X_{24}$ represents Gln, Ala, Arg, or Lys;
$X_{27}$ represents Met, Leu or Val;
$X_{28}$ represents Asn, Ser, or Lys;
$X_{29}$ represents Thr, Gly, or Lys; and
$X_{30}$ represents Lys, or $X_{30}$ is absent.

In one embodiment the glucagon derivative is of Formula I as described herein, wherein
$X_2$ represents Aib, Acb or Acpr;
$X_3$ represents Gln or His;
$X_{10}$ represents Leu;
$X_{12}$ represents Lys or Arg;
$X_{15}$ represents Asp or Glu;
$X_{16}$ represents Ser, Ala, Leu, Thr, Glu, or Lys;
$X_{17}$ represents Arg or Lys;
$X_{18}$ represents Arg, or Ala;
$X_{20}$ represents Gln, Arg, Glu, or Lys;
$X_{21}$ represents Asp, Glu or Lys;
$X_{24}$ represents Gln, Ala, Arg, or Lys;
$X_{27}$ represents Met, Leu or Val;
$X_{28}$ represents Asn, Ser, or Lys;
$X_{29}$ represents Thr, Gly, or Lys; and
$X_{30}$ represents Lys, or $X_{30}$ is absent.

In one embodiment the glucagon derivative is of Formula I as described herein, wherein $X_2$ represents Aib, Acb or Acpr. In one embodiment the glucagon derivative is of Formula I as described herein, wherein $X_2$ represents Aib. In one embodiment the glucagon derivative is of Formula I as described herein, wherein $X_2$ represents Acb. In one embodiment the glucagon derivative is of Formula I as described herein, wherein $X_2$ represents Acpr. In one embodiment the glucagon derivative is of Formula I as described herein, wherein $X_3$ represents Gln or His. In one embodiment the glucagon derivative is of Formula I as described herein, wherein $X_3$ represents Gln. In one embodiment the glucagon derivative is of Formula I as described herein, wherein $X_3$ represents His. In one embodiment the glucagon derivative is of Formula I as described herein, wherein $X_{10}$ represents Leu, Ile or Val. In one embodiment the glucagon derivative is of Formula I as described herein, wherein $X_{10}$ represents Leu. In one embodiment the glucagon derivative is of Formula I as described herein, wherein $X_{10}$ is Ile. In one embodiment the glucagon derivative is of Formula I as described herein, wherein $X_{10}$ represents Val. In one embodiment the glucagon derivative is of Formula I as described herein, wherein $X_{12}$ represents Lys or Arg. In one embodiment the glucagon derivative is of Formula I as described herein, wherein $X_{12}$ represents Lys. In one embodiment the glucagon derivative is of Formula I as described herein, wherein $X_{12}$ represents Arg. In one embodiment the glucagon derivative is of Formula I as described herein, wherein $X_{15}$ represents Asp or Glu. In one embodiment the glucagon derivative is of Formula I as described herein, wherein $X_{15}$ represents Asp. In one embodiment the glucagon derivative is as described herein, wherein $X_{15}$ represents Glu. In one embodiment the glucagon derivative is of Formula I as described herein, wherein $X_{16}$ represents Ser, Ala, Leu, Thr, Glu, Aib, Ile, Val or Lys. In one embodiment the glucagon derivative is of Formula I as described herein, wherein $X_{16}$ represents Ser, Ala, Leu, Thr, Glu, Aib, or Lys. In one embodiment the glucagon derivative is of Formula I as described herein, wherein $X_{16}$ represents Ser, Ala, Leu, Thr, Glu or Lys. In one embodiment the glucagon derivative is of Formula I as described herein, wherein $X_{16}$ represents Ala, Leu, Thr, Glu or Lys. In one embodiment the glucagon derivative is of Formula I as described herein, wherein $X_{16}$ represents Ser. In one embodiment the glucagon derivative is of Formula I as described herein, wherein $X_{16}$ represents Ala. In one embodiment the glucagon derivative is of Formula I as described herein, wherein $X_{16}$ represents Leu. In one embodiment the glucagon derivative is of Formula I as described herein, wherein $X_{16}$ represents Thr. In one embodiment the glucagon derivative is of Formula I as described herein, wherein $X_{16}$ represents Glu. In one embodiment the glucagon derivative is of Formula I as described herein, wherein $X_{16}$ represents Lys. In one embodiment the glucagon derivative is of Formula I as described herein, wherein $X_{17}$ represents Arg or Lys. In one embodiment the glucagon derivative is of Formula I as described herein, wherein $X_{17}$ represents Arg. In one embodiment the glucagon derivative is of Formula I as described herein, wherein $X_{17}$ represents Lys. In one embodiment the glucagon derivative is of Formula I as described herein, wherein $X_{18}$ represents Arg, or Ala. In one embodiment the glucagon derivative is of Formula I as described herein, wherein $X_{18}$ represents Arg. In one embodiment the glucagon derivative is of Formula I as described herein, wherein $X_{18}$ represents Ala. In one embodiment the glucagon derivative is of Formula I as described herein, wherein $X_{20}$ represents Gln, Arg, Glu, Aib or Lys. In one embodiment the glucagon derivative is of Formula I as described herein, wherein $X_{20}$ represents Gln, Arg, Glu, or Lys. In one embodiment the glucagon derivative is of Formula I as described herein, wherein $X_{20}$ represents Gln. In one embodiment the glucagon derivative is of Formula I as described herein, wherein $X_{20}$ represents Arg. In one embodiment the glucagon derivative is of Formula I as described herein, wherein $X_{20}$ represents Glu. In one embodiment the glucagon derivative is of Formula I as described herein, wherein $X_{20}$ represents Lys. In one embodiment the glucagon derivative is of Formula I as described herein, wherein $X_{21}$ represents Asp, Glu or Lys. In one embodiment the glucagon derivative is of Formula I as described herein, wherein $X_{21}$ represents Glu or Lys. In one embodiment the glucagon derivative is of Formula I as described herein, wherein $X_{21}$ represents Asp. In one embodiment the glucagon derivative is of Formula I as described herein, wherein $X_{21}$ represents Glu. In one embodiment the glucagon derivative is of Formula I as described herein, wherein $X_{21}$ represents Lys. In one embodiment the glucagon derivative is of Formula I as described herein, wherein $X_{24}$ represents Gln, Ala, Arg, Glu, Aib or Lys. In one embodiment the glucagon derivative is of Formula I as described herein, wherein $X_{24}$ represents Gln, Ala, Arg, or Lys. In one embodiment the glucagon derivative is of Formula I as described herein, wherein $X_{24}$ represents Gln. In one embodiment the glucagon derivative is of Formula I as described herein, wherein $X_{24}$ represents Ala. In one embodiment the glucagon derivative is of Formula I as described herein, wherein $X_{24}$ represents Arg. In one embodiment the glucagon derivative is of Formula I as described herein, wherein $X_{24}$ represents Lys. In one embodiment the glucagon derivative is of Formula I as described herein, wherein $X_{27}$ represents Met, Leu or Val. In one embodiment the glucagon derivative is of Formula I as described herein, wherein $X_{27}$ represents Leu or Val. In one embodiment the glucagon derivative is of Formula I as described herein, wherein $X_{27}$ represents Met. In one embodiment the glucagon derivative is of Formula I as described herein, wherein $X_{27}$ represents Leu. In one embodiment the glucagon derivative is of Formula I as described herein, wherein $X_{27}$ represents Val. In one embodiment the glucagon derivative is of Formula I as described herein, wherein $X_{28}$ represents Asn, Ser, Thr, Gln, Ala, Gly, Glu or Lys. In one embodiment the glucagon derivative is of Formula I as described herein, wherein $X_{28}$ represents Asn, Ser, or Lys. In one embodiment the glucagon derivative is of Formula I as described herein, wherein $X_{28}$ represents Asn. In one embodiment the glucagon derivative is of Formula I as described herein, wherein $X_{28}$ represents Ser. In one embodiment the glucagon derivative is of Formula I as described herein, wherein $X_{28}$ represents Lys. In one embodiment the glucagon derivative is of Formula I as described herein, wherein $X_{29}$ represents Thr, Gly, Ser, Gln, Ala, Glu or Lys. In one embodiment the glucagon derivative is of Formula I as described herein, wherein $X_{29}$ represents Thr, Gly, or Lys. In one embodiment the glucagon derivative is of Formula I as described herein, wherein $X_{29}$ represents Gly or Lys. In one embodiment the glucagon derivative is of Formula I as described herein, wherein $X_{29}$ represents Thr. In one embodiment the glucagon derivative is of Formula I as described herein, wherein $X_{29}$ represents Gly. In one embodiment the glucagon derivative is of Formula I as described herein, wherein $X_{29}$ represents Lys. In one embodiment the glucagon derivative is of Formula I as described herein, wherein $X_{30}$ represents Lys, or wherein $X_{30}$ is absent. In one embodiment the glucagon derivative is of Formula I as described herein, wherein $X_{30}$ represents Lys. In one embodiment the glucagon derivative is of Formula I as described herein, wherein $X_{30}$ is absent. In one embodiment the glucagon derivative is of Formula I as described herein, wherein $X_2$ represents Aib; $X_{20}$ represents Arg; and $X_{21}$ represents Glu.

In one embodiment the glucagon derivative is of Formula I as described herein, comprising an amino acid sequence with any one of the following amino acid substitutions:
[Aib2,Leu10,Lys16,Arg20,Leu27,Ser28];
[Aib2,Leu10,Arg20,Lys21,Leu27,Ser28];
[Aib2,Leu10,Arg20,Lys24,Leu27,Ser28];
[Aib2,Leu10,Arg20,Leu27,Lys28];
[Aib2,Leu10,Arg20,Leu27,Ser28,Lys29];
[Aib2,Leu10,Arg20,Leu27,Ser28];
[Aib2,Leu10,Lys16,Lys17,Glu21,Leu27];
[Aib2,Leu10,Lys17,Ala18,Glu21,Leu27,Lys29];
[Aib2,Leu10,Ala18,Arg20,Glu21,Leu27,Lys29];
[Aib2,Leu10,Lys16,Arg20,Glu21,Leu27];
[Aib2,Leu10,Thr16,Lys20,Leu27,Ser28,Lys29];
[Aib2,Leu10,Arg20,Glu21,Leu27,Lys29];
[Aib2,Leu10,Glu16,Lys20,Leu27,Ser28,Lys29];
[Aib2,Leu10,Lys16,Glu20,Leu27,Ser28,Lys29];
[Aib2,Leu10,Thr16,Arg24,Leu27,Ser28,Lys29];
[Acb2,Leu10,Glu15,Glu16,Arg20,Leu27,Lys28];
[Aib2,Leu10,Lys16,Lys17,Ala18,Arg20,Glu21,Ala24,Leu27];
[Aib2,Leu10,Lys16,Ala18,Arg20,Glu21,Ala24,Leu27];
[Aib2,Leu10,Lys16,Arg20,Glu21,Ala24,Leu27];
[Aib2,Leu10,Glu15,Arg20,Glu21,Leu27,Lys28];
[Aib2,Leu10,Glu15,Arg20,Glu21,Leu27,Lys29];
[Aib2,Leu10,Glu15,Lys17,Arg20,Glu21,Leu27,Lys28];
[Aib2,Leu10,Glu15,Lys17,Ala18,Arg20,Glu21,Leu27,Lys28];
[Aib2,Leu10,Leu16,Lys17,Arg20,Glu21,Leu27,Lys28];
[Aib2,His3,Leu10,Glu15,Lys17,Arg20,Glu21,Leu27,Lys28];
[Aib2,Leu10,Lys16,Glu21,Val27,Lys28,Gly29];
[Aib2,Leu10,Lys16,Glu21,Leu27];
[Aib2,His3,Leu10,Glu15,Arg20,Glu21,Leu27,Lys28];
[Aib2,His3,Leu10,Glu15,Arg20,Glu21,Ala24,Leu27,Lys28];
[Aib2,His3,Leu10,Glu15,Lys16,Arg20,Glu21,Ala24,Leu27,Ser28];
[Acb2,His3,Leu10,Glu15,Leu27,Lys28];
[Acb2,Leu10,Glu15,Lys17,Arg20,Glu21,Leu27,Lys28];
[Aib2,His3,Leu10,Glu15,Arg20,Leu27,Lys28];
[Aib2,Leu10,Leu16,Arg20,Glu21,Leu27,Lys29];
[Aib2,Leu10,Ala16,Arg20,Glu21,Leu27,Lys29];
[Aib2,Leu10,Ala16,Arg20,Glu21,Leu27,Lys28];
[Acb2,Leu10,Glu15,Arg20,Glu21,Leu27,Lys28];
[Acb2,Leu10,Leu16,Arg20,Leu27,Lys28];
[Acb2,Leu10,Arg12,Leu16,Arg20,Leu27,Lys28];
[Acb2,Leu10,Leu16,Lys17,Arg20,Glu21,Leu27,Lys28];
[Acb2,Leu10,Leu16,Arg20,Glu21,Leu27,Lys28];
[Acpr2,Leu10,Glu15,Arg20,Glu21,Leu27,Lys28];
[Aib2,Leu10,Aib16,Arg20,Glu21,Leu27,Lys28];
[Aib2,Leu10,Leu16,Leu27,Lys28];
[Aib2,Leu10,Leu16,Arg20,Leu27,Lys28];
[Aib2,Leu10,Arg20,Glu21,Leu27,Lys28];
[Aib2,Leu10,Glu15,Arg20,Leu27,Lys28];
[Aib2,Leu10,Ala16,Arg20,Leu27,Lys28];
[Acb2,Leu10,Arg12,Glu15,Arg20,Glu21,Leu27,Lys28];
[Aib2,Leu10,Arg12,Ala16,Arg20,Leu27,Lys28];
[Acb2,Leu10,Glu15,Leu27,Lys28];
[Aib2,Leu10,Arg12,Ala16,Leu27,Lys28];
[Aib2,Leu10,Ala16,Arg20,Leu27,Lys29];
[Aib2,Leu10,Ala16,Arg20,Leu27,Ser28,Lys29]; and
[Aib2,Leu10,Arg12,Glu15,Arg20,Glu21,Leu27,Lys28].

In one embodiment the glucagon derivative is of Formula I as described herein, comprising an amino acid sequence with any one of the following amino acid substitutions: [Aib2,Leu10,Lys16,Arg20,Leu27,Ser28]; [Aib2,Leu10,Arg20,Lys21,Leu27,Ser28]; and [Aib2,Leu10,Arg20,Lys24,Leu27,Ser28]. In one embodiment the glucagon derivative is of Formula I as described herein, comprising an amino acid sequence with any one of the following amino acid substitutions: [Aib2,Leu10,Arg20,Leu27,Lys28]; [Aib2,Leu10,Arg20,Leu27,Ser28,Lys29]; and [Aib2,Leu10,Arg20,Leu27,Ser28]. In one embodiment the glucagon derivative is of Formula I as described herein, comprising an amino acid sequence with any one of the following amino acid substitutions: [Aib2,Leu10,Lys16,Lys17,Glu21,Leu27]; [Aib2,Leu10,Lys17,Ala18,Glu21,Leu27,Lys29]; and [Aib2,Leu10,Ala18,Arg20,Glu21,Leu27,Lys29]. In one embodiment the glucagon derivative is of Formula I as described herein, comprising an amino acid sequence with any one of the following amino acid substitutions: [Aib2,Leu10,Lys16,Arg20,Glu21,Leu27]; [Aib2,Leu10,Thr16,Lys20,Leu27,Ser28,Lys29]; and [Aib2,Leu10,Arg20,Glu21,Leu27,Lys29]. In one embodiment the glucagon derivative is of Formula I as described herein, comprising an amino acid sequence with any one of the following amino acid substitutions: [Aib2,Leu10,Glu16,Lys20,Leu27,Ser28,Lys29]; [Aib2,Leu10,Lys16,Glu20,Leu27,Ser28,Lys29]; and [Aib2,Leu10,Thr16,Arg24,Leu27,Ser28,Lys29]. In one embodiment the glucagon derivative is of Formula I as described herein, comprising an amino acid sequence with any one of the following amino acid substitutions: [Acb2,Leu10,Glu15,Glu16,Arg20,Leu27,Lys28]; [Aib2,Leu10,Lys16,Lys17,Ala18,Arg20,Glu21,Ala24,Leu27]; and [Aib2,Leu10,Lys16,Ala18,Arg20,Glu21,Ala24,Leu27]. In one embodiment the glucagon derivative is of Formula I as described herein, comprising an amino acid sequence with any one of the following amino acid substitutions: [Aib2,Leu10,Lys16,Arg20,Glu21,Ala24,Leu27]; [Aib2,Leu10,Glu15,Arg20,Glu21,Leu27,Lys28]; and [Aib2,Leu10,Glu15,Arg20,Glu21,Leu27,Lys29]. In one embodiment the glucagon derivative is of Formula I as described herein, comprising an amino acid sequence with any one of the following amino acid substitutions: [Aib2,Leu10,Glu15,Lys17,Arg20,Glu21,Leu27,Lys28]; [Aib2,Leu10,Glu15,Lys17,Ala18,Arg20,Glu21,Leu27,Lys28]; and [Aib2,Leu10,Leu16,Lys17,Arg20,Glu21,Leu27,Lys28]. In one embodiment the glucagon derivative is of Formula I as described herein, comprising an amino acid sequence with any one of the following amino acid substitutions: [Aib2,His3,Leu10,Glu15,Lys17,Arg20,Glu21,Leu27,Lys28]; [Aib2,Leu10,Lys16,Glu21,Val27,Lys28,Gly29]; and [Aib2,Leu10,Lys16,Glu21,Leu27]. In one embodiment the glucagon derivative is of Formula I as described herein, comprising an amino acid sequence with any one of the following amino acid substitutions: [Aib2,His3,Leu10,Glu15,Arg20,Glu21,Leu27,Lys28]; [Aib2,His3,Leu10,Glu15,Arg20,Glu21,Ala24,Leu27,Lys28]; and [Aib2,His3,Leu10,Glu15,Lys16,Arg20,Glu21,Ala24,Leu27,Ser28]. In one embodiment the glucagon derivative is of Formula I as described herein, comprising an amino acid sequence with any one of the following amino acid substitutions: [Acb2,His3,Leu10,Glu15,Leu27,Lys28]; [Acb2,Leu10,Glu15,Lys17,Arg20,Glu21,Leu27,Lys28]; and [Aib2,His3,Leu10,Glu15,Arg20,Leu27,Lys28]. In one embodiment the glucagon derivative is of Formula I as described herein, comprising an amino acid sequence with any one of the following amino acid substitutions: [Aib2,Leu10,Leu16,Arg20,Glu21,Leu27,Lys29]; [Aib2,Leu10,Ala16,Arg20,Glu21,Leu27,Lys29]; and [Aib2,Leu10,Ala16,Arg20,Glu21,Leu27,Lys28]. In one embodiment the glucagon derivative is of Formula I as described herein, comprising an amino acid sequence with any one of the following amino acid substitutions: [Acb2,Leu10,Glu15,Arg20,Glu21,Leu27,Lys28]; [Acb2,Leu10,Leu16,Arg20,Leu27,Lys28]; and [Acb2,Leu10,Arg12,Leu16,Arg20,Leu27,Lys28]. In one embodiment the glucagon derivative is of Formula I as described herein, comprising an amino acid sequence with any one of the following amino acid substitutions: [Acb2,Leu10,Leu16,Lys17,Arg20,Glu21,Leu27,Lys28]; [Acb2,Leu10,Leu16,Arg20,Glu21,Leu27,Lys28]; and [Acpr2,Leu10,Glu15,Arg20,Glu21,Leu27,Lys28]. In one embodiment the glucagon derivative is of Formula I as described herein, comprising an amino acid sequence with any one of the following amino acid substitutions: [Aib2,Leu10,Aib16,Arg20,Glu21,Leu27,Lys28]; [Aib2,Leu10,Leu16,Leu27,Lys28]; and [Aib2,Leu10,Leu16,Arg20,Leu27,Lys28]. In one embodiment the glucagon derivative is of Formula I as described herein, comprising an amino acid sequence with any one of the following amino acid substitutions: [Aib2,Leu10,Arg20,Glu21,Leu27,Lys28]; [Aib2,Leu10,Glu15,Arg20,Leu27,Lys28]; and [Aib2,Leu10,Ala16,Arg20,Leu27,Lys28]. In one embodiment the glucagon derivative is of Formula I as described herein, comprising an amino acid sequence with any one of the following amino acid substitutions: [Acb2,Leu10,Arg12,Glu15,Arg20,Glu21,Leu27,Lys28]; [Aib2,Leu10,Arg12,Ala16,Arg20,Leu27,Lys28]; and [Acb2,Leu10,Glu15,Leu27,Lys28]. In one embodiment the glucagon derivative is of Formula I as described herein, comprising an amino acid sequence with any one of the following amino acid substitutions: [Aib2,Leu10,Arg12,Ala16,Leu27,Lys28]; [Aib2,Leu10,Ala16,Arg20,Leu27,Lys29]; [Aib2,Leu10,Ala16,Arg20,Leu27,Ser28,Lys29]; and [Aib2,Leu10,Arg12,Glu15,Arg20,Glu21,Leu27,Lys28]. In one embodiment the glucagon derivative is of Formula I as described herein, comprising an amino acid sequence with any one of the following amino acid substitutions: [Aib2,Leu10,Ala16,Arg20,Leu27,Lys28]; [Acb2,Leu10,Glu15,Arg20,Glu21,Leu27,Lys28]; and [Aib2,Leu10,Glu15,Lys17,Arg20,Glu21,Leu27,Lys28]. In one embodiment the glucagon derivative is of Formula I as described herein, comprising an amino acid sequence with any one of the following amino acid substitutions: [Aib2,Leu10,Glu15,Lys17,Arg20,Glu21,Leu27,Lys28]; [Acb2,Leu10,Glu15,Arg20,Glu21,Leu27,Lys28]; and [Aib2,Leu10,Ala16,Arg20,Leu27,Lys28]. In one embodiment the glucagon derivative is of Formula I as described herein, comprising an amino acid sequence with the following amino acid substitutions: [Aib2,Leu10,Glu15,Lys17,Arg20,Ser21,Leu27,Lys28]. In one embodiment the glucagon derivative is of Formula I as described herein, comprising an amino acid sequence with the following amino acid substitutions: [Aib2,Val10,Ala16,Leu27,Lys28].

In one embodiment the glucagon derivative is of Formula I as described herein, the amino acid sequence comprises a lysine residue at one or more of positions 12, 16, 17, 18, 20, 21, 24, 28, 29, and/or 30. In one embodiment the glucagon derivative is of Formula I as described herein, the amino acid sequence comprises a lysine residue at one, two or three of positions 12, 16, 17, 18, 20, 21, 24, 28, 29, and/or 30. In one embodiment the glucagon derivative is of Formula I as described herein, the amino acid sequence comprises a lysine residue at one or two of positions 12, 16, 17, 18, 20, 21, 24, 28, 29, and/or 30. In one embodiment the glucagon derivative is of Formula I as described herein, the amino acid sequence comprises a lysine residue at two of positions 12, 16, 17, 18, 20, 21, 24, 28, 29, and/or 30; in particular in positions 12 and 28. In one embodiment the glucagon derivative is of Formula I as described herein, the amino acid sequence comprises a lysine residue at position 12, 16, 17, 18, 20, 21, 24, 28, 29, or 30.

In one embodiment the amino acid sequence of Formula I consists of Formula I. In one embodiment $X_2$ is Aib, Acb, or Acpr. In one embodiment $X_3$ represents His. In one embodiment $X_{10}$ represents Leu or Val. In one embodiment $X_{12}$ represents Arg. In one embodiment $X_{15}$ represents Glu. In one embodiment $X_{16}$ represents Ala, Glu, Leu, Lys, Thr or Aib, such as Ala, Glu or Leu, or such as Lys, Thr or Aib. In one embodiment $X_{17}$ represents Lys. In one embodiment $X_{18}$ represents Ala. In one embodiment $X_{20}$ represents Arg, Lys or Glu. In one embodiment $X_{21}$ represents Lys, Glu or Ser. In one embodiment $X_{24}$ represents Ala, Arg or Lys. In one embodiment $X_{27}$ represents Leu or Val. In one embodiment $X_{28}$ represents Lys or Ser. In one embodiment $X_{29}$ represents Lys or Gly. In one embodiment $X_{30}$ represents Lys or $X_{30}$ is absent.

Glucagon Derivative

The invention relates to glucagon derivatives. The term "glucagon derivative" as used herein means chemically modified glucagon or an analogue thereof, wherein at least one substituent is not present in the unmodified peptide or an analogue thereof, i.e. where glucagon has been covalently modified. Typical modifications are amides, carbohydrates, alkyl groups, acyl groups, esters and the like. The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. In one embodiment the term "glucagon derivative" as used herein means glucagon derivative, glucagon compound, compound according to the invention, compound of the invention, compound of Formula I, a glucagon analogue, a glucagon derivative or a derivative of a glucagon analogue human glucagon, human glucagon (1-29), glucagon (1-30), glucagon (1-31), glucagon (1-32) as well as analogues, and fusion peptides thereof, which maintain glucagon activity.

In one embodiment the glucagon derivative comprises a substituent covalently attached to the glucagon analogue via the side chain of a lysine. The term "substituent" as used herein, means a chemical moiety or group replacing a hydrogen.

The term "distal" as used herein, means most remote (terminal) from the point of attachment.

In one embodiment the term "negatively charged moiety" as used herein, means a negatively chargeable chemical moiety, such as, but not limited to, a carboxylic acid (e.g. Glu, gamma-Glu, Asp or beta-Asp), sulphonic acid or a tetrazole moiety. In one embodiment the term "negatively charged moiety" as used herein, means a negatively chargeable chemical moiety such as, but not limited to a carboxylic acid, sulphonic acid or a tetrazole moiety. In one embodiment the substituent has three to ten negatively charged moieties. In one embodiment the substituent has 3, 4, 5, 6, 7, 8, 9 or 10 negatively charged moieties. In one embodiment the substituent is negatively charged at physiological pH. In one embodiment the number of "negatively charged moieties" is determined at physiological pH (pH 7.4). In one embodiment the "negatively charged moiety" is a carboxylic acid group.

The term "lipophilic moiety" as used herein, means an aliphatic or cyclic hydrocarbon moiety with more than 6 and less than 30 carbon atoms, wherein said hydrocarbon moiety may contain additional substituents.

The term "albumin binding residue" as used herein means a residue which binds non-covalently to human serum albumin. The albumin binding residue attached to the therapeutic polypeptide typically has an affinity below 10 µM to human serum albumin and preferably below 1 µM. A range of albumin binding residues are known among linear and branched lipohophillic moieties containing 4-40 carbon atoms.

The term "protracted effect" of the compounds of the invention means that the period of time in which they exert a biological activity is prolonged.

In the present context, the term "agonist" is intended to indicate a substance (ligand) that activates the receptor type in question.

In one embodiment the symbol "*" when used herein in a drawing of a chemical structure represents the point of attachment to the neighbouring position in the derivative.

In one embodiment the glucagon derivative of Formula I as described herein, wherein a substituent comprising a lipophilic moiety and three or more negatively charged moieties, wherein one of said negatively charged moieties is distal of a lipophilic moiety, and wherein said substituent is attached at the epsilon position of a Lys in one of the following amino acid positions of said glucagon derivative: 16, 17, 18, 20, 21, 24, 28, 29, and/or 30. In one embodiment the substituent comprising a lipophilic moiety and at least three negatively charged moieties, is attached at the epsilon position of a lysine residue in position 16, 21, 24, 28, 29, or 30. In one embodiment the substituent comprising a lipophilic moiety and at least three negatively charged moieties, is attached at the epsilon position of a lysine residue in position 16, 21, 24, 28, 29, or 30. In one embodiment the substituent comprising a lipophilic moiety and at least three negatively charged moieties, is attached at the epsilon position of a lysine residue in position 16, 24, 28, 29 or 30. In one embodiment the substituent comprising a lipophilic moiety and at least three negatively charged moieties, is attached at the epsilon position of a lysine residue in position 24, 28, 29 or 30. In one embodiment the substituent comprising a lipophilic moiety and at least three negatively charged moieties, is attached at the epsilon position of a lysine residue in position 28, 29 and 30. In one embodiment the substituent comprising a lipophilic moiety and at least three negatively charged moieties, is attached at the epsilon position of a lysine residue in position 28.

In one embodiment the substituent comprising a lipophilic moiety and three or more negatively charged moieties is a substituent of Formula II: $Z^1-Z^2-Z^3-Z^4-Z^5-Z^6-Z^7-Z^8-Z^9-Z^{10}$- (II), wherein, $Z^1$ - represents a structure of Formula IIa;

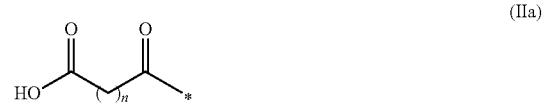

(IIa)

wherein n is 6-20; and the symbol * represents the attachment point to the nitrogen of the neighbouring linking group; and $Z^2-Z^3-Z^4-Z^5-Z^6-Z^7-Z^8-Z^9-Z^{10}$- represents a linking group, wherein each of $Z_2$ to $Z_{10}$ individually are represented by any one of the following amino acid residues: Glu, γGlu, Gly, Ser, Ala, Thr or Ado; or one or more of residues $Z^2$ to $Z^{10}$ are absent; provided, however, that at least two of residues $Z^2$ to $Z^{10}$ are present; and wherein $Z^1-Z^2-Z^3-Z^4-Z^5-Z^6-Z^7-Z^8-Z^9-Z^{10}$- together contains at least three negative charges; and wherein said substituent is attached at the epsilon position of a Lys residue according to Formula I.

In one embodiment the glucagon derivative is of Formula I as described herein, wherein $Z^1$ of Formula II represents a structure according to Formula IIa:

(IIa)

wherein n represents an integer in the range of from 6 to 20; the symbol * represents the attachment point to the nitrogen of the neighbouring group; and wherein $Z_2, Z_3, Z_4, Z_5, Z_6, Z_7, Z_8, Z^9, Z_{10}$ individually are represented by the following amino acids: Glu, γGlu, Gly, Ser, Ala, Thr and Ado; or one or more of $Z_2, Z_3, Z_4, Z_5, Z_6, Z_7, Z_8, Z_9, Z_{10}$ may be absent; provided, however, that at least two of residues $Z_2$ to $Z_{10}$ are present; wherein $Z_1-Z_2-Z_3-Z_4-Z_5-Z_6-Z_7-Z_8-Z_9-Z_{10}$ together contains at least three negative charges; and wherein said substituent is attached at the epsilon position of a Lys residue according to Formula I, herein.

In one embodiment n in $Z^1$ of Formula IIa is (i.e. represents) 14, 16 or 18. In one embodiment n in $Z^1$ of Formula IIa is 14. In one embodiment n in $Z^1$ of Formula IIa is 16. In one embodiment n in $Z^1$ of Formula IIa is 18.

In one embodiment $Z^2-Z^3-Z^4-Z^5-Z^6-Z^7-Z^8-Z^9-Z^{10}$- represents a linking group, wherein each of $Z_2$ to $Z_{10}$ individually are represented by any one of the following amino acid residues: Glu, γGlu, Gly, Ser, or Ado (such as Glu, γGlu, or Gly, or such as Ser, or Ado); or one or more of residues $Z^2$ to $Z^{10}$ are absent; provided, however, that at least two of residues $Z^2$ to $Z^{10}$ are present.

In one embodiment the substituent represents a structure according to any one of the following nine formulas (Chem.A-Chem.I), wherein * indicates the point of attachment to the nitrogen atom of the epsilon position of a Lys residue of Formula I:

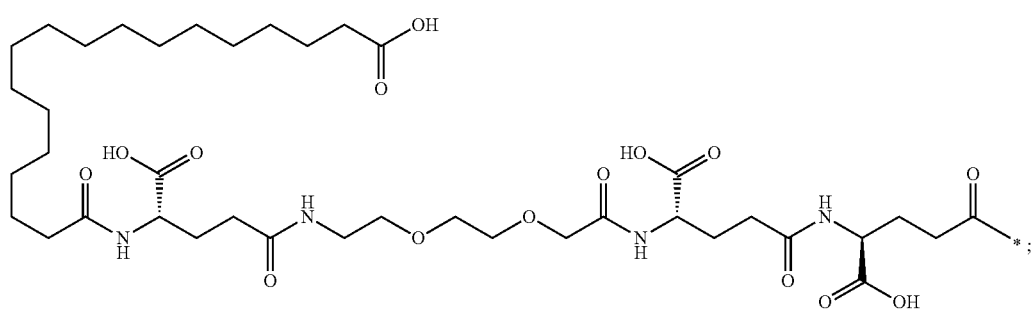
(Chem.A)
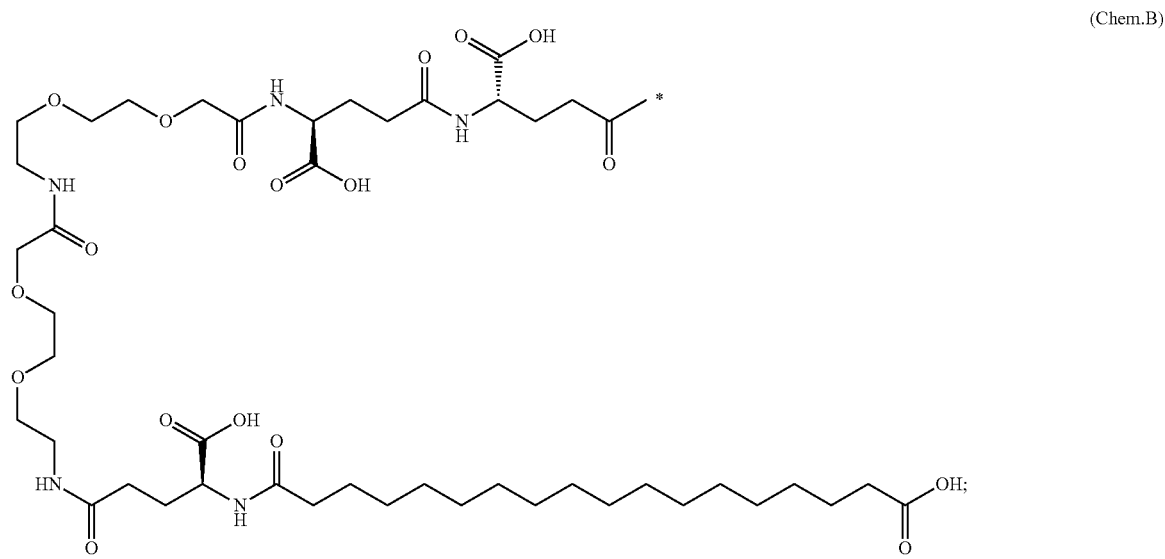
(Chem.B)
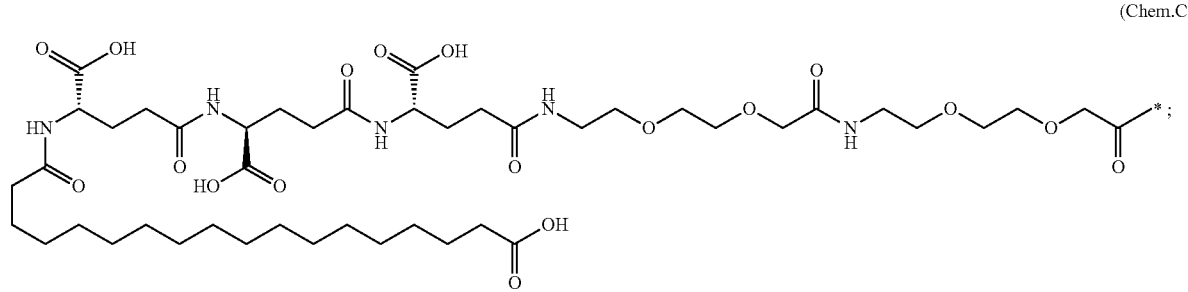
(Chem.C)
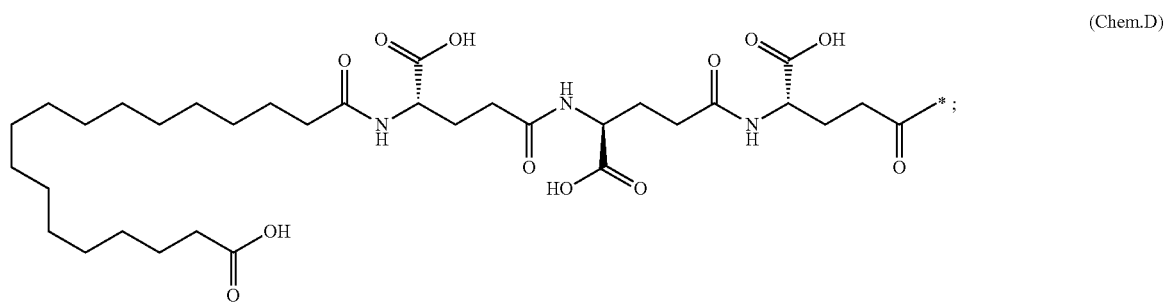
(Chem.D)
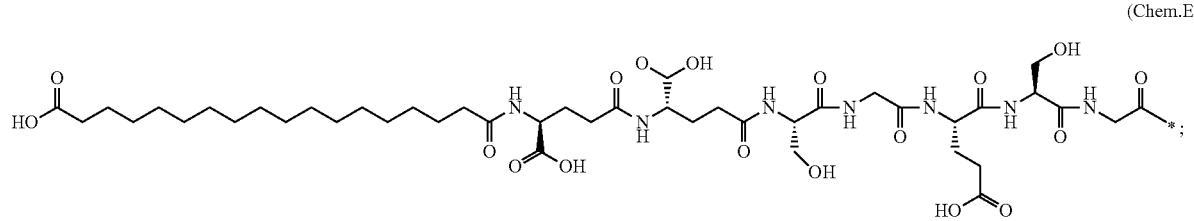
(Chem.E)

-continued
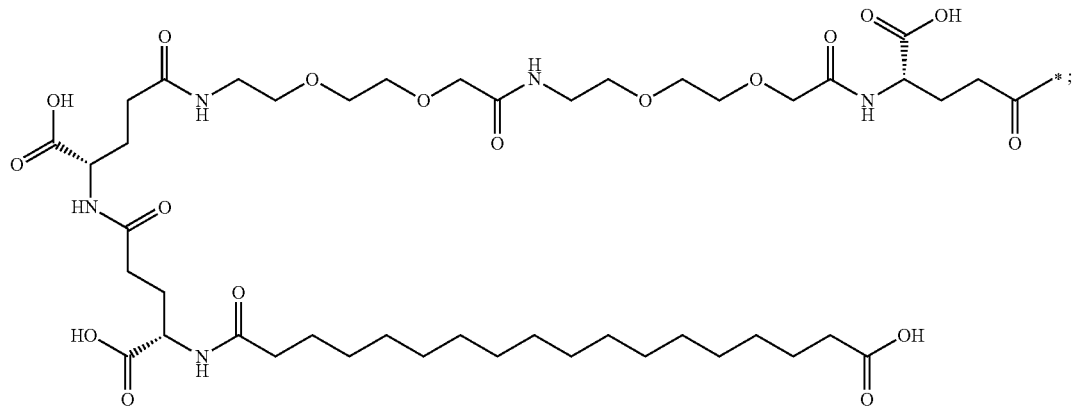
(Chem.F)
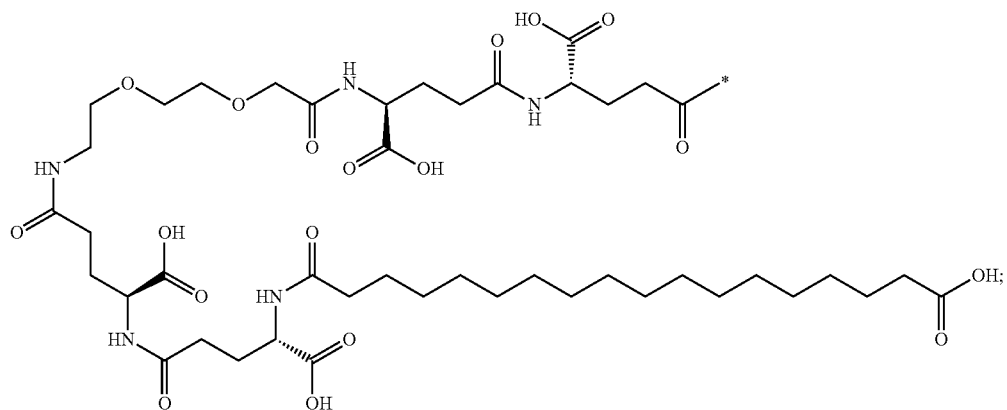
(Chem.G)
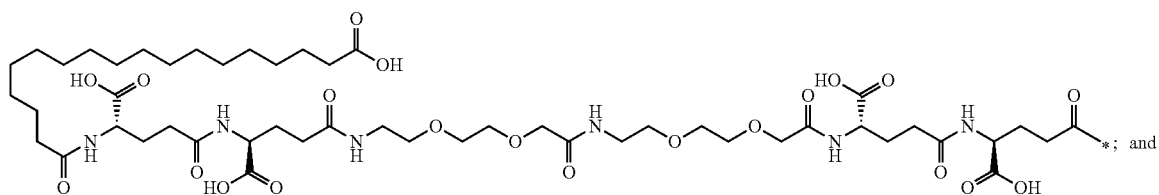
(Chem.H); and
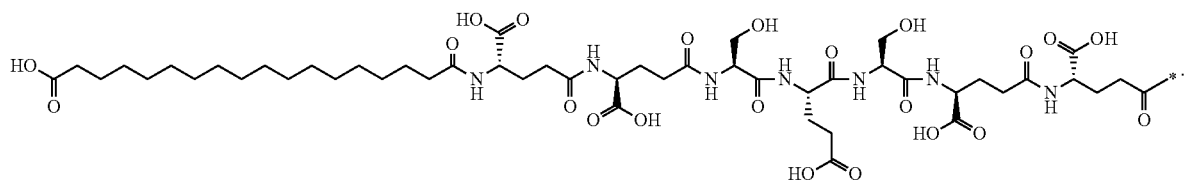
(Chem.I).

In one embodiment the substituent represents a structure according to the formula Chem.J, wherein * indicates the point of attachment to the nitrogen atom of the epsilon position of a Lys residue of Formula I:

wherein n in Formula IIa is 6-20, and the symbol * represents the attachment point to the nitrogen of the neighbouring group and wherein $Z_2, Z_3, Z_4, Z_5, Z_6, Z_7, Z_8, Z_9, Z_{10}$ individually are represented by the following amino acids:

(Chem.J)

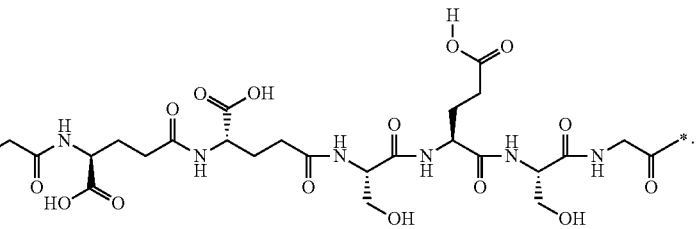

In one embodiment the substituent represents a structure according to any one of formulas Chem.A-Chem.I, as described herein, wherein * indicate the point of attachment to the nitrogen atom of the epsilon position of a Lys residue according to Formula I. In one embodiment the substituent represents a structure according to the formula Chem.J, as described herein, wherein * indicate the point of attachment to the nitrogen atom of the epsilon position of a Lys residue according to Formula I. In one embodiment the substituent represents a structure according to the formula Chem.B, Chem.C, or Chem.H, described herein, wherein * indicate the point of attachment to the nitrogen atom of the epsilon position of a Lys residue according to Formula I.

In one embodiment $Z_1$ represents a structure according to the Formula IIa;

Glu, γGlu, Gly, Ser, Ala, Thr, Ado or is absent. In one embodiment $Z_2, Z_3, Z_4, Z_5, Z_6, Z_7, Z_8, Z_9, Z_{10}$ individually are represented by the following amino acids: Glu, γGlu, Gly, Ser, Ado or is absent.

In one embodiment one of said negatively charged moieties is distal of said lipophilic moiety. In one embodiment the substituent binds non-covalently to albumin.

In one embodiment the glucagon derivative is $N^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Leu27,Ser28]-Glucagon amide

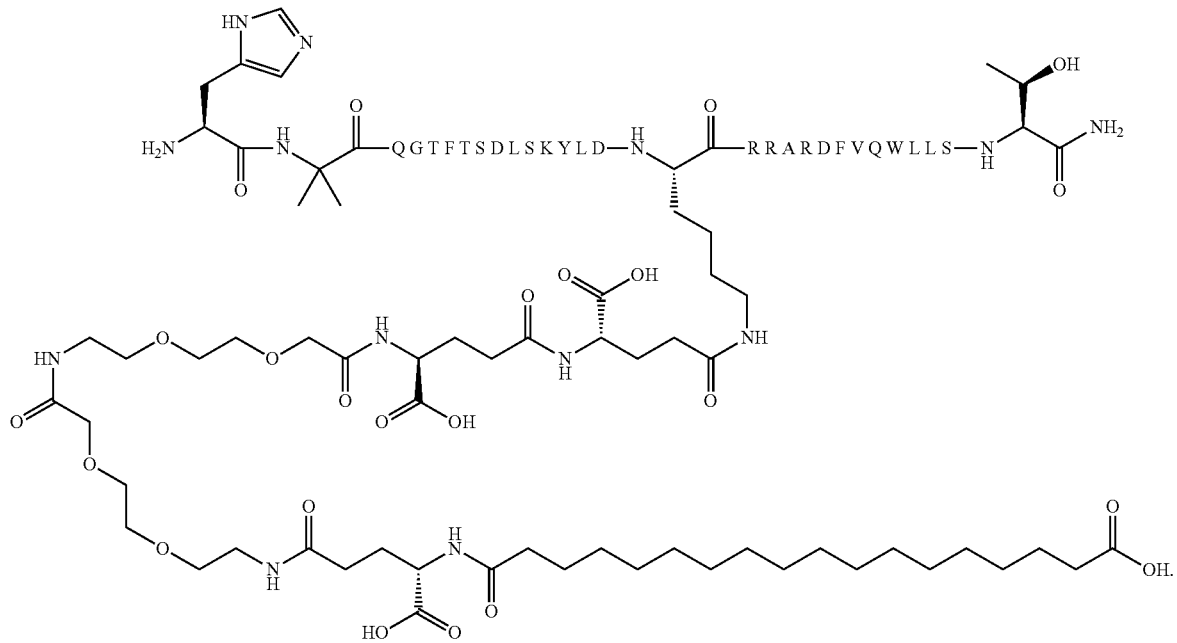

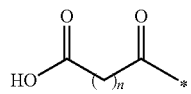
[IIa]

In one embodiment the glucagon derivative is $N^{\epsilon 21}$-(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys21,Leu27,Ser28]-Glucagon amide

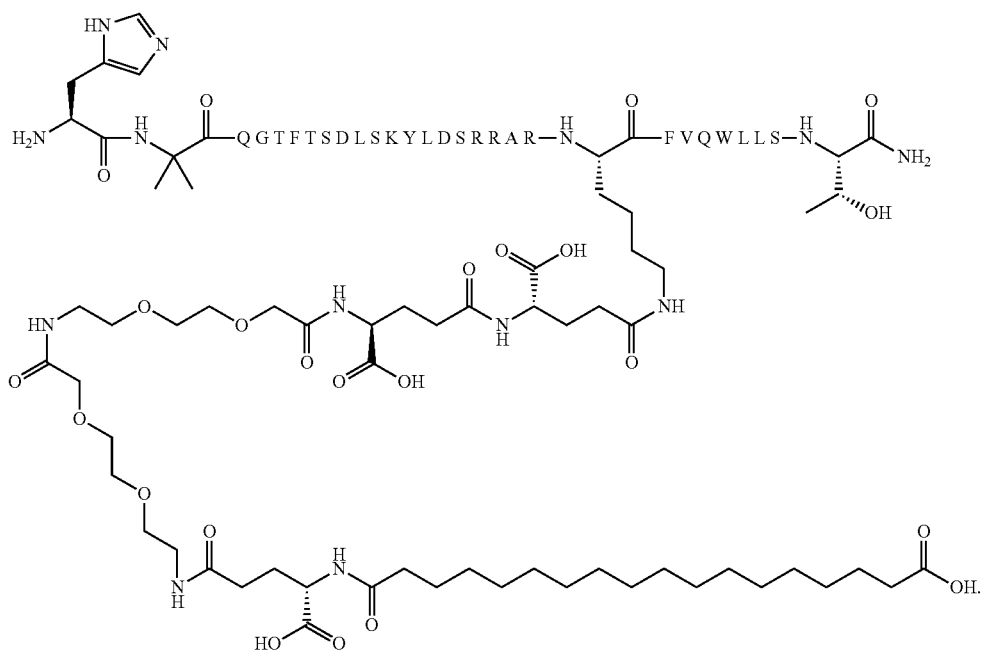

In one embodiment the glucagon derivative is $N^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys24,Leu27,Ser28]-Glucagon amide

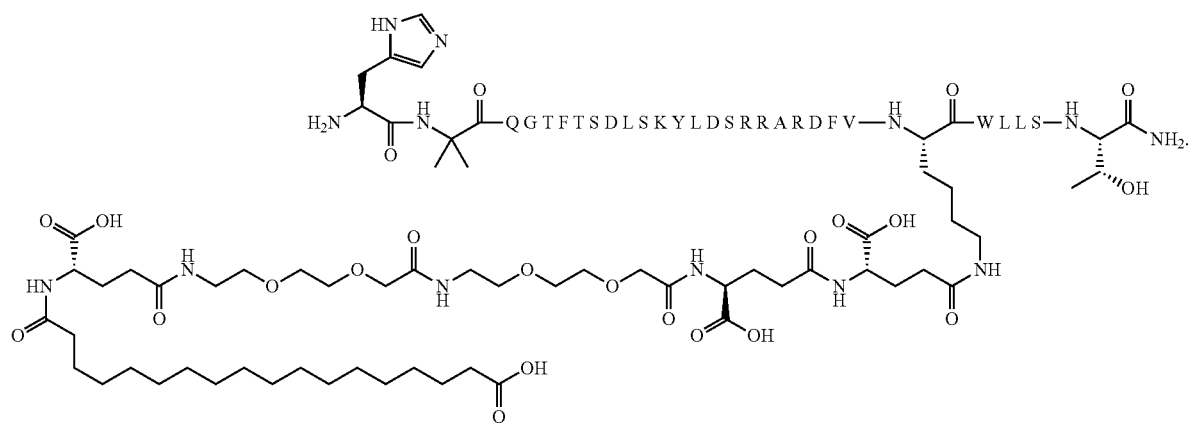

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Lys28]-Glucagon amide

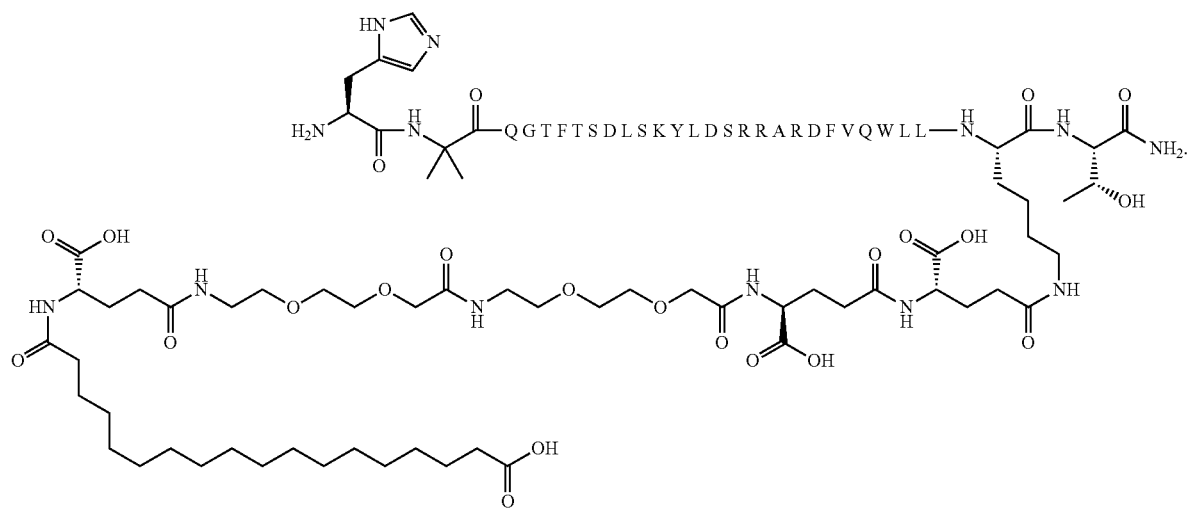

In one embodiment the glucagon derivative is $N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Ser28,Lys29]-Glucagon amide

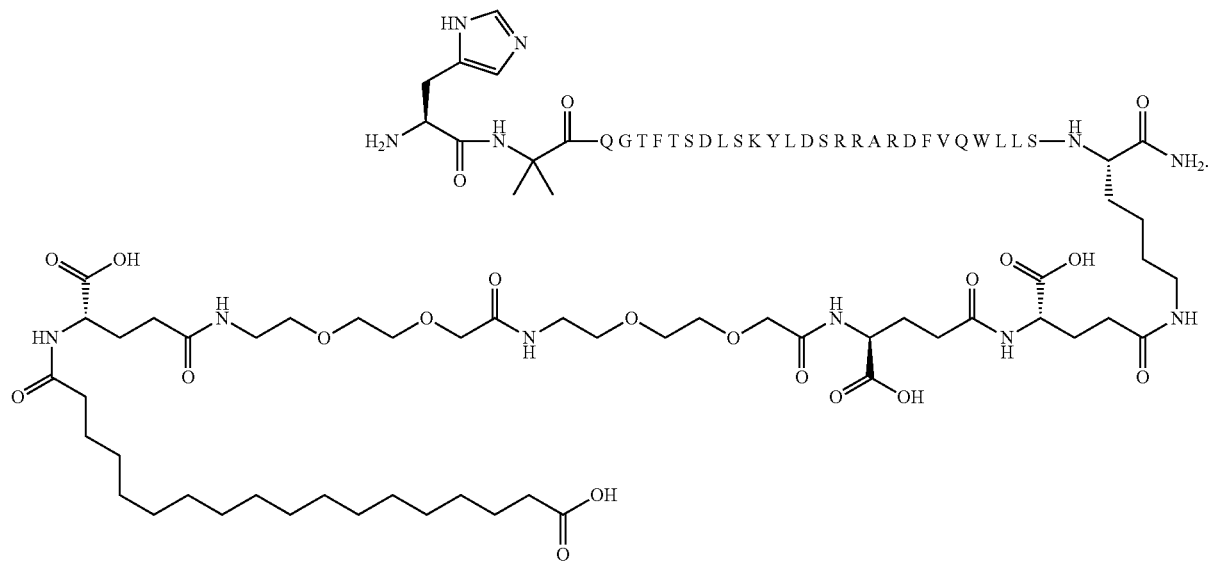

In one embodiment the glucagon derivative is $N^{\alpha}$-([Aib2,Leu10,Arg20,Leu27,Ser28]-Glucagonyl)-N{Epsilon}[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]Lys amide

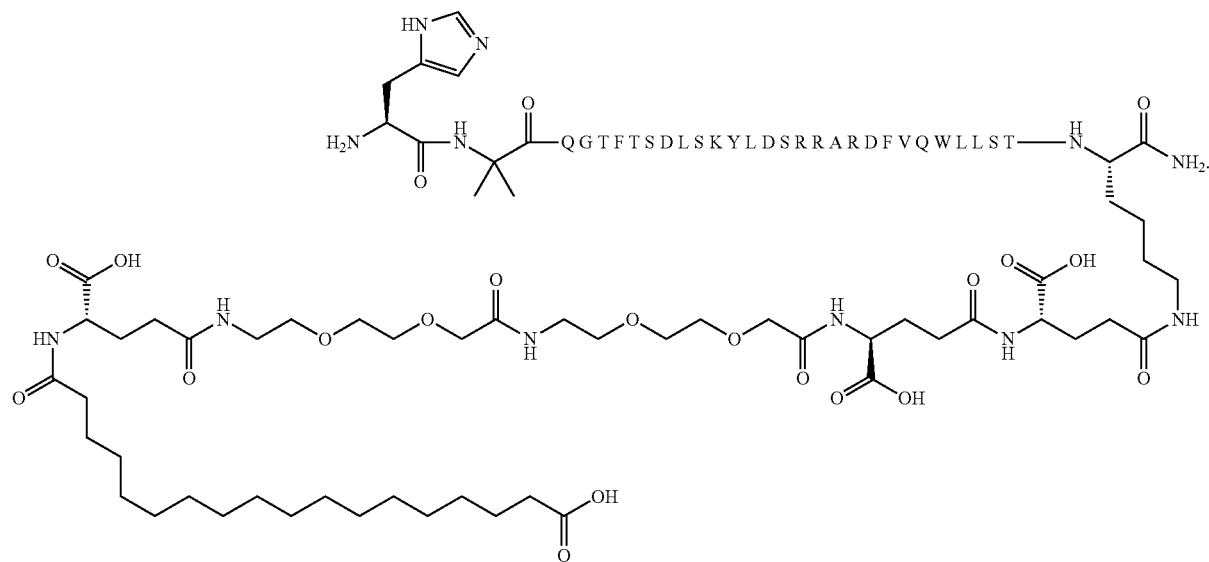

In one embodiment the glucagon derivative is N^ε16-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Glu21,Leu27]-Glucagon amide

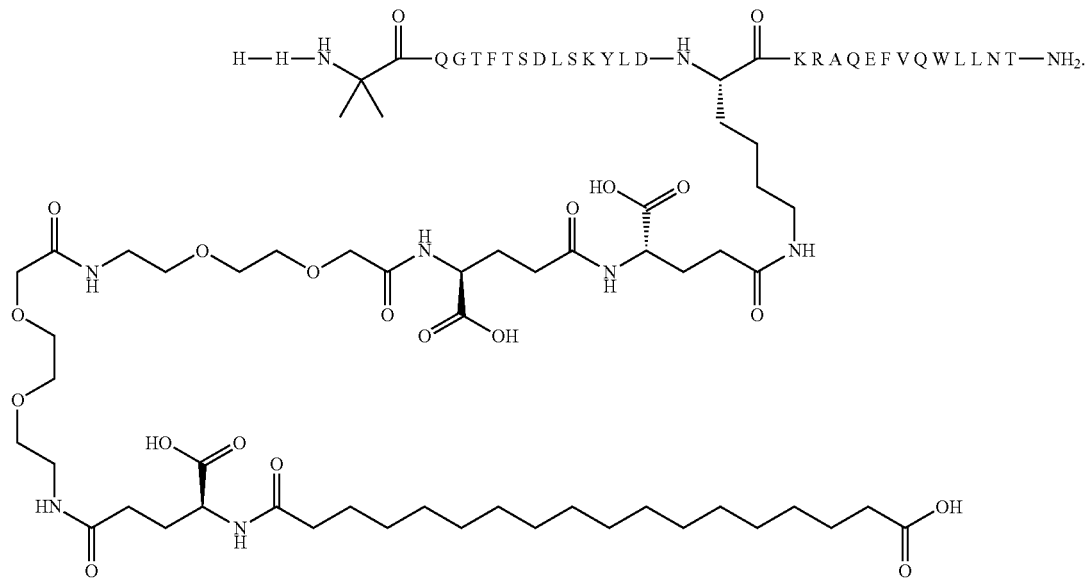

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys17,Ala18,Glu21,Leu27,Lys29]-Glucagon amide

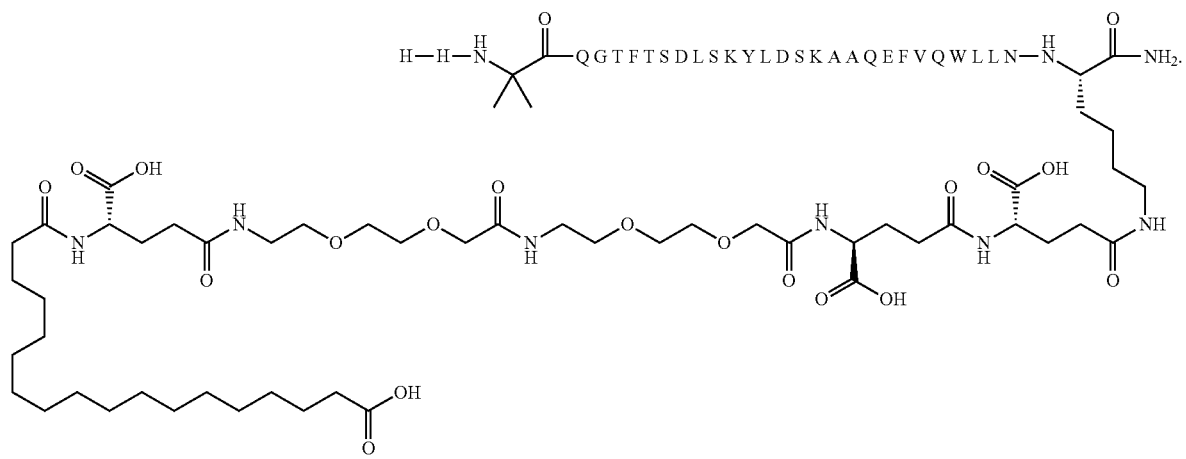

In one embodiment the glucagon derivative is N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala18,Arg20,Glu21,Leu27,Lys29]-Glucagon amide

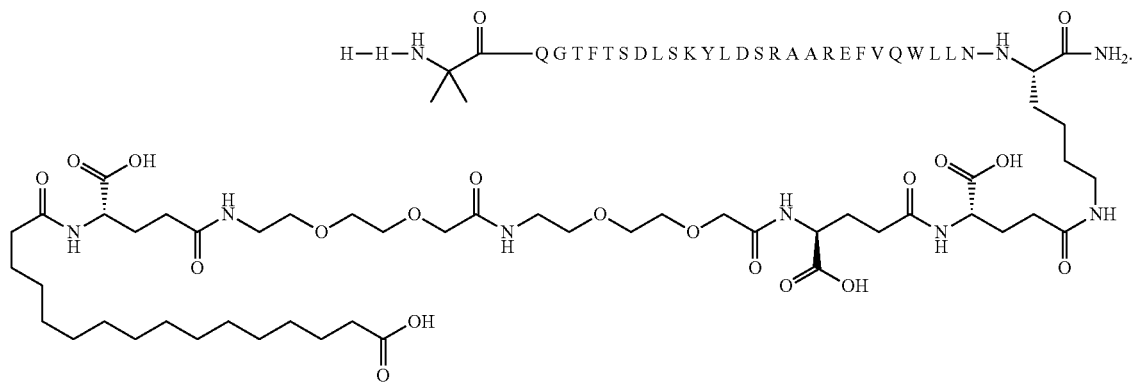

In one embodiment the glucagon derivative is N$^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Glu21,Leu27]-Glucagon amide

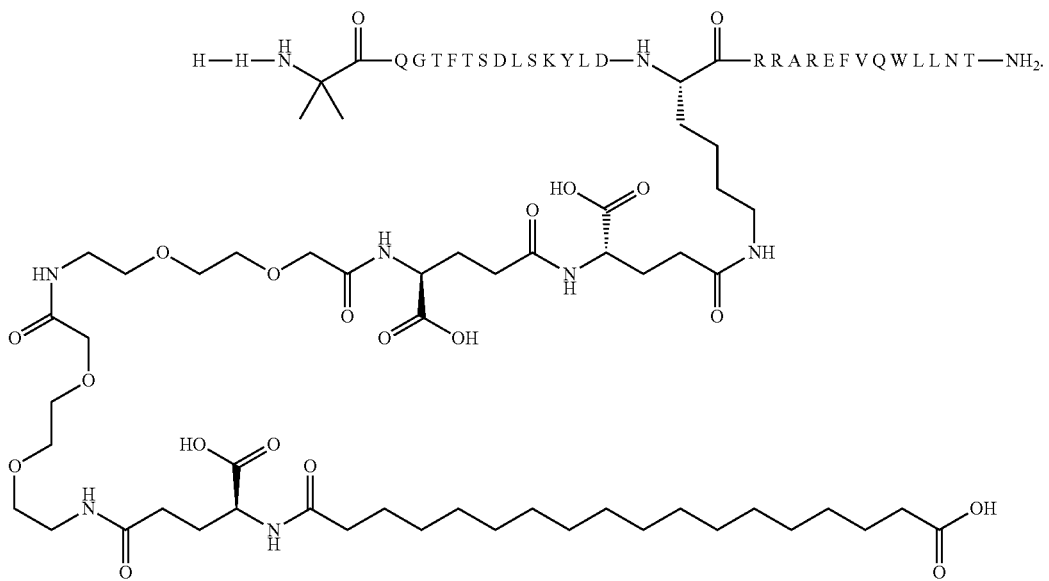

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Thr16,Lys20,Leu27,Ser28,Lys29]-Glucagon amide

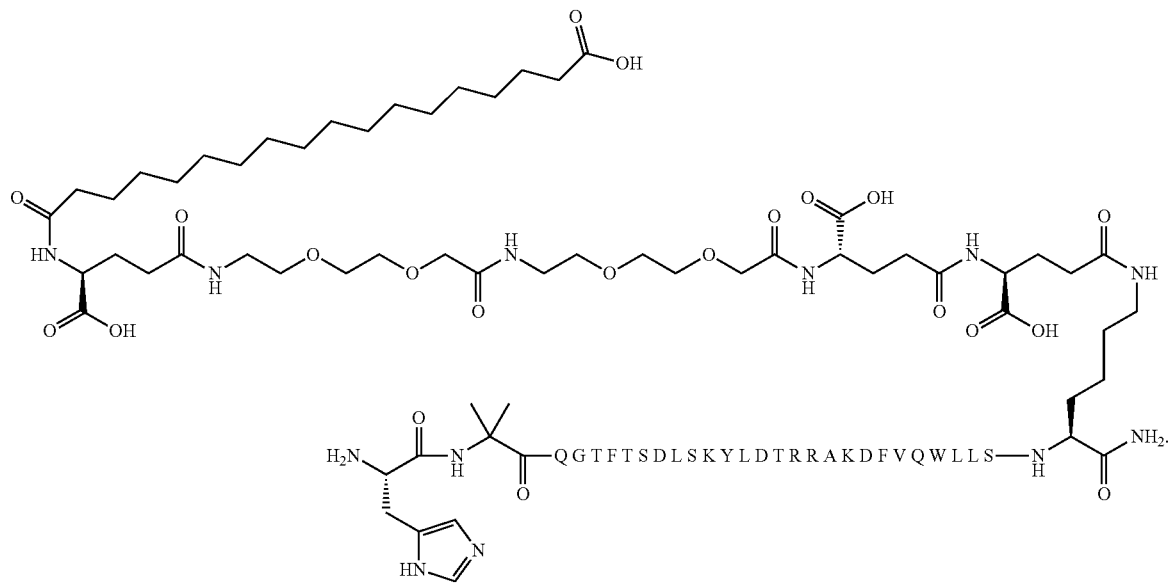

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys29]-Glucagon amide

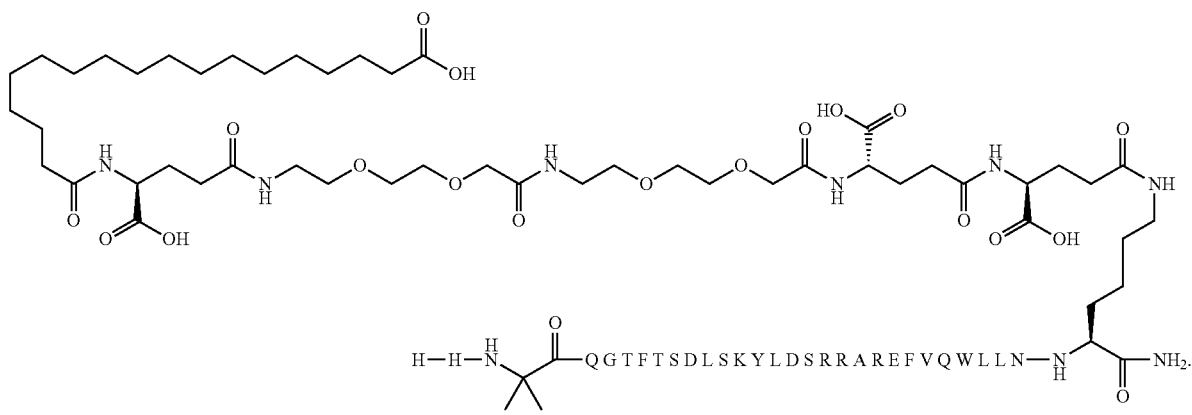

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu16,Lys20,Leu27,Ser28,Lys29]-Glucagon amide

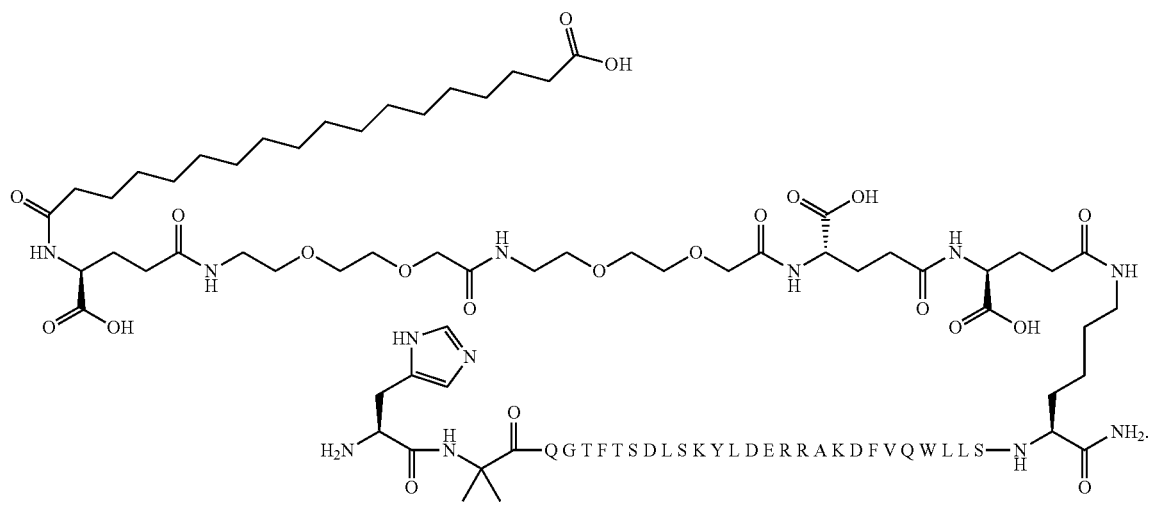

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Glu20,Leu27,Ser28,Lys29]-Glucagon amide

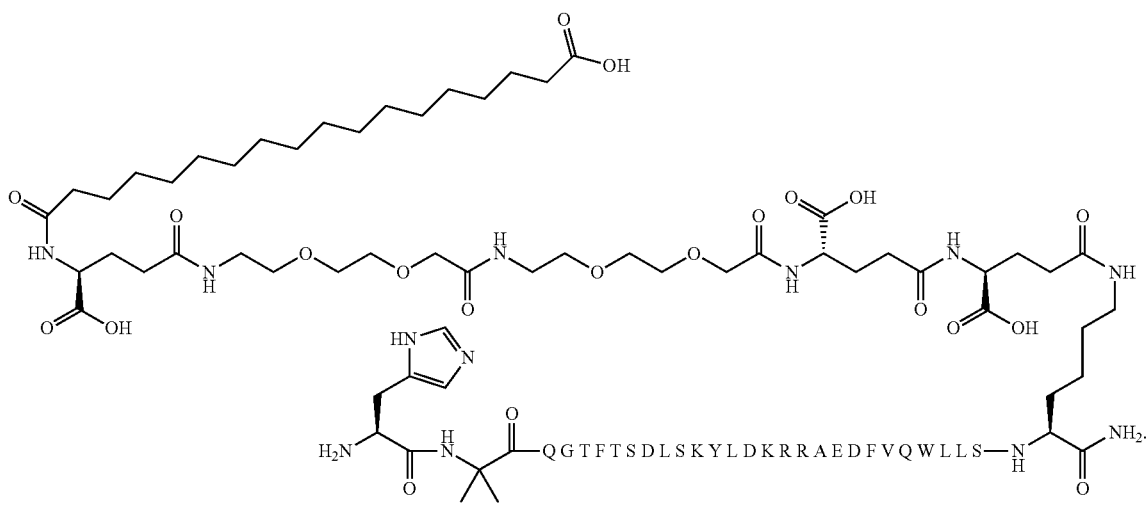

In one embodiment the glucagon derivative is $N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Thr16,Arg24,Leu27,Ser28,Lys29]-Glucagon amide 4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Glu16,Arg20,Leu27,Lys28]-Glucagon amide

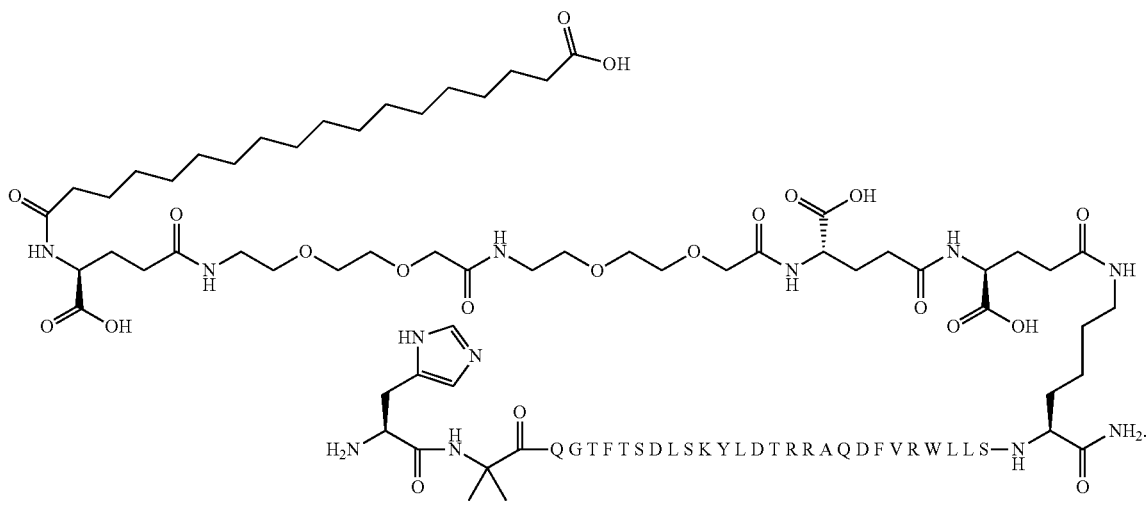

In one embodiment the glucagon derivative is $N^{\epsilon 28}$-[2-[[(2S)-2-[[(2S)-4-carboxy-2-[[2-[[(2S)-2-[[(4S)-4-carboxy-

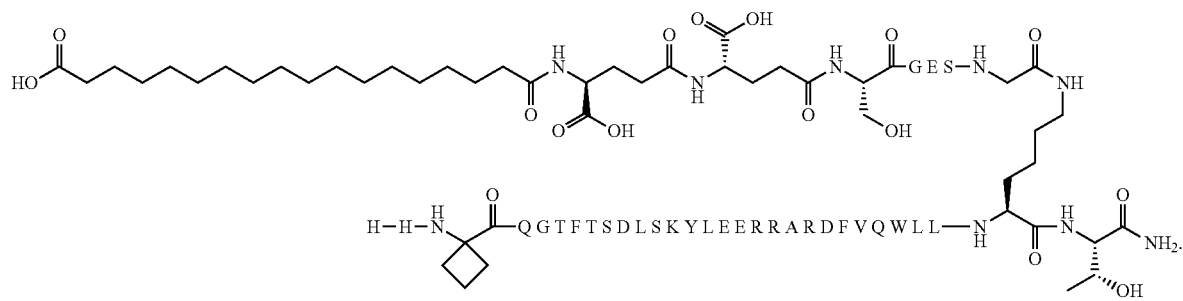

In one embodiment the glucagon derivative is $N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Ala18,Arg20,Glu21,Ala24,Leu27]-Glucagon amide

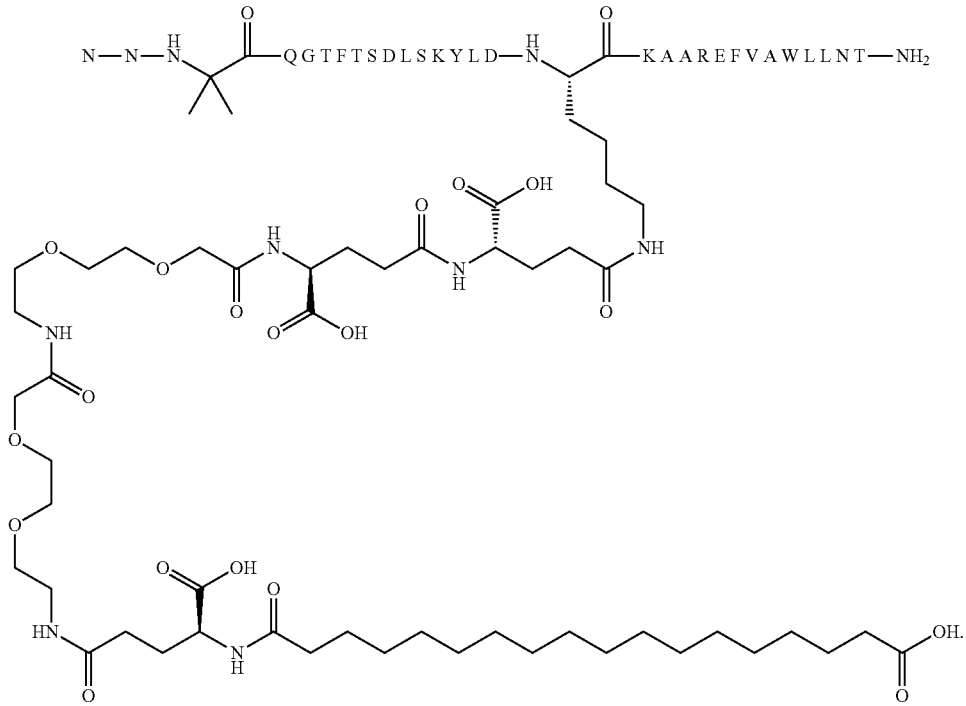

In one embodiment the glucagon derivative is $N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Ala18,Arg20,Glu21,Ala24,Leu27]-Glucagon amide

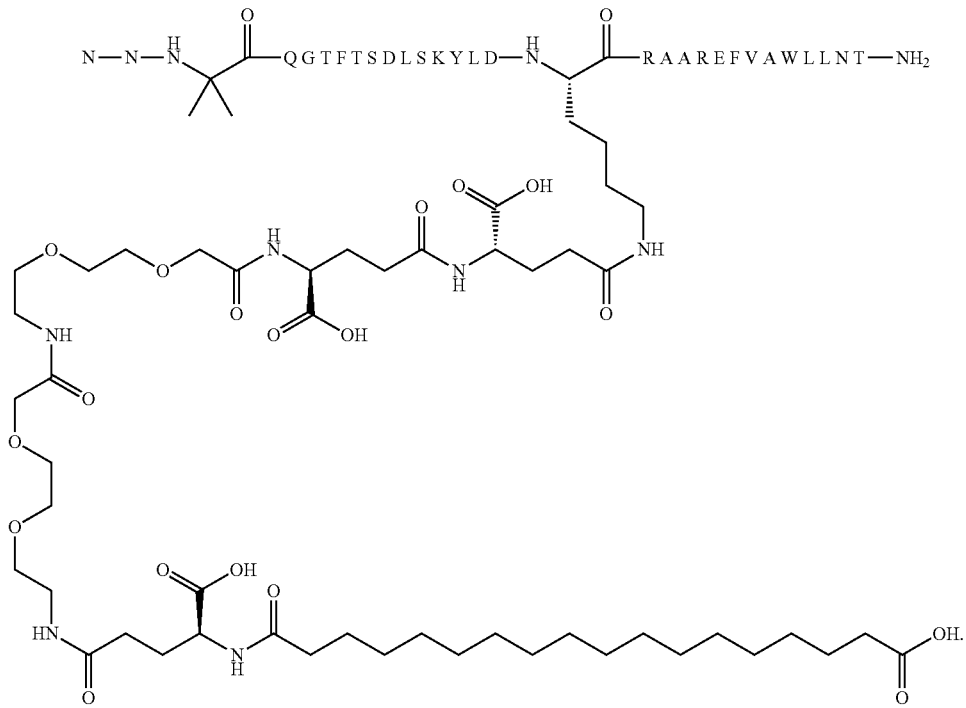

In one embodiment the glucagon derivative is $N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Lys16,Arg20,Glu21,Ala24,Leu27]-Glucagon amide

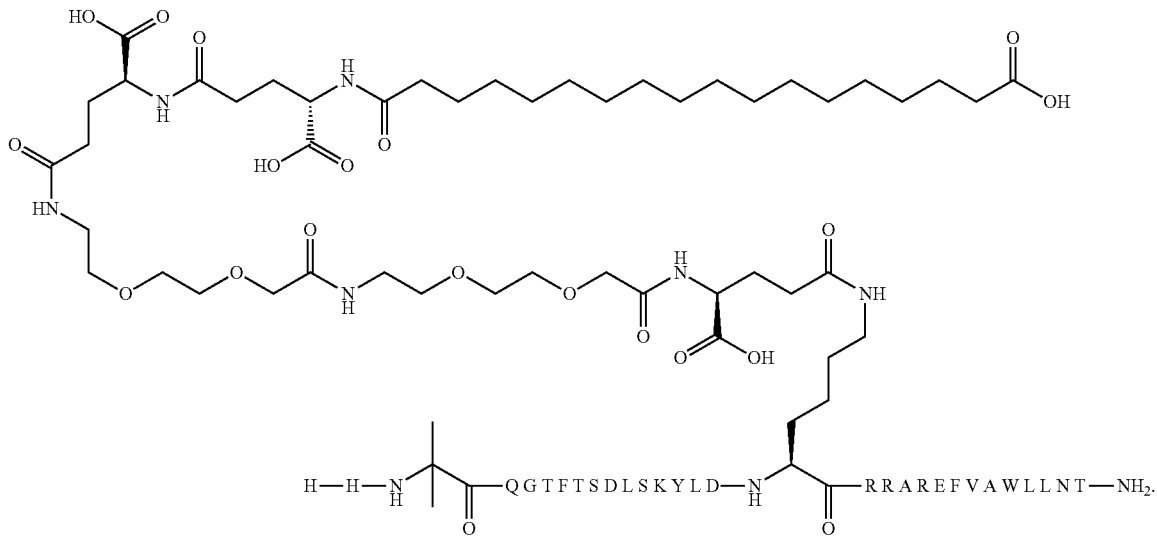

In one embodiment the glucagon derivative is $N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Glu15,Arg20,Glu21,Leu27,Lys28]-Glucagon amide

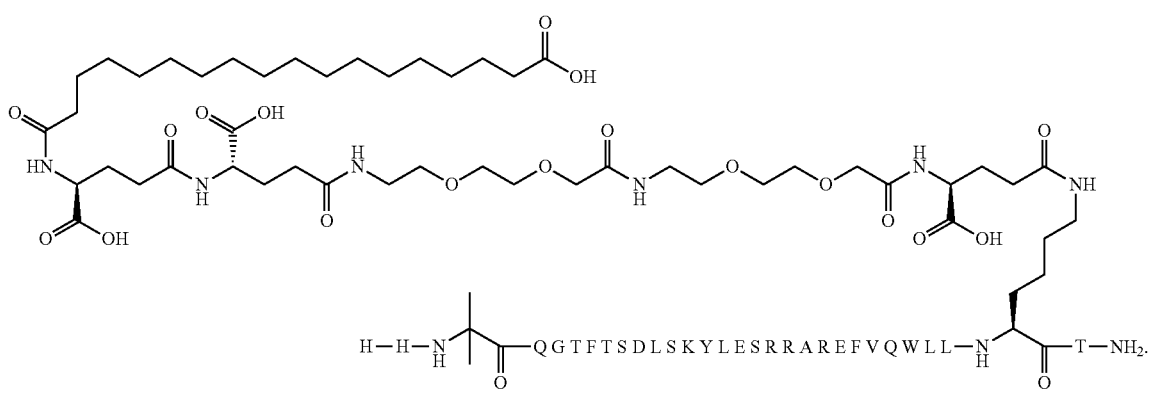

In one embodiment the glucagon derivative is $N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Glu15,Arg20,Glu21,Leu27,Lys29]-Glucagon amide

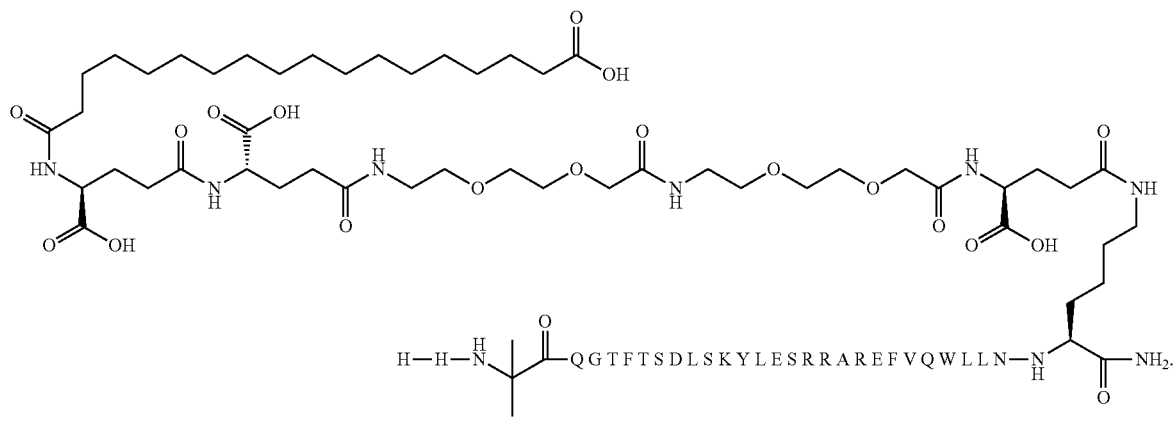

In one embodiment the glucagon derivative is $N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Arg20,Glu21,Leu27,Lys28]-Glucagon amide

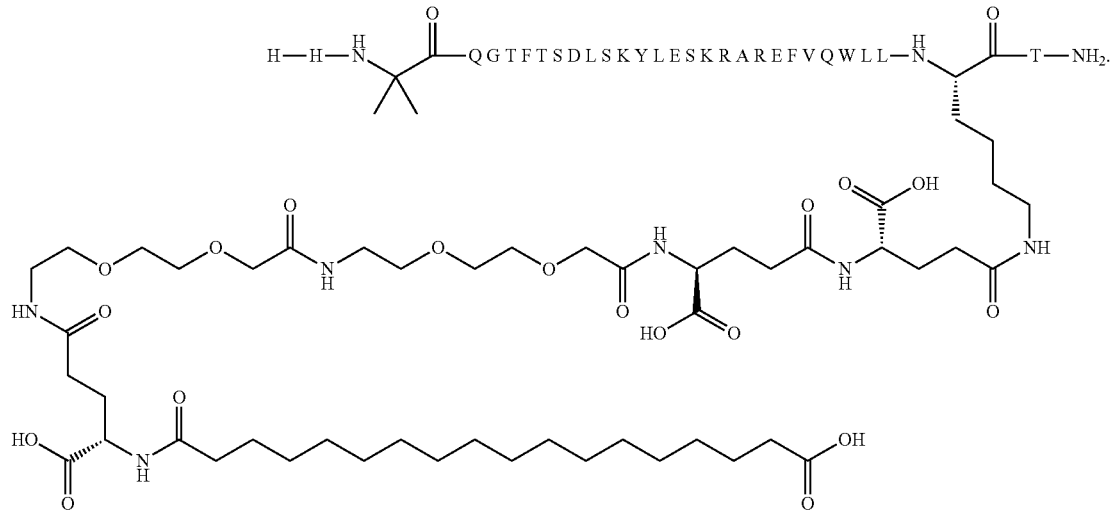

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys28]-Glucagon amide

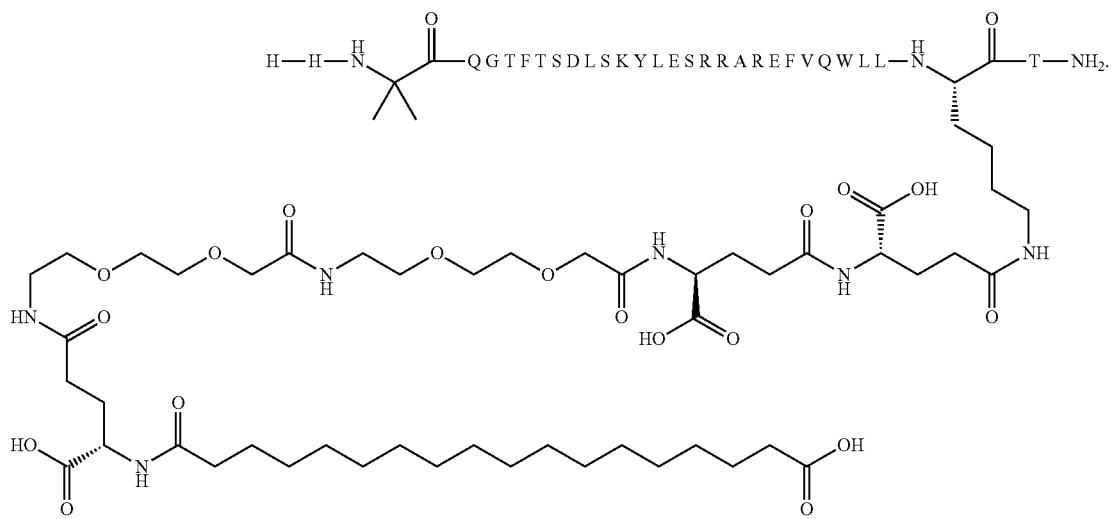

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Ala18,Arg20,Glu21,Leu27,Lys28]-Glucagon amide

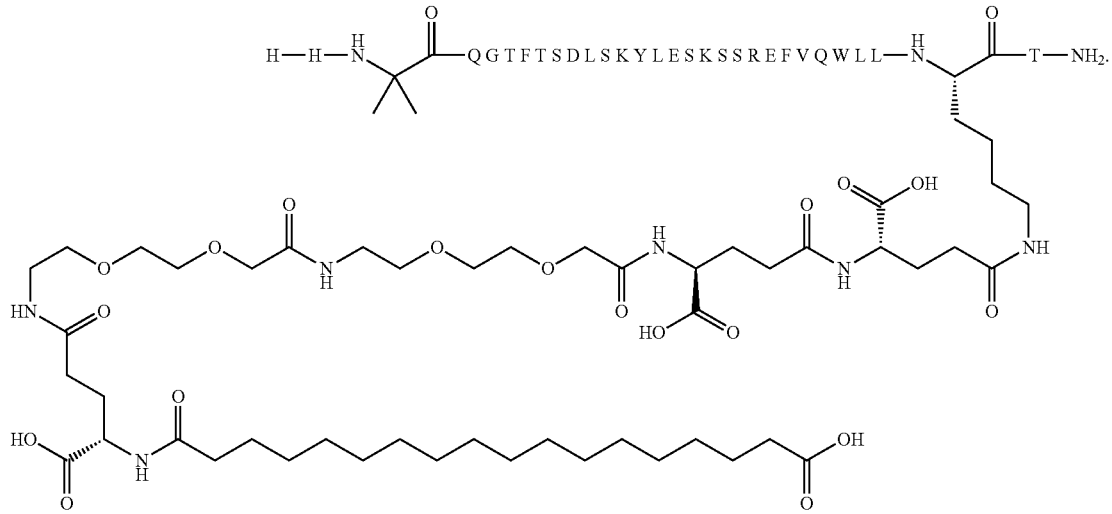

In one embodiment the glucagon derivative is $N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,Leu10,Glu15,Lys17,Arg20,Glu21,Leu27,Lys28]-Glucagon amide

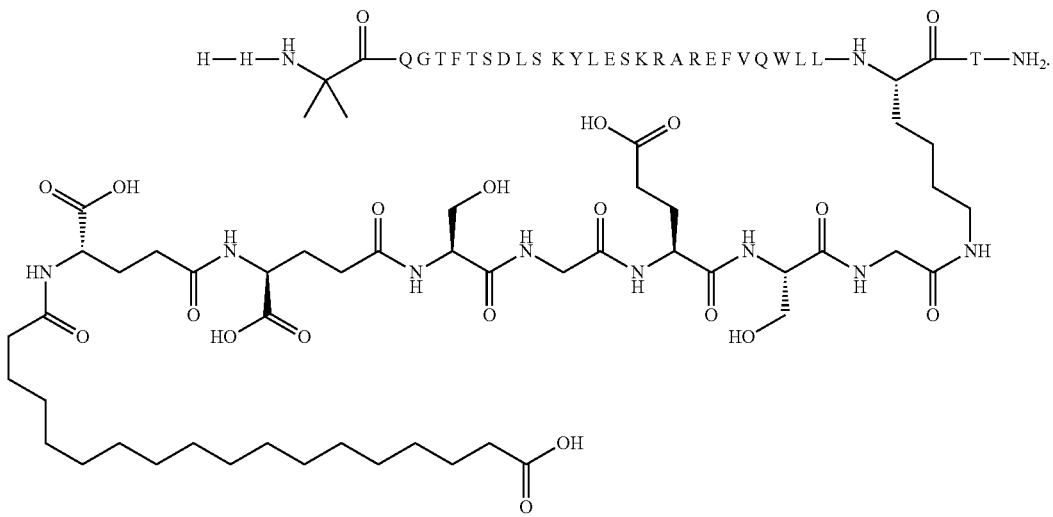

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]-acetyl]amino]ethoxy]ethoxy]acetyl]amino]butanoyl]amino]butanoyl]-[Aib2,Leu10,Leu16,Lys17,Arg20,Glu21,Leu27,Lys28]-Glucagon amide In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Lys17,Arg20,Glu21,Leu27,Lys28]-Glucagon amide

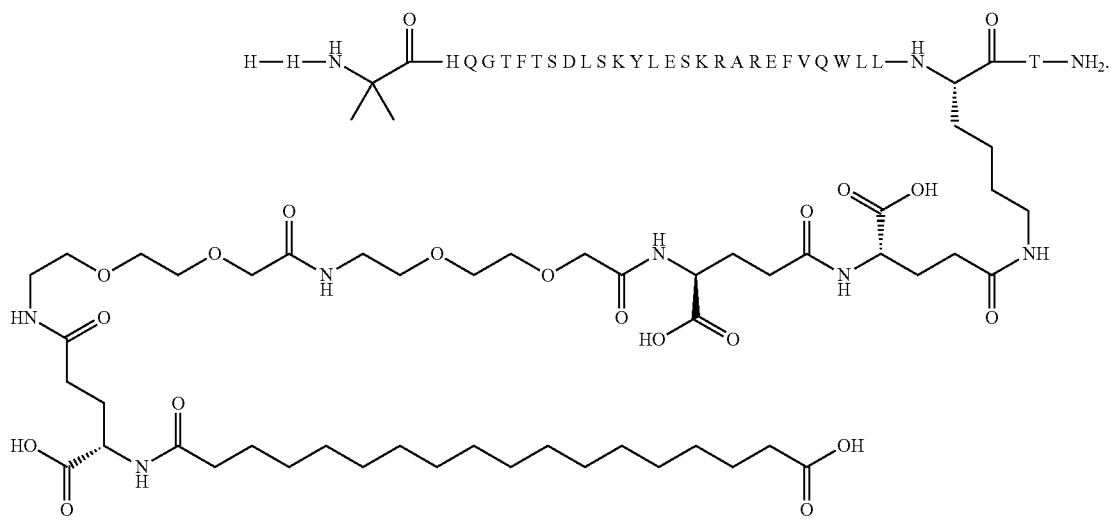

In one embodiment the glucagon derivative is N^ε16-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Aib2,Leu10,Lys16,Glu21,Val27,Lys28,Gly29]-Glucagon amide

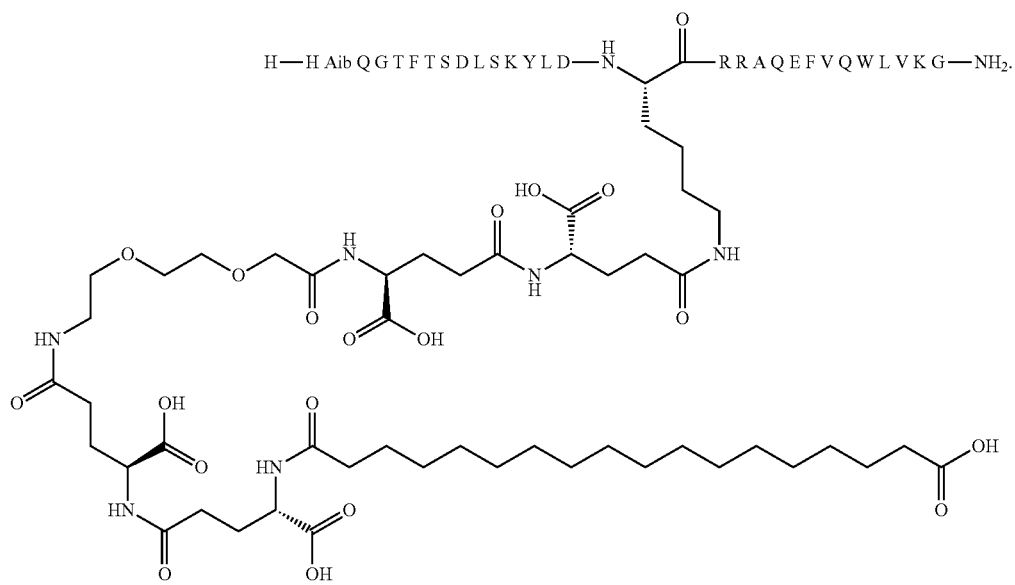

In one embodiment the glucagon derivative is N^ε16-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Aib2,Leu10,Lys16,Glu21,Leu27]-Glucagon amide

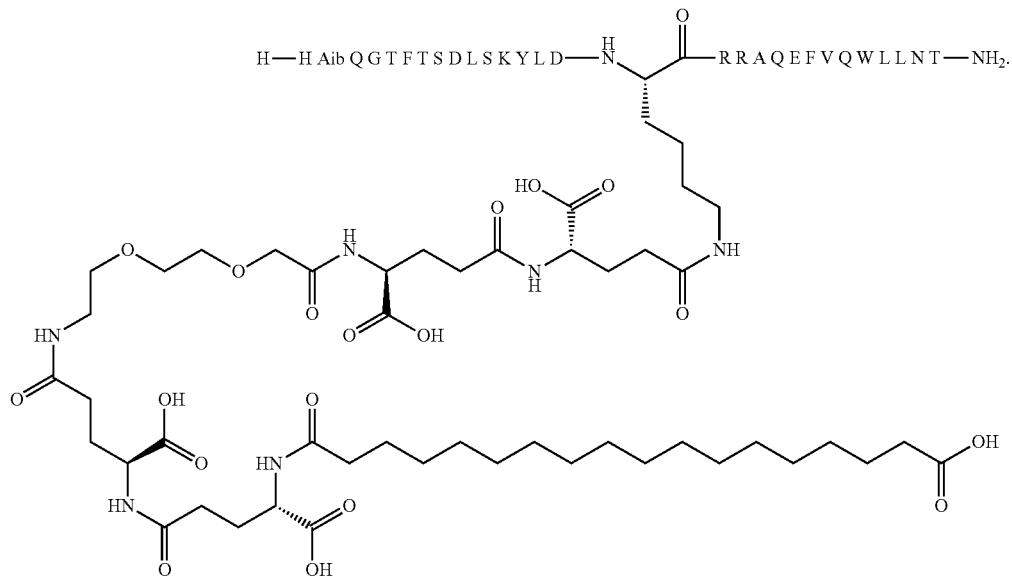

In one embodiment the glucagon derivative is $N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Leu27,Lys28]-Glucagon amide

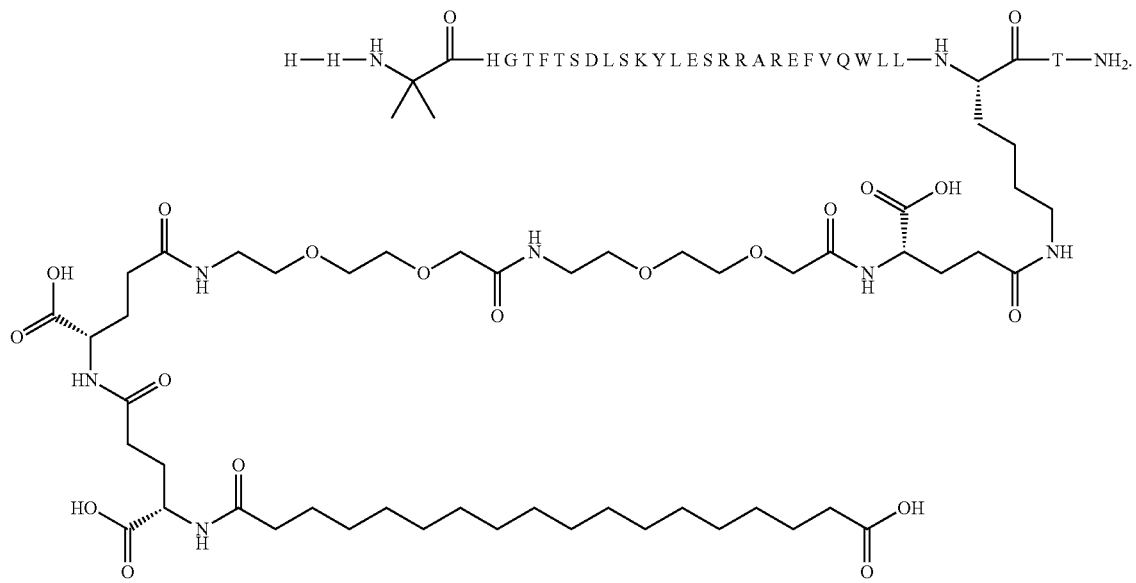

In one embodiment the glucagon derivative is $N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Ala24,Leu27,Lys28]-Glucagon amide

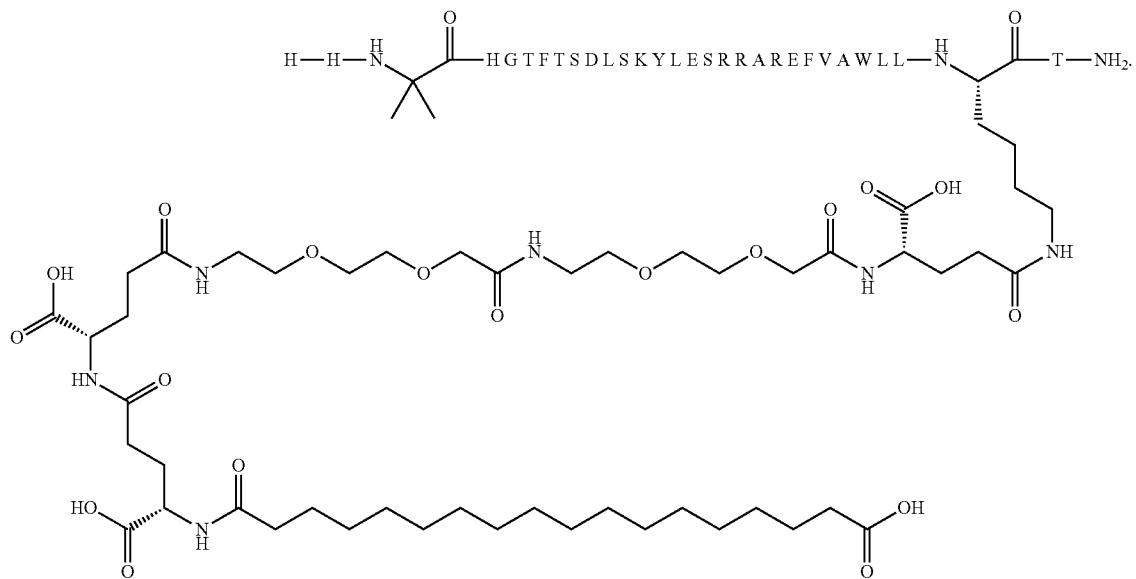

In one embodiment the glucagon derivative is N^ε16-[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]-[Aib2,His3,Leu10,Glu15,Lys16,Arg20,Glu21,Ala24,Leu27,Ser28]-Glucagon amide

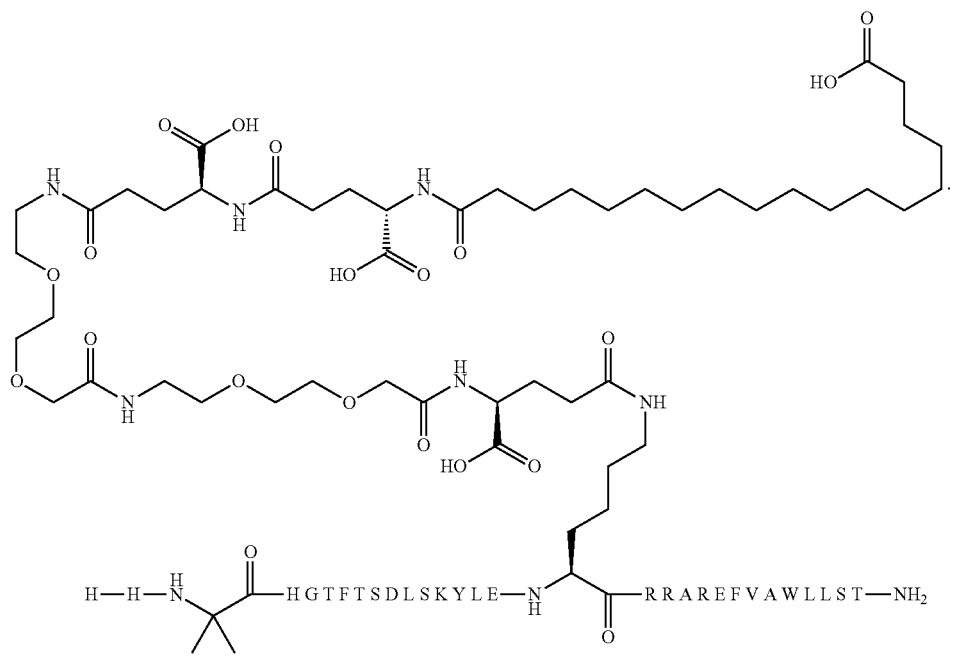

In one embodiment the glucagon derivative is N^ε28-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Arg20,Glu21,Leu27,Lys28]-Glucagon amide

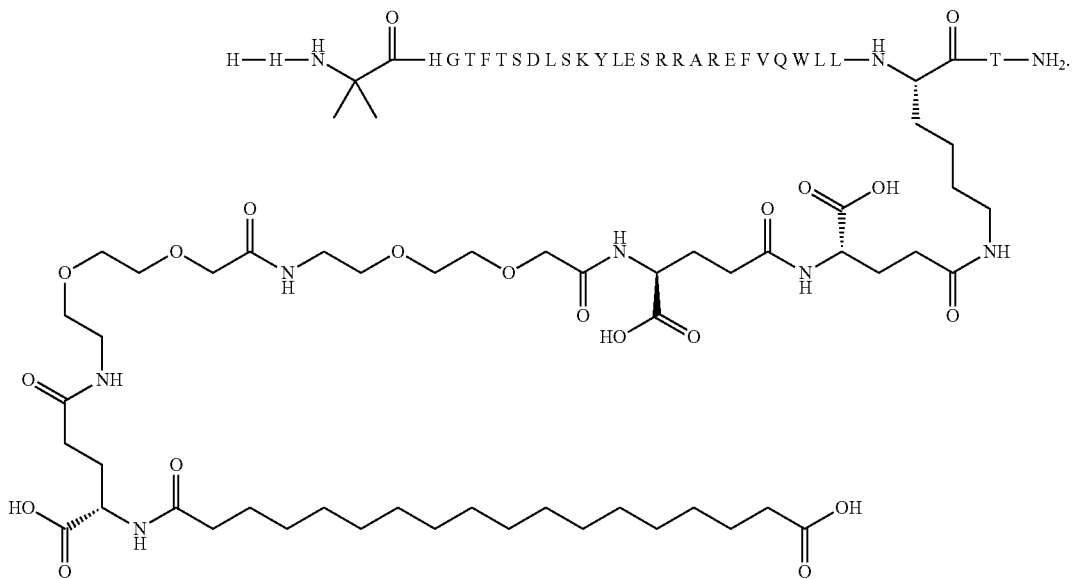

In one embodiment the glucagon derivative is $N^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,His3,Leu10,Glu15,Lys17,Arg20,Glu21,Leu27,Lys28]-Glucagon amide $N^{\epsilon 28}$-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,His3,Leu10,Glu15,Leu27,Lys28]-Glucagon amide

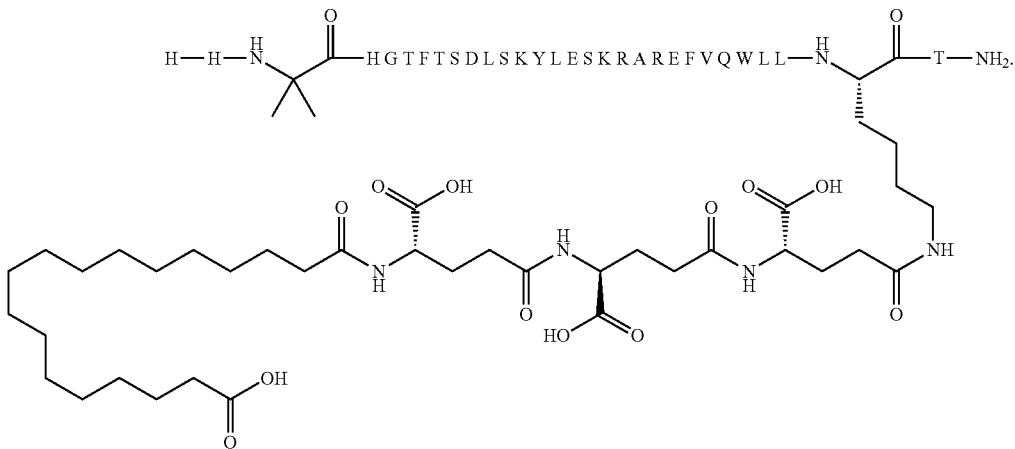

In one embodiment the glucagon derivative is $N^{\epsilon 28}$-[2-[[(2S)-2-[[(2S)-4-carboxy-2-[[2-[[(2S)-2-[[(4S)-4-carboxy-

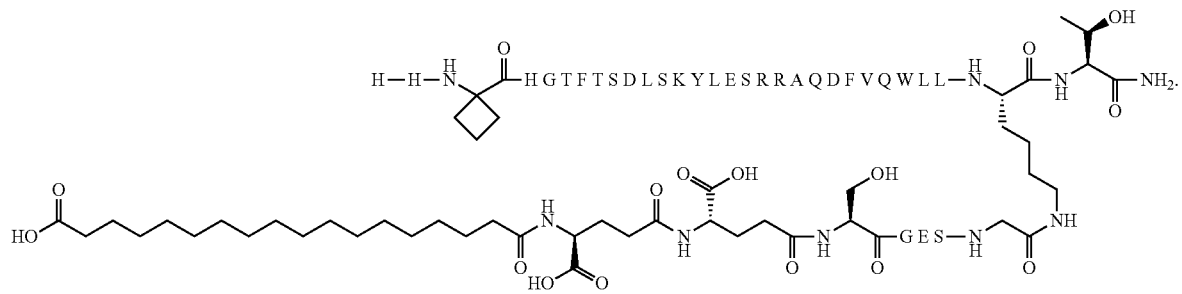

In one embodiment the glucagon derivative is N^ε28-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10, Glu15,Lys17,Arg20,Glu21, Leu27,Lys28]-Glucagon amide

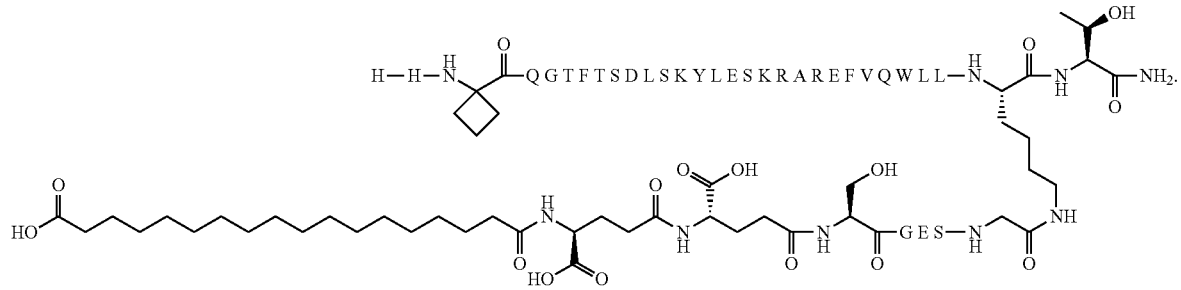

In one embodiment the glucagon derivative is N^ε28-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,His3,Leu10,Glu15,Arg20,Leu27, Lys28]-Glucagon amide

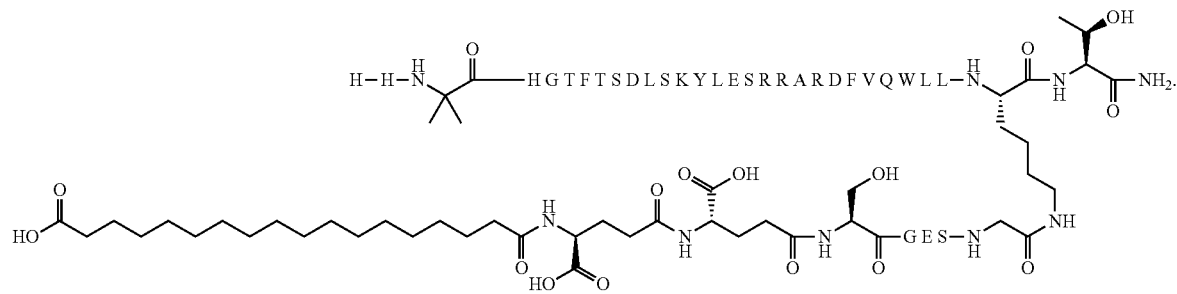

In one embodiment the glucagon derivative is N^ε29-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Leu16,Arg20,Glu21,Leu27,Lys29]-Glucagon amide

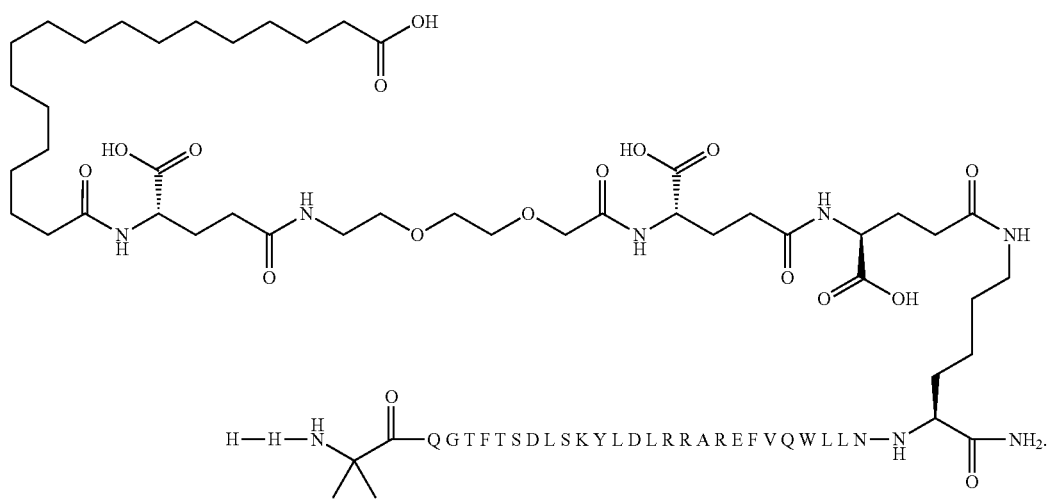

In one embodiment the glucagon derivative is N$^{\epsilon 29}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Ala16,Arg20,Glu21,Leu27,Lys29]-Glucagon amide

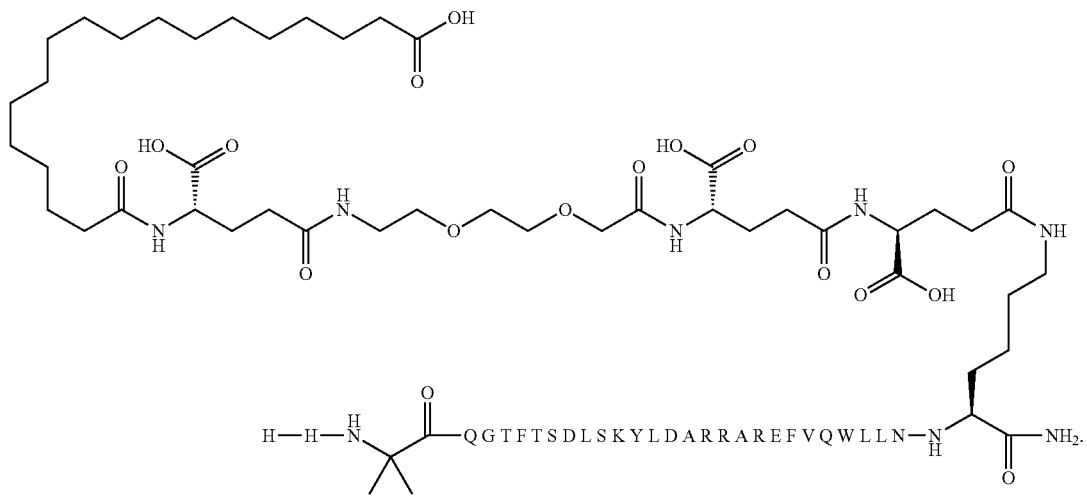

In one embodiment the glucagon derivative is N$^{\epsilon 29}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Glu15,Arg20,Glu21,Leu27,Lys29]-Glucagon amide

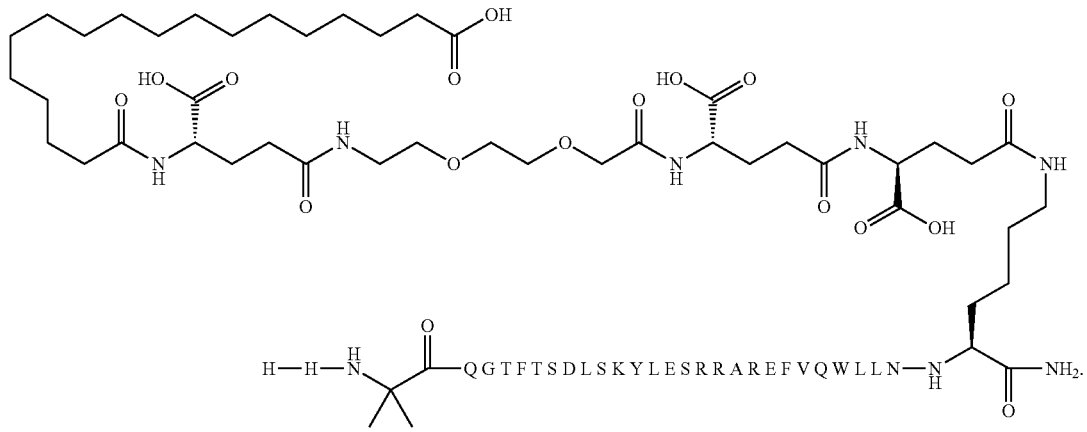

In one embodiment the glucagon derivative is N$^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Glu15,Arg20,Glu21,Leu27,Lys28]-Glucagon amide

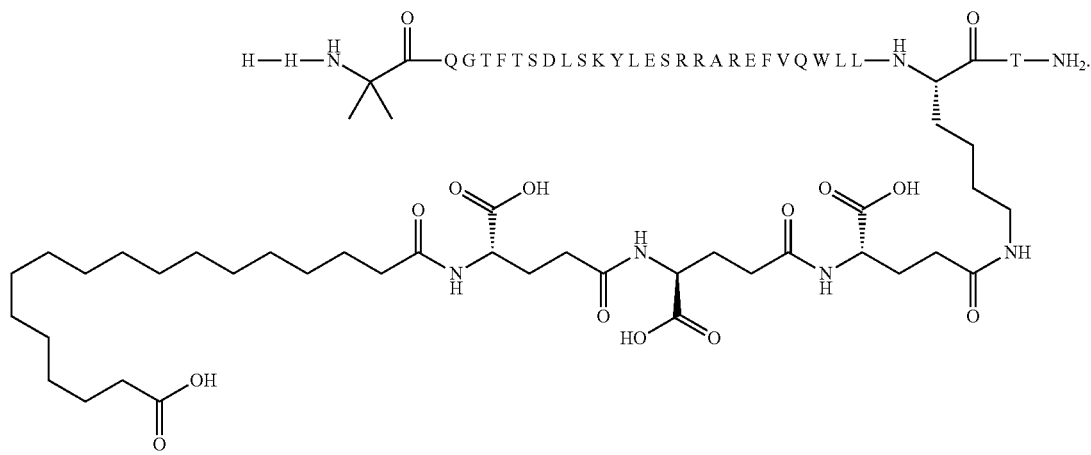

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]-[Aib2,Leu10,Glu15,Arg20,Glu21,Leu27,Lys28]-Glucagon amide

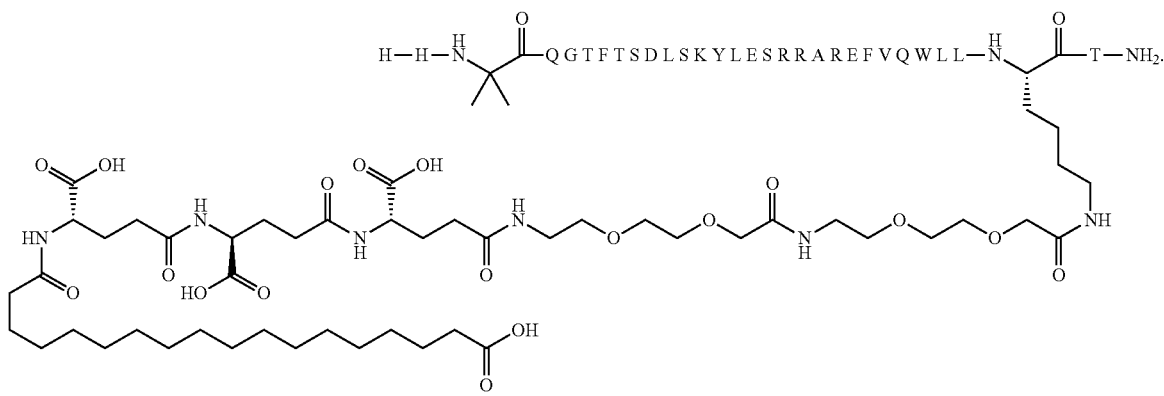

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Leu27,Lys28]-Glucagon amide

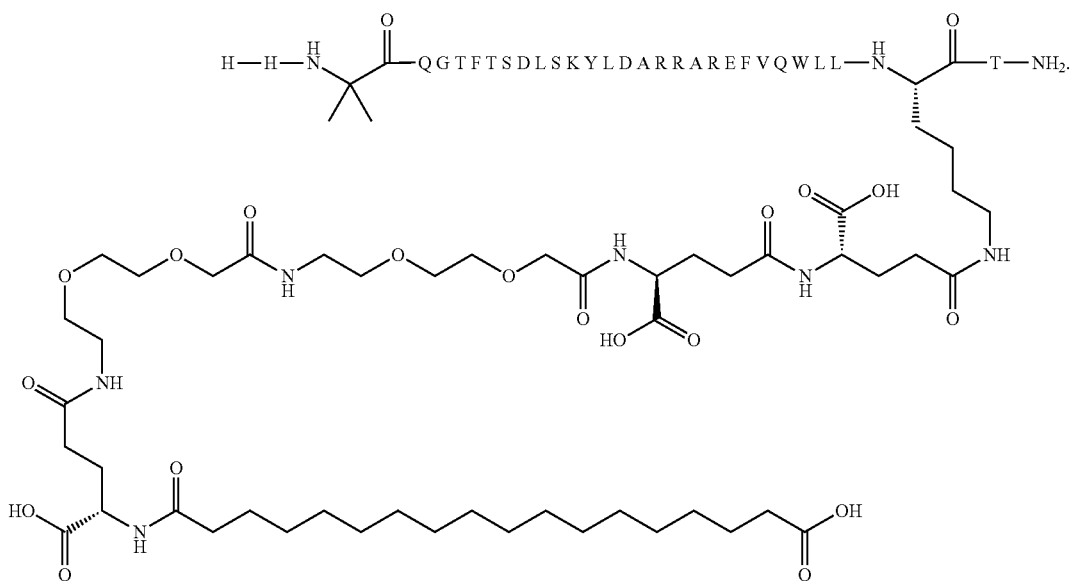

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Leu27,Lys28]-Glucagon amide

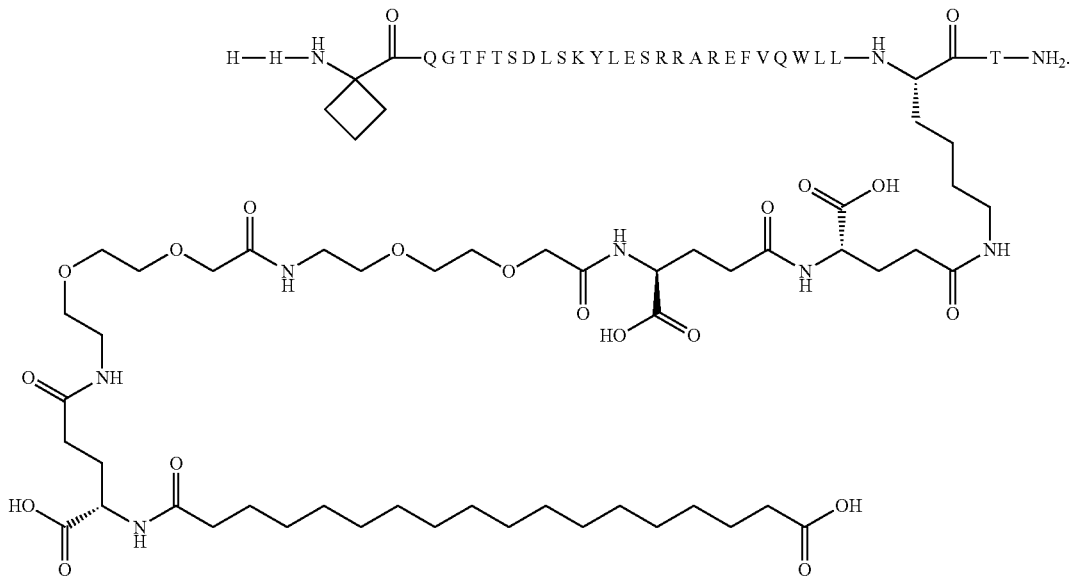

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Leu27,Lys28]-Glucagon amide

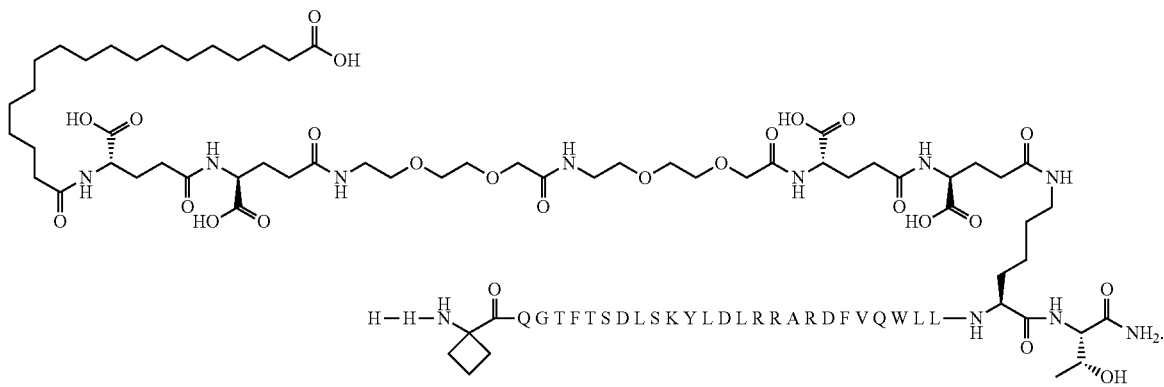

In one embodiment the glucagon derivative is N'-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Leu16,Arg20,Leu27,Lys28]-Glucagon amide In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide

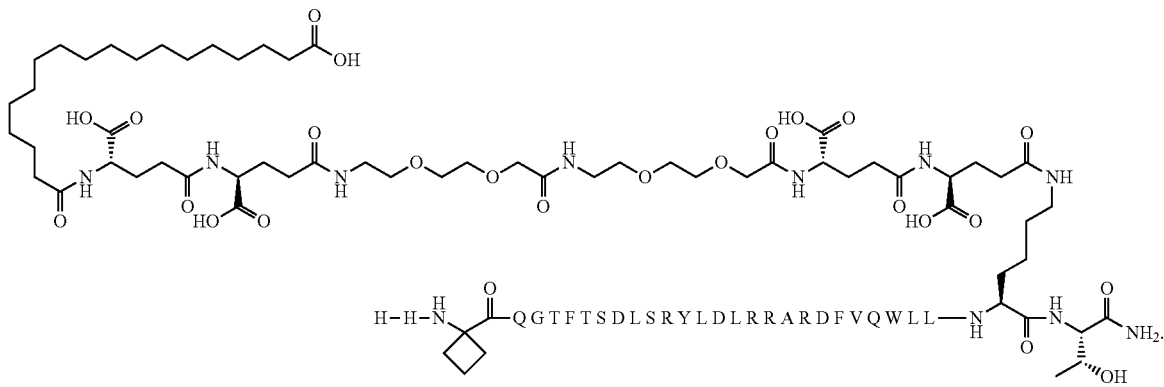

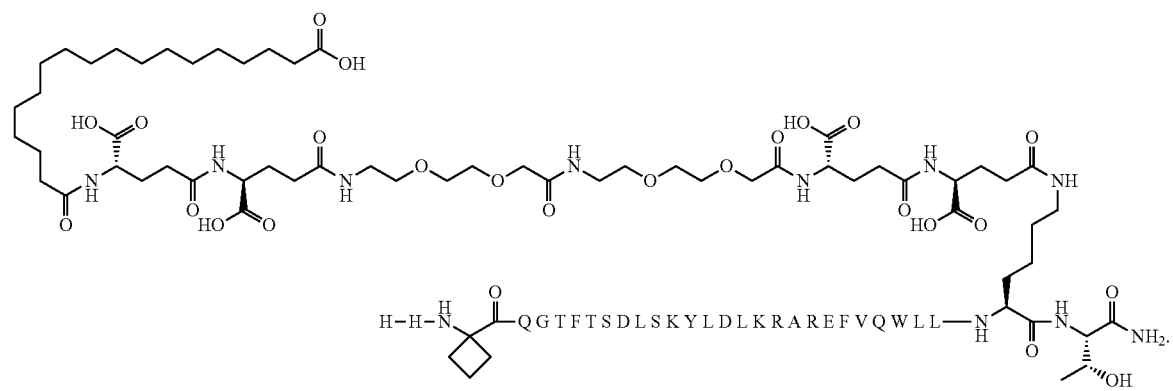

In one embodiment the glucagon derivative is $N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Leu16,Lys17,Arg20,Glu21,Leu27,Lys28]-Glucagon amide

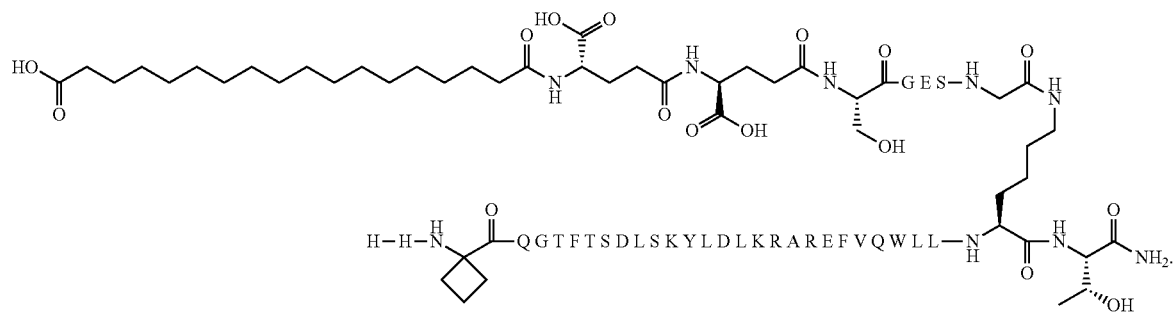

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Glu21,Leu27,Lys28]-Glucagon amide

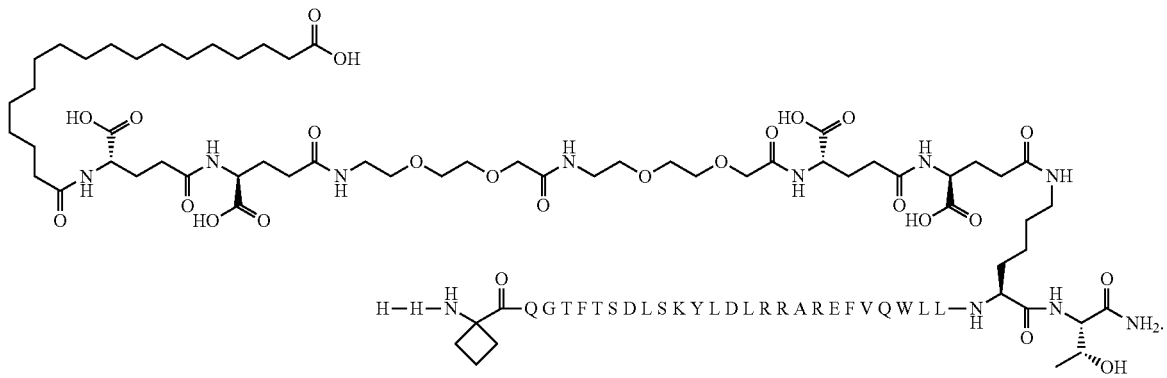

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Acpr2,Leu10,Glu15,Arg20,Glu21,Leu27,Lys28]-Glucagon amide

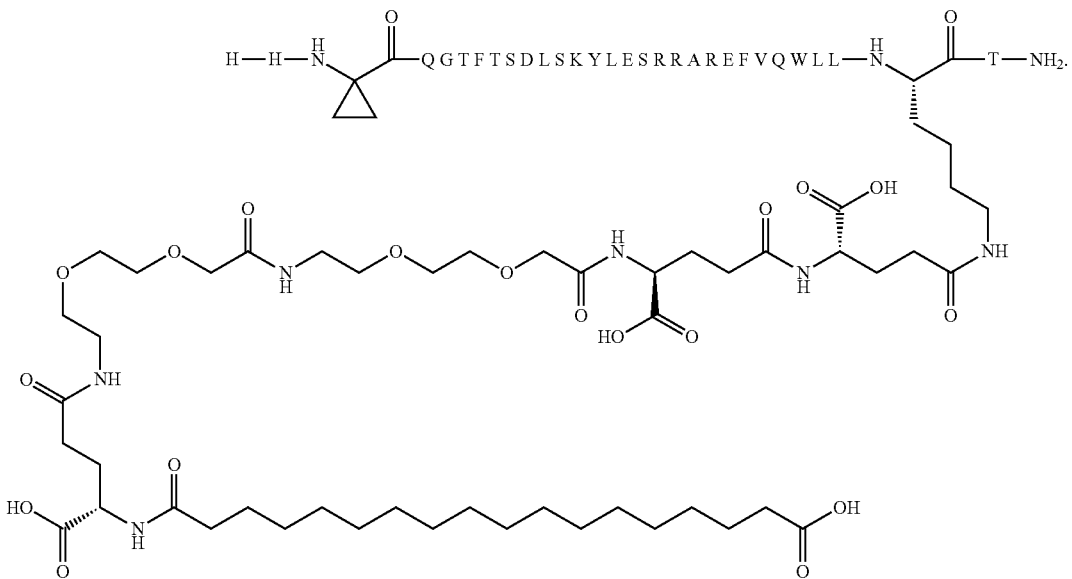

In one embodiment the glucagon derivative is N^ε28-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Aib16,Arg20,Glu21,Leu27,Lys28]-Glucagon amide

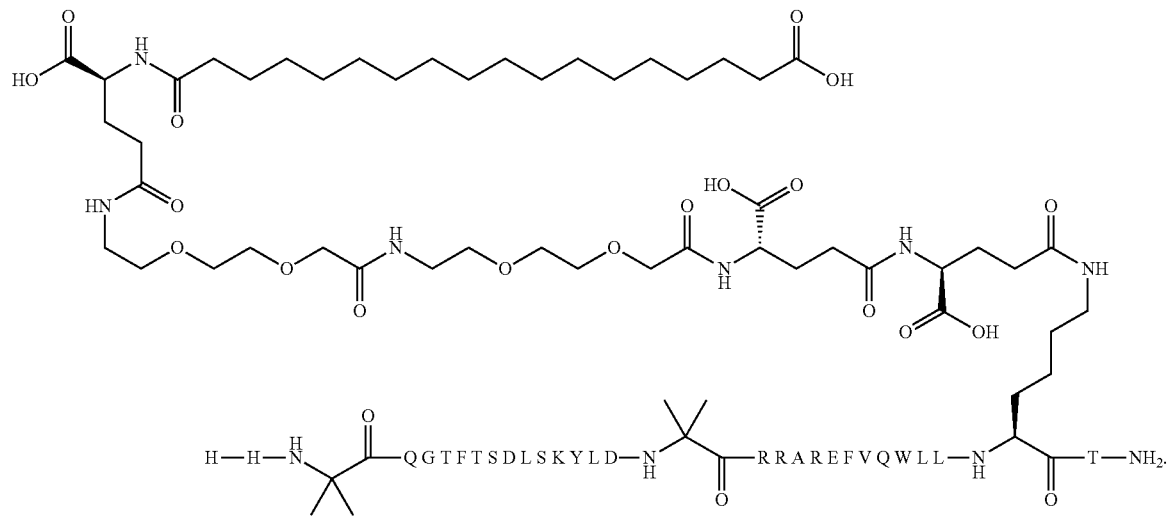

In one embodiment the glucagon derivative is N^ε28-(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide

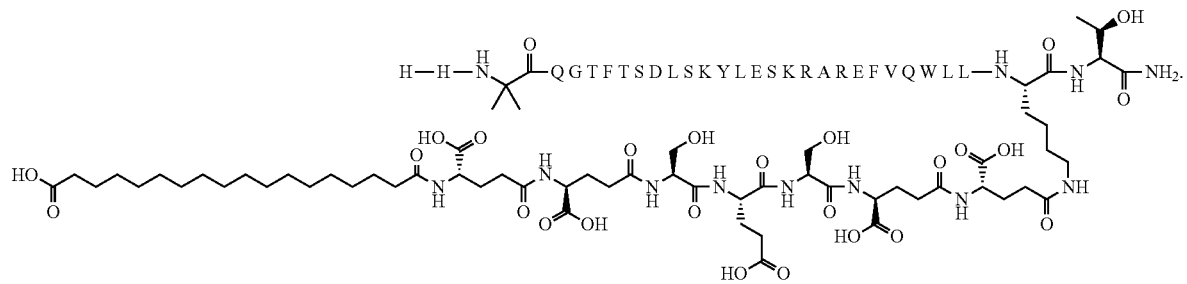

In one embodiment the glucagon derivative is N^ε28-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Leu16,Leu27,Lys28]-Glucagon amide

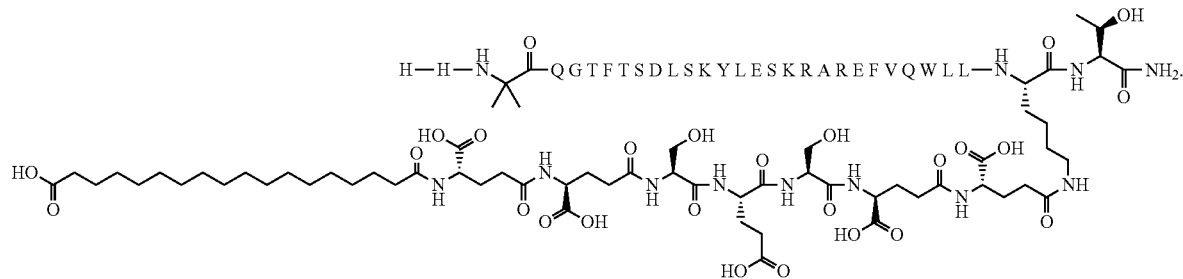

In one embodiment the glucagon derivative is N^ε28-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide

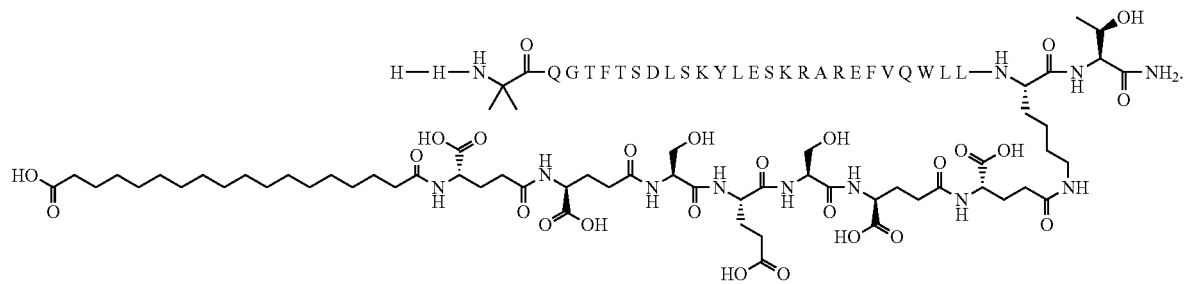

In one embodiment the glucagon derivative is N^ε28-[2-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypro panoyl]amino]butanoyl]amino]-3-hydroxypropanoyl]
amino]acetyl][Aib2,Leu10,Leu16,Arg20,Leu27,Lys28]-
Glucagon amide

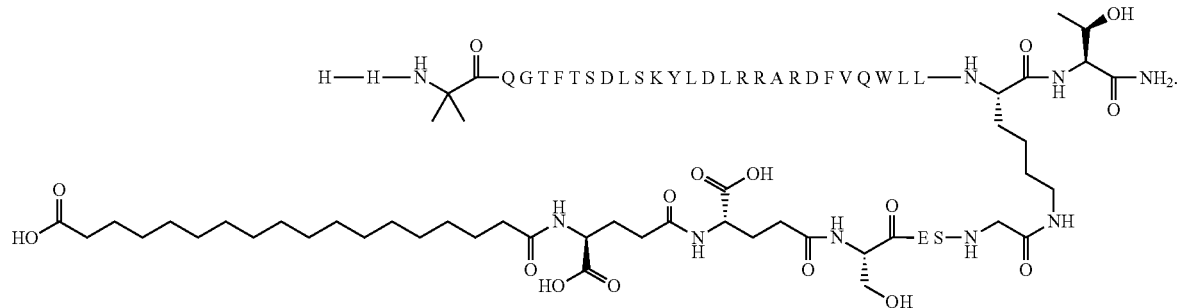

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys28]-Glucagon amide

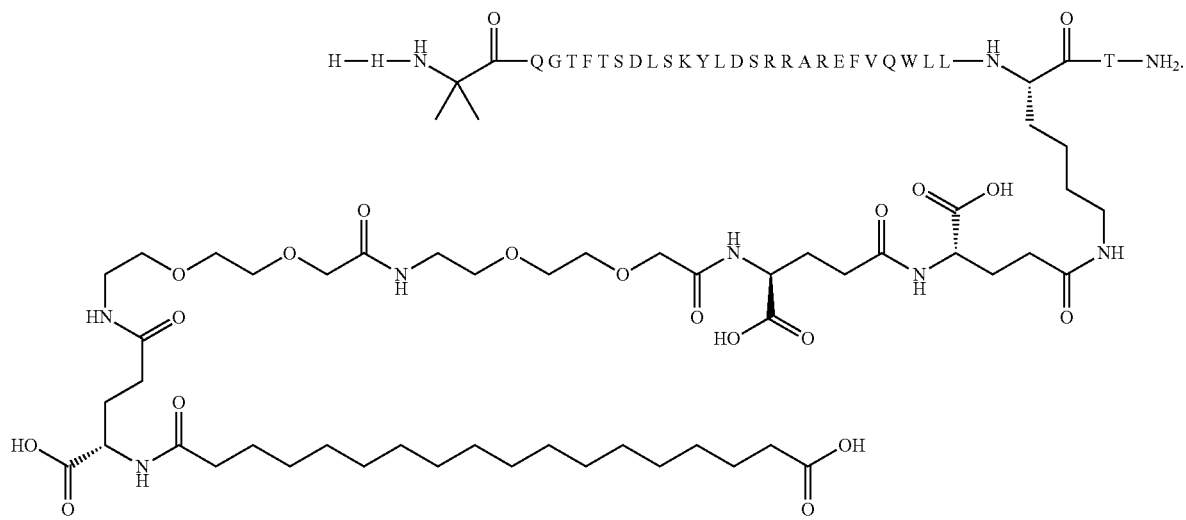

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Leu27,Lys28]-Glucagon amide

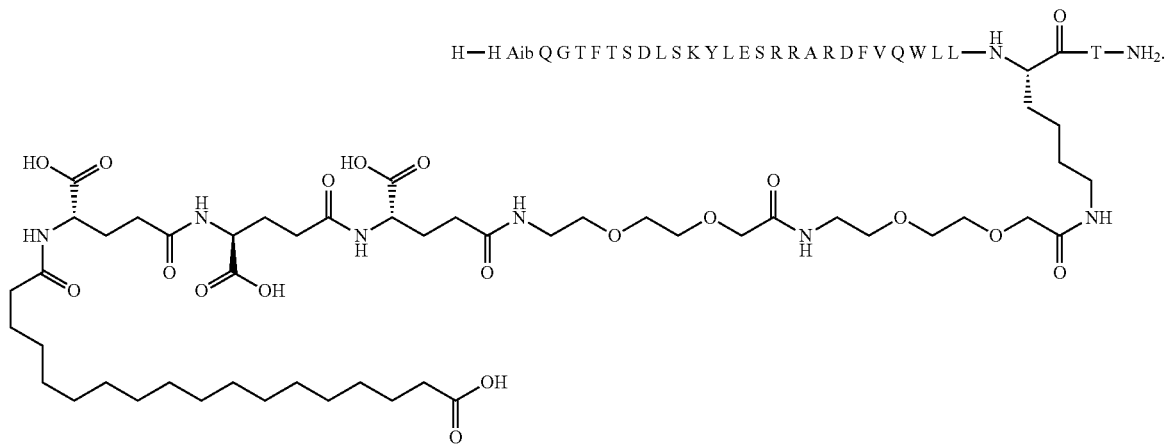

In one embodiment the glucagon derivative is $N^{\epsilon 28}$-[2-[2-[2-[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Leu27,Lys28]-Glucagon amide

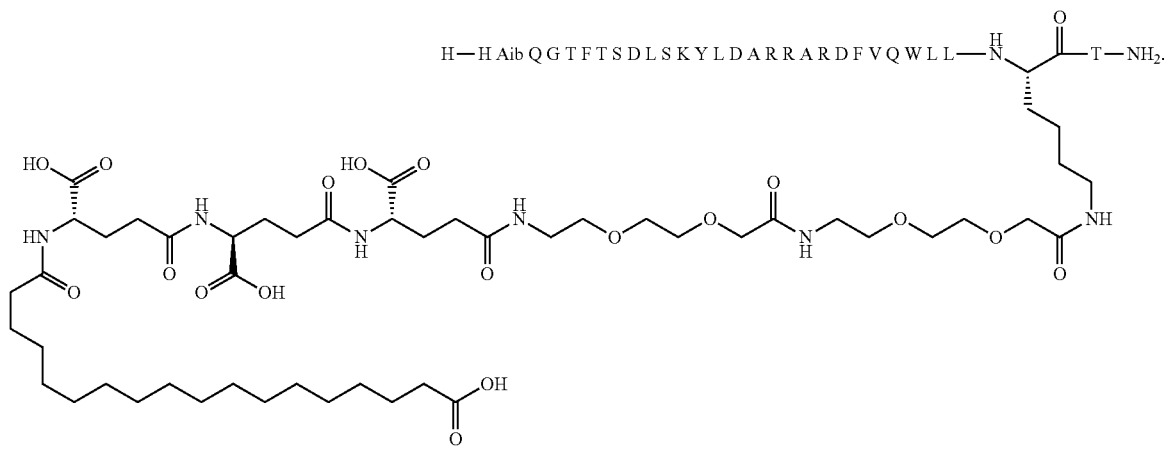

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy] acetyl]amino]ethoxy]ethoxy]acetyl]amino]butanoyl]amino] butanoyl]-[Acb2,Leu10,Arg12,Glu15,Arg20,Glu21,Leu27,Lys28]-Glucagon amide

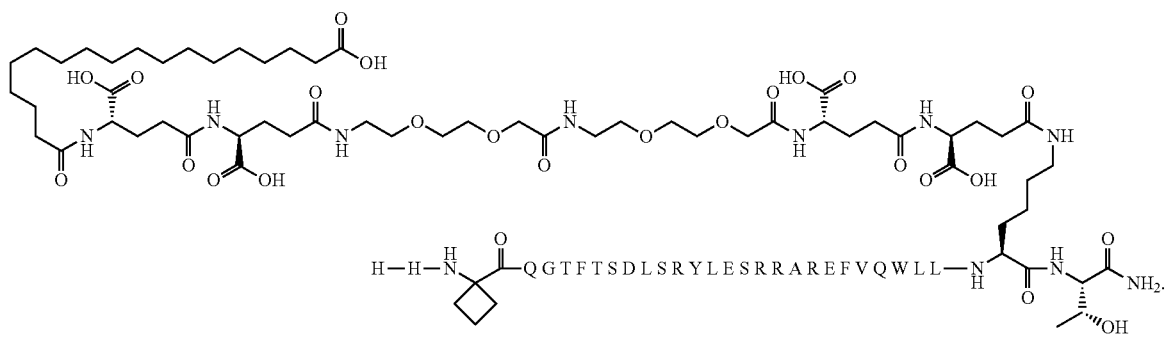

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Aib2,Leu10, Glu15,Arg20,Glu21,Leu27,Lys28]-Glucagon amide

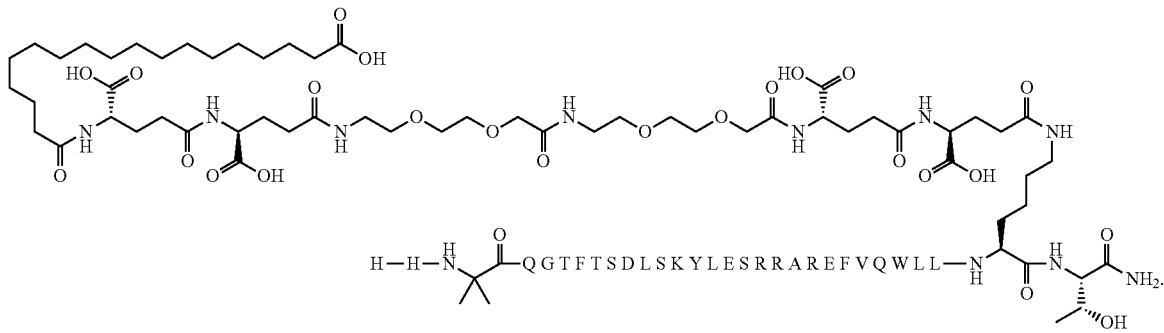

In one embodiment the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino) butanoyl]amino]butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Leu27,Lys28]-Glucagon amide

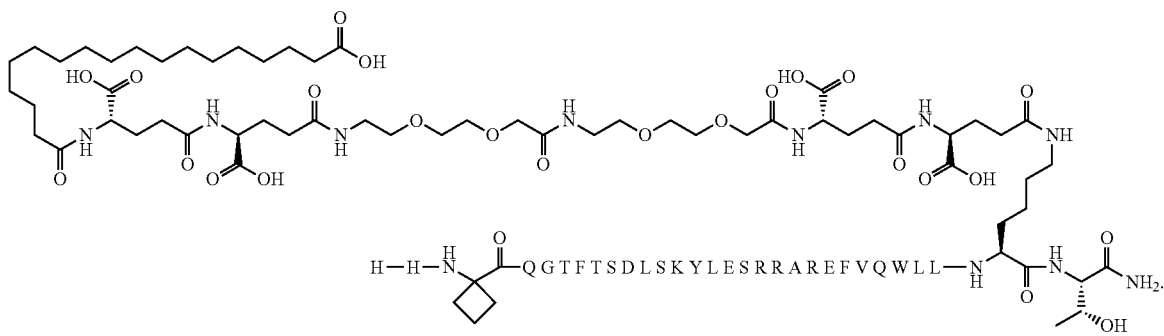

In one embodiment the glucagon derivative is $N^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Arg12,Ala16,Arg20,Leu27,Lys28]-Glucagon amide

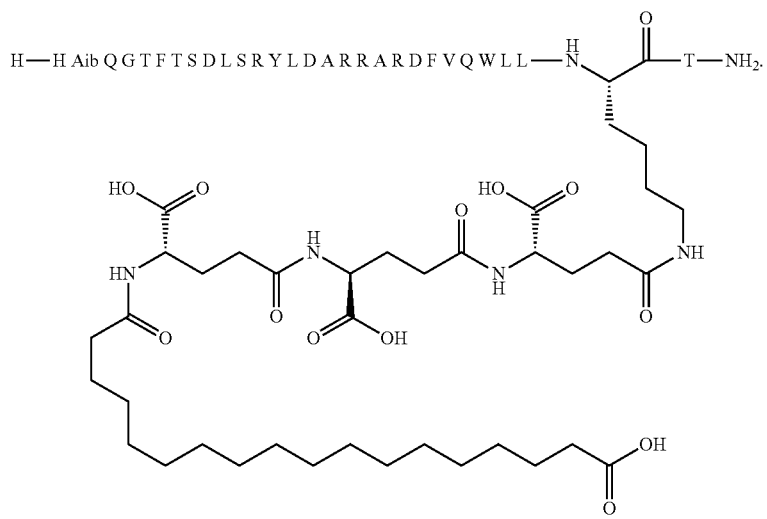

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Acb2,Leu10,Glu15,Leu27,Lys28]-Glucagon amide

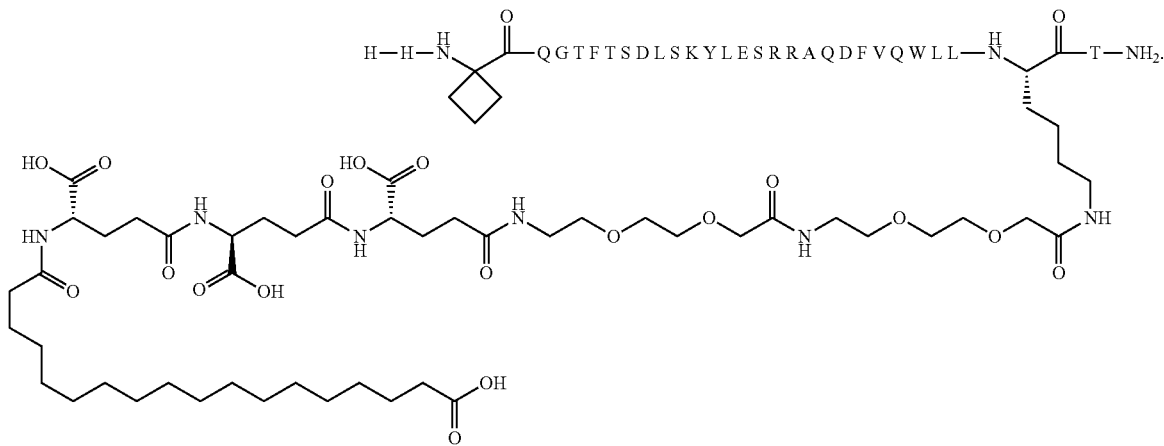

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Arg12,Ala16,Leu27,Lys28]-Glucagon amide

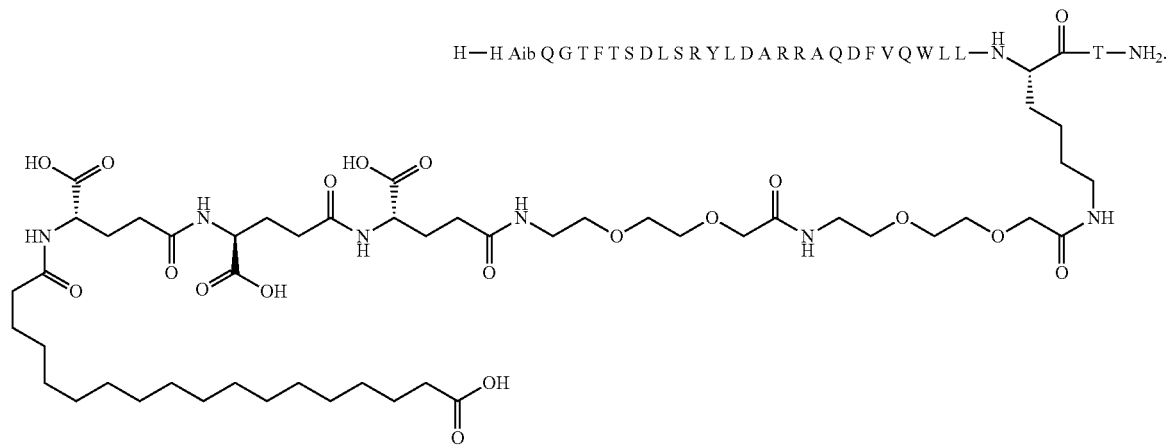

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Leu27,Lys29]-Glucagon amide

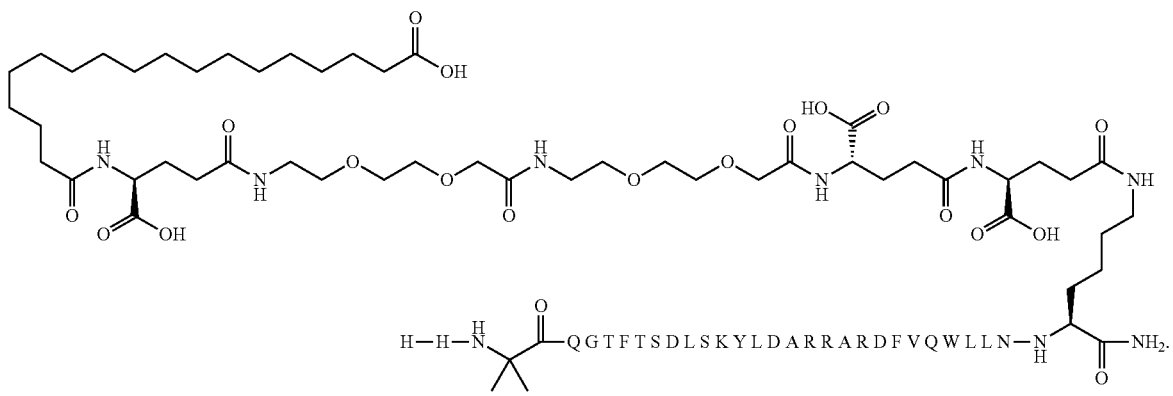

In one embodiment the glucagon derivative is N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Leu27,Ser28,Lys29]-Glucagon amide

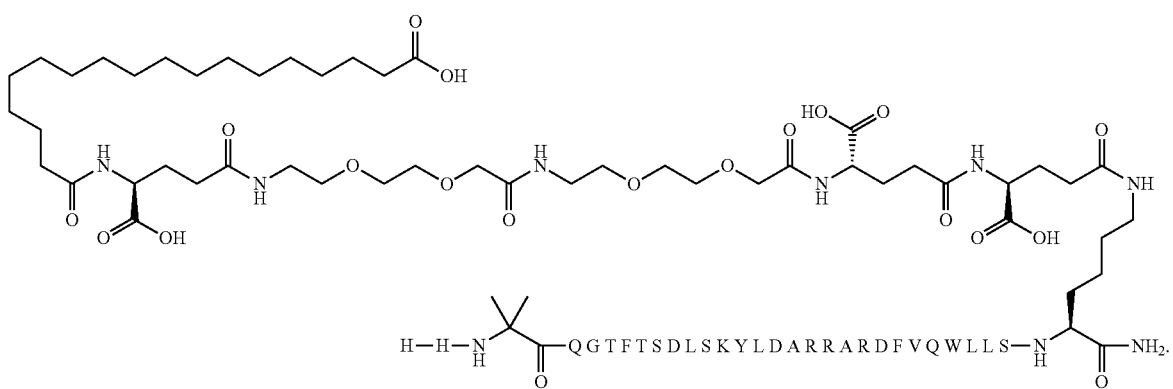

In one embodiment the glucagon derivative is N^ε28-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Arg20,Glu21,Leu27,Lys28]-Glucagon amide In one embodiment the glucagon derivative is N^ε28-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Ala16,Leu27,Lys28]-Glucagon amide

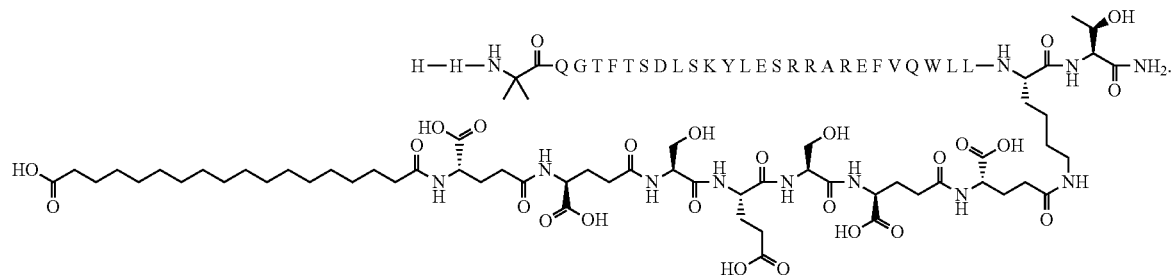

In one embodiment the glucagon derivative is N^ε28-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Acb2,Leu10,Glu15,Lys17,Arg20,Glu21,Leu27,Lys28]-Glucagon amide

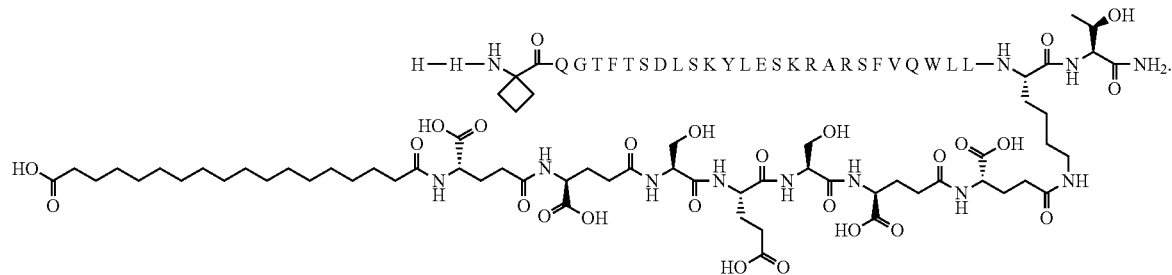

In one embodiment the glucagon derivative is N^ε28-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Ser21,Leu27,Lys28]-Glucagon amide

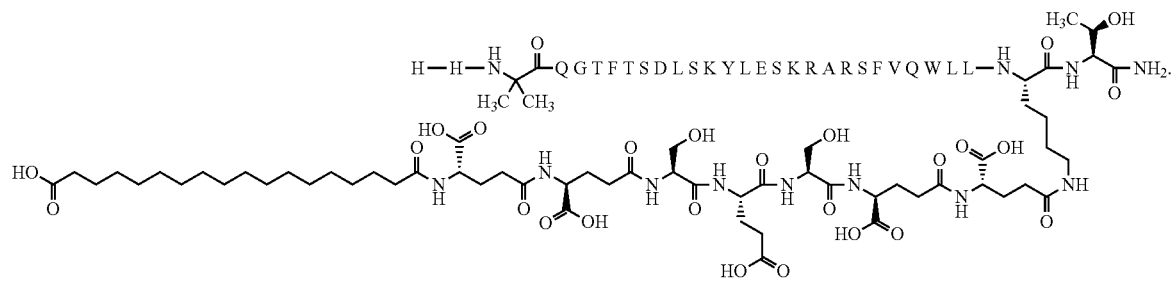

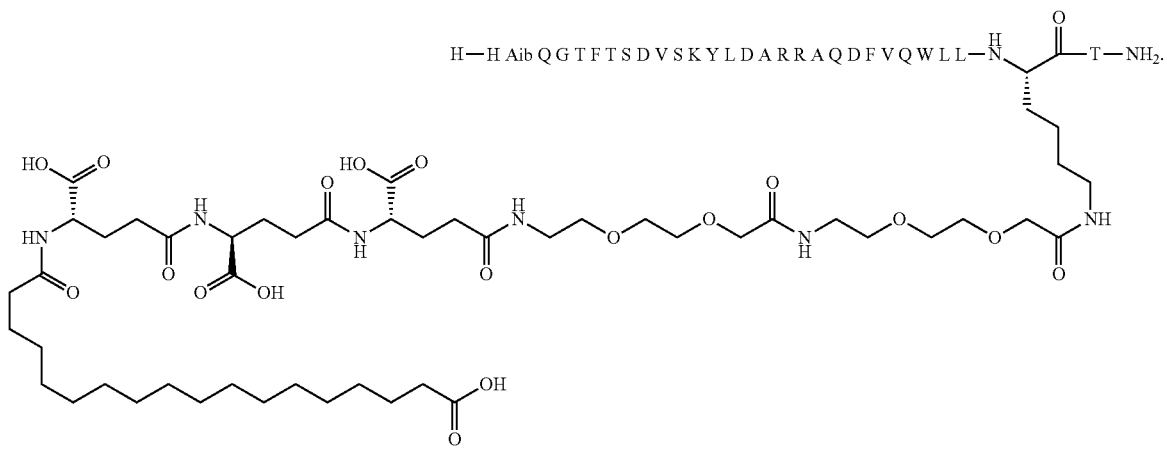

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Leu16,Leu27,Lys28]-Glucagon amide

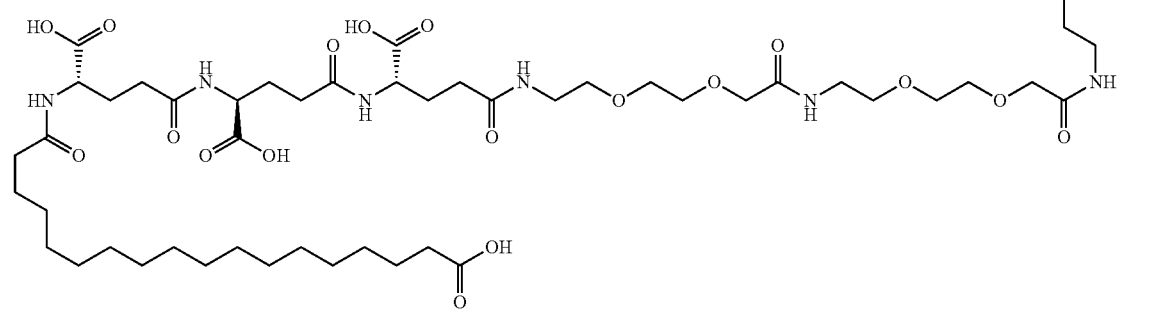

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Arg12,Ala16,Leu27,Lys28]-Glucagon amide

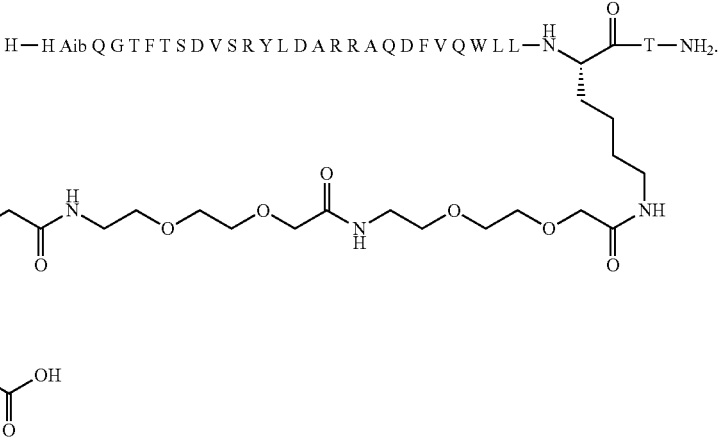

In one embodiment the glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Arg12,Leu16,Leu27,Lys28]-Glucagon amide minus of the peptide, and/or any free or substituted amino group of the peptide in the peptide and/or the side chain.

In one embodiment the derivative or peptide is in the form of a pharmaceutically acceptable salt. In another embodiment, the derivative or peptide is in the form of a pharmaceutically acceptable amide, preferably with an amide group

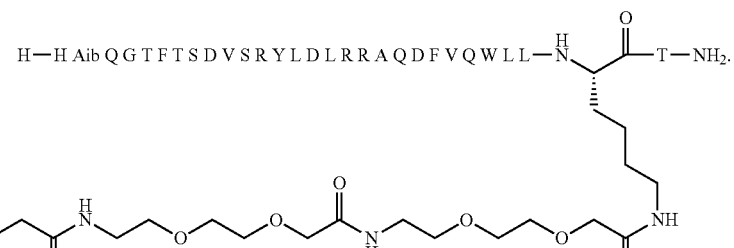

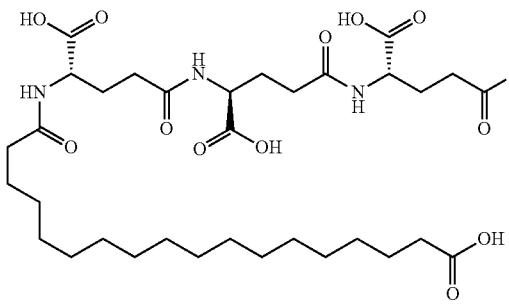

Pharmaceutically Acceptable Salt, Amide, or Ester

The derivatives, analogues and intermediate products of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivatives or analogues of the invention may be formed with added cations or anions between anionic or cationic groups, respectively. These groups may be situated in the peptide moiety, and/or in the side chain of the analogues of the invention.

Non-limiting examples of anionic groups of the derivatives or analogues of the invention include free carboxylic groups in the side chain, if any, as well as in the peptide moiety. The peptide moiety often includes free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivatives or analogues of the invention may e.g. be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivatives or analogues of the invention may e.g. be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terat the C-terminus of the peptide. In a still further embodiment, the derivative or peptide is in the form a pharmaceutically acceptable ester.

The term "pharmaceutical composition" as used herein means a product comprising an active compound, e.g. the glucagon derivative of the invention, or a salt thereof together with pharmaceutical excipients such as buffer, preservative, and optionally a tonicity modifier and/or a stabilizer. Thus a pharmaceutical composition is also known in the art as a pharmaceutical formulation.

In the present context, the term "pharmaceutically acceptable salt" is intended to indicate a salt which is not harmful to the patient. Such salts include pharmaceutically acceptable acid addition salts, pharmaceutically acceptable metal salts, ammonium and alkylated ammonium salts. Acid addition salts include salts of inorganic acids as well as organic acids.

The term "excipient" as used herein means the chemical compounds which are normally added to pharmaceutical compositions, e.g. buffers, tonicity agents, preservatives and the like.

As use herein, the term "therapeutically effective amount" of a compound, e.g. the glucagon derivative of the invention, refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the subject. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition, or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by beta-cell destruction, usually leading to absolute insulin deficiency.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

The term "euglycemia" as used herein means normal concentration of glucose in the blood. This is also referred to as normoglycemia.

The term "obesity" implies an excess of adipose tissue. When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity. In this context, obesity is best viewed as any degree of excess adipose tissue that imparts a health risk. The distinction between normal and obese individuals can only be approximated, but the health risk imparted by obesity is probably a continuum with increasing adipose tissue. However, in the context of the invention, individuals with a body mass index (BMI=body weight in kilograms divided by the square of the height in meters) above 25 are to be regarded as obese.

In the case of administration of a glucagon derivative of the invention, optionally in combination with one or more additional therapeutically active compounds or substances as disclosed above, for a purpose related to treatment or prevention of obesity or overweight, i.e. related to reduction or prevention of excess adiposity, it may be of relevance to employ such administration in combination with surgical intervention for the purpose of achieving weight loss or preventing weight gain, e.g. in combination with bariatric surgical intervention. Examples of frequently used bariatric surgical techniques include, but are not limited to, the following: vertical banded gastroplasty (also known as "stomach stapling"), wherein a part of the stomach is stapled to create a smaller pre-stomach pouch which serves as a new stomach; gastric banding, e.g. using an adjustable gastric band system (such as the Swedish Adjustable Gastric Band (SAGB), the LAP-BAND™ or the MIDband™), wherein a small pre-stomach pouch which is to serve as a new stomach is created using an elastomeric (e.g. silicone) band which can be adjusted in size by the patient; and gastric bypass surgery, e.g. "Roux-en-Y" bypass wherein a small stomach pouch is created using a stapler device and is connected to the distal small intestine, the upper part of the small intestine being reattached in a Y-shaped configuration.

The administration of a glucagon derivative of the invention (optionally in combination with one or more additional therapeutically active compounds or substances as disclosed above) may take place for a period prior to carrying out the bariatric surgical intervention in question and/or for a period of time subsequent thereto. In many cases it may be preferable to begin administration of a compound of the invention after bariatric surgical intervention has taken place.

The compounds of the invention and anti-obesity or anti-diabetic agents, as defined in the present specification, may be administered simultaneously or sequentially. The factors may be supplied in single-dosage form wherein the single-dosage form contains both compounds, or in the form of a kit-of-parts comprising a preparation of a compound of the invention as a first unit dosage form and a preparation of an anti-obesity or anti-diabetic agent as a second unit dosage form. Whenever a first or second or third, etc., unit dose is mentioned throughout this specification this does not indicate the preferred order of administration, but is merely done for convenience purposes.

By "simultaneous" dosing of a preparation of a compound of the invention and a preparation of anti-obesity or anti-diabetic agents is meant administration of the compounds in single-dosage form, or administration of a first agent followed by administration of a second agent with a time separation of no more than 15 minutes, preferably 10, more preferred 5, more preferred 2 minutes. Either factor may be administered first.

By "sequential" dosing is meant administration of a first agent followed by administration of a second agent with a time separation of more than 15 minutes. Either of the two unit dosage form may be administered first. Preferably, both products are injected through the same intravenous access.

As already indicated, in all of the therapeutic methods or indications disclosed above, a compound of the invention may be administered alone. However, it may also be administered in combination with one or more additional therapeutically active agents, substances or compounds, either sequentially or concomitantly.

A typical dosage of a compound of the invention when employed in a method according to the invention is in the range of from about 0.0001 to about 100 mg/kg body weight per day, preferably from about 0.001 to about 10 mg/kg body weight, more preferably from about 0.001 to about 5 mg/kg body weight per day, e.g. from about 0.001 to about 10 mg/kg body weight per day or from about 0.001 to about 5 mg/kg body weight per day administered in one or more doses, such as from 1 to 3 doses. The exact dosage will depend upon the frequency and mode of administration, the sex, age, weight and general condition of the treated subject, the nature and severity of the condition treated, any concomitant diseases to be treated and other factors evident to those skilled in the art.

Compounds of the invention comprise compounds that are believed to be well-suited to administration with longer intervals than, for example, once daily, thus, appropriately formulated compounds of the invention may be suitable for e.g. twice-weekly or once-weekly administration by a suitable route of administration, such as one of the routes disclosed herein.

As described above, compounds of the invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from, or associated with, diabetes.

Preparation of Derivatives of Glucagon Peptides

In one embodiment the invention relates to a process for making a glucagon derivative according the invention. The derivative of the invention may be prepared by the method described below.

SPPS General Methods

The Fmoc-protected amino acid derivatives to be used may be the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH supplied from e.g. Anaspec, Bachem, Iris Biotech, or NovabioChem. Where nothing else is specified the natural L-form of the amino acids are used. The N-terminal amino acid is Boc protected at the alpha amino group (e.g. Boc-His(Boc)-OH, or Boc-His(Trt)-OH for peptides with His at the N-terminus). SPPS may be performed using Fmoc based chemistry on a Prelude Solid Phase Peptide Synthesizer from Protein Technologies (Tucson, Ariz. 85714 U.S.A.). A suitable resin for the preparation of C-terminal peptide amides is H-Rink Amide-ChemMatrix resin (loading e.g. 0.52 nmol/g) or Rink Amide AM polystyrene resin (Novabiochem, loading e.g. 0.62 mmol/g) or the like. Fmoc-deprotection is achieved with 20% piperidine in NMP. Peptide couplings are performed by using either DIC/HOAt/collidine or DIC/Oxyma Pure/collidine without preactivation. Amino acid/HOAt or amino acid/Oxyma Pure solutions (0.3 M/0.3 M in NMP at a molar excess of 3-10 fold) are added to the resin followed by the same molar equivalent of DIC (3 M in NMP) followed by collidine (3 M in NMP). For example, the following amounts of 0.3 M amino acid/HOAt solution can be used per coupling for the following scale reactions: Scale/mL, 0.05 mmol/1.5 mL, 0.10 mmol/3.0 mL, 0.25 mmol/7.5 mL. The Mtt group may be removed by washing the resin with HFIP/DCM (75:25) (2×2 min), washing with DCM and suspending the resin in HFIP/DCM (75:25)(2×20 min) and subsequently washing in sequence with Piperidine/NMP (20:80), DCM(1×), NMP(1×), DCM(1×), NMP(1×).

Attachment of the Substituent

The substituent can be introduced in a stepwise procedure by the Prelude peptide synthesizer as described above using suitably protected building blocks, such as the standard amino acids described above, Fmoc-8-amino-3,6-dioxaoctanoic acid and Fmoc-Glu-OtBu. Introduction of the fatty acid moiety can be achieved using a building block, such as, but not limited to, octadecanedioic acid mono-tert-butylester. After each coupling step, unreacted peptide intermediate can be capped using acetic acid anhydride and collidine in excess (>10 eq.).

The introduction of a substituent on the epsilon-nitrogen of a lysine is achieved using a Lysine protected with Mtt (Fmoc-Lys(Mtt)-OH). The MTT group can be removed using standard procedure such as Alternatively, the epsilon-nitrogen of a lysine could be protected with an ivDde group (Fmoc-Lys(ivDde)-OH). The incorporation of gamma-Glu moieties in the substituent may be achieved by coupling with the amino acid Fmoc-Glu-OtBu.

Introduction of each moiety in the substituent can be achieved using prolonged coupling time (1×6 hours) followed by capping with acetic anhydride or alternatively acetic acid/DIC/HOAt/collidine.

Cleavage from the Resin

After synthesis the resin is washed with DCM, and the peptide is cleaved from the resin by a 2-3 hour treatment with TFA/TIS/water (95/2.5/2.5) followed by precipitation with diethylether. The precipitate is washed with diethylether.

Purification and Quantification

The crude peptide is dissolved in a suitable mixture of water and MeCN, such as water/MeCN (4:1), and purified by reversed-phase preparative HPLC (Waters Deltaprep 4000 or Gilson) on a column containing C18-silica gel. Elution is performed with an increasing gradient of MeCN in water containing 0.1% TFA. Relevant fractions are checked by analytical HPLC or UPLC. Fractions containing the pure target peptide are mixed and concentrated under reduced pressure. The resulting solution is analyzed (HPLC, LCMS) and the product (i.e. the derivative) is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Functional Properties

In a first functional embodiment, the peptides of the invention are able to bind to both the GLP-1 receptor and glucagon receptor with good affinity. In a second functional embodiment, the peptides of the invention preferably are GLP-1 and glucagon receptor agonists as is reflected by their potency on both receptors. Also, in a third functional embodiment, they have improved pharmacokinetic properties. Also, or alternatively, in a fourth functional embodiment, they have good biophysical properties.

In one embodiment the invention provides novel GLP-1/glucagonR co-agonists with an improved receptor potency and/or affinity on the GLP-1 receptor or the glucagon receptor or on both receptors. In another embodiment, the invention provides novel GLP-1/glucagonR co-agonists with improved stability. In another embodiment, the invention provides novel GLP-1/glucagonR co-agonists with improved solubility. In another embodiment, the invention provides novel GLP-1/glucagonR co-agonists with increased half-life.

The potency (i.e. receptor activation) and affinity (i.e. receptor binding) on the glucagon and GLP-1 receptors may be determined according to the assays described in Examples 74-75 herein.

The solubility of the compounds of the invention at different pH values may be measured as described in the Functional Properties section herein.

The physical stability of the compounds of the invention may be measured by the Thioflavin (ThT) fibrillation assay described in Example 76 herein.

The chemical stability of the glucagon derivatives or analogues of the invention may be determined as described in Example 79 herein.

The peptides of the invention also have prolonged in vivo half-life. The half-life of the glucagon derivatives or analogues of the invention may be determined in a pharmacokinetic study in various species, including mice (as described in Example 78 herein), rats and minipigs.

The effect of the glucagon derivatives of the invention on the reduction of body weight may be determined in DIO mice as described in Example 77 herein.

In one embodiment the glucagon derivative of the invention is as selective for glucagon receptor as for GLP-1 receptor.

GLP-1/Glucagon Receptor Co-Agonists

In one embodiment the invention provides novel stable and protracted GLP-1/glucagon receptor co-agonists. A GLP-1/glucagon receptor co-agonist may be defined as a peptide that is able to activate both the GLP-1 and the glucagon receptors.

The derivatives of the invention show an $EC_{50}$ below 1 nM on the GLP-1 receptor and an $EC_{50}$ below 10 nM on the glucagon receptor, or below 100 pM on the GLP-1 receptor and below 100 pM on the glucagon receptor, or below 50 pM on the GLP-1 receptor and below 100 pM on the glucagon receptor, or below 10 pM on the GLP-1 receptor and below 50 pM on the glucagon receptor. As mentioned, the receptor potencies may be determined using the assay described in Example 74 herein.

In one embodiment the glucagon derivative is an agonist of the GLP-1 receptor with an $EC_{50}<100$ pM and an $EC_{50}<1$ nM on the glucagon receptor. In one embodiment the glucagon derivative is an agonist of the GLP-1 receptor with an $EC_{50}<50$ pM and an $EC_{50}<1$ nM on the glucagon receptor. In one embodiment the glucagon derivative is an agonist of the GLP-1 receptor with an $EC_{50}<10$ pM and an $EC_{50}<1$ nM on the glucagon receptor. In one embodiment the glucagon derivative is an agonist of the GLP-1 receptor with an $EC_{50}<50$ pM and an $EC_{50}<100$ pM on the glucagon receptor. In one embodiment the glucagon derivative is an agonist of the GLP-1 receptor with an $EC_{50}<10$ pM and an $EC_{50}<100$ pM on the glucagon receptor. In one embodiment the glucagon derivative is an agonist of the GLP-1 receptor with an $EC_{50}<10$ pM and an $EC_{50}<50$ pM on the glucagon receptor. In one embodiment the glucagon derivative is an agonist of the GLP-1 receptor with an $EC_{50}<1$ pM and an $EC_{50}<50$ pM on the glucagon receptor. In one embodiment the glucagon derivative is an agonist of the GLP-1 receptor with an $EC_{50}<10$ pM and an $EC_{50}<10$ pM on the glucagon receptor. In one embodiment the glucagon derivative is a GLP-1/glucagon co-agonist with an $EC_{50}$ on the GLP-1 receptor<the $EC_{50}$ on the glucagon receptor. In one embodiment the glucagon derivative is a GLP-1/glucagon co-agonist with an $EC_{50}$ on the GLP-1 receptor (e.g. in pM) greater than the $EC_{50}$ on the glucagon receptor (e.g. in pM).

Glucagon Receptor Agonist

A receptor agonist may be defined as a peptide that binds to a receptor and elicits a response typical of the natural ligand. The term "glucagon agonist" as used herein refers to any glucagon derivative which binds to and fully or partially activates the human glucagon receptor. In one embodiment, the "glucagon agonist" is any glucagon derivative that activates the glucagon receptor, with a potency ($EC_{50}$) below 10 nM or below 1 nM or 100 pM or below 10 pM, as measured by the assay described in Example 74 herein.

In one embodiment the glucagon derivative is an agonist of the glucagon receptor. In one embodiment the glucagon derivative is an agonist of the glucagon receptor, with an $EC_{50}<10$ nM. In one embodiment the glucagon derivative is an agonist of the glucagon receptor, with an $EC_{50}<1$ nM. In one embodiment the glucagon derivative is an agonist of the glucagon receptor, with an $EC_{50}<100$ pM. In one embodiment the glucagon derivative is an agonist of the glucagon receptor, with an $EC_{50}<10$ pM. The potency, i.e. $EC_{50}$, of the glucagon derivative on the glucagon receptor may be determined by the assay described in Example 74 herein.

GLP-1 Receptor Agonist

A receptor agonist may be defined as a peptide that binds to a receptor and elicits a response typical of the natural ligand. Thus, for example, a "GLP-1 receptor agonist" or "GLP-1 receptor agonist peptide" may be defined as a compound which is capable of binding to the GLP-1 receptor and capable of activating it.

The co-agonist peptides of the invention have GLP-1 activity. This term refers to the ability to bind to the GLP-1 receptor and initiate a signal transduction pathway resulting in insulinotropic action or other physiological effects as is known in the art. The derivatives of the invention shows an $EC_{50}$ below 1 nM or below 100 pM or below 50 pM or below 10 pM using the assay described in Example 74 herein.

In one embodiment the glucagon derivative is an agonist of the GLP-1 receptor. In one embodiment the glucagon derivative is an agonist of the GLP-1 receptor, with an $EC_{50}<100$ pM. In one embodiment the glucagon derivative is an agonist of the GLP-1 receptor, with an $EC_{50}<50$ pM. In one embodiment the glucagon derivative is an agonist of the GLP-1 receptor, with an $EC_{50}<10$ pM. The potency, i.e. $EC_{50}$, of the glucagon derivative on the GLP-1 receptor may be determined by the assay described in Example 74 herein.

Biological Activity—In Vitro Affinity and Potency

In one embodiment affinity refers to in vitro binding affinity, i.e. performance in a GLP-1 receptor binding affinity assay and in a glucagon receptor binding affinity assay, more in particular to the capability of binding the human GLP-1 receptor and to the human glucagon receptor. The binding affinity of the human GLP-1 receptor may be measured in a binding assay, e.g. in a stably transfected BHK cell line that expresses the human GLP-1 receptor. Radioactively labelled GLP-1 binds to the receptor and may be displaced competitively by a compound. Binding of radioligand may be determined in the presence of scintillation proximity assay (SPA) beads which bind to cell membranes and when radioactivity is close to the bead it produces light which is measured and is a measure of the in vitro binding affinity. One non-limiting example of such an assay is described in Example 75 herein. The binding affinity of the human glucagon receptor may be measured in a binding affinity assay, e.g. in a stably transfected BHK cell line that expresses the human glucagon receptor. Radioactively-labelled glucagon binds to the receptor and may be displaced competively by a compound. Binding of radioligand may be determined in the presence of scintillation proximity assay (SPA) beads which bind to cell membranes and when radioactivity is close to the bead it produces light which is measured and is a measure of the in vitro binding affinity.

The term half maximal inhibitory concentration ($IC_{50}$) generally refers to the concentration of competing compound which displaces 50% of the specific binding of the radioligand binding corresponding to halfway between the baseline and maximum, by reference to the dose response curve. $IC_{50}$ is used as a measure of the binding affinity of a compound and represents the concentration where 50% of its maximal binding is observed.

The in vitro binding of the peptides of the invention may be determined as described above, and the $IC_{50}$ of the peptide in question determined. The lower the $IC_{50}$ value, the better the binding affinity.

The affinity, i.e. $IC_{50}$, of the glucagon derivative on the GLP-1 receptor may be determined by the assay described in Example 75 herein. In another embodiment, the peptide of the invention has an in vitro binding affinity on the GLP-1 receptor determined using the method of Example 75 herein corresponding to an $IC_{50}$ at or below 100 nM, more preferably below 10 nM, even more preferably below 5 nM, or most preferably below 1 nM.

The affinity, i.e. $IC_{50}$, of the glucagon derivative on the glucagon receptor may be determined by the assay described in Example 75 herein. In another embodiment, the peptide of the invention has an in vitro binding affinity on the glucagon receptor determined using the method of Example 75 herein corresponding to an $IC_{50}$ at or below 100 nM, or below 50 nM or below 10 nM In one embodiment potency refers to in vitro potency, i.e. performance in a functional GLP-1 receptor assay and glucagon receptor assay, more in particular to the capability of activating the human GLP-1 receptor and the human glucagon receptor. The response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase expression may be determined by adding luciferin, which by the enzyme is converted to oxyluciferin and produces bioluminescence, which is measured and is a measure of the in vitro potency. One non-limiting example of such an assay is described in Example 74 herein. The response of the human glucagon receptor may be measured in a reporter gene assay, e.g. in a stably transfected BHK cell line that expresses the human glucagon receptor and contains the DNA for the cAMP response element (CRE) coupled to a promoter and the gene for firefly luciferase (CRE luciferase). When cAMP is produced as a result of activation of the glucagon receptor this in turn results in the luciferase being expressed. Luciferase expression may be determined by adding luciferin, which by the enzyme is converted to oxyluciferin and produces bioluminescence, which is measured and is a measure of the in vitro potency. One non-limiting example of such an assay is described in Example 74 herein.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the peptides of the invention may be determined as described above, and the $EC_{50}$ of the peptide in question determined. The lower the $EC_{50}$ value, the better the potency.

Biological Activity—In Vivo Pharmacology

In another embodiment the derivatives or peptides of the invention (or analogues thereof), are potent in vivo, which may be determined as is known in the art in any suitable animal model, as well as in clinical trials.

The diet-induced obese (DIO) mouse is one example of a suitable animal model and the effect on body weight, food intake and glucose tolerance can be assessed during subchronic dosing in this model. Effect on body weight and blood glucose may be determined in such mice in vivo, e.g. as described in Example 77 herein. Food intake can be assessed by single housing animals and weighing food consumed per day. This model can also be used to evaluate effects on glucose tolerance by performing an oral or i.p. glucose tolerance test (OGTT or IPGTT). These tests are performed by administration of a glucose load orally or i.p. to semi-fasted animals and subsequent blood glucose measure for up to three hours.

Pharmacokinetics Profile

According to the third functional embodiment, the peptides of the invention have improved pharmacokinetic properties such as increased terminal half-life.

The pharmacokinetic properties of the peptides of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the peptides of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $T_{1/2}=\ln(2)/\lambda_z$ (see e.g. Johan Gabrielsson and Daniel Weiner: Pharmacokinetics and Pharmacodynamic Data Analysis. Concepts & Applications, 3rd Ed., Swedish Pharmaceutical Press, Stockholm, 2000).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Pharmacokinetics Profile—Half Life In Vivo in Rats

According to the third functional embodiment, the peptides of the invention have improved pharmacokinetic properties compared to hGLP-1 or hglucagon. Preferably the peptides of the invention have pharmacokinetic properties suitable for once daily administration or less.

In one embodiment the pharmacokinetic properties may be determined as terminal half-life ($T_{1/2}$) in vivo in rats after i.v. and s.c. administration. In additional embodiments, the terminal half-life is at least 1 hour, preferably at least 3 hours, preferably at least 4 hours, even more preferably at least 5 hours, or most preferably at least 6 hours.

Pharmacokinetics Profile—Half Life In Vivo in Mice

According to the third functional embodiment, the peptides of the invention have improved pharmacokinetic properties compared to hGLP-1 or hglucagon. Preferably the peptides of the invention have pharmacokinetic properties suitable for once daily administration or less.

In one embodiment the pharmacokinetic properties may be determined as terminal half-life ($T_{1/2}$) in vivo in mice after i.v. and s.c. administration. In additional embodiments, the terminal half-life is at least 1 hour, preferably at least 3 hours, preferably at least 4 hours, even more preferably at least 5 hours, or most preferably at least 6 hours. A suitable assay for determining terminal half-life in mice after s.c. administration is disclosed in Example 78 herein.

Pharmacokinetics Profile—Half Life In Vivo in Minipigs

According to the third functional embodiment, the peptides of the invention have improved pharmacokinetic properties compared to hGLP-1 (i.e. human GLP-1) or hglucagon (i.e. human glucagon) and preferably suitable for once daily or once weekly administration. In one embodiment the pharmacokinetic properties may be determined as terminal half-life ($T_{1/2}$) in vivo in minipigs after i.v. administration, e.g. as described below.

In one embodiments, the terminal half-life in minipigs is at least 5 hours, preferably at least 10 hours, even more preferably at least 15 hours, or most preferably at least 20 hours.

The half-life in vivo in minipigs of the glucagon derivative may be determined according to the following method:

The purpose of this study is to determine the pharmacokinetic properties in vivo of the glucagon derivatives after i.v. administration to minipigs. This is done in a pharmacokinetic (PK) study, where among other parameters the terminal half-life and the clearance of the derivative in question is determined. Increasing the terminal half-life and decreasing the clearance means that the compound of study is eliminated slower from the body. For glucagon derivatives or analogues this entails an extended duration of pharmacological effect.

Female Göttingen minipigs are obtained from Ellegaard Göttingen Minipigs (Dalmose, Denmark) approximately 7-14 months of age and weighing from approximately 16-35 kg are used in the studies. The minipigs are housed either individually (pigs with permanent catheters) or in a group, and are fed restrictedly once or twice daily with SDS minipig diet (Special Diets Services, Essex, UK).

In some studies two permanent central venous catheters are implanted in vena cava caudalis or cranialis in each animal after at least 2 weeks of acclimatiation. The animals are allowed 1 week recovery after the surgery, and are then used for repeated pharmacokinetic studies with a suitable wash-out period between successive glucagon derivative dosings. In other studies the animals are acclimatized for 1 week, after which they are used for repeated pharmacokinetic studies with a suitable wash-out period between successive glucagon derivative dosings. On each dosing occasion these pigs are instrumented with a venflon in one ear vein through which the derivatives were dosed. Blood sampling are performed by venipuncture in v. jugularis or v. cava cranialis The animals are either unfasted or fasted for approximately 18 h before dosing and from 0 to 4 h after dosing, but have ad libitum access to water during the whole period.

The glucagon derivatives are usually dissolved in 50 mM sodium phosphate, 145 mM sodium chloride, 0.05% TWEEN® 80 (nonionic surfactant), pH 7.4 to a concentration of usually from 20-60 nmol/ml. Intravenous injections (the volume corresponding to usually 2-3 nmol/kg, for example 0.1 ml/kg) of the compounds are given through one catheter or through the venflon, and blood are sampled at predefined time points for up till 13 days post dosing (preferably through the other catheter or by venipuncture). Blood samples (for example 0.8 ml) are collected in tubes with EDTA buffer (8 mM) (sometimes aprotinin 500 KIU/ml blood was added) and then centrifuged at 4° C. and 1942 G for 10 minutes. Plasma is pippetted into Micronic tubes on dry ice, and kept at −20° C. until analyzed for plasma concentration of the respective glucagon derivative using an appropriate quantitative assay like ELISA or LC-MS.

Based on these measurements, time-plasma concentration profiles for the compound of study are plotted and a so-called non-compartmental pharmacokinetic analysis of the data is performed in WinNonlin v. 5.0 or Phoenix v. 6.2 (Pharsight Inc., Mountain View, Calif., USA) or other relevant software for PK analysis. For most compounds, the terminal part of the plasma-concentration profiles will be linear when drawn in a semi-logarithmic plot, reflecting that after the initial distribution, drug is removed from the body at a constant fractional rate. The rate (lambda Z or λz) is equal to minus the slope of the terminal part of the plot. From this rate, also the terminal half-life may be calculated, as T½=ln(2)/λz (see e.g. Johan Gabrielsson and Daniel Weiner: Pharmacokinetics and Pharmacodynamic Data Analysis. Concepts & Applications, 3rd Ed., Swedish Pharmaceutical Press, Stockholm (2000)). Clearance is defined as the dose (D) divided by area under the curve (AUC) on the plasmaconcentration versus time profile (Rowland, M and Tozer T N: Clinical Pharmacokinetics: Concepts and Applications, 3rd edition, 1995 Williams Wilkins).

Physicochemical Properties

According to the fourth embodiment, the peptides of the invention have advantageous physicochemical properties. These properties include but are not limited to physical stability, chemical stability and/or solubility. These and other physicochemical properties may be measured using standard methods known in the art of protein chemistry. In one embodiment these properties are improved as compared to native glucagon (SEQ ID NO:1). More pronounced self-association of the peptides self-association properties of the peptides may be at least partly responsible for the improved physical stability and/or solubility.

Non-limiting examples of assays to investigate biophysical properties are described in Example 76 and Example 79 herein.

In one embodiment the glucagon derivative of the invention has more than 70% recovery in the ThT fibrillation assay. In one embodiment the glucagon derivative of the invention has more than 90% recovery in the ThT fibrillation assay. In one embodiment the glucagon derivative of the invention has about 100% recovery in the ThT fibrillation assay. In one embodiment the glucagon derivative of the invention has more than 7 hours lag time in the ThT fibrillation assay. In one embodiment the glucagon derivative of the invention has more than 20 hours lag time in the ThT fibrillation assay. In one embodiment the glucagon derivative of the invention has 45 hours lag time or more in the ThT fibrillation assay. A glucagon derivative as described herein, wherein said ThT fibrillation assay is as described in Example 76 herein.

In one embodiment the glucagon derivative of the invention has less than 14% degradation in the chemical stability assay. In one embodiment the glucagon derivative of the invention has less than 13% degradation in the chemical stability assay. In one embodiment the glucagon derivative of the invention has less than 12% degradation in the chemical stability assay. In one embodiment the glucagon derivative of the invention has less than 10% degradation in the chemical stability assay. In one embodiment the glucagon derivative of the invention has less than 9% degradation in the chemical stability assay. In one embodiment the glucagon derivative of the invention has less than 7% degradation in the chemical stability assay. In one embodiment the glucagon derivative of the invention has less than 5% degradation in the chemical stability assay. In one embodiment the glucagon derivative of the invention has less than 3% degradation in the chemical stability assay. In one embodiment the glucagon derivative of the invention has less than 2% degradation in the chemical stability assay. In one embodiment the chemical stability assay is as described in Example 79 herein.

Stability

The term "physical stability" of the GLP-1 receptor agonist peptide preparation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein preparations is evaluated by means of visual inspection and/or turbidity measurements after exposing the preparation filled in suitable containers (e.g. cartridges or vials) to mechanical/physical stress (e.g. agitation) at different temperatures for various time periods. Visual inspection of the preparations is performed in a sharp focused light with a dark background. The turbidity of the preparation is characterized by a visual score ranking the degree of turbidity for instance on a scale from 0 to 3 (a preparation showing no turbidity corresponds to a visual score 0, and a preparation showing visual turbidity in daylight corresponds to visual score 3). A preparation is classified physically unstable with respect to protein aggregation, when it shows visual turbidity in daylight. Alternatively, the turbidity of the preparation can be evaluated by simple turbidity measurements well-known to the skilled person. Physical stability of the aqueous protein preparations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

The term "chemical stability" of the protein preparation as used herein refers to changes in the covalent protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Increasing amounts of chemical degradation products is often seen during storage and use of the protein preparation. Most proteins are prone to deamidation, a process in which the side chain amide group in glutaminyl or asparaginyl residues is hydrolysed to form a free carboxylic acid or asparaginyl residues to form an IsoAsp derivative. Other degradations pathways involves formation of high molecular weight products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein preparation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC). Since HMWP products are potentially immunogenic and not biologically active, low levels of HMWP are advantageous.

The term "stabilized preparation" refers to a preparation with increased physical stability, increased chemical stability or increased physical and chemical stability. In general, a preparation must be stable during use and storage (in compliance with recommended use and storage conditions) until the expiration date is reached.

Solubility

In the present context, if not stated otherwise, the terms "soluble", "solubility", "soluble in aqueous solution", "aqueous solubility", "water soluble", "water-soluble", "water solubility" and "water-solubility", refer to the solubility of a compound in water or in an aqueous salt or aqueous buffer solution, for example a 10 mM phosphate solution, or in an aqueous solution containing other compounds. Solubility may be assessed using the following assay.

pH Dependent Solubility Assay

The solubility of peptides and proteins depends on the pH of the solution. Often a protein or peptide precipitates at or close to its isoelectric point (pI), at which its net charge is zero. At low pH (i.e. lower than the pI) proteins and peptides are typically positively charged, at pH higher than the pI they are negatively charged.

It is advantageous for a therapeutic peptide if it is soluble in a sufficient concentration at a given pH, which is suitable for both formulating a stable drug product and for administrating the drug product to the patient e.g. by subcutaneous injection.

Solubility versus pH curves are measured as described: a formulation or a peptide solution in water is prepared and aliquots are adjusted to pH values in the desired range by adding HCl and NaOH. These samples are left equilibrating at room temperature for 2-4 days. Then the samples are centrifuged. A small aliquot of each sample is withdrawn for reverse HPLC analysis for determination of the concentration of the proteins in solution. The pH of each sample is measured after the centrifugation, and the concentration of each protein is depicted versus the measured pH.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The compounds of the invention may be a soluble glucagon/GLP-1 receptor co-agonist, for example with solubility of at least 0.1 mmol/l, 0.2 mmol/l, at least 0.5 mmol/l, at least 2 mmol/l, at least 4 mmol/l, at least 8 mmol/l, at least 10 mmol/l, or at least 15 mmol/l.

DPP-IV Stability

In one embodiment the glucagon derivative of the invention is DPP-IV protected. The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. glucagon, GLP-1, GLP-2, oxyntomodulin etc. Thus, a considerable effort is being made to develop analogues and derivatives of the polypeptides susceptible to DPP-IV mediated hydrolysis in order to reduce the rate of degradation by DPP-IV. In one embodiment the glucagon derivative is a DPPIV protected compound. In one embodiment the glucagon derivative is DPPIV stabilised.

In one embodiment the compounds of the invention may be stabilized against DPP-IV cleavage in an albumin free assay:

10 μM of peptide is incubated with DPP-IV (2 μg/ml) in duplicate at 37° C. in a HEPES buffer to which 0.005% TWEEN® 20 (nonionic surfactant) is added. In the experiment human GLP-1 is used as a positive control. Aliqouts of sample are taken at 3, 15, 30, 60, 120 and 240 min and three volumes of ethanol are added to stop the reaction. The samples are analysed by LC-MS for parent peptide. Data are plotted according to $1^{st}$ kinetics and the stability is reported as half-lives.

Combinations

In one embodiment the invention relates to the glucagon derivative as described herein in combination with a GLP-1 compound or with an insulin compound. In one embodiment the invention relates to the glucagon derivative as described herein in combination with a GLP-1 compound. In one embodiment the invention relates to the glucagon derivative as described herein in combination with an insulin compound.

In one embodiment the GLP-1 compound of the combination is N-epsilon26-((S)-4-Carboxy-4-hexadecanoylamino-butyryl)[Arg34]GLP-1-(7-37):

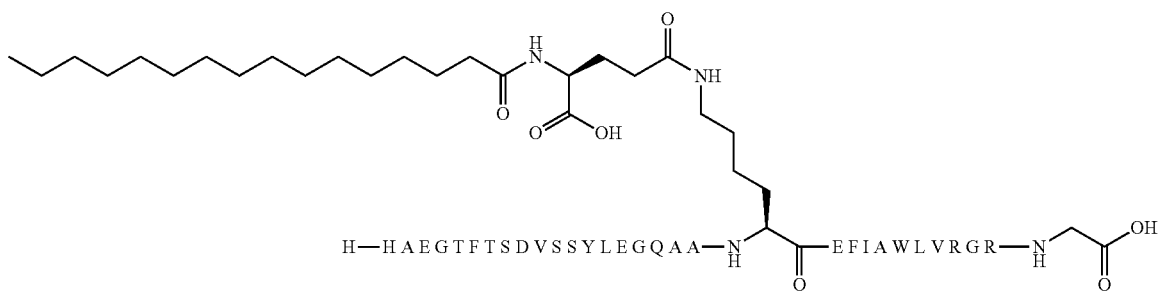

(Compound G1); or a pharmaceutically acceptable salt, amide, alkyl, or ester thereof. In one embodiment the GLP-1 compound of the combination is N-epsilon37-[2-(2-{2-[2-(2-{2-[(S)-4-Carboxy-4-({trans-4-[(19-carboxynonadecanoylamino) methyl]cyclohexanecarbonyl}amino)butyrylamino]ethoxy}ethoxy)acetylamino]ethoxy}ethoxy) acetyl][DesaminoHis7,Glu22,Arg26,Arg34,Lys37]GLP-1-(7-37):

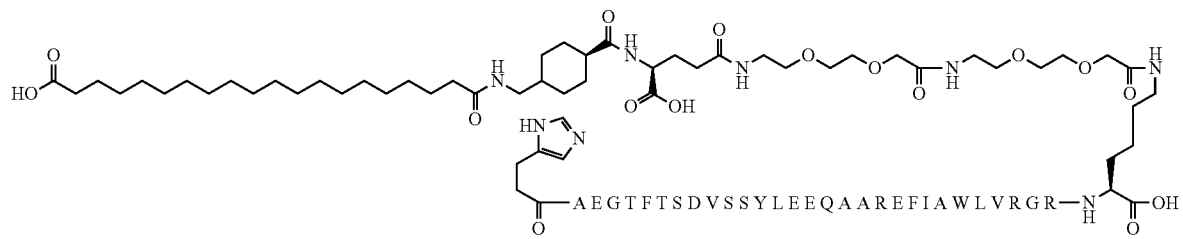

(Compound G2); or a pharmaceutically acceptable salt, amide, alkyl, or ester thereof. In one embodiment the GLP-1 compound of the combination is N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy) acetyl][Aib8,Arg34]GLP-1-(7-37):

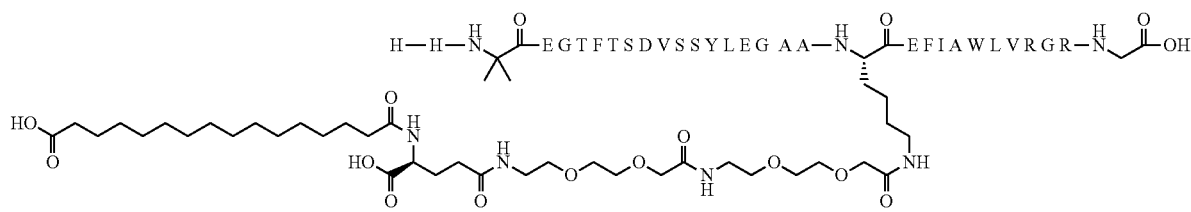

(Compound G3); or a pharmaceutically acceptable salt, amide, alkyl, or ester thereof. In one embodiment the GLP-1 compound of the combination is N-epsilon-37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl][Aib8,22,35,Lys37]GLP-1-(7-37):

about 0.5 mg to about 5 mg, e.g. from about 0.5 mg to about 200 mg, of a glucagon derivative as described herein. In one embodiment the invention relates to a pharmaceutical composition comprising a derivative of the invention, wherein said derivative is present in a concentration from about 0.01 mg/mL to about 25 mg/mL, such as from about 0.05 mg/mL

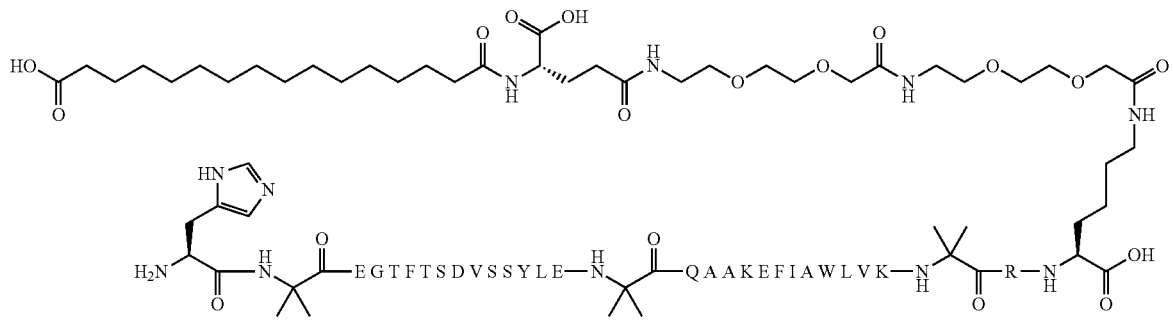

(Compound G4); or a pharmaceutically acceptable salt, amide, alkyl, or ester thereof.

In one embodiment the insulin compound of the combination is N-epsilon-B29-[(S)-4-Carboxy-4-(15-carboxypentadecanoylamino)butyryl]desB30 human insulin to about 5 mg/mL and from about 0.1 mg/mL to about 2 mg/mL, and wherein said composition has a pH from 2.0 to 10.0. The pharmaceutical composition may comprise a derivative of the invention, wherein said derivative is present in a concentration from about 0.01 mg/mL to about 50

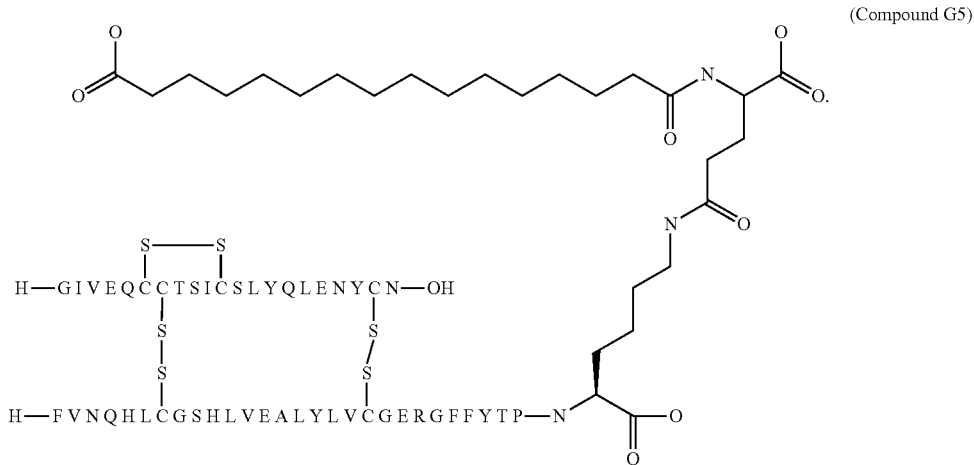

(Compound G5)

Pharmaceutical Compositions

In one embodiment the invention relates to a pharmaceutical composition comprising the derivative of the invention and one or more pharmaceutically acceptable excipients. In one embodiment the composition is suited for parenteral administration, such as SC, IM or IV administration. The terms "pharmaceutical composition" and "composition" are used interchangeably herein.

Pharmaceutical compositions containing a derivative of the invention may be prepared by conventional techniques, e.g. as described in Remington's Pharmaceutical Sciences, 1985 or in Remington: The Science and Practice of Pharmacy, 19th edition, 1995.

In one embodiment the pharmaceutical composition in unit dosage form comprises from about 0.01 mg to about 1000 mg, such as from about 0.1 mg to about 500 mg, from mg/mL, and wherein said composition has a pH from 2.0 to 10.0.

In one embodiment the pharmaceutical composition comprises an aqueous solution of a derivative of the invention, and a buffer, wherein said derivative is present in a concentration from 0.01 mg/mL or above, and wherein said composition has a pH from about 2.0 to about 10.0. In another embodiment the pharmaceutical composition comprises an aqueous solution of a derivative of the invention, and a buffer, wherein said derivative is present in a concentration from 0.01 mg/mL or above, and wherein said composition has a pH from about 6.5 to about 8.5.

In one embodiment the composition of the invention has a pH from about 2.0 to about 10.0. In another embodiment the composition has a pH from about 6.5 to about 8.5. In a further embodiment the composition has a pH from about 7.0 to about 8.5, such as from about 7.2 to about 8.2.

The composition may further comprise a buffer system, preservative(s), isotonicity agent(s), chelating agent(s), stabilizers and surfactants. In one embodiment the pharmaceutical composition is an aqueous composition, i.e. a composition comprising water. Such composition is typically a solution or a suspension. In a further embodiment of the invention the pharmaceutical composition is an aqueous solution. The term "aqueous composition" is defined as a composition comprising at least 50% w/w water. Likewise, the term "aqueous solution" is defined as a solution comprising at least 50% w/w water. In one embodiment the composition comprises a non-aqeuous organic solvent.

In another embodiment the pharmaceutical composition is a freeze-dried composition to which solvents and/or diluents are added prior to use, e.g. by the physician or the patient.

In another embodiment the pharmaceutical composition is a dried composition (e.g. freeze-dried or spray-dried) ready for use without any prior dissolution.

In one embodiment the invention relates to a composition comprising the derivative of the invention and one or more other active ingredients, such as GLP-1, insulin or analogues and/or derivatives thereof. In one embodiment the invention relates to a composition comprising the derivative of the invention and GLP-1 or analogues and/or derivatives thereof. In one embodiment the invention relates to a composition comprising the derivative of the invention and insulin or analogues and/or derivatives thereof. A composition comprising the derivative of the invention and one or more other active ingredients may be referred to as a "co-formulation". In one embodiment such co-formulations are physically stable and/or chemically stable compositions.

The fact that the derivatives of the invention may be soluble at neutral pH, may allow a co-formulation with insulin and allow for more stable blood glucose levels and a reduced number of hypoglycaemic episodes, as well as a reduced risk of diabetes related complications.

In one embodiment the pharmaceutical composition further comprises one or more additional therapeutically active compounds or substances. In one embodiment the additional therapeutically active compound is a GLP-1 compound or an insulin compound. In one embodiment the additional therapeutically active compound is a GLP-1 compound. In one embodiment the additional therapeutically active compound is an insulin compound. In one embodiment the additional therapeutically active compound is the GLP-1 compound N-epsilon26-((S)-4-Carboxy-4-hexadecanoylamino-butyryl)[Arg34]GLP-1-(7-37):

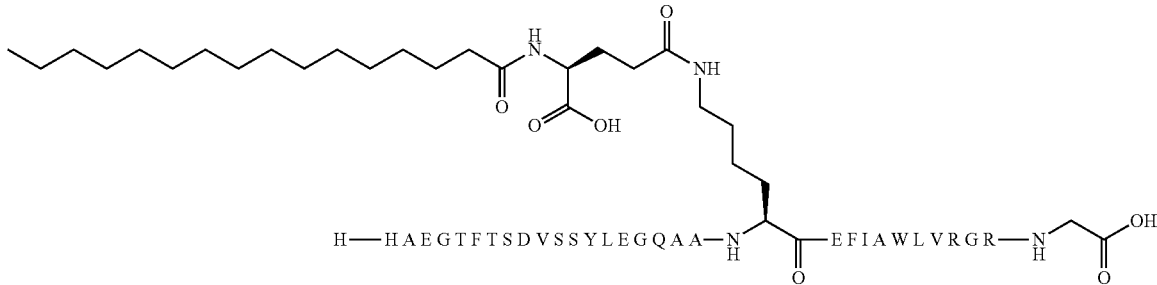

(Compound G1); or a pharmaceutically acceptable salt, amide, alkyl, or ester thereof. In one embodiment the additional therapeutically active compound is the GLP-1 compound N-epsilon37-[2-(2-{2-[2-(2-{2-[(S)-4-Carboxy-4-({trans-4-[(19-carboxynonadecanoylamino)methyl] cyclohexanecarbonyl}amino)butyrylamino]ethoxy}ethoxy) acetylamino]ethoxy}ethoxy)acetyl][DesaminoHis7,Glu22, Arg26,Arg34,Lys37]GLP-1-(7-37):

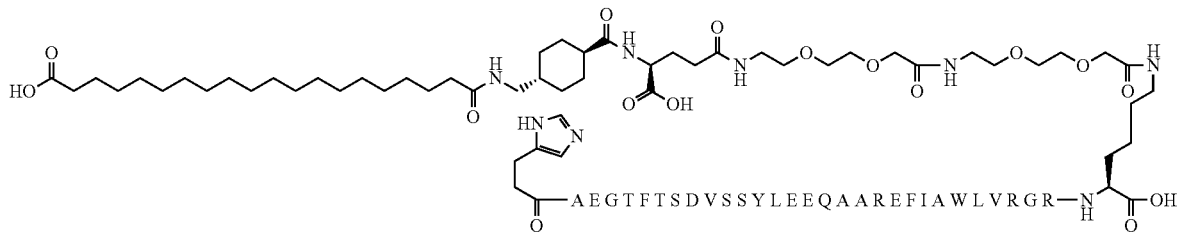

(Compound G2); or a pharmaceutically acceptable salt, amide, alkyl, or ester thereof. In one embodiment the additional therapeutically active compound is the GLP-1 compound N-epsilon26-[2-(2-{2-[2-(2-{2-[(S)-4-Carboxy-4-(17-carboxyheptadecanoylamino)butyrylamino] ethoxy}ethoxy)acetylamino]ethoxy}ethoxy)acetyl][Aib8, Arg34]GLP-1-(7-37):

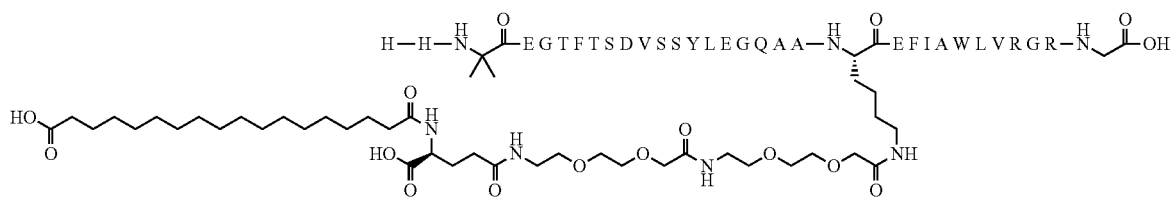

(Compound G3); or a pharmaceutically acceptable salt, amide, alkyl, or ester thereof. In one embodiment the additional therapeutically active compound is the GLP-1 compound N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

Pharmaceutical Administration

The derivative of the invention may be administered parenterally to a patient. The route of administration of the derivative may be intramuscular (IM), subcutaneous (SC), or intravenous (IV). It is recommended that the dosage of the

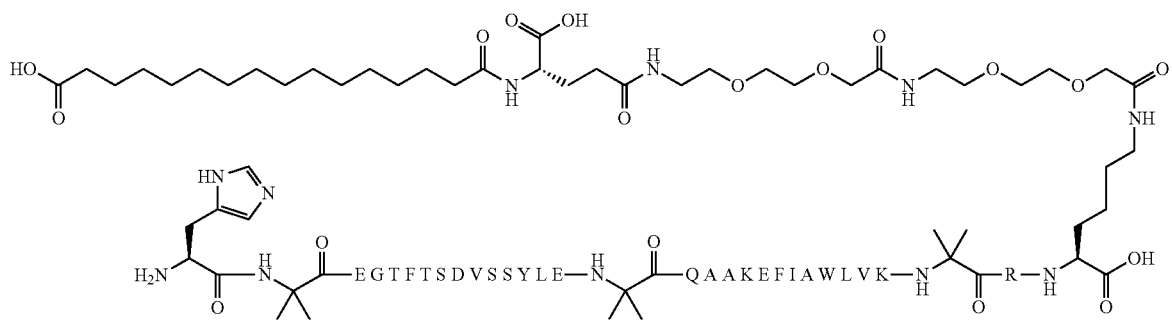

(Compound G4); or a pharmaceutically acceptable salt, amide, alkyl, or ester thereof.

In one embodiment the additional therapeutically active compound is the insulin compound N-epsilon-B29-[(S)-4-Carboxy-4-(15-carboxypentadecanoylamino)butyryl] desB30 human insulin compositions comprising the derivative of this invention which is to be administered to the patient be selected by a physician.

Parenteral administration may be performed by subcutaneous, intramuscular, intraperitoneal or intravenous injection by means of a syringe, optionally a pen-like syringe. In (Compound G5)

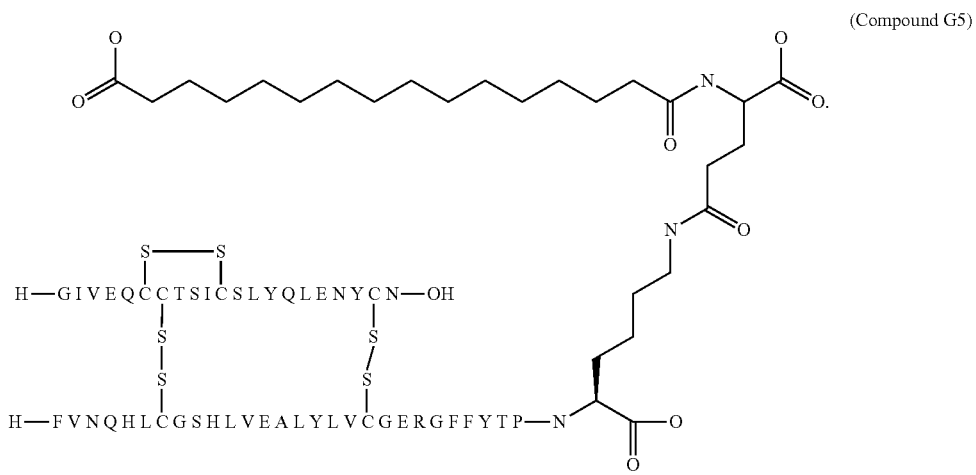

In one embodiment the additional therapeutically active compound is a pharmaceutically acceptable salt, amide, alkyl, or ester of Compound G5.

one embodiment the compositions comprising the derivative of the invention can be used in ready to use pen devices for glucagon administration. Alternatively, parenteral administration can be performed by means of an infusion pump. In one embodiment the compositions comprising the derivative of the invention can be used in pumps for glucagon administration. Parenteral administration may be nasal administration. As a further option, the glucagon preparations containing the derivative of the invention can also be adapted to transdermal administration, e.g. by needle-free injection or from a patch, optionally an iontophoretic patch, or transmucosal, e.g. buccal, administration.

A typical dosage of a derivative or composition of the invention when employed in a method according to the invention is in the range of from about 0.0001 to about 1 mg/kg body weight per day, preferably from about 0.001 to about 1 mg/kg body weight, more preferably from about 0.005 to about 0.02 mg/kg body. As described above, derivatives of the invention may be administered or applied in combination with one or more additional therapeutically active compounds or substances, and suitable additional compounds or substances may be selected, for example, from antidiabetic agents, antihyperlipidemic agents, antiobesity agents, antihypertensive agents and agents for the treatment of complications resulting from, or associated with, diabetes.

Suitable antidiabetic agents include insulin, insulin derivatives or analogues, GLP-1 (glucagon like peptide-1) derivatives or analogues [such as those disclosed in WO 98/08871 (Novo Nordisk A/S), or other GLP-1 analogues such as exenatide (Byetta, Eli Lilly/Amylin; AVE0010, Sanofi-Aventis), taspoglutide (Roche), albiglutide (Syncria, GlaxoSmithKline)], amylin, amylin analogues (e.g. Symlin/Pramlintide) as well as orally active hypoglycemic agents.

Pharmaceutical Indications

The invention also relates to a derivative of the invention, for use in medicine. In one embodiment the invention relates to the glucagon derivative, optionally in combination with one or more additional therapeutically active compounds, for use in therapy. In one embodiment the terms "glucagon derivative" and "derivative" are used interchangeably herein in connection with a medical use and refers to the glucagon derivative of the invention. In one embodiment the terms "medicine" and "therapy" are used interchangeably herein. In one embodiment the invention relates to a method of treatment or prevention of a disease or disorder, e.g. one or more of the diseases or disorders mentioned herein in relation to specific medical uses. In one embodiment the invention relates to a method for the preparation of a medicament for use in therapy, e.g. in the specific medical uses defined herein.

In one embodiment the invention relates to a glucagon derivative of the invention, optionally in combination with one or more additional therapeutically active compounds, for use in medicine.

In one embodiment the derivative is used for treating and/or preventing hypoglycemia. In one embodiment the invention relates to a method for treating and/or preventing hypoglycemia comprising administering a therapeutically effective amount of the derivative of the invention to a patient in need thereof.

In one embodiment the invention relates to the glucagon derivative for use in treating or preventing type 2 diabetes. In one embodiment the glucagon derivative of the invention is for use in treating impaired glucose tolerance. In one embodiment the invention relates to the glucagon derivative for use in delaying or preventing disease progression in type 2 diabetes. In one embodiment the invention relates to a glucagon derivative of the invention, optionally in combination with one or more additional therapeutically active compounds, for use in delaying the progression from type 2 diabetes to insulin-requiring diabetes, for use regulating appetite, for use in preventing weight regain after successful weight loss, for use in inducing satiety, for use in preventing weight regain after successful weight loss, for use in treating a disease or state related to overweight or obesity. In one embodiment the invention relates to the glucagon derivative for use in delaying the progression from impaired glucose tolerance (IGT) to type 2 diabetes. In one embodiment the invention relates to the glucagon derivative for use in delaying the progression from type 2 diabetes to insulin-requiring diabetes.

In one embodiment the invention relates to a method for treating or preventing hypoglycemia, type 2 diabetes, impaired glucose tolerance, type 1 diabetes and obesity, comprising administering to a patient in need thereof, an effective amount of a glucagon derivative according to the invention, optionally in combination with one or more additional therapeutically active compounds. In one embodiment the invention relates to the glucagon derivative for use in treating or preventing hypoglycemia, type 2 diabetes, impaired glucose tolerance, type 1 diabetes and obesity.

In one embodiment the invention relates to the glucagon derivative for use in treating obesity or preventing overweight. In one embodiment the invention relates to a method for treating obesity or preventing overweight, comprising administering to a patient in need thereof, an effective amount of a glucagon derivative according to the invention, optionally in combination with one or more additional therapeutically active compounds.

In one embodiment the invention relates to a method for use in reducing body weight, for use in regulating appetite, for use in increasing energy expenditure, for use in inducing satiety, for use in preventing weight regain after successful weight loss, for use in treating a disease or state related to overweight or obesity, comprising administering to a patient in need thereof, an effective amount of a glucagon derivative according to the invention, optionally in combination with one or more additional therapeutically active compounds. In one embodiment the invention relates to the glucagon derivative for use in decreasing food intake. In one embodiment the invention relates to the glucagon derivative for use in increasing energy expenditure. In one embodiment the invention relates to the glucagon derivative for use in reducing body weight. In one embodiment the invention relates to the glucagon derivative for use in regulating appetite. In one embodiment the invention relates to the glucagon derivative for use in inducing satiety. In one embodiment the invention relates to the glucagon derivative for use in preventing weight regain after successful weight loss. In one embodiment the invention relates to the glucagon derivative for use in treating a disease or state related to overweight or obesity. In one embodiment the invention relates to the glucagon derivative for use in treating bulimia. In one embodiment the invention relates to the glucagon derivative for use in treating binge-eating.

In one embodiment the invention relates to use of a glucagon derivative according to the invention, for the preparation of a medicament.

In one embodiment the invention relates to use of a glucagon derivative according to the invention, for the preparation of a medicament for the treatment or prevention of hyperglycemia, type 2 diabetes, impaired glucose tolerance, type 1 diabetes and obesity. In one embodiment the glucagon derivative of the invention is for use in the treatment or prevention of hyperglycemia, type 2 diabetes, impaired glucose tolerance, type 1 diabetes and obesity.

In one embodiment the glucagon derivative of the invention is for use in the treatment or prevention of atherosclerosis. In one embodiment the glucagon derivative of the invention is for use in treating hypertension. In one embodiment the glucagon derivative of the invention is for use in treating dyslipidemia. In one embodiment the glucagon derivative of the invention is for use in treating coronary heart disease. In one embodiment the glucagon derivative of the invention is for use in treating hepatic steatosis.

In one embodiment the invention relates to a method for decreasing food intake, comprising administering to a patient in need thereof, an effective amount of a glucagon derivative as described herein, optionally in combination with one or more additional therapeutically active compounds.

In one embodiment the invention relates to a method for use in increasing energy expenditure, comprising administering to a patient in need thereof, an effective amount of a glucagon derivative as described herein, optionally in combination with one or more additional therapeutically active compounds.

In one embodiment the invention relates to a method for use in reducing body weight, comprising administering to a patient in need thereof, an effective amount of a glucagon derivative as described herein, optionally in combination with one or more additional therapeutically active compounds.

In one embodiment the invention relates to a method for use in delaying the progression from impaired glucose tolerance (IGT) to type 2 diabetes, comprising administering to a patient in need thereof, an effective amount of a glucagon derivative as described herein, optionally in combination with one or more additional therapeutically active compounds.

In one embodiment the invention relates to a method for use in delaying the progression from type 2 diabetes to insulin-requiring diabetes, comprising administering to a patient in need thereof, an effective amount of a glucagon derivative as described herein, optionally in combination with one or more additional therapeutically active compounds.

In one embodiment the invention relates to a method for use in regulating appetite, comprising administering to a patient in need thereof, an effective amount of a glucagon derivative as described herein, optionally in combination with one or more additional therapeutically active compounds.

In one embodiment the invention relates to a method for use in inducing satiety, comprising administering to a patient in need thereof, an effective amount of a glucagon derivative as described herein, optionally in combination with one or more additional therapeutically active compounds.

In one embodiment the invention relates to a method for use in preventing weight regain after successful weight loss, comprising administering to a patient in need thereof, an effective amount of a glucagon derivative as described herein, optionally in combination with one or more additional therapeutically active compounds.

In one embodiment the invention relates to a method for use in treating a disease or state related to overweight or obesity, comprising administering to a patient in need thereof, an effective amount of a glucagon derivative as described herein, optionally in combination with one or more additional therapeutically active compounds.

In one embodiment the invention relates to a method for use in treating bulimia, comprising administering to a patient in need thereof, an effective amount of a glucagon derivative as described herein, optionally in combination with one or more additional therapeutically active compounds.

In one embodiment the invention relates to a method for use in treating binge-eating, comprising administering to a patient in need thereof, an effective amount of a glucagon derivative as described herein, optionally in combination with one or more additional therapeutically active compounds.

In one embodiment the invention relates to a method for use in treating atherosclerosis, comprising administering to a patient in need thereof, an effective amount of a glucagon derivative as described herein, optionally in combination with one or more additional therapeutically active compounds.

In one embodiment the invention relates to a method for use in treating hypertension, comprising administering to a patient in need thereof, an effective amount of a glucagon derivative as described herein, optionally in combination with one or more additional therapeutically active compounds.

In one embodiment the invention relates to a method for use in treating type 2 diabetes, comprising administering to a patient in need thereof, an effective amount of a glucagon derivative as described herein, optionally in combination with one or more additional therapeutically active compounds.

In one embodiment the invention relates to a method for use in treating impaired glucose tolerance, comprising administering to a patient in need thereof, an effective amount of a glucagon derivative as described herein, optionally in combination with one or more additional therapeutically active compounds.

In one embodiment the invention relates to a method for use in treating dyslipidemia, comprising administering to a patient in need thereof, an effective amount of a glucagon derivative as described herein, optionally in combination with one or more additional therapeutically active compounds.

In one embodiment the invention relates to a method for use in treating coronary heart disease, comprising administering to a patient in need thereof, an effective amount of a glucagon derivative as described herein, optionally in combination with one or more additional therapeutically active compounds.

In one embodiment the invention relates to a method for use in treating hepatic steatosis, comprising administering to a patient in need thereof, an effective amount of a glucagon derivative as described herein, optionally in combination with one or more additional therapeutically active compounds.

In one embodiment the invention relates to use of a glucagon derivative as described herein, for the preparation of a medicament for delaying or preventing disease progression in type 2 diabetes, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge-eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as x-ray, CT- and NMR-scanning.

In one embodiment the invention relates to novel stable and protracted GLP-1/glucagon receptor co-agonists, to the use of said peptides in therapy, to methods of treatment comprising administration of said peptides to patients, and to the use of said peptides in the manufacture of medicaments for use in the treatment of diabetes, obesity and related diseases and conditions.

In one embodiment the derivative of the invention is used for treatment or prevention of hypoglycemia, insulin induced hypoglycemia, reactive hypoglycemia, diabetic hypoglycemia, non-diabetic hypoglycemia, fasting hypoglycemia, drug-induced hypoglycemia, gastric by-pass induced hypoglycemia, hypoglycemia in pregnancy, alcohol induced hypoglycemia, insulinoma and/or Von Girkes disease.

In one embodiment the derivatives of the invention are for use in inhibition of the motility of the gastrointestinal tract, which is useful in connection with investigations of the gastrointestinal tract using techniques such as x-ray, CT- and NMR-scanning.

In one embodiment the derivative is for use in treatment of beta-blocker poisoning. In one embodiment the derivative is for use in treatment or prevention of hepatic steatosis. In one embodiment the derivative is for use in treatment or prevention of hypoglycaemia. In one embodiment the derivative is for use in treatment or prevention of insulin induced hypoglycaemia. In one embodiment the derivative is for use in treatment or prevention of reactive hypoglycaemia. In one embodiment the derivative is for use in treatment or prevention of diabetic hypoglycaemia. In one embodiment the derivative is for use in treatment or prevention of non-diabetic hypoglycaemia. In one embodiment the derivative is for use in treatment or prevention of fasting hypoglycaemia. In one embodiment the derivative is for use in treatment or prevention of drug-induced hypoglycaemia. In one embodiment the derivative is for use in treatment or prevention of gastric by-pass induced hypoglycaemia. In one embodiment the derivative is for use in treatment or prevention of hypoglycemia in pregnancy. In one embodiment the derivative is for use in treatment or prevention of alcohol-induced hypoglycaemia. In one embodiment the derivative is for use in treatment or prevention of insulinoma. In one embodiment the derivative is for use in treatment or prevention of Von Girkes disease.

In one embodiment the derivative is administered in a dosage regime which provides a therapeutically effective amount of said derivative. As used herein, the term "therapeutically effective amount" of a derivative of the invention refers to an amount sufficient to cure, alleviate or partially arrest the clinical manifestations of a given disease and/or its complications. An amount adequate to accomplish this is defined as a "therapeutically effective amount". Effective amounts for each purpose will depend on the severity of the disease or injury, as well as on the weight and general state of the patient. It will be understood that determination of an appropriate dosage may be achieved using routine experimentation, by constructing a matrix of values and testing different points in the matrix, all of which is within the level of ordinary skill of a trained physician or veterinarian.

The terms "treatment", "treating" and other variants thereof as used herein refer to the management and care of a patient or patient for the purpose of combating a condition, such as a disease or a disorder. The terms are intended to include the full spectrum of treatments for a given condition from which the patient is suffering, such as administration of the active compound(s) in question to alleviate symptoms or complications thereof, to delay the progression of the disease, disorder or condition, to cure or eliminate the disease, disorder or condition, and/or to prevent the condition, in that prevention is to be understood as the management and care of a patient for the purpose of combating the disease, condition, or disorder, and includes the administration of the active compound(s) in question to prevent the onset of symptoms or complications. The patient to be treated is preferably a mammal, in particular a human being, but treatment of other animals, such as dogs, cats, cows, horses, sheep, goats or pigs, is within the scope of the invention.

Intermediate Products

In one embodiment the invention relates to an intermediate product in the form of a glucagon peptide which comprises a C-terminal amide and any one of the following modifications as compared to glucagon (SEQ ID NO: 1):
  a) [Aib2,Leu10,Lys16,Arg20,Leu27,Ser28];
  b) [Aib2,Leu10,Arg20,Lys21,Leu27,Ser28];
  c) [Aib2,Leu10,Arg20,Lys24,Leu27,Ser28];
  d) [Aib2,Leu10,Arg20,Leu27,Lys28];
  e) [Aib2,Leu10,Arg20,Leu27,Ser28,Lys29];
  f) [Aib2,Leu10,Arg20,Leu27,Ser28];
  g) [Aib2,Leu10,Lys16,Lys17,Glu21,Leu27];
  h) [Aib2,Leu10,Lys17,Ala18,Glu21,Leu27,Lys29];
  i) [Aib2,Leu10,Ala18,Arg20,Glu21,Leu27,Lys29];
  j) [Aib2,Leu10,Lys16,Arg20,Glu21,Leu27];
  k) [Aib2,Leu10,Thr16,Lys20,Leu27,Ser28,Lys29];
  l) [Aib2,Leu10,Arg20,Glu21,Leu27,Lys29];
  m) Aib2,Leu10,Glu16,Lys20,Leu27,Ser28,Lys29];
  n) [Aib2,Leu10,Lys16,Glu20,Leu27,Ser28,Lys29];
  o) [Aib2,Leu10,Thr16,Arg24,Leu27,Ser28,Lys29];
  p) [Acb2,Leu10,Glu15,Glu16,Arg20,Leu27,Lys28];
  q) [Aib2,Leu10,Lys16,Lys17,Ala18,Arg20,Glu21,Ala24,Leu27];
  r) [Aib2,Leu10,Lys16,Ala18,Arg20,Glu21,Ala24,Leu27];
  s) [Aib2,Leu10,Lys16,Arg20,Glu21,Ala24,Leu27];
  t) [Aib2,Leu10,Glu15,Arg20,Glu21,Leu27,Lys28];
  u) [Aib2,Leu10,Glu15,Arg20,Glu21,Leu27,Lys29];
  v) [Aib2,Leu10,Glu15,Lys17,Arg20,Glu21,Leu27,Lys28];
  w) [Aib2,Leu10,Glu15,Arg20,Glu21,Leu27,Lys28];
  x) [Aib2,Leu10,Glu15,Lys17,Ala18,Arg20,Glu21,Leu27,Lys28];
  y) [Aib2,Leu10,Glu15,Lys17,Arg20,Glu21,Leu27,Lys28];
  z) [Aib2,Leu10,Leu16,Lys17,Arg20,Glu21,Leu27,Lys28];
  aa) [Aib2,His3,Leu10,Glu15,Lys17,Arg20,Glu21,Leu27,Lys28];
  bb) [Aib2,Leu10,Lys16,Glu21,Val27,Lys28,Gly29];
  cc) [Aib2,Leu10,Lys16,Glu21,Leu27];
  dd) [Aib2,His3,Leu10,Glu15,Arg20,Glu21,Leu27,Lys28];
  ee) [Aib2,His3,Leu10,Glu15,Arg20,Glu21,Ala24,Leu27,Lys28];
  ff) [Aib2,His3,Leu10,Glu15,Lys16,Arg20,Glu21,Ala24,Leu27,Ser28];
  gg) [Aib2,His3,Leu10,Glu15,Arg20,Glu21,Leu27,Lys28];
  hh) [Aib2,His3,Leu10,Glu15,Lys17,Arg20,Glu21,Leu27,Lys28];

ii) [Acb2,His3,Leu10,Glu15,Leu27,Lys28];
jj) [Acb2,Leu10,Glu15,Lys17,Arg20,Glu21,Leu27,Lys28]
kk) [Aib2,His3,Leu10,Glu15,Arg20,Leu27,Lys28];
ll) [Aib2,Leu10,Leu16,Arg20,Glu21,Leu27,Lys29];
mm) [Aib2,Leu10,Ala16,Arg20,Glu21,Leu27,Lys29];
nn) [Aib2,Leu10,Glu15,Arg20,Glu21,Leu27,Lys29];
oo) [Aib2,Leu10,Glu15,Arg20,Glu21,Leu27,Lys28];
pp) [Aib2,Leu10,Glu15,Arg20,Glu21,Leu27,Lys28];
qq) [Aib2,Leu10,Ala16,Arg20,Glu21,Leu27,Lys28];
rr) [Acb2,Leu10,Glu15,Arg20,Glu21,Leu27,Lys28];
ss) [Acb2,Leu10,Leu16,Arg20,Leu27,Lys28];
tt) [Acb2,Leu10,Arg12,Leu16,Arg20,Leu27,Lys28];
uu) [Acb2,Leu10,Leu16,Lys17,Arg20,Glu21,Leu27,Lys28];
vv) [Acb2,Leu10,Leu16,Lys17,Arg20,Glu21,Leu27,Lys28];
ww) [Acb2,Leu10,Leu16,Arg20,Leu27,Lys28];
xx) [Acpr2,Leu10,Glu15,Arg20,Glu21,Leu27,Lys28];
yy) [Aib2,Leu10,Aib16,Arg20,Glu21,Leu27,Lys28];
zz) [Aib2,Leu10,Glu15,Lys17,Arg20,Glu21,Leu27,Lys28];
aaa) [Aib2,Leu10,Leu16,Leu27,Lys28];
bbb) [Aib2,Leu10,Glu15,Lys17,Arg20,Glu21,Leu27,Lys28];
ccc) [Aib2,Leu10,Leu16,Arg20,Leu27,Lys28];
ddd) [Aib2,Leu10,Arg20,Glu21,Leu27,Lys28];
eee) [Aib2,Leu10,Glu15,Arg20,Leu27,Lys28];
fff) [Aib2,Leu10,Ala16,Arg20,Leu27,Lys28];
ggg) [Acb2.Leu10.Arg12.Glu15.Arg20,Glu21,Leu27,Lys28];
hhh) [Aib2.Leu10.Glu15,Arg20,Glu21,Leu27,Lys28];
iii) [Acb2,Leu10,Glu15,Arg20,Glu21,Leu27,Lys28];
jjj) [Aib2,Leu10,Arg12,Ala16,Arg20,Leu27,Lys28];
kkk) [Acb2,Leu10,Glu15,Leu27,Lys28];
lll) [Aib2,Leu10,Arg12,Ala16,Leu27,Lys28];
mmm) [Aib2,Leu10,Ala16,Arg20,Leu27,Lys29];
nnn) [Aib2,Leu10,Ala16,Arg20,Leu27,Ser28,Lys29];
ooo) [Aib2,Leu10,Glu15,Arg20,Glu21,Leu27,Lys28];
ppp) [Aib2,Leu10,Arg12,Glu15,Arg20,Glu21,Leu27,Lys28];
qqq) [Acb2,Leu10,Glu15,Lys17,Arg20,Glu21,Leu27,Lys28];
rrr) [Aib2,Leu10,Glu15,Lys17,Arg20,Ser21,Leu27,Lys28];
sss) [Aib2,Val10,Ala16,Leu27,Lys28];
ttt) [Aib2,Val10,Leu16,Leu27,Lys28];
uuu) [Aib2,Val10,Arg12,Ala16,Leu27,Lys28]; or
vvv) [Aib2,Val10,Arg12,Leu16,Leu27,Lys28];
or a pharmaceutically acceptable salt, amide, or ester thereof.

In one embodiment the invention relates to an intermediate product in the form of a glucagon peptide having a C-terminal amide and consisting of one of the modifications a) to ppp) as defined above as compared to glucagon (SEQ ID NO: 1), or a pharmaceutically acceptable salt, amide, or ester thereof.

The glucagon derivatives of the invention may be prepared by the following a stepwise synthesis method comprising (i) preparation of the intermediate glucagon peptide followed by (ii) attachment of the substituent. Step (i) of this method can be achieved using standard solid phase synthesis as described in the experimental section using protected amino acids; after cleavage from the resin the glucagon peptide can be subjected to purification using preparative HPLC as described in the experimental section herein to give the intermediate product. Alternatively, step (i) of this method, preparation of the intermediate product, can be carried out using a semirecombinant synthesis as described in WO2009/083549. Step (ii) of this method, i.e. the attachment of the substituent to the intermediate product leading to the final product, as well as preparation of the substituent itself can be achieved using methods described in WO2009/083549.

EMBODIMENTS OF THE INVENTION

The glucagon derivatives of the invention may further be characterised by one or more of the following non-limiting embodiments:

1. A glucagon derivative comprising the amino acid sequence of Formula I (corresponding to SEQ ID NO:4 and SEQ ID NO:5):

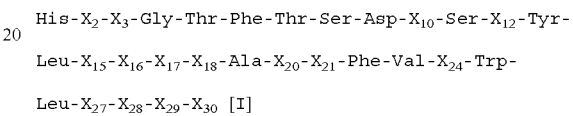

wherein
$X_2$ represents Aib, Acb or Acpr;
$X_3$ represents Gln or His;
$X_{10}$ represents Leu, Ile or Val;
$X_{12}$ represents Lys or Arg;
$X_{15}$ represents Asp or Glu;
$X_{16}$ represents Ser, Ala, Leu, Thr, Glu, Aib, Ile, Val or Lys;
$X_{17}$ represents Arg or Lys;
$X_{18}$ represents Arg, Ala or Lys;
$X_{20}$ represents Gln, Arg, Glu, Aib or Lys;
$X_{21}$ represents Asp, Glu, Ser or Lys;
$X_{24}$ represents Gln, Ala, Arg, Glu, Aib or Lys;
$X_{27}$ represents Met, Leu or Val;
$X_{28}$ represents Asn, Ser, Thr, Gln, Ala, Gly, Glu or Lys;
$X_{29}$ represents Thr, Gly, Ser, Gln, Ala, Glu or Lys;
$X_{30}$ represents Lys, or $X_{30}$ is absent;
which amino acid sequence comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, is attached at the epsilon position of a lysine residue in one of the amino acid positions 16, 17, 18, 20, 21, 24, 28, 29, or 30; and wherein said glucagon derivative is a C-terminal amide, or a pharmaceutically acceptable salt or prodrug thereof.

2. A glucagon derivative comprising the amino acid sequence of Formula I (corresponding to SEQ ID NO:2 and SEQ ID NO:3):

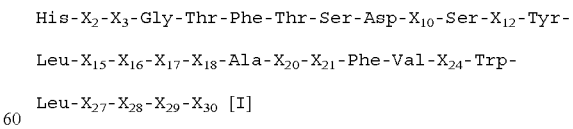

wherein
$X_2$ represents Aib, Acb or Acpr;
$X_3$ represents Gln or His;
$X_{10}$ represents Leu, Ile or Val;
$X_{12}$ represents Lys or Arg;
$X_{15}$ represents Asp or Glu;
$X_{16}$ represents Ser, Ala, Leu, Thr, Glu, Aib, Ile, Val or Lys;

$X_{17}$ represents Arg or Lys;
$X_{18}$ represents Arg, Ala or Lys;
$X_{20}$ represents Gln, Arg, Glu, Aib or Lys;
$X_{21}$ represents Asp, Glu or Lys;
$X_{24}$ represents Gln, Ala, Arg, Glu, Aib or Lys;
$X_{27}$ represents Met, Leu or Val;
$X_{28}$ represents Asn, Ser, Thr, Gln, Ala, Gly, Glu or Lys;
$X_{29}$ represents Thr, Gly, Ser, Gln, Ala, Glu or Lys;
$X_{30}$ represents Lys, or $X_{30}$ is absent;
which amino acid sequence comprises a lysine residue at one or more of positions 12, 16, 17, 18, 20, 21, 24, 28, 29, and/or 30; and wherein said glucagon derivative comprises a substituent comprising a lipophilic moiety and at least three negatively charged moieties, wherein one of said negatively charged moieties is distal of a lipophilic moiety, is attached at the epsilon position of a lysine residue in one of the amino acid positions 16, 17, 18, 20, 21, 24, 28, 29, or 30; and wherein said glucagon derivative is a C-terminal amide, or a pharmaceutically acceptable salt or prodrug thereof.

3. A glucagon derivative of Formula I as described above, wherein
$X_2$ represents Aib, Acb or Acpr;
$X_3$ represents Gln or His;
$X_{10}$ represents Leu;
$X_{12}$ represents Lys or Arg;
$X_{15}$ represents Asp or Glu;
$X_{16}$ represents Ser, Ala, Leu, Thr, Glu, Aib, or Lys;
$X_{17}$ represents Arg or Lys;
$X_{18}$ represents Arg, or Ala;
$X_{20}$ represents Gln, Arg, Glu, or Lys;
$X_{21}$ represents Asp, Glu or Lys;
$X_{24}$ represents Gln, Ala, Arg, or Lys;
$X_{27}$ represents Met, Leu or Val;
$X_{28}$ represents Asn, Ser, or Lys;
$X_{29}$ represents Thr, Gly, or Lys; and
$X_{30}$ represents Lys, or $X_{30}$ is absent.

4. A glucagon derivative of Formula I as described above, wherein a substituent comprising a lipophilic moiety and three or more negatively charged moieties, wherein one of said negatively charged moieties is distal of a lipophilic moiety, and wherein said substituent is attached at the epsilon position of a Lys in one of the following amino acid positions of said glucagon derivative: 16, 17, 18, 20, 21, 24, 28, 29, and/or 30.

5. A glucagon derivative of Formula I as described above, wherein
$X_2$ represents Aib, Acb or Acpr;
$X_3$ represents Gln or His;
$X_{10}$ represents Leu;
$X_{12}$ represents Lys or Arg;
$X_{15}$ represents Asp or Glu;
$X_{16}$ represents Ser, Ala, Leu, Thr, Glu, or Lys;
$X_{17}$ represents Arg or Lys;
$X_{18}$ represents Arg, or Ala;
$X_{20}$ represents Gln, Arg, Glu, or Lys;
$X_{21}$ represents Asp, Glu or Lys;
$X_{24}$ represents Gln, Ala, Arg, or Lys;
$X_{27}$ represents Met, Leu or Val;
$X_{28}$ represents Asn, Ser, or Lys;
$X_{29}$ represents Thr, Gly, or Lys; and
$X_{30}$ represents Lys, or $X_{30}$ is absent.

6. The glucagon derivative of Formula I as described above, wherein $X_2$ represents Aib, Acb or Acpr.

7. The glucagon derivative of Formula I as described above, wherein $X_2$ represents Aib.

8. The glucagon derivative of Formula I as described above, wherein $X_2$ represents Acb.

9. The glucagon derivative of Formula I as described above, wherein $X_2$ represents Acpr.

10. The glucagon derivative of Formula I as described above, wherein $X_3$ represents Gln or His.

11. The glucagon derivative of Formula I as described above, wherein $X_3$ represents Gln.

12. The glucagon derivative of Formula I as described above, wherein $X_3$ represents His.

13. The glucagon derivative of Formula I as described above, wherein $X_{10}$ represents Leu, Ile or Val.

14. The glucagon derivative of Formula I as described above, wherein $X_{10}$ represents Leu.

15. The glucagon derivative of Formula I as described above, wherein $X_{10}$ is Ile.

16. The glucagon derivative of Formula I as described above, wherein $X_{10}$ represents Val.

17. The glucagon derivative of Formula I as described above, wherein $X_{12}$ represents Lys or Arg.

18. The glucagon derivative of Formula I as described above, wherein $X_{12}$ represents Lys.

19. The glucagon derivative of Formula I as described above, wherein $X_{12}$ represents Arg.

20. The glucagon derivative of Formula I as described above, wherein $X_{15}$ represents Asp or Glu.

21. The glucagon derivative of Formula I as described above, wherein $X_{15}$ represents Asp.

22. The glucagon derivative according to any one of the previous embodiments, wherein $X_{15}$ represents Glu.

23. The glucagon derivative of Formula I as described above, wherein $X_{16}$ represents Ser, Ala, Leu, Thr, Glu, Aib, Ile, Val or Lys.

24. The glucagon derivative of Formula I as described above, wherein $X_{16}$ represents Ser, Ala, Leu, Thr, Glu, Aib, or Lys.

25. The glucagon derivative of Formula I as described above, wherein $X_{16}$ represents Ser, Ala, Leu, Thr, Glu or Lys.

26. The glucagon derivative of Formula I as described above, wherein $X_{16}$ represents Ala, Leu, Thr, Glu or Lys.

27. The glucagon derivative of Formula I as described above, wherein $X_{16}$ represents Ser.

28. The glucagon derivative of Formula I as described above, wherein $X_{16}$ represents Ala.

29. The glucagon derivative of Formula I as described above, wherein $X_{16}$ represents Leu.

30. The glucagon derivative of Formula I as described above, wherein $X_{16}$ represents Thr.

31. The glucagon derivative of Formula I as described above, wherein $X_{16}$ represents Glu.

32. The glucagon derivative of Formula I as described above, wherein $X_{16}$ represents Lys.

33. The glucagon derivative of Formula I as described above, wherein $X_{17}$ represents Arg or Lys.

34. The glucagon derivative of Formula I as described above, wherein $X_{17}$ represents Arg.

35. The glucagon derivative of Formula I as described above, wherein $X_{17}$ represents Lys.

36. The glucagon derivative of Formula I as described above, wherein $X_{18}$ represents Arg, or Ala.

37. The glucagon derivative of Formula I as described above, wherein $X_{18}$ represents Arg.

38. The glucagon derivative of Formula I as described above, wherein $X_{18}$ represents Ala.

39. The glucagon derivative of Formula I as described above, wherein $X_{20}$ represents Gln, Arg, Glu, Aib or Lys.

40. A glucagon derivative of Formula I as described above, wherein $X_{20}$ represents Gln, Arg, Glu, or Lys.

41. The glucagon derivative of Formula I as described above, wherein $X_{20}$ represents Gln.

42. The glucagon derivative of Formula I as described above, wherein $X_{20}$ represents Arg.

43. The glucagon derivative of Formula I as described above, wherein $X_{20}$ represents Glu.

44. The glucagon derivative of Formula I as described above, wherein $X_{20}$ represents Lys.

45. A glucagon derivative of Formula I as described above, wherein $X_{21}$ represents Asp, Glu or Lys.

46. The glucagon derivative of Formula I as described above, wherein $X_{21}$ represents Glu or Lys.

47. The glucagon derivative of Formula I as described above, wherein $X_{21}$ represents Asp.

48. The glucagon derivative of Formula I as described above, wherein $X_{21}$ represents Glu.

49. The glucagon derivative of Formula I as described above, wherein $X_{21}$ represents Lys.

50. A glucagon derivative of Formula I as described above, wherein $X_{24}$ represents Gln, Ala, Arg, Glu, Aib or Lys.

51. A glucagon derivative of Formula I as described above, wherein $X_{24}$ represents Gln, Ala, Arg, or Lys.

52. The glucagon derivative of Formula I as described above, wherein $X_{24}$ represents Gln.

53. The glucagon derivative of Formula I as described above, wherein $X_{24}$ represents Ala.

54. The glucagon derivative of Formula I as described above, wherein $X_{24}$ represents Arg.

55. The glucagon derivative of Formula I as described above, wherein $X_{24}$ represents Lys.

56. A glucagon derivative of Formula I as described above, wherein $X_{27}$ represents Met, Leu or Val.

57. A glucagon derivative of Formula I as described above, wherein $X_{27}$ represents Leu or Val.

58. The glucagon derivative of Formula I as described above, wherein $X_{27}$ represents Met.

59. The glucagon derivative of Formula I as described above, wherein $X_{27}$ represents Leu.

60. The glucagon derivative of Formula I as described above, wherein $X_{27}$ represents Val.

61. A glucagon derivative of Formula I as described above, wherein $X_{28}$ represents Asn, Ser, Thr, Gln, Ala, Gly, Glu or Lys.

62. A glucagon derivative of Formula I as described above, wherein $X_{28}$ represents Asn, Ser, or Lys.

63. The glucagon derivative of Formula I as described above, wherein $X_{28}$ represents Asn.

64. The glucagon derivative of Formula I as described above, wherein $X_{28}$ represents Ser.

65. The glucagon derivative of Formula I as described above, wherein $X_{28}$ represents Lys.

66. A glucagon derivative of Formula I as described above, wherein $X_{29}$ represents Thr, Gly, Ser, Gln, Ala, Glu or Lys.

67. A glucagon derivative of Formula I as described above, wherein $X_{29}$ represents Thr, Gly, or Lys.

68. The glucagon derivative of Formula I as described above, wherein $X_{29}$ represents Gly or Lys.

69. The glucagon derivative of Formula I as described above, wherein $X_{29}$ represents Thr.

70. The glucagon derivative of Formula I as described above, wherein $X_{29}$ represents Gly.

71. The glucagon derivative of Formula I as described above, wherein $X_{29}$ represents Lys.

72. A glucagon derivative of Formula I as described above, wherein $X_{30}$ represents Lys, or wherein $X_{30}$ is absent.

73. The glucagon derivative of Formula I as described above, wherein $X_{30}$ represents Lys.

74. The glucagon derivative of Formula I as described above, wherein $X_{30}$ is absent.

75. The glucagon derivative of Formula I as described above, wherein $X_2$ represents Aib;

$X_{20}$ represents Arg; and $X_{21}$ represents Glu.

76. The glucagon derivative of Formula I as described above, comprising an amino acid sequence with any one of the following amino acid substitutions:

[Aib2,Leu10,Lys16,Arg20,Leu27,Ser28];
[Aib2,Leu10,Arg20,Lys21,Leu27,Ser28];
[Aib2,Leu10,Arg20,Lys24,Leu27,Ser28];
[Aib2,Leu10,Arg20,Leu27,Lys28];
[Aib2,Leu10,Arg20,Leu27,Ser28,Lys29];
[Aib2,Leu10,Arg20,Leu27,Ser28];
[Aib2,Leu10,Lys16,Lys17,Glu21,Leu27];
[Aib2,Leu10,Lys17,Ala18,Glu21,Leu27,Lys29];
[Aib2,Leu10,Ala18,Arg20,Glu21,Leu27,Lys29];
[Aib2,Leu10,Lys16,Arg20,Glu21,Leu27];
[Aib2,Leu10,Thr16,Lys20,Leu27,Ser28,Lys29];
[Aib2,Leu10,Arg20,Glu21,Leu27,Lys29];
[Aib2,Leu10,Glu16,Lys20,Leu27,Ser28,Lys29];
[Aib2,Leu10,Lys16,Glu20,Leu27,Ser28,Lys29];
[Aib2,Leu10,Thr16,Arg24,Leu27,Ser28,Lys29];
[Acb2,Leu10,Glu15,Glu16,Arg20,Leu27,Lys28];
[Aib2,Leu10,Lys16,Lys17,Ala18,Arg20,Glu21,Ala24,Leu27];
[Aib2,Leu10,Lys16,Ala18,Arg20,Glu21,Ala24,Leu27];
[Aib2,Leu10,Lys16,Arg20,Glu21,Ala24,Leu27];
[Aib2,Leu10,Glu15,Arg20,Glu21,Leu27,Lys28];
[Aib2,Leu10,Glu15,Arg20,Glu21,Leu27,Lys29];
[Aib2,Leu10,Glu15,Lys17,Arg20,Glu21,Leu27,Lys28];
[Aib2,Leu10,Glu15,Lys17,Ala18,Arg20,Glu21,Leu27,Lys28];
[Aib2,Leu10,Leu16,Lys17,Arg20,Glu21,Leu27,Lys28];
[Aib2,His3,Leu10,Glu15,Lys17,Arg20,Glu21,Leu27,Lys28];
[Aib2,Leu10,Lys16,Glu21,Val27,Lys28,Gly29];
[Aib2,Leu10,Lys16,Glu21,Leu27];
[Aib2,His3,Leu10,Glu15,Arg20,Glu21,Leu27,Lys28];
[Aib2,His3,Leu10,Glu15,Arg20,Glu21,Ala24,Leu27,Lys28];
[Aib2,His3,Leu10,Glu15,Lys16,Arg20,Glu21,Ala24,Leu27,Ser28];
[Acb2,His3,Leu10,Glu15,Leu27,Lys28];
[Acb2,Leu10,Glu15,Lys17,Arg20,Glu21,Leu27,Lys28];
[Aib2,His3,Leu10,Glu15,Arg20,Leu27,Lys28];
[Aib2,Leu10,Leu16,Arg20,Glu21,Leu27,Lys29];
[Aib2,Leu10,Ala16,Arg20,Glu21,Leu27,Lys29];
[Aib2,Leu10,Ala16,Arg20,Glu21,Leu27,Lys28];
[Acb2,Leu10,Glu15,Arg20,Glu21,Leu27,Lys28];
[Acb2,Leu10,Leu16,Arg20,Leu27,Lys28];
[Acb2,Leu10,Arg12,Leu16,Arg20,Leu27,Lys28];
[Acb2,Leu10,Leu16,Lys17,Arg20,Glu21,Leu27,Lys28];
[Acb2,Leu10,Leu16,Arg20,Glu21,Leu27,Lys28];
[Acpr2,Leu10,Glu15,Arg20,Glu21,Leu27,Lys28];
[Aib2,Leu10,Aib16,Arg20,Glu21,Leu27,Lys28];
[Aib2,Leu10,Leu16,Leu27,Lys28];
[Aib2,Leu10,Leu16,Arg20,Leu27,Lys28];
[Aib2,Leu10,Arg20,Glu21,Leu27,Lys28];
[Aib2,Leu10,Glu15,Arg20,Leu27,Lys28];
[Aib2,Leu10,Ala16,Arg20,Leu27,Lys28];

[Acb2,Leu10,Arg12,Glu15,Arg20,Glu21,Leu27,Lys28];
[Aib2,Leu10,Arg12,Ala16,Arg20,Leu27,Lys28];
[Acb2,Leu10,Glu15,Leu27,Lys28];
[Aib2,Leu10,Arg12,Ala16,Leu27,Lys28];
[Aib2,Leu10,Ala16,Arg20,Leu27,Lys29];
[Aib2,Leu10,Ala16,Arg20,Leu27,Ser28,Lys29]; and
[Aib2,Leu10,Arg12,Glu15,Arg20,Glu21,Leu27,Lys28].

77. The glucagon derivative of Formula I as described above, comprising an amino acid sequence with any one of the following amino acid substitutions:
[Aib2,Leu10,Ala16,Arg20,Leu27,Lys28];
[Acb2,Leu10,Glu15,Arg20,Glu21,Leu27,Lys28]; and
[Aib2,Leu10,Glu15,Lys17,Arg20,Glu21,Leu27,Lys28].

78. The glucagon derivative of Formula I as described above, comprising an amino acid sequence with any one of the following amino acid substitutions:
[Aib2,Leu10,Glu15,Lys17,Arg20,Glu21,Leu27,Lys28];
[Acb2,Leu10,Glu15,Arg20,Glu21,Leu27,Lys28]; and
[Aib2,Leu10,Ala16,Arg20,Leu27,Lys28].

79. The glucagon derivative of Formula I as described above, comprising an amino acid sequence with the following amino acid substitutions:
[Aib2,Leu10,Glu15,Lys17,Arg20,Ser21,Leu27,Lys28].

80. The glucagon derivative of Formula I as described above, comprising an amino acid sequence with the following amino acid substitutions:
[Aib2,Val10,Ala16,Leu27,Lys28].

81. A glucagon derivative of Formula I as described above, the amino acid sequence comprises a lysine residue at one or more of positions 12, 16, 17, 18, 20, 21, 24, 28, 29, and/or 30.

82. The glucagon derivative of Formula I as described above, the amino acid sequence comprises a lysine residue at one, two or three of positions 12, 16, 17, 18, 20, 21, 24, 28, 29, and/or 30.

83. The glucagon derivative of Formula I as described above, the amino acid sequence comprises a lysine residue at one or two of positions 12, 16, 17, 18, 20, 21, 24, 28, 29, and/or 30.

84. The glucagon derivative of Formula I as described above, the amino acid sequence comprises a lysine residue at two of positions 12, 16, 17, 18, 20, 21, 24, 28, 29, and/or 30; in particular in positions 12 and 28.

85. The glucagon derivative of Formula I as described above, the amino acid sequence comprises a lysine residue at position 12, 16, 17, 18, 20, 21, 24, 28, 29, or 30.

86. A glucagon derivative of Formula I as described above, wherein the substituent comprising a lipophilic moiety and at least three negatively charged moieties, is attached at the epsilon position of a lysine residue in position 16, 21, 24, 28, 29, or 30.

87. The glucagon derivative of Formula I as described above, wherein the substituent comprising a lipophilic moiety and at least three negatively charged moieties, is attached at the epsilon position of a lysine residue in position 16, 21, 24, 28, 29, or 30.

88. The glucagon derivative of Formula I as described above, wherein the substituent comprising a lipophilic moiety and at least three negatively charged moieties, is attached at the epsilon position of a lysine residue in position 16, 24, 28, 29 or 30.

89. The glucagon derivative of Formula I as described above, wherein the substituent comprising a lipophilic moiety and at least three negatively charged moieties, is attached at the epsilon position of a lysine residue in position 24, 28, 29 or 30.

90. The glucagon derivative of Formula I as described above, wherein the substituent comprising a lipophilic moiety and at least three negatively charged moieties, is attached at the epsilon position of a lysine residue in position 28, 29 and 30.

91. The glucagon derivative of Formula I as described above, wherein the substituent comprising a lipophilic moiety and at least three negatively charged moieties, is attached at the epsilon position of a lysine residue in position 28.

92. The glucagon derivative of Formula I as described above, wherein the substituent comprising a lipophilic moiety and three or more negatively charged moieties is a substituent of Formula II:

$Z^1$-$Z^2$-$Z^3$-$Z^4$-$Z^5$-$Z^6$-$Z^7$-$Z^8$-$Z^9$-$Z^{10}$- wherein,
$Z^1$- represents a structure of Formula IIa;

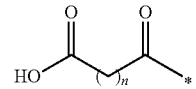

wherein n is 6-20; and the symbol * represents the attachment point to the nitrogen of the neighbouring linking group; and
$Z^2$-$Z^3$-$Z^4$-$Z^5$-$Z^6$-$Z^7$-$Z^8$-$Z^9$-$Z^{10}$- represents a linking group, wherein each of $Z_2$ to $Z_{10}$ individually are represented by any one of the following amino acid residues: Glu, γGlu, Gly, Ser, Ala, Thr or Ado; or one or more of residues $Z^2$ to $Z^{10}$ are absent; provided, however, that at least two of residues $Z^2$ to $Z^{10}$ are present; and
wherein $Z^1$-$Z^2$-$Z^3$-$Z^4$-$Z^5$-$Z^6$-$Z^7$-$Z^8$-$Z^9$-$Z^{10}$- together contains at least three negative charges; and
wherein said substituent is attached at the epsilon position of a Lys residue according to Formula I.

93. The glucagon derivative of Formula I as described above, wherein $Z^1$ of Formula II represents a structure according to Formula IIa:

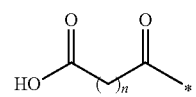

wherein n represents an integer in the range of from 6 to 20;
the symbol * represents the attachment point to the nitrogen of the neighbouring group; and
wherein $Z_2$, $Z_3$, $Z_4$, $Z_5$, $Z_6$, $Z_7$, $Z_8$, $Z_9$, $Z_{10}$ individually are represented by the following amino acids: Glu, γGlu, Gly, Ser, Ala, Thr and Ado; or one or more of $Z_2$, $Z_3$, $Z_4$, $Z_5$, $Z_6$, $Z_7$, $Z_8$, $Z_9$, $Z_{10}$ may be absent; provided, however, that at least two of residues $Z_2$ to $Z_{10}$ are present;
wherein $Z_1$-$Z_2$-$Z_3$-$Z_4$-$Z_5$-$Z_6$-$Z_7$-$Z_8$-$Z_9$-$Z_{10}$ together contains at least three negative charges; and
wherein said substituent is attached at the epsilon position of a Lys residue according to Formula I, above.

94. The glucagon derivative of Formula I as described above, wherein n in $Z^1$ of Formula IIa represents 14, 16 or 18.

95. The glucagon derivative of Formula I as described above, wherein n in $Z^1$ of Formula IIa represents 14.

96. The glucagon derivative of Formula I as described above, wherein n in $Z^1$ of Formula IIa represents 16.

97. The glucagon derivative of Formula I as described above, wherein n in $Z^1$ of Formula IIa represents 18.

98. The glucagon derivative of Formula I as described above, wherein said substituent represents a structure according to any one of the following nine formulas (Chem.A-Chem.I), wherein * indicates the point of attachment to the nitrogen atom of the epsilon position of a Lys residue of Formula I:
(Chem. A)
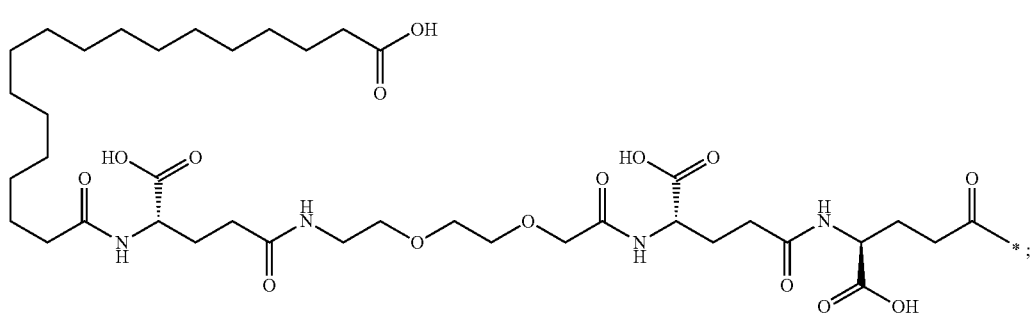
(Chem. B)
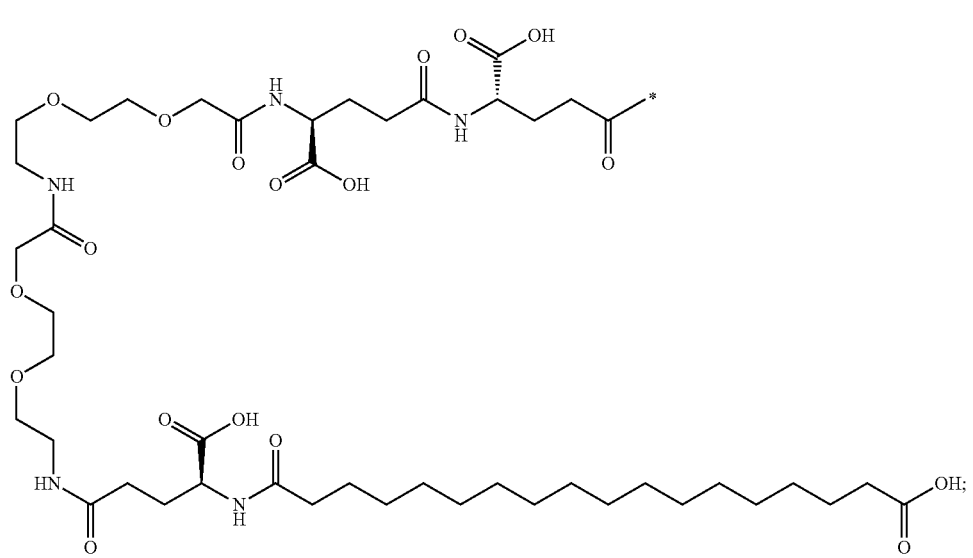
(Chem. C)
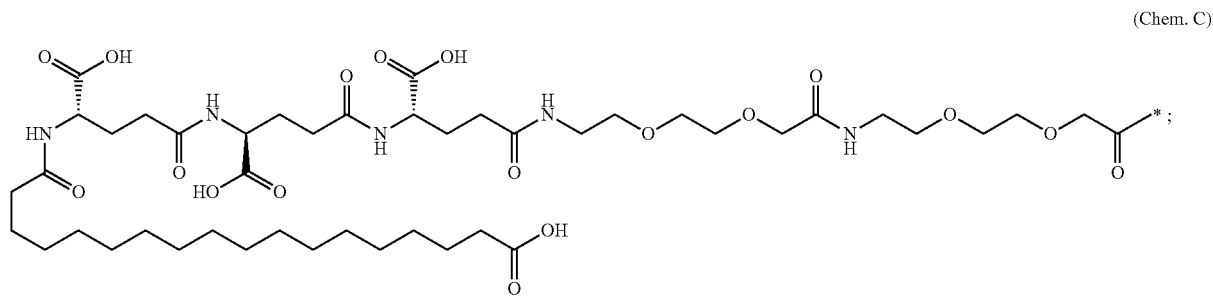
(Chem. D)
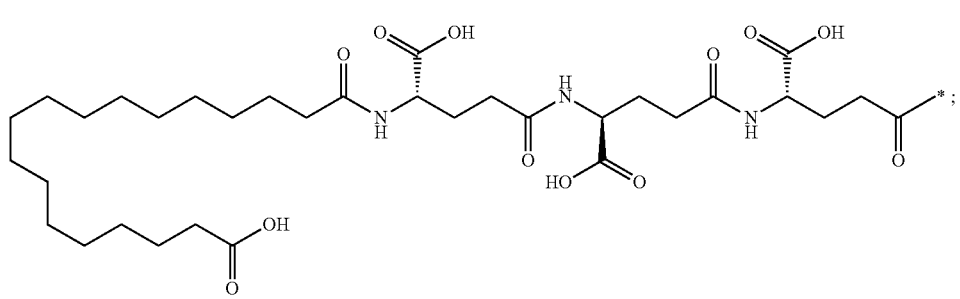

-continued
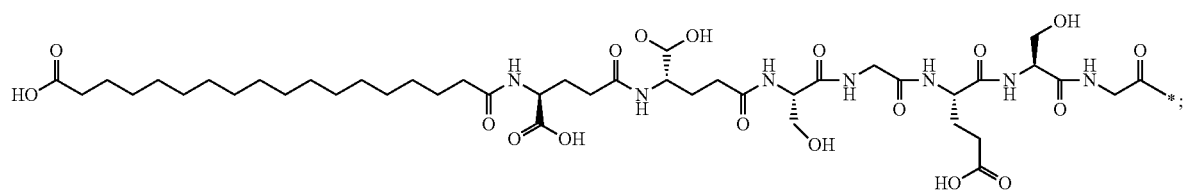
(Chem. E)
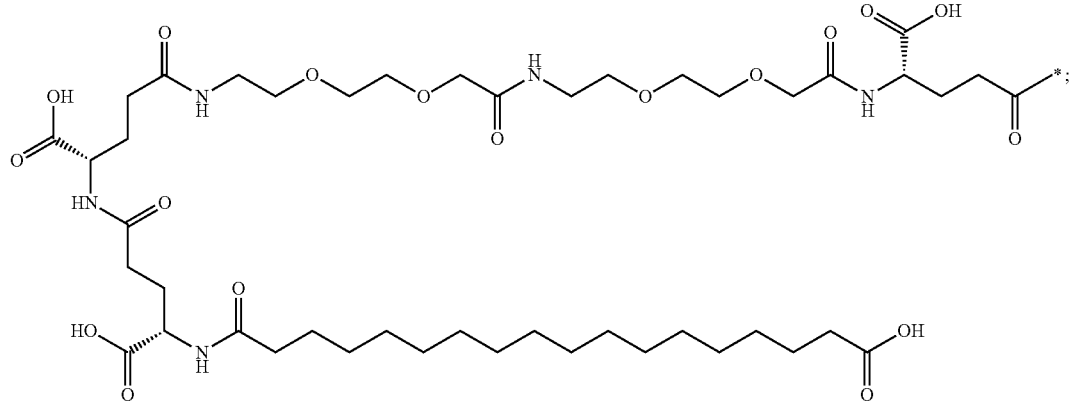
(Chem. F)
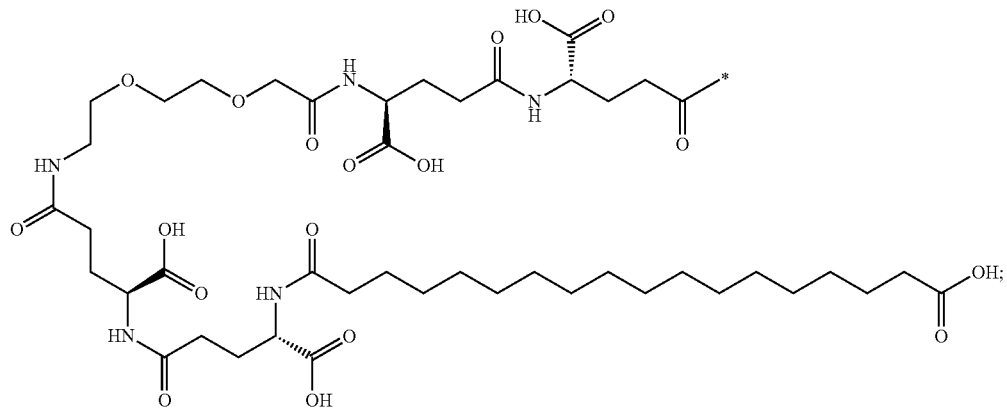
(Chem. G)
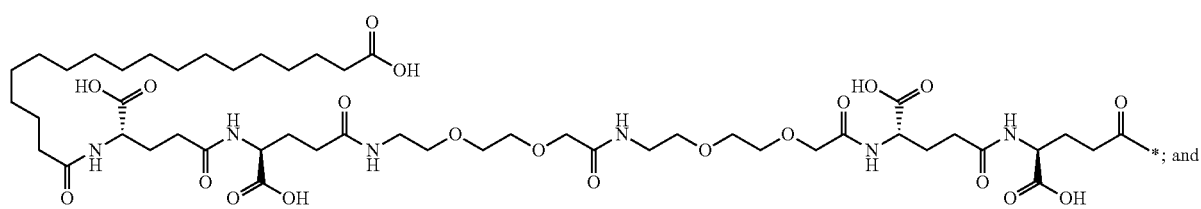
(Chem. H)
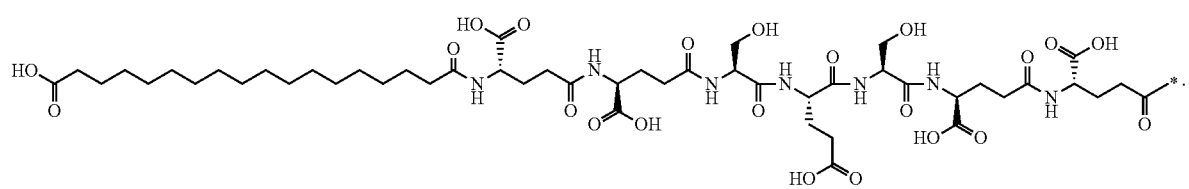
(Chem. I)
99. The glucagon derivative of Formula I as described above, wherein said substituent represents a structure according to the following formula (Chem.J), wherein * indicates the point of attachment to the nitrogen atom of the epsilon position of a Lys residue of Formula I:

(Chem.J)

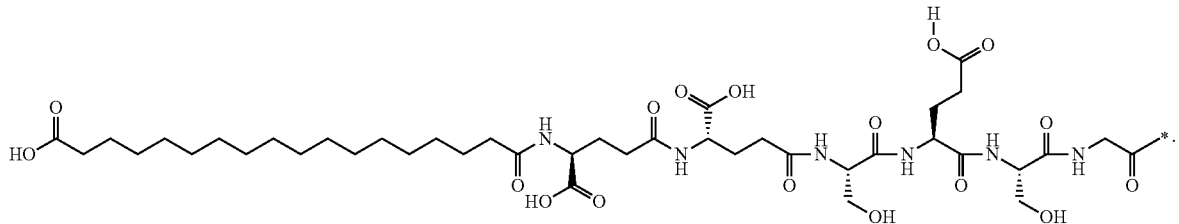

100. The glucagon derivative of Formula I as described above, wherein said substituent represents a structure according to any one of formulas Chem.A-Chem.I or Chem.J, as described above, wherein * indicate the point of attachment to the nitrogen atom of the epsilon position of a Lys residue according to Formula I.

101. The glucagon derivative of Formula I as described above, wherein said substituent represents a structure according to the formula Chem.B, Chem.C, or Chem.H, or according to the formula Chem.J, described above, wherein * indicate the point of attachment to the nitrogen atom of the epsilon position of a Lys residue according to Formula I.

102. A glucagon derivative of the invention selected from the group consisting of:

$N^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Leu27,Ser28]-Glucagon amide;

$N^{\epsilon 21}$-(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys21,Leu27,Ser28]-Glucagon amide;

$N^{\epsilon 24}$-[(4S)-4-carboxy-4-[[(4S)-4-carboxy-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys24,Leu27,Ser28]-Glucagon amide;

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Lys28]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Ser28,Lys29]-Glucagon amide;

$N^{\alpha}$-([Aib2,Leu10,Arg20,Leu27,Ser28]-Glucagonyl)-$N^{\epsilon}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]Lys amide;

$N^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Glu21,Leu27]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys17,Ala18,Glu21,Leu27,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala18,Arg20,Glu21,Leu27,Lys29]-Glucagon amide;

$N^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Glu21,Leu27]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Thr16,Lys20,Leu27,Ser28,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu16,Lys20,Leu27,Ser28,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Glu20,Leu27,Ser28,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Thr16,Arg24,Leu27,Ser28,Lys29]-Glucagon amide;

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3- hydroxypropanoyl]amino]acetyl]-[Acb2,Leu10,Glu15, Glu16,Arg20,Leu27,Lys28]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Ala18,Arg20,Glu21,Ala24,Leu27]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Ala18,Arg20,Glu21,Ala24,Leu27]-Glucagon amide;

$N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Lys16,Arg20,Glu21,Ala24,Leu27]-Glucagon amide;

$N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Glu15,Arg20,Glu21,Leu27,Lys28]-Glucagon amide;

$N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,Leu10,Glu15,Arg20,Glu21,Leu27,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Arg20,Glu21,Leu27,Lys28]-Glucagon amide;

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys28]-Glucagon amide;

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Ala18,Arg20,Glu21,Leu27,Lys28]-Glucagon amide;

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,Leu10, Glu15, Lys17,Arg20,Glu21,Leu27,Lys28]-Glucagon amide;

$N^{\epsilon 28}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy-acetyl]amino]ethoxy]ethoxy]acetyl]amino]butanoyl]amino]butanoyl]-[Aib2,Leu10,Leu16,Lys17,Arg20,Glu21,Leu27,Lys28]-Glucagon amide;

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Lys17,Arg20,Glu21,Leu27, Lys28]-Glucagon amide;

$N^{\epsilon 16}$-[(4S)-4-carboxy-4-[[(4S)-4-carboxy-4-[[2-[2-[2-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Aib2,Leu10,Lys16, Glu21,Val27,Lys28,Gly29]-Glucagon amide;

$N^{\epsilon 16}$-[(4S)-4-carboxy-4-[[(4S)-4-carboxy-4-[[2-[2-[2-[[(4S)-4-carboxy-4-(17-carboxyheptadecanoylamino)butanoyl]amino]butanoyl]amino]ethoxy]ethoxy]acetyl]amino]butanoyl]amino]butanoyl]-[Aib2,Leu10,Lys16, Glu21,Leu27]-Glucagon amide;

$N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Leu27,Lys28]-Glucagon amide;

$N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Ala24,Leu27, Lys28]-Glucagon amide;

$N^{\epsilon 16}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Lys16,Arg20,Glu21,Ala24, Leu27,Ser28]-Glucagon amide;

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Arg20,Glu21,Leu27,Lys28]-Glucagon amide;

$N^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,His3,Leu10, Glu15,Lys17,Arg20,Glu21,Leu27,Lys28]-Glucagon amide;

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,His3,Leu10, Glu15,Leu27,Lys28]-Glucagon amide;

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15, Lys17,Arg20,Glu21,Leu27,Lys28]-Glucagon amide;

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,His3,Leu10, Glu15,Arg20,Leu27,Lys28]-Glucagon amide;

$N^{\epsilon 29}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Leu16,Arg20,Glu21, Leu27,Lys29]-Glucagon amide;

$N^{\epsilon 29}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Ala16,Arg20,Glu21,Leu27,Lys29]-Glucagon amide;

N$^{\epsilon 29}$-[(4S)-4-carboxy-4-[[(4S)-4-carboxy-4-[[2-[2-[2-[[(4S)-4-carboxy-4-(17-carboxyheptadecanoylamino)butanoyl]amino]ethoxy]ethoxy]acetyl]amino]butanoyl]amino]butanoyl]-[Aib2,Leu10,Glu15,Arg20,Glu21,Leu27,Lys29]-Glucagon amide;

N$^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Glu15,Arg20,Glu21,Leu27,Lys28]-Glucagon amide;

N$^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Leu16,Arg20,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide;

N$^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Leu16,Lys17,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Acpr2,Leu10,Glu15,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Aib16,Arg20,Glu21,Leu27,Lys28]-Glucagon amide;

N$^{\epsilon 28}$4 S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide;

N$^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Leu16,Leu27,Lys28]-Glucagon amide;

N$^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide;

N$^{\epsilon 28}$-[2-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]acetyl]-[Aib2,Leu10,Leu16,Arg20,Leu27,Lys28]-Glucagon amide;

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys28]-Glucagon amide;

N$^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Leu27,Lys28]-Glucagon amide;

N$^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Glu15,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys28]-Glucagon amide;

N$^{\epsilon 28}$-[(4S)-4-carboxy-4-[[(4S)-4-carboxy-4-[[2-[2-[2-[[2-[2-[[(4S)-4-carboxy-4-[[(4S)-4-carboxy-4-(17-carboxyheptadecanoylamino)butanoyl]amino]butanoyl]

amino]ethoxy]ethoxy]acetyl]amino]ethoxy]ethoxy] acetyl]amino]butanoyl]amino]butanoyl]-[Acb2,Leu10, Glu15,Arg20,Glu21,Leu27,Lys28]-Glucagon amide;

$N^{\epsilon 28}$-[(4S)-4-carboxy-4-[[(4S)-4-carboxy-4-[[(4S)-4-carboxy-4-(17-carboxyheptadecanoylamino)butanoyl] amino]butanoyl]amino]butanoyl]-[Aib2,Leu10,Arg12, Ala16,Arg20,Leu27,Lys28]-Glucagon amide;

$N^{\epsilon 28}$-[2-[2-[2-[[2-[2-[2-[[(4S)-4-carboxy-4-[[(4S)-4-carboxy-4-(17-carboxyheptadecanoylamino)butanoyl]amino]butanoyl]amino]butanoyl] amino]ethoxy]ethoxy]acetyl]amino]ethoxy]ethoxy] acetyl]-[Acb2,Leu10,Glu15,Leu27,Lys28]-Glucagon amide;

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl] amino]ethoxy]ethoxy]acetyl]amino]ethoxy]ethoxy] acetyl]-[Aib2,Leu10,Arg12,Ala16,Leu27,Lys28]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino] ethoxy]ethoxy]acetyl]amino]butanoyl]amino]butanoyl]-[Aib2,Leu10,Ala16,Arg20,Leu27,Lys29]-Glucagon amide;

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino] ethoxy]ethoxy]acetyl]amino]butanoyl]amino]butanoyl]-[Aib2,Leu10,Ala16,Arg20,Leu27,Ser28,Lys29]-Glucagon amide;

$N^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl] amino]butanoyl]amino]-3-hydroxypropanoyl]amino] butanoyl]amino]-3-hydroxypropanoyl]amino]butanoyl] amino]butanoyl]-[Aib2,Leu10,Glu15,Arg20,Glu21, Leu27,Lys28]-Glucagon amide; and $N^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl] amino]butanoyl]amino]-3-hydroxypropanoyl]amino] butanoyl]amino]-3-hydroxypropanoyl]amino]butanoyl] amino]butanoyl]-[Acb2,Leu10,Glu15,Lys17,Arg20, Glu21,Leu27,Lys28]-Glucagon amide.

103. A glucagon derivative of the invention, wherein said glucagon derivative is selected from the group consisting of:

$N^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl] amino]butanoyl]amino]-3-hydroxypropanoyl]amino] butanoyl]amino]-3-hydroxypropanoyl]amino]butanoyl] amino]butanoyl]-[Aib2,Leu10,Glu15,Lys17,Arg20, Ser21,Leu27,Lys28]-Glucagon amide;

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl] amino]ethoxy]ethoxy]acetyl]amino]ethoxy]ethoxy] acetyl]-[Aib2,Val10,Leu16,Leu27,Lys28]-Glucagon amide;

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl] amino]ethoxy]ethoxy]acetyl]amino]ethoxy]ethoxy] acetyl]-[Aib2,Val10,Arg12,Ala16,Leu27,Lys28]-Glucagon amide; and $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl] amino]ethoxy]ethoxy]acetyl]amino]ethoxy]ethoxy] acetyl]-[Aib2,Val10,Arg12,Leu16,Leu27,Lys28]-Glucagon amide.

104. A glucagon derivative of the invention, wherein said glucagon derivative is $N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino] butanoyl]amino]ethoxy]ethoxy]acetyl]amino]ethoxy] ethoxy]acetyl]-[Aib2,Val10,Ala16,Leu27,Lys28]-Glucagon amide.

Further embodiments of the invention relate to:

105. The glucagon derivative of Formula I as described above, wherein said glucagon derivative is a GLP-1 and glucagon receptor co-agonist.

106. The glucagon derivative according to any of the previous embodiments, wherein said substituent binds non-covalently to albumin.

107. The glucagon derivative according to any of the previous embodiments, wherein said substituent is negatively charged at physiological pH.

108. The glucagon derivative according to any of the previous embodiments, wherein said glucagon derivative is a DPPIV protected compound.

109. The glucagon derivative according to any of the previous embodiments, wherein said glucagon derivative is DPPIV stabilised.

110. The glucagon derivative according to any of the previous embodiments, wherein said glucagon derivative is an agonist of the glucagon receptor.

111. The glucagon derivative according to any of the previous embodiments, wherein said glucagon derivative is an agonist of the glucagon receptor, with an $EC_{50}<10$ nM.

112. The glucagon derivative according to any of the previous embodiments, wherein said glucagon derivative is an agonist of the glucagon receptor, with an $EC_{50}<1$ nM.

113. The glucagon derivative according to any of the previous embodiments, wherein said glucagon derivative is an agonist of the glucagon receptor, with an $EC_{50}<100$ pM.

114. The glucagon derivative according to any of the previous embodiments, wherein said glucagon derivative is an agonist of the glucagon receptor, with an $EC_{50}<10$ pM.

115. The glucagon derivative according to any of the previous embodiments, wherein said glucagon derivative is an agonist of the GLP-1 receptor.

116. The glucagon derivative according to any of the previous embodiments, wherein said glucagon derivative is an agonist of the GLP-1 receptor, with an $EC_{50}<100$ pM.

117. The glucagon derivative according to any of the previous embodiments, wherein said glucagon derivative is an agonist of the GLP-1 receptor, with an $EC_{50}<50$ pM.

118. The glucagon derivative according to any of the previous embodiments, wherein said glucagon derivative is an agonist of the GLP-1 receptor, with an $EC_{50}<10$ pM.

119. The glucagon derivative according to any of the previous embodiments, wherein said glucagon derivative is an agonist of the GLP-1 receptor with an $EC_{50}<100$ pM and an $EC_{50}<1$ nM on the glucagon receptor.

120. The glucagon derivative according to any of the previous embodiments, wherein said glucagon derivative is an agonist of the GLP-1 receptor with an $EC_{50}<50$ pM and an $EC_{50}<1$ nM on the glucagon receptor.

121. The glucagon derivative according to any of the previous embodiments, wherein said glucagon derivative is an agonist of the GLP-1 receptor with an $EC_{50}$<10 pM and an $EC_{50}$<1 nM on the glucagon receptor.

122. The glucagon derivative according to any of the previous embodiments, wherein said glucagon derivative is an agonist of the GLP-1 receptor with an $EC_{50}$<50 pM and an $EC_{50}$<100 pM on the glucagon receptor.

123. The glucagon derivative according to any of the previous embodiments, wherein said glucagon derivative is an agonist of the GLP-1 receptor with an $EC_{50}$<10 pM and an $EC_{50}$<100 pM on the glucagon receptor.

124. The glucagon derivative according to any of the previous embodiments, wherein said glucagon derivative is an agonist of the GLP-1 receptor with an $EC_{50}$<10 pM and an $EC_{50}$<50 pM on the glucagon receptor.

125. The glucagon derivative according to any of the previous embodiments, wherein said glucagon derivative is an agonist of the GLP-1 receptor with an $EC_{50}$<1 pM and an $EC_{50}$<50 pM on the glucagon receptor.

126. The glucagon derivative according to any of the previous embodiments, wherein said glucagon derivative is an agonist of the GLP-1 receptor with an $EC_{50}$<10 pM and an $EC_{50}$<10 pM on the glucagon receptor.

127. The glucagon derivative according to any of the previous embodiments, wherein said glucagon derivative is a GLP-1/glucagon co-agonist with an $EC_{50}$ on the GLP-1 receptor<the $EC_{50}$ on the glucagon receptor.

128. The glucagon derivative according to any of the previous embodiments, wherein said glucagon derivative is a GLP-1/glucagon co-agonist with an $EC_{50}$ on the GLP-1 receptor (e.g. in pM) greater than the $EC_{50}$ on the glucagon receptor (e.g. in pM).

Further embodiments of the invention relate to combinations:

129. The glucagon derivative according to any one of the previous embodiments, in combination with a GLP-1 compound or with an insulin compound.

130. The glucagon derivative according to any one of the previous embodiments, in combination with a GLP-1 compound.

131. The glucagon derivative according to any one of the previous embodiments, in combination with an insulin compound.

132. The glucagon derivative according to any one of embodiments 123-125, wherein the GLP-1 compound is selected from the group consisting of:

N-epsilon26-((S)-4-Carboxy-4-hexadecanoylamino-butyryl)[Arg34]GLP-1-(7-37):

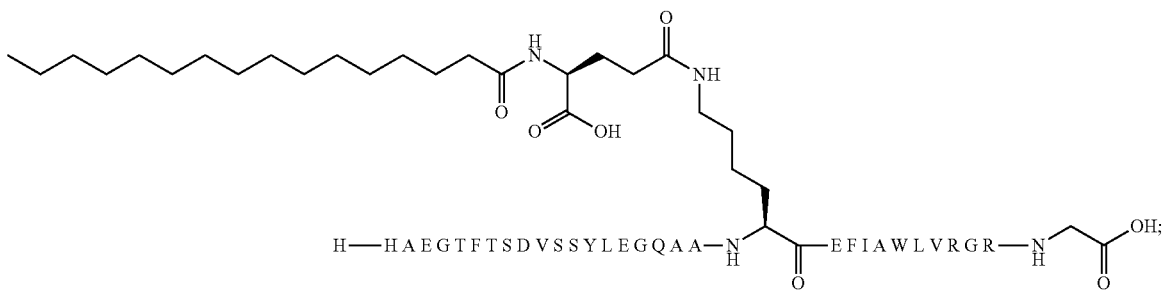

(Compound G1)

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37):

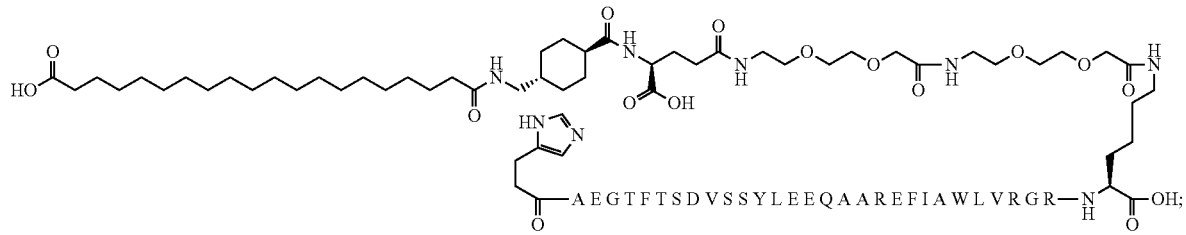

(Compound G2)

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8,Arg34]GLP-1-(7-37):

(Compound G3)

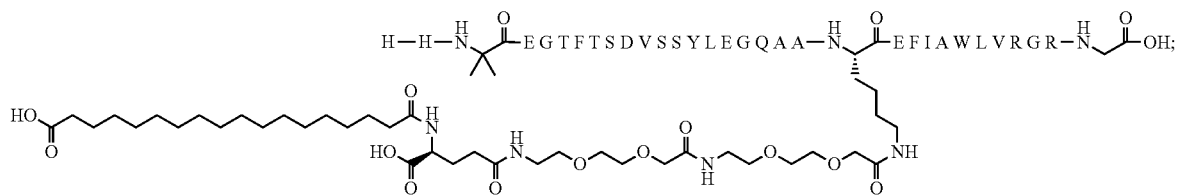

and
N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

and their pharmaceutically acceptable salts, amides, alkyls, or esters.

133. The glucagon derivative according to any one of embodiments 129-132, wherein the insulin compound is: N-epsilon-B29-[(S)-4-Carboxy-4-(15-carboxypentadecanoylamino)butyryl] desB30 human insulin Other embodiments of the present relates to pharmaceutical compositions:

134. A pharmaceutical composition comprising a glucagon derivative according to any one of embodiments 1-128 and optionally one or more pharmaceutically acceptable excipients.

(Compound G4)

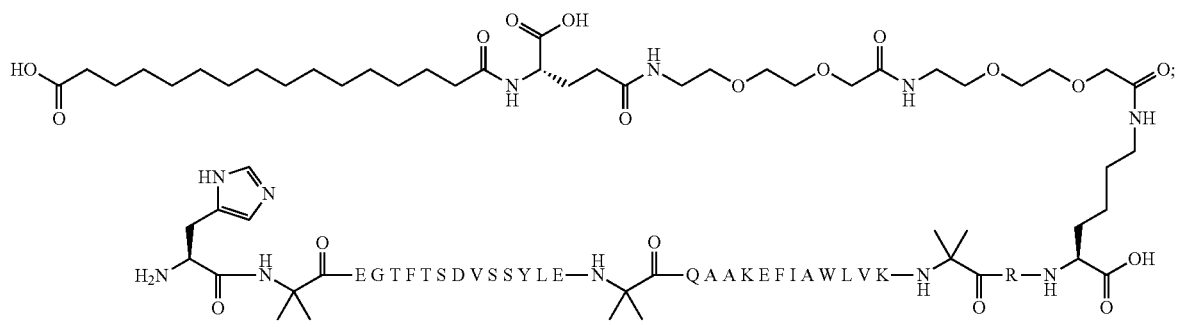

135. The pharmaceutical composition according to embodiment 134, further comprising one or more additional therapeutically active compounds or substances.

136. The pharmaceutical composition according to embodiment 135, wherein said additional therapeutically active compound is a GLP-1 compound or an insulin compound.

(Compound G5)

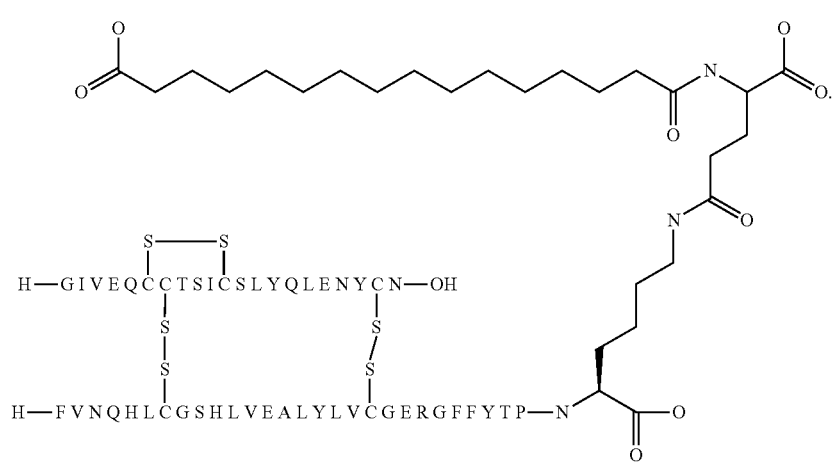

137. The pharmaceutical composition according to embodiment 136, wherein said additional therapeutically active compound is a GLP-1 compound.

138. The pharmaceutical composition according to embodiment 136 or 137, wherein said additional therapeutically active compound is an insulin compound.

139. The pharmaceutical composition according to any one of embodiments 136-138, wherein the GLP-1 compound is selected from the group consisting of:

N-epsilon26-((S)-4-Carboxy-4-hexadecanoylamino-butyryl)[Arg34]GLP-1-(7-37):

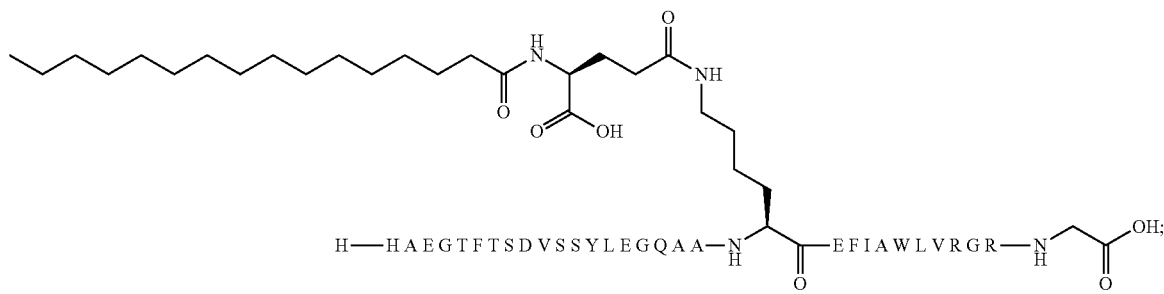

(Compound G1)

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37):

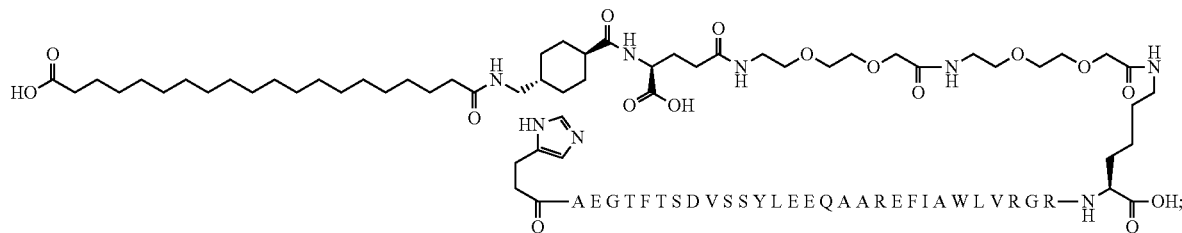

(Compound G2)

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8,Arg34]GLP-1-(7-37):

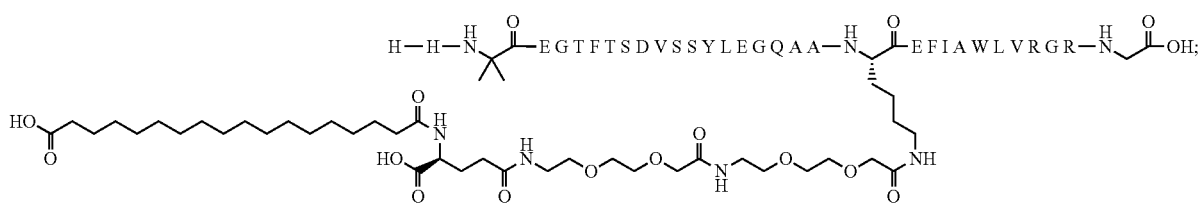

(Compound G3)

and
N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

additional therapeutically active compounds, for use in treatment or prevention of hyperglycemia, type 2 diabetes, impaired glucose tolerance, type 1 diabetes and obesity.

145. The glucagon derivative according to any of embodiments 1-128, optionally in combination with one or more (Compound G4)

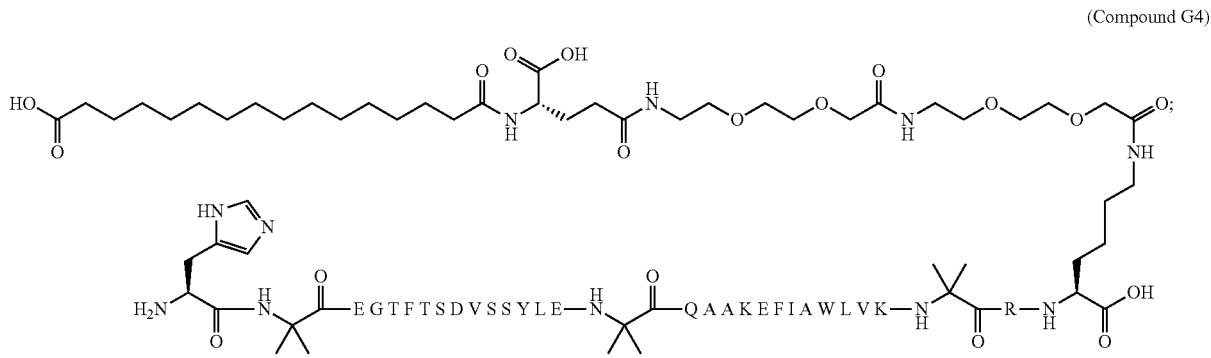

and their pharmaceutically acceptable salts, amides, alkyls, or esters.

140. The pharmaceutical composition according to any one of embodiments 130-133, wherein the insulin compound is:
N-epsilon-B29-[(S)-4-Carboxy-4-(15-carboxypentadecanoylamino)butyryl] desB30 human insulin additional therapeutically active compounds, for use in delaying or preventing disease progression in type 2 diabetes.

146. The glucagon derivative according to any of embodiments 1-128, optionally in combination with one or more additional therapeutically active compounds, for use treating obesity or preventing overweight.

(Compound G5)

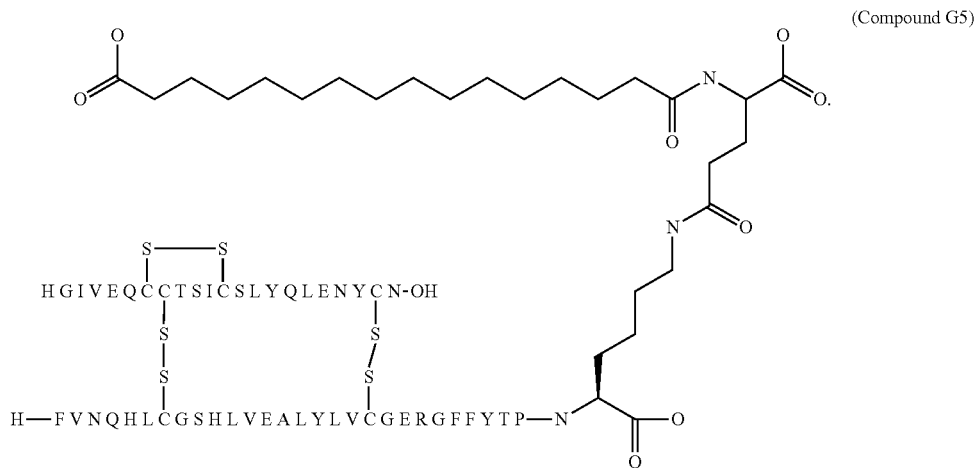

141. The pharmaceutical composition according to any one of embodiments 128-134, in unit dosage form comprising from about 0.01 mg to about 1000 mg, such as from about 0.1 mg to about 500 mg, from about 0.5 mg to about 5 mg, e.g. from about 0.5 mg to about 200 mg, of a glucagon derivative according to any of embodiments 1-128.

142. The pharmaceutical composition according to any one of embodiments 126-138, which is suited for parenteral administration.

143. The glucagon derivative according to any one of embodiments 1-128, optionally in combination with one or more additional therapeutically active compounds, for use in therapy.

Further embodiments of the invention relate to the following:

144. The glucagon derivative according to any of embodiments 1-128, optionally in combination with one or more 147. The glucagon derivative according to any of embodiments 1-128, optionally in combination with one or more additional therapeutically active compounds, for use in for decreasing food intake.

148. The glucagon derivative according to any of embodiments 1-128, optionally in combination with one or more additional therapeutically active compounds, for use in increasing energy expenditure.

149. The glucagon derivative according to any of embodiments 1-128, optionally in combination with one or more additional therapeutically active compounds, for use in reducing body weight.

150. The glucagon derivative according to any of embodiments 1-128, optionally in combination with one or more additional therapeutically active compounds, for use in delaying the progression from impaired glucose tolerance (IGT) to type 2 diabetes.

151. The glucagon derivative according to any of embodiments 1-128, optionally in combination with one or more additional therapeutically active compounds, for use in delaying the progression from type 2 diabetes to insulin-requiring diabetes.

152. The glucagon derivative according to any of embodiments 1-128, optionally in combination with one or more additional therapeutically active compounds, for use in regulating appetite.

153. The glucagon derivative according to any of embodiments 1-128, optionally in combination with one or more additional therapeutically active compounds, for use in inducing satiety.

154. The glucagon derivative according to any of embodiments 1-128, optionally in combination with one or more additional therapeutically active compounds, for use in preventing weight regain after successful weight loss.

155. The glucagon derivative according to any of embodiments 1-128, optionally in combination with one or more additional therapeutically active compounds, for use in treating a disease or state related to overweight or obesity.

156. The glucagon derivative according to any of embodiments 1-128, optionally in combination with one or more additional therapeutically active compounds, for use in treating bulimia.

157. The glucagon derivative according to any of embodiments 1-128, optionally in combination with one or more additional therapeutically active compounds, for use in treating binge-eating.

158. The glucagon derivative according to any of embodiments 1-128, optionally in combination with one or more additional therapeutically active compounds, for use in treating atherosclerosis.

159. The glucagon derivative according to any of embodiments 1-128, optionally in combination with one or more additional therapeutically active compounds, for use in treating hypertension.

160. The glucagon derivative according to any of embodiments 1-128, optionally in combination with one or more additional therapeutically active compounds, for use in treating type 2 diabetes.

161. The glucagon derivative according to any of embodiments 1-128, optionally in combination with one or more additional therapeutically active compounds, for use in treating impaired glucose tolerance.

162. The glucagon derivative according to any of embodiments 1-128, optionally in combination with one or more additional therapeutically active compounds, for use in treating dyslipidemia.

163. The glucagon derivative according to any of embodiments 1-128, optionally in combination with one or more additional therapeutically active compounds, for use in treating coronary heart disease.

164. The glucagon derivative according to any of embodiments 1-128, optionally in combination with one or more additional therapeutically active compounds, for use in treating hepatic steatosis.

Further embodiments of the invention relate to the following methods:

165. A method for treating or preventing hypoglycemia, type 2 diabetes, impaired glucose tolerance, type 1 diabetes and obesity, comprising administering to a patient in need thereof, an effective amount of a glucagon derivative according to any of embodiments 1-128, optionally in combination with one or more additional therapeutically active compounds.

166. A method for delaying or preventing disease progression in type 2 diabetes, comprising administering to a patient in need thereof, an effective amount of a glucagon derivative according to any of embodiments 1-128, optionally in combination with one or more additional therapeutically active compounds.

167. A method for treating obesity or preventing overweight, comprising administering to a patient in need thereof, an effective amount of a glucagon derivative according to any of embodiments 1-128, optionally in combination with one or more additional therapeutically active compounds.

168. A method for decreasing food intake, comprising administering to a patient in need thereof, an effective amount of a glucagon derivative according to any of embodiments 1-128, optionally in combination with one or more additional therapeutically active compounds.

169. A method for use in increasing energy expenditure, comprising administering to a patient in need thereof, an effective amount of a glucagon derivative according to any of embodiments 1-128, optionally in combination with one or more additional therapeutically active compounds.

170. A method for use in reducing body weight, comprising administering to a patient in need thereof, an effective amount of a glucagon derivative according to any of embodiments 1-128, optionally in combination with one or more additional therapeutically active compounds.

171. A method for use in delaying the progression from impaired glucose tolerance (IGT) to type 2 diabetes, comprising administering to a patient in need thereof, an effective amount of a glucagon derivative according to any of embodiments 1-128, optionally in combination with one or more additional therapeutically active compounds.

172. A method for use in delaying the progression from type 2 diabetes to insulin-requiring diabetes, comprising administering to a patient in need thereof, an effective amount of a glucagon derivative according to any of embodiments 1-128, optionally in combination with one or more additional therapeutically active compounds.

173. A method for use in regulating appetite, comprising administering to a patient in need thereof, an effective amount of a glucagon derivative according to any of embodiments 1-128, optionally in combination with one or more additional therapeutically active compounds.

174. A method for use in inducing satiety, comprising administering to a patient in need thereof, an effective amount of a glucagon derivative according to any of embodiments 1-128, optionally in combination with one or more additional therapeutically active compounds.

175. A method for use in preventing weight regain after successful weight loss, comprising administering to a patient in need thereof, an effective amount of a glucagon derivative according to any of embodiments 1-128, optionally in combination with one or more additional therapeutically active compounds.

176. A method for use in treating a disease or state related to overweight or obesity, comprising administering to a patient in need thereof, an effective amount of a glucagon derivative according to any of embodiments 1-128, optionally in combination with one or more additional therapeutically active compounds.

177. A method for use in treating bulimia, comprising administering to a patient in need thereof, an effective amount of a glucagon derivative according to any of embodiments 1-128, optionally in combination with one or more additional therapeutically active compounds.

178. A method for use in treating binge-eating, comprising administering to a patient in need thereof, an effective amount of a glucagon derivative according to any of embodiments 1-128, optionally in combination with one or more additional therapeutically active compounds.

179. A method for use in treating atherosclerosis, comprising administering to a patient in need thereof, an effective amount of a glucagon derivative according to any of embodiments 1-128, optionally in combination with one or more additional therapeutically active compounds.

180. A method for use in treating hypertension, comprising administering to a patient in need thereof, an effective amount of a glucagon derivative according to any of embodiments 1-128, optionally in combination with one or more additional therapeutically active compounds.

181. A method for use in treating type 2 diabetes, comprising administering to a patient in need thereof, an effective amount of a glucagon derivative according to any of embodiments 1-128, optionally in combination with one or more additional therapeutically active compounds.

182. A method for use in treating impaired glucose tolerance, comprising administering to a patient in need thereof, an effective amount of a glucagon derivative according to any of embodiments 1-128, optionally in combination with one or more additional therapeutically active compounds.

183. A method for use in treating dyslipidemia, comprising administering to a patient in need thereof, an effective amount of a glucagon derivative according to any of embodiments 1-128, optionally in combination with one or more additional therapeutically active compounds.

184. A method for use in treating coronary heart disease, comprising administering to a patient in need thereof, an effective amount of a glucagon derivative according to any of embodiments 1-128, optionally in combination with one or more additional therapeutically active compounds.

185. A method for use in treating hepatic steatosis, comprising administering to a patient in need thereof, an effective amount of a glucagon derivative according to any of embodiments 1-128, optionally in combination with one or more additional therapeutically active compounds.

Further embodiments of the invention relate to the following uses:

186. Use of a glucagon derivative according to any one of the embodiments 1-128, for the preparation of a medicament.

187. Use of a glucagon derivative according to any one of embodiments 1-128, for the preparation of a medicament for the treatment or prevention of hyperglycemia, type 2 diabetes, impaired glucose tolerance, type 1 diabetes and obesity.

188. Use of a glucagon derivative according to any one of the embodiments 1-128, for the preparation of a medicament for delaying or preventing disease progression in type 2 diabetes, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge-eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as x-ray, CT- and NMR-scanning.

Further embodiments of the invention relate to the following:

189. A glucagon derivative according to any of the previous embodiments, wherein said glucagon derivative has more than 70% recovery in the ThT fibrillation assay.

190. A glucagon derivative according to any of the previous embodiments, wherein said glucagon derivative has more than 90% recovery in the ThT fibrillation assay.

191. A glucagon derivative according to any of the previous embodiments, wherein said glucagon derivative has about 100% recovery in the ThT fibrillation assay.

192. A glucagon derivative according to any of the previous embodiments, wherein said glucagon derivative has more than 7 hours lag time in the ThT fibrillation assay.

193. A glucagon derivative according to any of the previous embodiments, wherein said glucagon derivative has more than 20 hours lag time in the ThT fibrillation assay.

194. A glucagon derivative according to any of the previous embodiments, wherein said glucagon derivative has 45 hours lag time or more in the ThT fibrillation assay.

195. A glucagon derivative according to any of the previous embodiments, wherein said ThT fibrillation assay is as described in Example 76 herein.

196. A glucagon derivative according to any of the previous embodiments, wherein said glucagon derivative has less than 14% degradation in the chemical stability assay.

197. A glucagon derivative according to any of the previous embodiments, wherein said glucagon derivative has less than 13% degradation in the chemical stability assay.

198. A glucagon derivative according to any of the previous embodiments, wherein said glucagon derivative has less than 12% degradation in the chemical stability assay.

199. A glucagon derivative according to any of the previous embodiments, wherein said glucagon derivative has less than 10% degradation in the chemical stability assay.

200. A glucagon derivative according to any of the previous embodiments, wherein said glucagon derivative has less than 9% degradation in the chemical stability assay.

201. A glucagon derivative according to any of the previous embodiments, wherein said glucagon derivative has less than 7% degradation in the chemical stability assay.

202. A glucagon derivative according to any of the previous embodiments, wherein said glucagon derivative has less than 5% degradation in the chemical stability assay.

203. A glucagon derivative according to any of the previous embodiments, wherein said glucagon derivative has less than 3% degradation in the chemical stability assay.

204. A glucagon derivative according to any of the previous embodiments, wherein said glucagon derivative has less than 2% degradation in the chemical stability assay.

205. A glucagon derivative according to any of the previous embodiments, wherein said chemical stability assay is as described in Example 79 herein.

206. A glucagon derivative according to any of the previous embodiments, wherein said glucagon derivative is as selective for glucagon receptor as for GLP-1 receptor.

207. A glucagon derivative as defined in any of the previous embodiments, optionally in combination with one or more additional therapeutically active compounds, for use in medicine.

208. The glucagon derivative according to embodiment 207, optionally in combination with one or more additional therapeutically active compounds, for i) treating obesity, preventing overweight, and/or reducing body weight, and/or ii) treatment or prevention of hyperglycemia, type 2 diabetes, impaired glucose tolerance, and/or type 1 diabetes.

FURTHER EMBODIMENTS OF THE INVENTION

The invention can further be described by the following further non-limiting embodiments:

1. A glucagon derivative comprising (formula I) (SEQ ID NO:2 and SEQ ID NO:3):

His-$X_2$-$X_3$-Gly-Thr-Phe-Thr-Ser-Asp-$X_{10}$-Ser-$X_{12}$-Tyr-Leu-$X_{15}$-$X_{16}$-$X_{17}$-$X_{18}$-Ala-$X_{20}$-$X_{21}$-Phe-Val-$X_{24}$-Trp-Leu-$X_{27}$-$X_{28}$-$X_{29}$-$X_{30}$ (formula I), wherein
$X_2$ is Aib, Acb or Acpr,
$X_3$ is Gln or His,
$X_{10}$ is Leu, Ile or Val,
$X_{12}$ is Lys or Arg,
$X_{15}$ is Asp or Glu
$X_{16}$ is Ser, Ala, Leu, Thr, Glu, Aib, Ile, Val or Lys,
$X_{17}$ is Arg or Lys,
$X_{18}$ is Arg, Ala or Lys,
$X_{20}$ is Gln, Arg, Glu, Aib or Lys,
$X_{21}$ is Asp, Glu or Lys,
$X_{24}$ is Gln, Ala, Arg, Glu, Aib or Lys,
$X_{27}$ is Met, Leu or Val,
$X_{28}$ is Asn, Ser, Thr, Gln, Ala, Gly, Glu or Lys,
$X_{29}$ is Thr, Gly, Ser, Gln, Ala, Glu or Lys,
$X_{30}$ is absent or is Lys,
and a substituent comprising a lipophilic moiety and three or more negatively charged moieties, wherein one of said negatively charged moieties is distal of a lipophilic moiety, and wherein said substituent is attached at the epsilon position of a Lys in one of the following amino acid positions of said glucagon derivative: 16, 17, 18, 20, 21, 24, 28, 29, and/or 30, wherein said glucagon derivative is a C-terminal amide or a pharmaceutically acceptable salt or prodrug thereof.

2. The glucagon derivative according to embodiment 1, wherein said glucagon derivative is a GLP-1 and glucagon receptor co-agonist.
3. The glucagon derivative according to embodiment 2, wherein $X_2$ is Aib.
4. The glucagon derivative according to embodiment 2, wherein $X_2$ is Acb.
5. The glucagon derivative according to embodiment 2, wherein $X_2$ is Acpr.
6. The glucagon derivative according to any one of the previous embodiments, wherein $X_3$ is Gln.
7. The glucagon derivative according to any one of the previous embodiments, wherein $X_3$ is His.
8. The glucagon derivative according to any one of the previous embodiments, wherein $X_{10}$ is Leu.
9. The glucagon derivative according to any one of the previous embodiments, wherein $X_{10}$ is Ile.
10. The glucagon derivative according to any one of the previous embodiments, wherein $X_{10}$ is Val.
11. The glucagon derivative according to any one of the previous embodiments, wherein $X_{12}$ is Lys.
12. The glucagon derivative according to any one of the previous embodiments, wherein $X_{12}$ is Arg.
13. The glucagon derivative according to any one of the previous embodiments, wherein $X_{15}$ is Asp.
14. The glucagon derivative according to any one of the previous embodiments, wherein $X_{15}$ is Glu.
15. The glucagon derivative according to any one of the previous embodiments, wherein $X_{16}$ is Ser, Ala, Leu, Thr, Glu or Lys.
16. The glucagon derivative according to embodiment 15, wherein $X_{16}$ is Ser.
17. The glucagon derivative according to embodiment 15, wherein $X_{16}$ is Ala, Leu, Thr, Glu or Lys.
18. The glucagon derivative according to embodiment 15, wherein $X_{16}$ is Ala.
19. The glucagon derivative according to embodiment 15, wherein $X_{16}$ is Leu.
20. The glucagon derivative according to embodiment 15, wherein $X_{16}$ is Thr.
21. The glucagon derivative according to embodiment 15, wherein $X_{16}$ is Glu.
22. The glucagon derivative according to embodiment 15, wherein $X_{16}$ is Lys.
23. The glucagon derivative according to any one of the previous embodiments, wherein $X_{17}$ is Arg.
24. The glucagon derivative according to any one of the previous embodiments, wherein $X_{17}$ is Lys.
25. The glucagon derivative according to any one of the previous embodiments, wherein $X_{18}$ is Arg or Ala.
26. The glucagon derivative according to embodiment 25, wherein $X_{18}$ is Arg.
27. The glucagon derivative according to embodiment 25, wherein $X_{18}$ is Ala.
28. The glucagon derivative according to any one of the previous embodiments, wherein $X_{20}$ is Gln, Arg, Glu or Lys.
29. The glucagon derivative according to embodiment 28, wherein $X_{20}$ is Gln.
30. The glucagon derivative according to embodiment 28, wherein $X_{20}$ is Arg.
31. The glucagon derivative according to embodiment 28, wherein $X_{20}$ is Glu.
32. The glucagon derivative according to embodiment 28, wherein $X_{20}$ is Lys.
33. The glucagon derivative according to any one of the previous embodiments, wherein $X_{21}$ is Asp.
34. The glucagon derivative according to any one of the previous embodiments, wherein $X_{21}$ is Glu or Lys.
35. The glucagon derivative according to embodiment 34, wherein $X_{21}$ is Glu.
36. The glucagon derivative according to embodiment 34, wherein $X_{21}$ is Lys.
37. The glucagon derivative according to any one of the previous embodiments, wherein $X_{24}$ is Gln, Ala, Arg or Lys.
38. The glucagon derivative according to embodiment 37, wherein $X_{24}$ is Gln.
39. The glucagon derivative according to embodiment 37, wherein $X_{24}$ is Ala.
40. The glucagon derivative according to embodiment 37, wherein $X_{24}$ is Arg.
41. The glucagon derivative according to embodiment 37, wherein $X_{24}$ is Lys.
42. The glucagon derivative according to any one of the previous embodiments, wherein $X_{27}$ is Met, Leu or Val.
43. The glucagon derivative according to embodiment 42, wherein $X_{27}$ is Met.
44. The glucagon derivative according to embodiment 42, wherein $X_{27}$ is Leu.
45. The glucagon derivative according to embodiment 42, wherein $X_{27}$ is Val.
46. The glucagon derivative according to any one of the previous embodiments, wherein $X_{28}$ is Asn, Ser or Lys.
47. The glucagon derivative according to embodiment 46, wherein $X_{28}$ is Asn.

48. The glucagon derivative according to embodiment 46, wherein $X_{28}$ is Ser.
49. The glucagon derivative according to embodiment 46, wherein $X_{28}$ is Lys.
50. The glucagon derivative according to any one of the previous embodiments, wherein $X_{29}$ is Thr, Gly or Lys.
51. The glucagon derivative according to embodiment 50, wherein $X_{29}$ is Gly or Lys.
52. The glucagon derivative according to embodiment 50, wherein $X_{29}$ is Thr.
53. The glucagon derivative according to embodiment 50, wherein $X_{29}$ is Gly.
54. The glucagon derivative according to embodiment 50, wherein $X_{29}$ is Lys.
55. The glucagon derivative according to any one of the previous embodiments, wherein $X_{30}$ is absent.
56. The glucagon derivative according to any one of embodiments 1-54, wherein $X_{30}$ is Lys.
57. The glucagon derivative according to any one of the previous embodiments, wherein $X_2$ represents Aib, $X_{20}$ represents Arg and $X_{21}$ represents Glu.
58. The glucagon derivative according to any of the previous embodiments, wherein the amino acid substitutions are:
 (i) 2Acb, 10L, 12R, 16L, 20R, 27L, 28K;
 (ii) 2Acb, 10L, 15E, 16E, 20R, 27L 28K;
 (iii) 2Acb, 10L, 15E, 17K, 20R, 21E, 27L, 28K;
 (iv) 2Acb, 10L, 15E, 20R, 21E, 27L, 28K;
 (v) 2Acb, 10L, 16L, 17K, 20R, 21E, 27L, 28K;
 (vi) 2Acb, 10L, 16L, 20R, 21E, 27L, 28K;
 (vii) 2Acb, 10L, 16L, 20R, 27L, 28K;
 (viii) 2Acb, 3H, 10L, 15E, 27L, 28K;
 (ix) 2Acpr, 10L, 15E, 20R, 21E, 27L, 28K;
 (x) 2Aib, 10L, 15E, 17K, 18A, 20R, 21E, 27L, 28K;
 (xi) 2Aib, 10L, 15E, 17K, 20R, 21E, 27L, 28K;
 (xii) 2Aib, 10L, 15E, 20R, 21E, 27L, 28K;
 (xiii) 2Aib, 10L, 16A, 20R, 21E, 27L, 28K;
 (xiv) 2Aib, 10L, 16E, 20K, 27L, 28S, 29K;
 (xv) 2Aib, 10L, 16K, 17K, 18A, 20R, 21E, 24A, 27L;
 (xvi) 2Aib, 10L, 16K, 17K, 21E, 27L;
 (xvii) 2Aib, 10L, 16K, 18A, 20R, 21E, 24A, 27L;
 (xviii) 2Aib, 10L, 16K, 20E, 27L, 28S, 29K;
 (xix) 2Aib, 10L, 16K, 20R, 21E, 24A, 27L;
 (xx) 2Aib, 10L, 16K, 20R, 21E, 27L;
 (xxi) 2Aib, 10L, 16K, 20R, 27L, 28S;
 (xxii) 2Aib, 10L, 16K, 21E, 27L;
 (xxiii) 2Aib, 10L, 16K, 21E, 27V, 28K, 29G;
 (xxiv) 2Aib, 10L, 16L, 17K, 20R, 21E, 27L, 28K;
 (xxv) 2Aib, 10L, 16L, 20R, 21E, 27L, 29K;
 (xxvi) 2Aib, 10L, 16T, 20K, 27L, 28S, 29K;
 (xxvii) 2Aib, 10L, 16T, 24R, 27L, 28S, 29K;
 (xxviii) 2Aib, 10L, 17K, 18A, 21E, 27L, 29K;
 (xxix) 2Aib, 10L, 18A, 20R, 21E, 27L, 29K;
 (xxx) 2Aib, 10L, 20R, 21E, 23I, 27L, 29K;
 (xxxi) 2Aib, 10L, 20R, 21E, 27L, 29K;
 (xxxii) 2Aib, 10L, 20R, 21K, 27L, 28S;
 (xxxiii) 2Aib, 10L, 20R, 24K, 27L, 28S;
 (xxxiv) 2Aib, 10L, 20R, 27L, 28K;
 (xxxv) 2Aib, 10L, 20R, 27L, 28S, 29K;
 (xxxvi) 2Aib, 10L, 20R, 27L, 28S, 30K;
 (xxxvii) 2Aib, 3H, 10L, 15E, 16K, 20R, 21E, 24A, 27L, 28S;
 (xxxviii) 2Aib, 3H, 10L, 15E, 17K, 20R, 21E, 27L, 28K;
 (xxxix) 2Aib, 3H, 10L, 15E, 20R, 21E, 24A, 27L, 28K;
 (xl) 2Aib, 3H, 10L, 15E, 20R, 21E, 27L, 28K or
 (xli) 2Aib, 3H, 10L, 15E, 20R, 27L, 28K.
59. The glucagon derivative according to any one of the previous embodiments, wherein said substituent has formula II:

$$Z_1\text{-}Z_2\text{-}Z_3\text{-}Z_4\text{-}Z_5\text{-}Z_6\text{-}Z_7\text{-}Z_8\text{-}Z_9\text{-}Z_{10}\text{-} \qquad [II]$$

wherein,
$Z_1$ represents a structure according to the formula IIa;

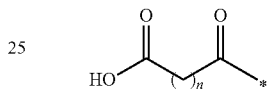

wherein n in formula IIa is 6-20,
the symbol * in formula $Z_1$ represents the attachment point to the nitrogen of the neighbouring group and wherein $Z_2$, $Z_3$, $Z_4$, $Z_5$, $Z_6$, $Z_7$, $Z_8$, $Z_9$, $Z_{10}$ individually are represented by the following amino acids;
Glu, γGlu, Gly, Ser, Ala, Thr, Ado or are absent,
wherein at least two of residues $Z_2$ to $Z_{10}$ are present, wherein said substituent is attached at the epsilon position of a Lys of formula I and wherein $Z_1\text{-}Z_2\text{-}Z_3\text{-}Z_4\text{-}Z_5\text{-}Z_6\text{-}Z_7\text{-}Z_8\text{-}Z_9\text{-}Z_{10}$ together contains at least three negative charges.
60. The glucagon derivative according to embodiment 59, wherein n in Z1 of formula II is 14, 16 or 18.
61. The glucagon derivative according to embodiment 59, wherein n in Z1 of formula II is 14.
62. The glucagon derivative according to embodiment 59, wherein n in Z1 of formula II is 16.
63. The glucagon derivative according to embodiment 59, wherein n in Z1 of formula II is 18.
64. The glucagon derivative according to any one of the previous embodiments, wherein said substituent represents a structure according to one of the formulas and wherein * indicates the point of attachment to the nitrogen at the epsilon position of a Lys of formula I:

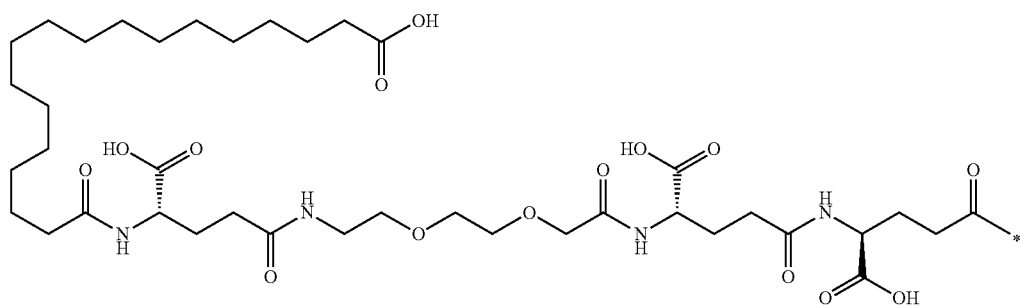

-continued
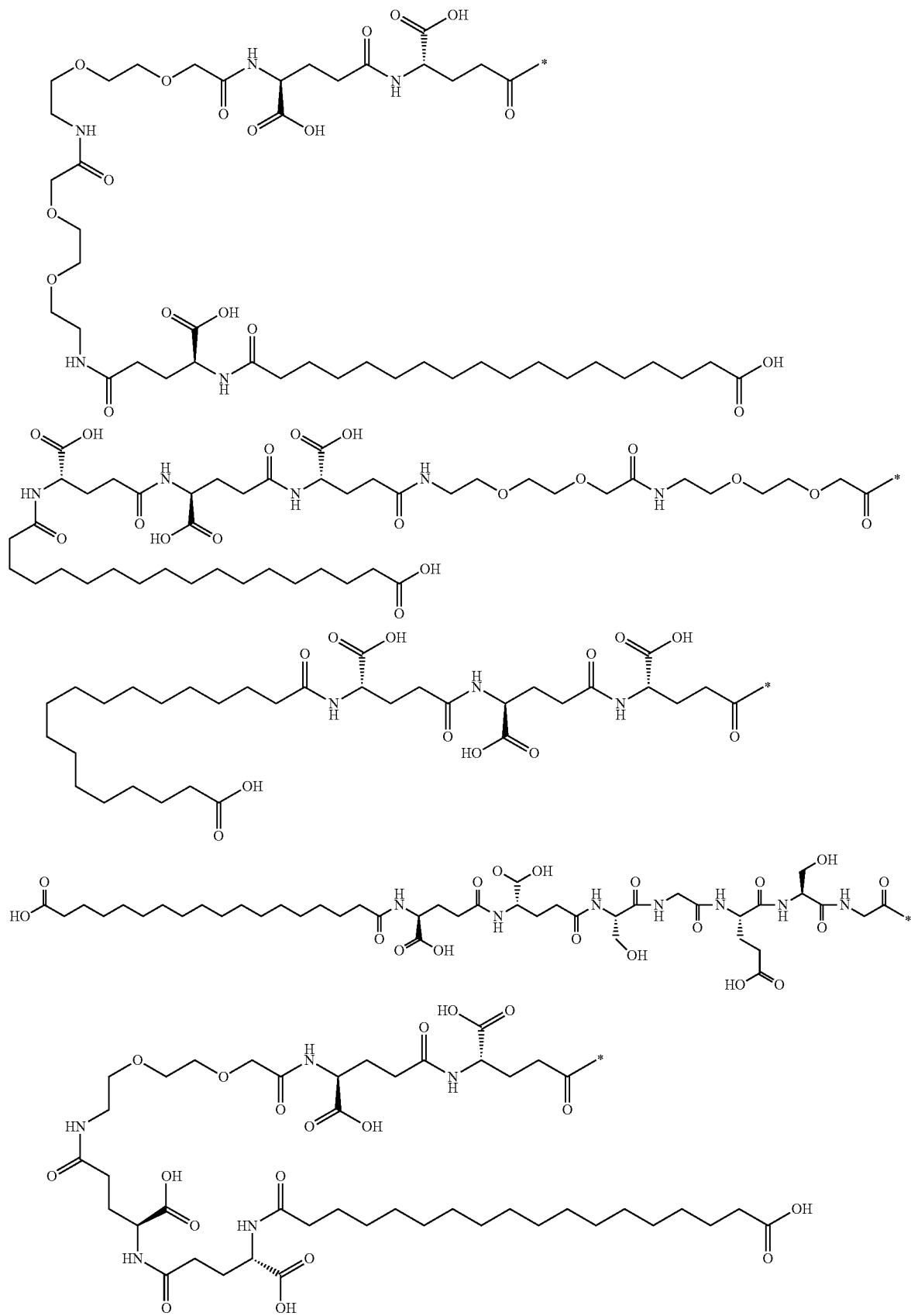

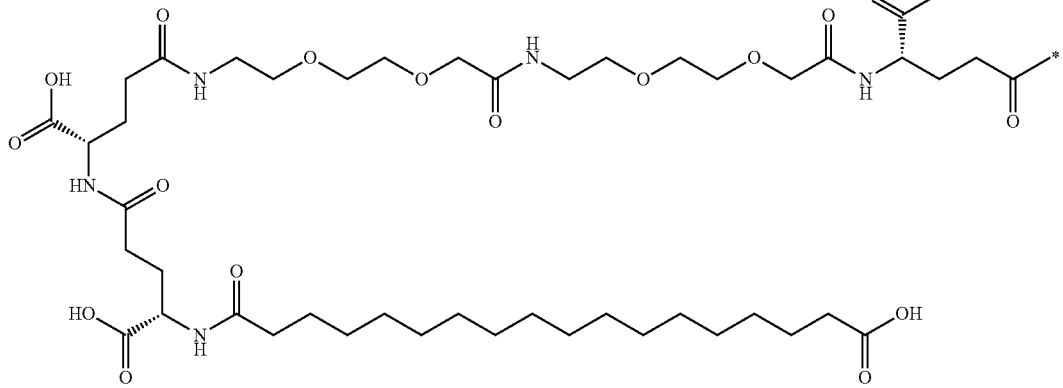

-continued

65. The glucagon derivative according to any of the previous embodiments, wherein said substituent binds non-covalently to albumin.
66. The glucagon derivative according to any of the previous embodiments, wherein said substituent is negatively charged at physiological pH.
67. The glucagon derivative according to any one of the previous embodiments, selected from the group consisting of: Chem.1; Chem.2; Chem.3; Chem.4; Chem.5; Chem.6; Chem.7; Chem.8; Chem.9; Chem.10; Chem.11; Chem.12; Chem.13; Chem.14; Chem.15; Chem.16; Chem.17; Chem.18; Chem.19; Chem.20; Chem.21; Chem.22; Chem.23; Chem.24; Chem.25; Chem.26; Chem.27; Chem.28; Chem.29; Chem.30; Chem.31; Chem.32; Chem.33; Chem.34; Chem.35; Chem.36; Chem.37; Chem.38; Chem.39; Chem.40; Chem.41; Chem.42; Chem.43; Chem.44; Chem.45; Chem.46; Chem.47; Chem.48; Chem.49 and Chem.50.

Further embodiments of the invention relate to:

68. The glucagon derivative according to any of the previous embodiments, wherein said glucagon derivative is a DPPIV protected compound.
69. The glucagon derivative according to any of the previous embodiments, wherein said glucagon derivative is DPPIV stabilised.
70. The glucagon derivative according to any of the previous embodiments, wherein said glucagon derivative is an agonist of the glucagon receptor.
71. The glucagon derivative according to any of the previous embodiments, wherein said glucagon derivative is an agonist of the glucagon receptor, with an EC50<10 nM.
72. The glucagon derivative according to any of the previous embodiments, wherein said glucagon derivative is an agonist of the glucagon receptor, with an EC50<1 nM.
73. The glucagon derivative according to any of the previous embodiments, wherein said glucagon derivative is an agonist of the glucagon receptor, with an EC50<100 pM.
74. The glucagon derivative according to any of the previous embodiments, wherein said glucagon derivative is an agonist of the glucagon receptor, with an EC50<10 pM.
75. The glucagon derivative according to any of the previous embodiments, wherein said glucagon derivative is an agonist of the GLP-1 receptor.
76. The glucagon derivative according to any of the previous embodiments, wherein said glucagon derivative is an agonist of the GLP-1 receptor, with an EC50<100 pM.
77. The glucagon derivative according to any of the previous embodiments, wherein said glucagon derivative is an agonist of the GLP-1 receptor, with an EC50<50 pM.
78. The glucagon derivative according to any of the previous embodiments, wherein said glucagon derivative is an agonist of the GLP-1 receptor, with an EC50<10 pM.
79. The glucagon derivative according to any of the previous embodiments, wherein said glucagon derivative is an agonist of the GLP-1 receptor with an EC50<100 pM and an EC50<1 nM on the glucagon receptor.
80. The glucagon derivative according to any of the previous embodiments, wherein said glucagon derivative is an agonist of the GLP-1 receptor with an EC50<50 pM and an EC50<1 nM on the glucagon receptor.
81. The glucagon derivative according to any of the previous embodiments, wherein said glucagon derivative is an agonist of the GLP-1 receptor with an EC50<10 pM and an EC50<1 nM on the glucagon receptor.
82. The glucagon derivative according to any of the previous embodiments, wherein said glucagon derivative is an agonist of the GLP-1 receptor with an EC50<50 pM and an EC50<100 pM on the glucagon receptor.
83. The glucagon derivative according to any of the previous embodiments, wherein said glucagon derivative is an agonist of the GLP-1 receptor with an EC50<10 pM and an EC50<100 pM on the glucagon receptor.
84. The glucagon derivative according to any of the previous embodiments, wherein said glucagon derivative is an agonist of the GLP-1 receptor with an EC50<10 pM and an EC50<50 pM on the glucagon receptor.
85. The glucagon derivative according to any of the previous embodiments, wherein said glucagon derivative is an agonist of the GLP-1 receptor with an EC50<10 pM and an EC50<10 pM on the glucagon receptor.
86. The glucagon derivative according to any of the previous embodiments, wherein said glucagon derivative is a GLP-1/glucagon co-agonist with an EC50 on the GLP-1 receptor<the EC50 on the glucagon receptor.

Further embodiments of the invention relate to combinations:

87. The glucagon derivative according to any one of the previous embodiments, in combination with a GLP-1 compound or with an insulin compound.
88. The glucagon derivative according to any one of the previous embodiments, in combination with a GLP-1 compound.
89. The glucagon derivative according to any one of the previous embodiments, in combination with an insulin compound.
90. The glucagon derivative according to embodiment 88, wherein the GLP-1 compound is selected from the group consisting of:

N$^{\epsilon 26}$-((S)-4-Carboxy-4-hexadecanoylamino-butyryl) [Arg34]GLP-1-(7-37):

(compound G1)

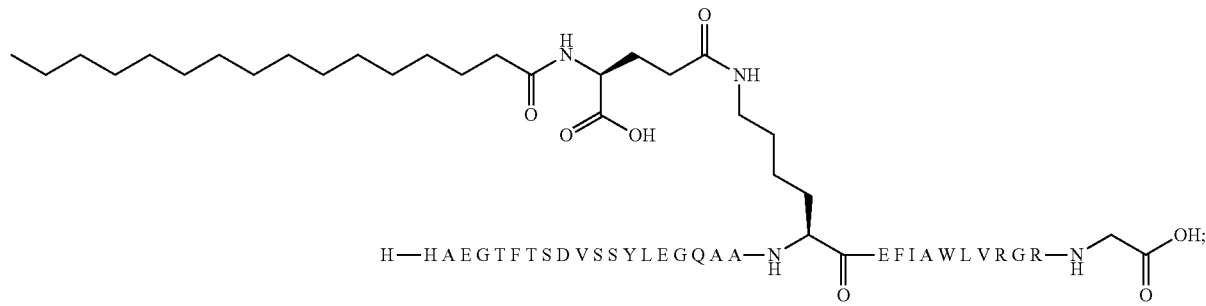

N$^{\epsilon 37}$-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl] [DesaminoHis7,Glu22,Arg26,Arg34,Lys37]GLP-1-(7-37):

(compound G2)

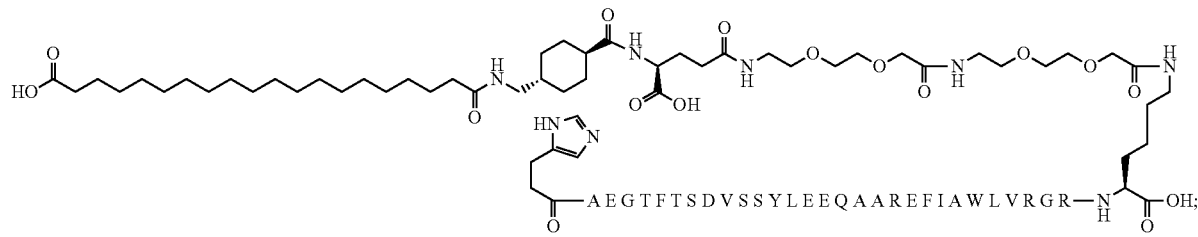

N$^{\epsilon 26}$-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8,Arg34]GLP-1-(7-37):

(compound G3)

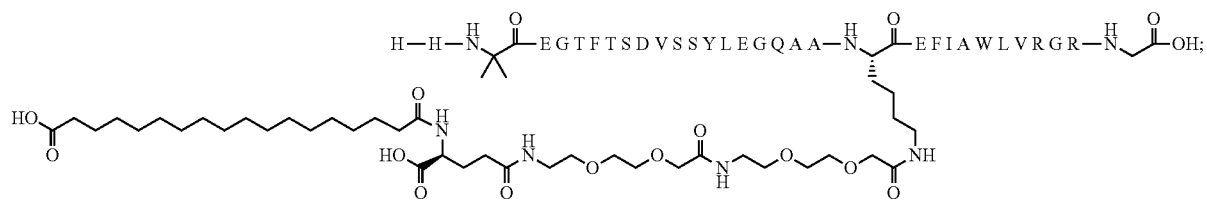

N$^{\epsilon 37}$-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

(compound G4)

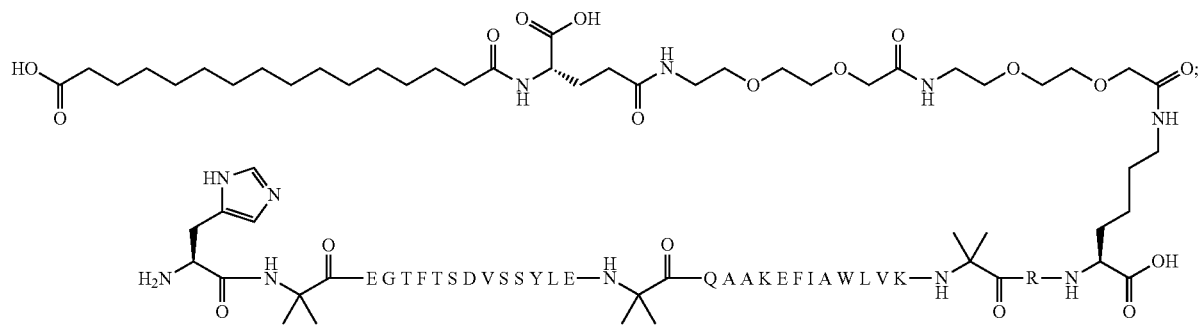

and their pharmaceutically acceptable salts, amides, alkyls, or esters.

91. The glucagon derivative according to embodiment 89, wherein the insulin compound is: N-epsilon-B29-[(S)-4-Carboxy-4-(15-carboxypentadecanoylamino)butyryl] desB30 human insulin Other embodiments of the present relates to pharmaceutical compositions:

92. A pharmaceutical composition comprising a glucagon derivative according to any one of embodiments 1-91.

93. The pharmaceutical composition according to embodiment 92, further comprising one or more additional therapeutically active compounds or substances.

94. The pharmaceutical composition according to embodiment 93, wherein said additional therapeutically active compound is a GLP-1 compound or an insulin compound.

95. The pharmaceutical composition according to embodiment 94, wherein said additional therapeutically active compound is a GLP-1 compound.

(compound G5)

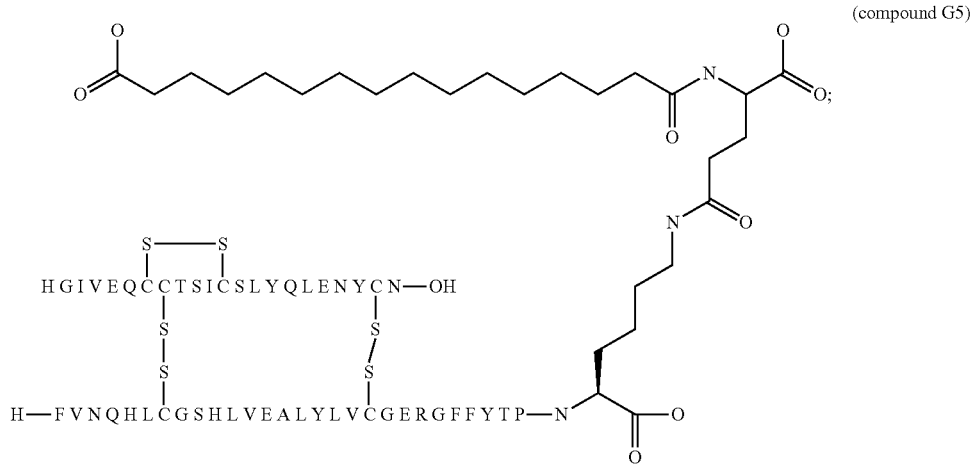

96. The pharmaceutical composition according to embodiment 94, wherein said additional therapeutically active compound is an insulin compound.

97. The pharmaceutical composition according to embodiment 95, wherein the GLP-1 compound is selected from the group consisting of:

N-epsilon26-((S)-4-Carboxy-4-hexadecanoylamino-butyryl)[Arg34]GLP-1-(7-37):

(compound G1)

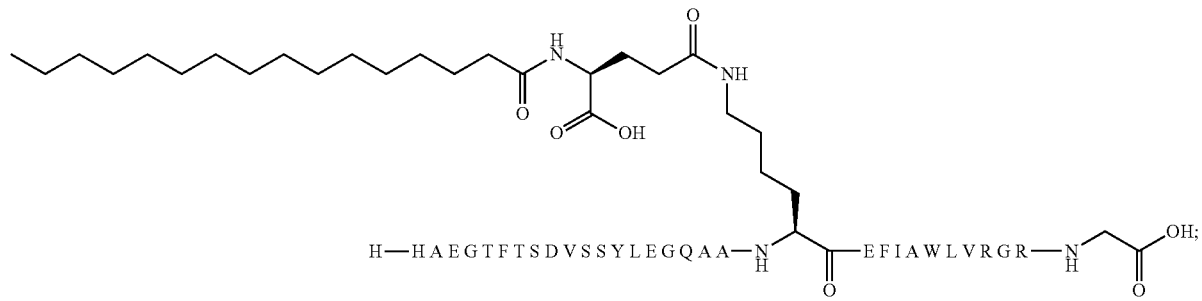

N-epsilon37-[2-(2-{2-[2-(2-{2-[(S)-4-Carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl][DesaminoHis7,Glu22,Arg26,Arg34,Lys37]GLP-1-(7-37]:

(compound G2)

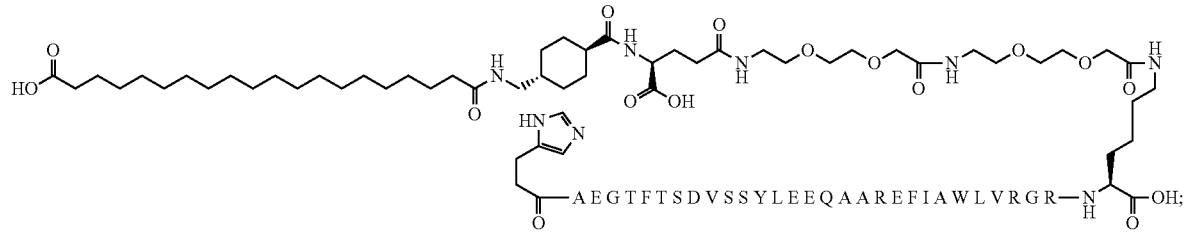

N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl] [Aib8,Arg34]GLP-1-(7-37):

(compound G3)

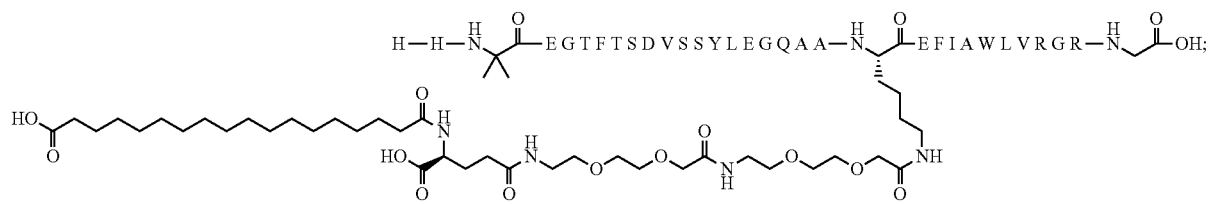

N-epsilon37-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)-acetyl] [Aib8,22,35,Lys37]GLP-1-(7-37):

(compound G4)

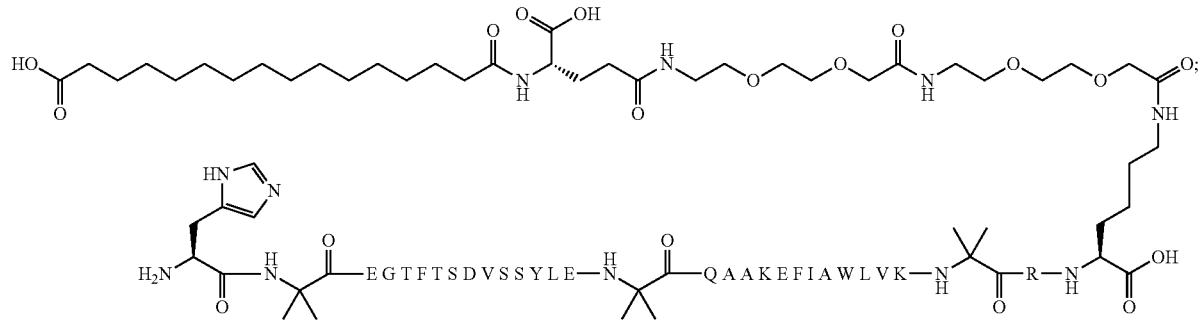

and their pharmaceutically acceptable salts, amides, alkyls, or esters.

98. The pharmaceutical composition according to embodiment 96, wherein the insulin compound is: N-epsilon-B29-[(S)-4-Carboxy-4-(15-carboxypentadecanoylamino)butyryl] desB30 human insulin

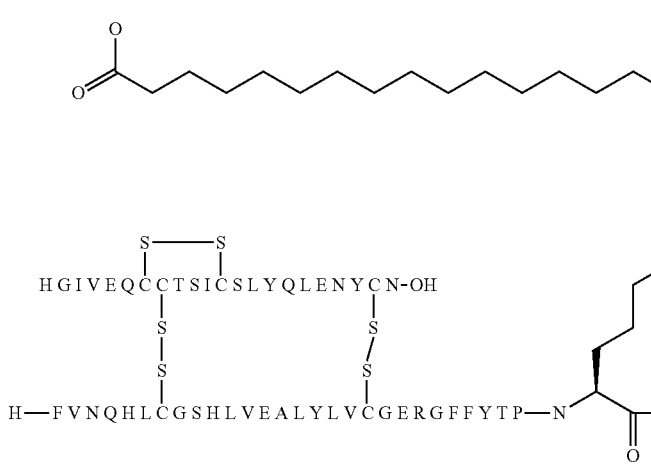

(compound G5)

99. The pharmaceutical composition according to any one of embodiments 92-98, in unit dosage form comprising from about 0.01 mg to about 1000 mg, such as from about 0.1 mg to about 500 mg, from about 0.5 mg to about 5 mg, e.g. from about 0.5 mg to about 200 mg, of a glucagon derivative according to any of embodiments 1-91.

100. The pharmaceutical composition according to any one of embodiments 92-99, which is suited for parenteral administration.

101. The glucagon derivative according to any one of embodiments 1-91, for use in therapy.

Further embodiments of the invention relate to the following:

102. The glucagon derivative according to any of embodiments 1-91, optionally in combination with one or more additional therapeutically active compounds, for use in treatment or prevention of hyperglycemia, type 2 diabetes, impaired glucose tolerance, type 1 diabetes and obesity.

103. The glucagon derivative according to any of embodiments 1-91, optionally in combination with one or more additional therapeutically active compounds, for use in delaying or preventing disease progression in type 2 diabetes.

104. The glucagon derivative according to any of embodiments 1-91, optionally in combination with one or more additional therapeutically active compounds, for use treating obesity or preventing overweight.

105. The glucagon derivative according to any of embodiments 1-91, optionally in combination with one or more additional therapeutically active compounds, for use in for decreasing food intake.

106. The glucagon derivative according to any of embodiments 1-91, optionally in combination with one or more additional therapeutically active compounds, for use in increasing energy expenditure.

107. The glucagon derivative according to any of embodiments 1-91, optionally in combination with one or more additional therapeutically active compounds, for use in reducing body weight.

108. The glucagon derivative according to any of embodiments 1-91, optionally in combination with one or more additional therapeutically active compounds, for use in delaying the progression from impaired glucose tolerance (IGT) to type 2 diabetes.

109. The glucagon derivative according to any of embodiments 1-91, optionally in combination with one or more additional therapeutically active compounds, for use in delaying the progression from type 2 diabetes to insulin-requiring diabetes.

110. The glucagon derivative according to any of embodiments 1-91, optionally in combination with one or more additional therapeutically active compounds, for use regulating appetite.

111. The glucagon derivative according to any of embodiments 1-91, optionally in combination with one or more additional therapeutically active compounds, for use inducing satiety.

112. The glucagon derivative according to any of embodiments 1-91, optionally in combination with one or more additional therapeutically active compounds, for use in preventing weight regain after successful weight loss.

113. The glucagon derivative according to any of embodiments 1-91, optionally in combination with one or more additional therapeutically active compounds, for use in treating a disease or state related to overweight or obesity.

114. The glucagon derivative according to any of embodiments 1-91, optionally in combination with one or more additional therapeutically active compounds, for use in treating bulimia.

115. The glucagon derivative according to any of embodiments 1-91, optionally in combination with one or more additional therapeutically active compounds, for use in treating binge-eating.

116. The glucagon derivative according to any of embodiments 1-91, optionally in combination with one or more additional therapeutically active compounds, for use in treating atherosclerosis.

117. The glucagon derivative according to any of embodiments 1-91, optionally in combination with one or more additional therapeutically active compounds, for use in treating hypertension.

118. The glucagon derivative according to any of embodiments 1-91, optionally in combination with one or more additional therapeutically active compounds, for use in treating type 2 diabetes.

119. The glucagon derivative according to any of embodiments 1-91, optionally in combination with one or more additional therapeutically active compounds, for use in treating impaired glucose tolerance.

120. The glucagon derivative according to any of embodiments 1-91, optionally in combination with one or more additional therapeutically active compounds, for use in treating dyslipidemia.

121. The glucagon derivative according to any of embodiments 1-91, optionally in combination with one or more additional therapeutically active compounds, for use in treating coronary heart disease.

122. The glucagon derivative according to any of embodiments 1-91, optionally in combination with one or more additional therapeutically active compounds, for use in treating hepatic steatosis.

Further embodiments of the invention relate to the following methods:

123. A method for treating or preventing hypoglycemia, type 2 diabetes, impaired glucose tolerance, type 1 diabetes and obesity, comprising administering to a patient in need thereof, an effective amount of a glucagon derivative according to any of embodiments 1-91, optionally in combination with one or more additional therapeutically active compounds.

124. A method for delaying or preventing disease progression in type 2 diabetes, comprising administering to a patient in need thereof, an effective amount of a glucagon derivative according to any of embodiments 1-91, optionally in combination with one or more additional therapeutically active compounds.

125. A method for treating obesity or preventing overweight, comprising administering to a patient in need thereof, an effective amount of a glucagon derivative according to any of embodiments 1-91, optionally in combination with one or more additional therapeutically active compounds.

126. A method for decreasing food intake, comprising administering to a patient in need thereof, an effective amount of a glucagon derivative according to any of embodiments 1-91, optionally in combination with one or more additional therapeutically active compounds.

127. A method for use in increasing energy expenditure, comprising administering to a patient in need thereof, an effective amount of a glucagon derivative according to any of embodiments 1-91, optionally in combination with one or more additional therapeutically active compounds.

128. A method for use in reducing body weight, comprising administering to a patient in need thereof, an effective amount of a glucagon derivative according to any of embodiments 1-91, optionally in combination with one or more additional therapeutically active compounds.

129. A method for use in delaying the progression from impaired glucose tolerance (IGT) to type 2 diabetes, comprising administering to a patient in need thereof, an effective amount of a glucagon derivative according to any of embodiments 1-91, optionally in combination with one or more additional therapeutically active compounds.

130. A method for use in delaying the progression from type 2 diabetes to insulin-requiring diabetes, comprising administering to a patient in need thereof, an effective amount of a glucagon derivative according to any of embodiments 1-91, optionally in combination with one or more additional therapeutically active compounds.

131. A method for use in regulating appetite, comprising administering to a patient in need thereof, an effective amount of a glucagon derivative according to any of embodiments 1-91, optionally in combination with one or more additional therapeutically active compounds.

132. A method for use in inducing satiety, comprising administering to a patient in need thereof, an effective amount of a glucagon derivative according to any of embodiments 1-91, optionally in combination with one or more additional therapeutically active compounds.

133. A method for use in preventing weight regain after successful weight loss, comprising administering to a patient in need thereof, an effective amount of a glucagon derivative according to any of embodiments 1-91, optionally in combination with one or more additional therapeutically active compounds.

134. A method for use in treating a disease or state related to overweight or obesity, comprising administering to a patient in need thereof, an effective amount of a glucagon derivative according to any of embodiments 1-91, optionally in combination with one or more additional therapeutically active compounds.

135. A method for use in treating bulimia, comprising administering to a patient in need thereof, an effective amount of a glucagon derivative according to any of embodiments 1-91, optionally in combination with one or more additional therapeutically active compounds.

136. A method for use in treating binge-eating, comprising administering to a patient in need thereof, an effective amount of a glucagon derivative according to any of embodiments 1-91, optionally in combination with one or more additional therapeutically active compounds.

137. A method for use in treating atherosclerosis, comprising administering to a patient in need thereof, an effective amount of a glucagon derivative according to any of embodiments 1-91, optionally in combination with one or more additional therapeutically active compounds.

138. A method for use in treating hypertension, comprising administering to a patient in need thereof, an effective amount of a glucagon derivative according to any of embodiments 1-91, optionally in combination with one or more additional therapeutically active compounds.

139. A method for use in treating type 2 diabetes, comprising administering to a patient in need thereof, an effective amount of a glucagon derivative according to any of embodiments 1-91, optionally in combination with one or more additional therapeutically active compounds.

140. A method for use in treating impaired glucose tolerance, comprising administering to a patient in need thereof, an effective amount of a glucagon derivative according to any of embodiments 1-91, optionally in combination with one or more additional therapeutically active compounds.

141. A method for use in treating dyslipidemia, comprising administering to a patient in need thereof, an effective amount of a glucagon derivative according to any of embodiments 1-91, optionally in combination with one or more additional therapeutically active compounds.

142. A method for use in treating coronary heart disease, comprising administering to a patient in need thereof, an effective amount of a glucagon derivative according to any of embodiments 1-91, optionally in combination with one or more additional therapeutically active compounds.

143. A method for use in treating hepatic steatosis, comprising administering to a patient in need thereof, an effective amount of a glucagon derivative according to any of embodiments 1-91, optionally in combination with one or more additional therapeutically active compounds.

Further embodiments of the invention relate to the following uses:

144. Use of a glucagon derivative according to any one of the embodiments 1-91, for the preparation of a medicament.

145. Use of a glucagon derivative according to any one of embodiments 1-91, for the preparation of a medicament for the treatment or prevention of hyperglycemia, type 2 diabetes, impaired glucose tolerance, type 1 diabetes and obesity.

146. Use of a glucagon derivative according to any one of the embodiments 1-91, for the preparation of a medicament for delaying or preventing disease progression in type 2 diabetes, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes; regulating appetite; inducing satiety; preventing weight regain after successful weight loss; treating a disease or state related to overweight or obesity; treating bulimia; treating binge-eating; treating atherosclerosis, hypertension, type 2 diabetes, IGT, dyslipidemia, coronary heart disease, hepatic steatosis, treatment of beta-blocker poisoning, use for inhibition of the motility of the gastrointestinal tract, useful in connection with investigations of the gastrointestinal tract using techniques such as x-ray, CT- and NMR-scanning.

Further embodiments of the invention relate to the following:

147. A glucagon derivative according to any of the previous embodiments, wherein said glucagon derivative has more than 70% recovery in the ThT fibrillation assay.
148. A glucagon derivative according to any of the previous embodiments, wherein said glucagon derivative has more than 90% recovery in the ThT fibrillation assay.
149. A glucagon derivative according to any of the previous embodiments, wherein said glucagon derivative has about 100% recovery in the ThT fibrillation assay.
150. A glucagon derivative according to any of the previous embodiments, wherein said glucagon derivative has more than 7 hours lag time in the ThT fibrillation assay.
151. A glucagon derivative according to any of the previous embodiments, wherein said glucagon derivative has more than 20 hours lag time in the ThT fibrillation assay.
152. A glucagon derivative according to any of the previous embodiments, wherein said glucagon derivative has 45 hours lag time or more in the ThT fibrillation assay.
153. A glucagon derivative according to any of the previous embodiments, wherein said glucagon derivative has less than 14% degradation in the chemical stability assay.
154. A glucagon derivative according to any of the previous embodiments, wherein said glucagon derivative has less than 13% degradation in the chemical stability assay.
155. A glucagon derivative according to any of the previous embodiments, wherein said glucagon derivative has less than 12% degradation in the chemical stability assay.
156. A glucagon derivative according to any of the previous embodiments, wherein said glucagon derivative has less than 10% degradation in the chemical stability assay.
157. A glucagon derivative according to any of the previous embodiments, wherein said glucagon derivative has less than 9% degradation in the chemical stability assay.
158. A glucagon derivative according to any of the previous embodiments, wherein said glucagon derivative has less than 7% degradation in the chemical stability assay.
159. A glucagon derivative according to any of the previous embodiments, wherein said glucagon derivative has less than 5% degradation in the chemical stability assay.
160. A glucagon derivative according to any of the previous embodiments, wherein said glucagon derivative has less than 3% degradation in the chemical stability assay.
161. A glucagon derivative according to any of the previous embodiments, wherein said glucagon derivative has less than 2% degradation in the chemical stability assay.
162. A glucagon derivative according to any of the previous embodiments, wherein said glucagon derivative is as selective for glucagon receptor as for GLP-1 receptor.

EXAMPLES

The invention is further illustrated with reference to the following examples, which are not intended to be in any way limiting to the scope of the invention as claimed.

List of Abbreviations
  BOC: tert-Butyl oxycarbonyl
  DCM: Dichloromethane
  DIC: Diisopropylcarbodiimide
  Fmoc: 9-fluorenylmethyloxycarbonyl
  HOAt: 1-hydroxy-7-azabenzotriazole
  HPLC: High Performance Liquid Chromatography
  LCMS: Liquid Chromatography Mass Spectroscopy
  MeCN: Acetonitrile
  Mtt: 4-Methyltrityl
  NMP: N-methyl pyrrolidone
  Oxyma Pure: Cyano-hydroxyimino-acetic acid ethyl ester
  RP: Reverse Phase
  RP-HPLC: Reverse Phase High Performance Liquid Chromatography
  RT: Room Temperature
  Rt: Retention time
  SPPS: Solid Phase Peptide Synthesis
  TFA: Trifluoroacetic acid
  TIPS: Triisopropylsilane
  UPLC: Ultra Performance Liquid Chromatography General Methods This section relates to methods for synthesising resin bound peptide (SPPS methods, including methods for de-protection of amino acids, methods for cleaving the peptide from the resin, and for its purification), as well as methods for detecting and characterising the resulting peptide (LCMS and UPLC methods).

The compounds in Examples 1-73 herein were prepared, purified and analysed according to the procedures described below.

SPPS General Methods

The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(BOC)-OH, Fmoc-Met-OH, Fmoc-Phe-OH, Fmoc-Pro-OH, Fmoc-Ser(tBu)-OH, Fmoc-Thr(tBu)-OH, Fmoc-Trp(BOC)-OH, Fmoc-Tyr(tBu)-OH, Fmoc-Val-OH and Fmoc-Lys(Mtt)-OH supplied from e.g. Anaspec, Bachem, Iris Biotech, or NovabioChem.

The N-terminal amino acid is Boc protected at the alpha amino group (e.g. Boc-His(Trt)-OH for peptides with His at the N-terminus).

The introduction of the substituent on the epsilon-nitrogen of a lysine was achieved using a Lysine protected with Mtt (Fmoc-Lys(Mtt)-OH). Suitably protected building blocks such as Fmoc-8-amino-3,6-dioxaoctanoic acid, Fmoc-Glu-OtBu as well as the protected standard amino acids described above were used for the introduction of the substituent. Introduction of the fatty acid moiety was achieved using octadecanedioic acid mono-tert-butyl-ester.

SPPS was performed on a Prelude Solid Phase Peptide Synthesizer from Protein Technologies (Tucson, Ariz. 85714 U.S.A.) at 100 or 250-pmol scale using six fold excess of Fmoc-amino acids (300 mM in NMP with 300 mM HOAt or Oxyma Pure®) relative to resin loading. H-Rink Amide-ChemMatrix resin (loading e.g. 0.52 nmol/g) or Rink Amide AM polystyrene resin (Novabiochem, loading e.g. 0.62 mmol/g) was used as the solid support. Fmoc-deprotection was performed using 20% piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH as well as the building blocks leading to the substituent were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min). The Mtt group was removed by washing the resin with HFIP/DCM (75:25) (2×2 min), washed with DCM and suspending the resin in HFIP/DCM (75:25)(2×20 min) and subsequently washed in sequence with Piperidine/NMP (20:80), DCM (1×), NMP(1×), DCM(1×), NMP(1×).

Cleavage from the Resin

After synthesis the resin was washed with DCM, and the peptide was cleaved from the resin by a 2-3 hour treatment with TFA/TIS/water (95/2.5/2.5) followed by precipitation with diethylether. The precipitate was washed with diethylether.

Purification and Quantification

The crude peptide was dissolved in a suitable mixture of water and MeCN such as water/MeCN (4:1) and purified by reversed-phase preparative HPLC (Waters Deltaprep 4000 or Gilson) on a column containing C18-silica gel. Elution was performed with an increasing gradient of MeCN in water containing 0.1% TFA. Relevant fractions are checked by analytical HPLC or UPLC. Fractions containing the pure target peptide were pooled and concentrated under reduced pressure. The resulting solution was analyzed (HPLC, LCMS) and the product is quantified using a chemiluminescent nitrogen specific HPLC detector (Antek 8060 HPLC-CLND) or by measuring UV-absorption at 280 nm. The product is dispensed into glass vials. The vials are capped with Millipore glassfibre prefilters. Freeze-drying affords the peptide trifluoroacetate as a white solid.

Methods for Detection and Characterization

LCMS Methods

Method: LCMS 4

LCMS_4 was performed on a setup consisting of Waters Acquity UPLC system and LCT Premier XE mass spectrometer from Micromass.

Eluents:
A: 0.1% Formic acid in water
B: 0.1% Formic acid in acetonitrile

The analysis was performed at RT by injecting an appropriate volume of the sample (preferably 2-100) onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% acetonitrile during 4.0 min (alternatively 8.0 min) at 0.4 ml/min. Detection: 214 nm (derivative/analogue output from TUV (Tunable UV detector)) MS ionisation mode: API-ES Scan: 100-2000 amu (alternatively 500-2000 amu), step 0.1 amu.

Method: LCMS01v01

| System | LC-system: Waters Acquity UPLC |
| --- | --- |
| | Column: Waters Acquity UPLC BEH, C-18, 1.7 μm, 2.1 mm × 50 mm |
| | Detector: Waters (Micromass) LCT Premier XE |
| Detector setup | Ionisation method: ES |
| | Scanning range: 500-2000 amu |
| | Operating mode: W mode |
| | positive/negative: positive mode |
| | Cone Voltage: 50 V |
| | Scantime 1 |
| | Interscandelay: 0.0 |

-continued

| Conditions | Linear gradient: 5% to 95% B |
| --- | --- |
| | Gradient run-time: 4.0 minutes |
| | Total run-time: 7.0 minutes |
| | Flow rate: 0.4 ml/min |
| | Column temperature: 40° C. |
| Eluents | Solvent A: 99.90% MQ-water, 0.1% formic acid |
| | Solvent B: 99.90% acetonitrile, 0.1% formic acid |
| | Solvent C: NA |
| Results specification and validation | Mass found is the mass found of the compound M/z found is the molecular ion found ((M + z)/z) of the compound Calculated Mass is the molecular weight of the desired compound Calculated M/z is the molecular weight (M + z)/z of the desired compound |

Method: LCMS13v01

| System | System: Waters Acquity UPLC SQD 2000 |
| --- | --- |
| | Column: Acquity UPLC BEH 1.7μ C18 100 Å 2.1 × 100 mm |
| | Detector: UV: PDA, SQD 2000 |
| Detector setup | Ionisation method: ES+ |
| | Scanning range: 500-2000 |
| | Cone Voltage: 60 V |
| | Scantime 0.5 |
| Conditions | Linear gradient: 10% to 90% B |
| | Gradient run-time: 3 min |
| | Total run-time: 4 min |
| | Flow rate: 0.3 ml/min |
| | Column temperature: 40° C. |
| | PDA: 210-400 nm |
| Eluents | Solvent A: 99.90% H2O, 0.1% TFA |
| | Solvent B: 99.90% CH3CN, 0.1% TFA |
| | Solvent C: NA |
| Results specification and validation | Mass found is the mass found of the compound M/z found is the molecular ion found ((M + z)/z) of the compound Calculated Mass is the molecular weight of the desired compound Calculated M/z is the molecular weight (M + z)/z of the desired compound |

UPLC Methods

Method: 04 A9 1

The RP-analysis was performed using a Waters UPLC system fitted with a dual band detector. UV detections at 214 nm and 254 nm were collected using an ACQUITY UPLC BEH Shield RP18, C18, 1.7 um, 2.1 mm×150 mm column, 60° C.

The UPLC system was connected to two eluent reservoirs containing:

A: 200 mM Na2SO4+20 mM Na2HPO4+20 mM NaH2PO4 in 90% H2O/10% CH3CN, pH 7.2;
B: 70% CH3CN, 30% H2O.

The following step gradient was used: 90% A, 10% B to 80% A, 20% B over 3 minutes, 80% A, 20% B to 50% A, 50% B over 17 minutes at a flow-rate of 0.40 ml/min.

Method: 09 B2 1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:

A: 99.95% H2O, 0.05% TFA;
B: 99.95% CH3CN, 0.05% TFA.

The following linear gradient was used: 95% A, 5% B to 40% A, 60% B over 16 minutes at a flow-rate of 0.40 ml/min.

Method: 09 B4 1

The RP-analysis was performed using a Waters UPLC system fitted with a dual band detector. UV detections at 214 nm and 254 nm were collected using an ACQUITY UPLC BEH130, C18, 130 Å, 1.7 um, 2.1 mm×150 mm column, 40° C.

The UPLC system was connected to two eluent reservoirs containing:
A: 99.95% H2O, 0.05% TFA;
B: 99.95% CH3CN, 0.05% TFA.

The following linear gradient was used: 95% A, 5% B to 5% A, 95% B over 16 minutes at a flow-rate of 0.40 ml/min.

Method: 10 B4 1

The RP-analysis was performed using a Waters UPLC system fitted with a dual band detector. UV detections at 214 nm and 254 nm were collected using an ACQUITY UPLC BEHC18, 1.7 um, 2.1 mm×150 mm column, 40° C.

The UPLC system was connected to two eluent reservoirs containing:
A: 99.95% H2O, 0.05% TFA;
B: 99.95% CH3CN, 0.05% TFA.

The following linear gradient was used: 95% A, 5% B to 5% A, 95% B over 16 minutes at a flow-rate of 0.40 ml/min.

Method: UPLC01 v01

| System | System: Waters Acquity UPLC system<br>Column: ACQUITY UPLC BEH C18, 1.7 um,<br>2.1 mm × 150 mm column |
|---|---|
| Detector setup | Detectors: Waters Acquity TUV Detector<br>214 nm and 254 nm |
| Conditions | Linear gradient: 5% to 60% B<br>Gradient run-time: 16 minutes<br>Total run-time: 20 minutes |
| | Flow rate: 0.40 ml/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

Method: UPLC02v01

| System | System: Waters Acquity UPLC system<br>Column: ACQUITY UPLC BEH C18, 1.7 um,<br>2.1 mm × 150 mm column |
|---|---|
| Detector setup | Detectors: Waters Acquity TUV Detector<br>214 nm and 254 nm |
| Conditions | Linear gradient: 5% to 95% B<br>Gradient run-time: 16 minutes<br>Flow rate: 0.40 ml/min fixed<br>Column temperature: 40° C. |
| Eluents | Solvent A: 99.95% Water, 0.05% Trifluoroacetic acid<br>Solvent B: 99.95% Acetonitrile, 0.05% Trifluoroacetic acid |

Example 1

$N^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Leu27,Ser28]-Glucagon amide

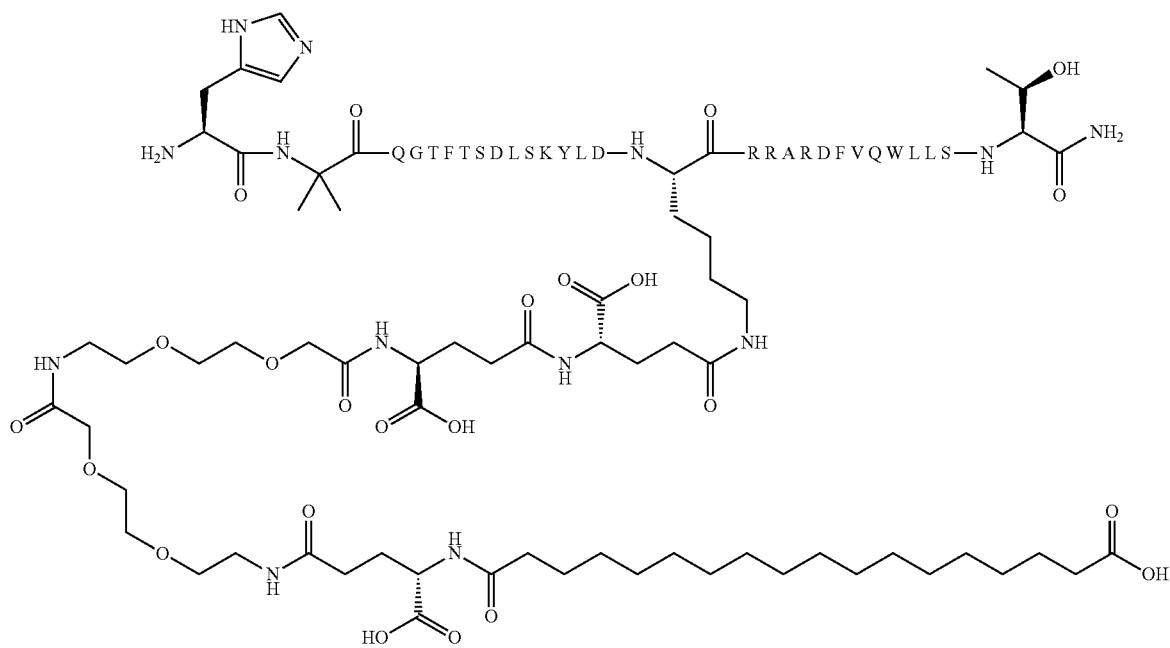

UPLC Method: 04_A9_1; Rt=15.8 min
LC-MS Method: LCMS_4; Rt=2.3 min; m/3: 1429; m/4: 1108; m/5: 887
UPLC Method: 10_B4_1; Rt=8.2 min Example 2

N$^{\epsilon 21}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys21,Leu27,Ser28]-Glucagon amide

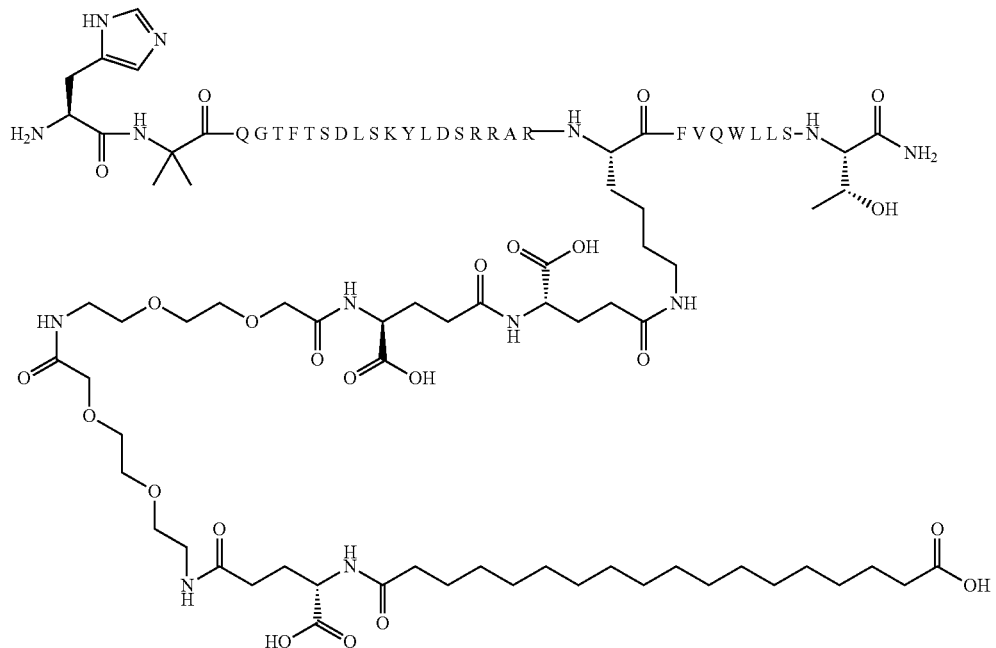

UPLC Method: 10_B4_1; Rt=8.18 min
UPLC Method: 04_A9_1; Rt=17.4 min
LC-MS Method: LCMS_4; Rt=2.29; m/3:1468; m/4: 1101; m/5: 885

Example 3

N$^{\epsilon 24}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Lys24,Leu24,Ser28]-Glucagon amide

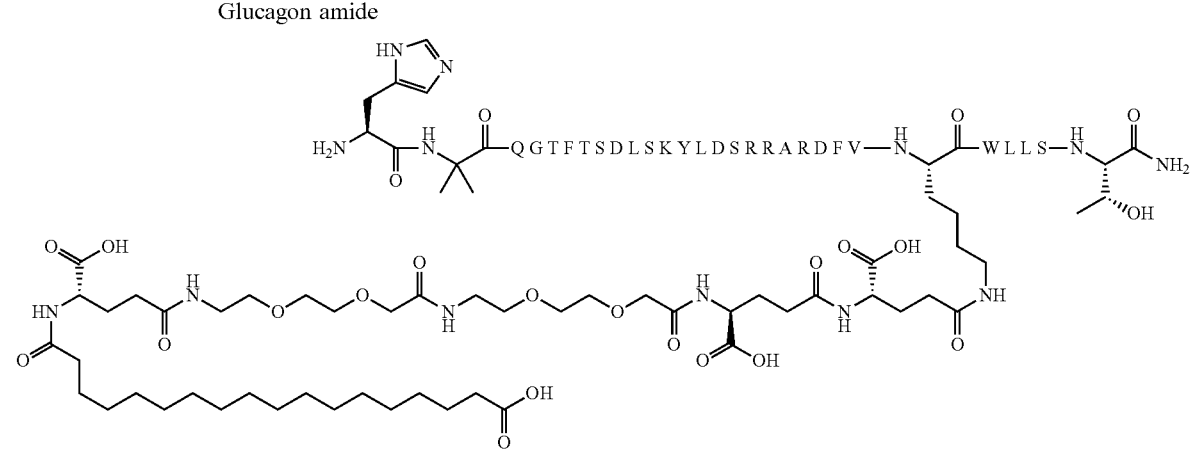

UPLC Method: 09_B4_1; Rt=8.4 min
UPLC Method: 04_A9_1; Rt=17.4 min
LC-MS Method: LCMS_4; Rt=2.4 min; m/3:1464; m/4: 1098; m/5: 879

Example 4

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Lys28]-Glucagon amide

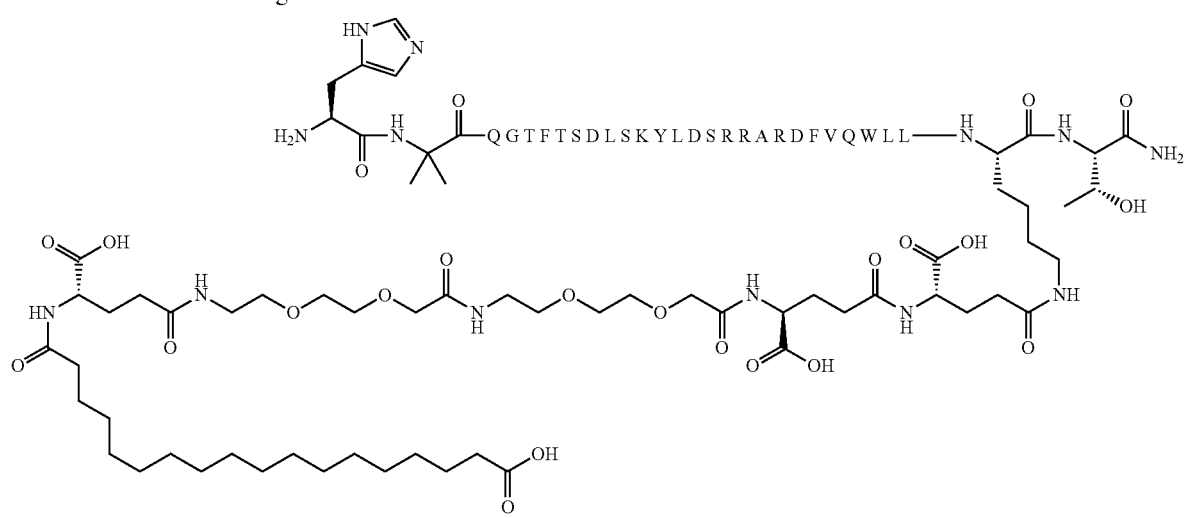

UPLC Method: 10_B4_1; Rt=8.2 min
UPLC Method: 04_A9_1; Rt=16.2 min
LC-MS Method: LCMS_4; Rt=2.3 min; m/3:1477; m/4: 1108; m/5: 887

Example 5

N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Leu27,Ser28,Lys29]-Glucagon amide

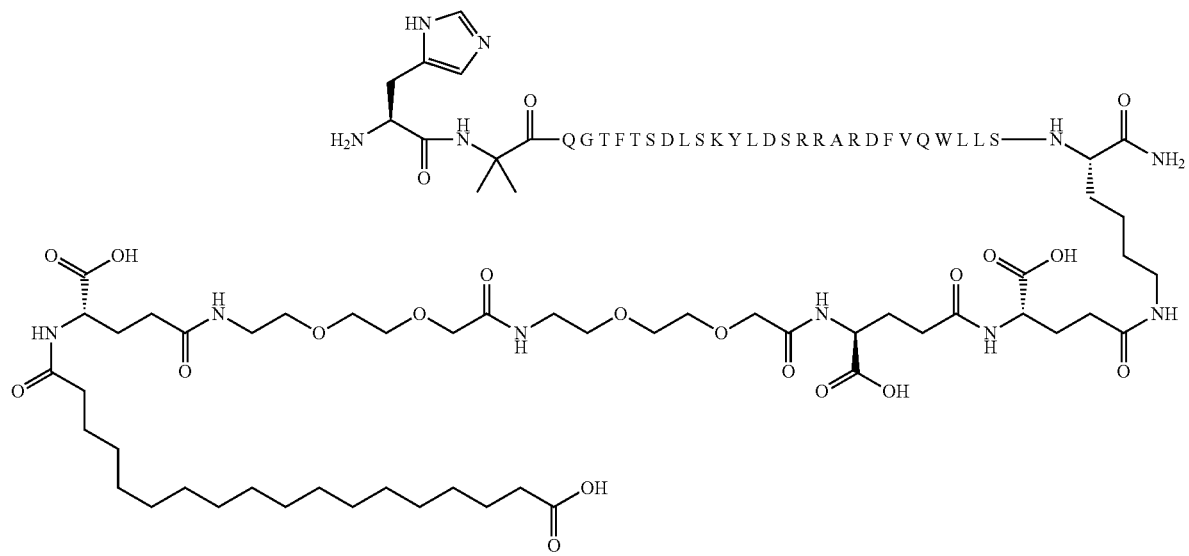

UPLC Method: 10_B4_1; Rt=8.3 min
UPLC Method: 04_A9_1; Rt=15.2 min
LC-MS Method: LCMS_4; Rt=2.3 min; m/3:1473; m/4: 1105; m/5: 884

Example 6

N$^\alpha$-([Aib2,Leu10,Arg20,Leu27,Ser28]-Glucagonyl)-N{Epsilon}[(4S)-4-carboxy-4-[[(4S)-4-carboxy-4-[[2-[2-[2-[[2-[2-[2-[[(4S)-4-carboxy-4-(17-carboxy-heptadecanoylamino)butanoyl]amino]ethoxy]ethoxy]acetyl]amino]ethoxy]ethoxy]acetyl]amino]butanoyl]amino]butanoyl]Lys amide

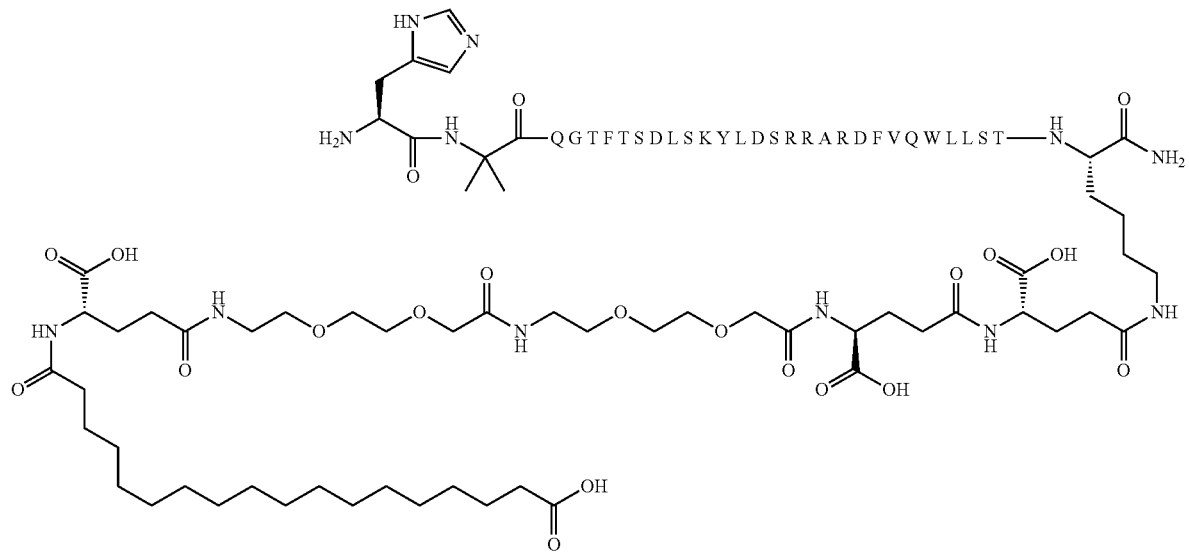

UPLC Method: 10_B4_1; Rt=8.0 min
UPLC Method: 04_A9_1; Rt=14.2 min
LC-MS Method: LCMS_4; Rt=2.3 min; m/4:1130; m/5: 904; m/6: 754

Example 7

N$^{\epsilon 16}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Glu21Leu27]-Glucagon amide

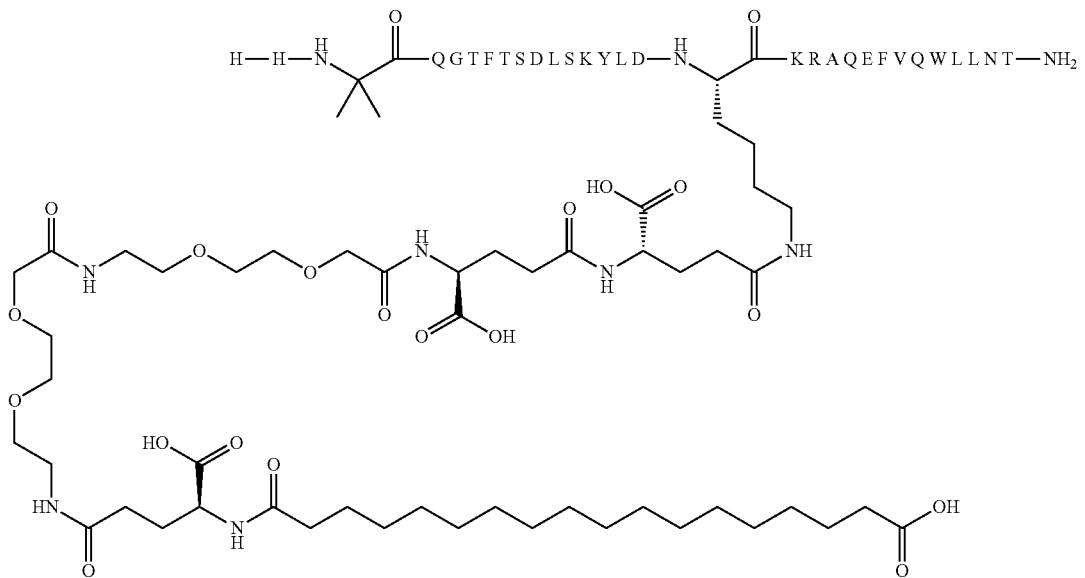

UPLC Method: 10_B4_1; Rt=8.3 min
UPLC Method: 04_A9_1; Rt=15.3 min
LC-MS Method: LCMS_4; Rt=2.3 min, m/3: 1472; m/4: 1104; m/5:883

Example 8

N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys17,Ala18,Glu21,Leu27,Lys29]-Glucagon amide

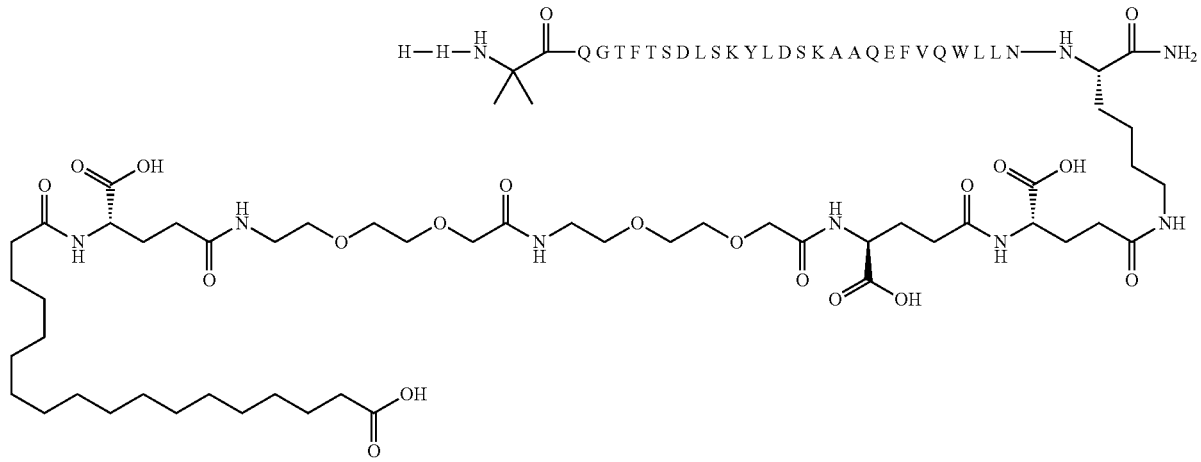

UPLC Method: 10_B4_1; Rt=8.9 min
UPLC Method: 04_A9_1; Rt=16.2 min
LC-MS Method: LCMS_4; Rt=2.3 min, m/3: 1439; m/4: 1079; m/5: 863

Example 9

N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala18,Arg20,Glu21,Leu27,Lys29]-Glucagon amide

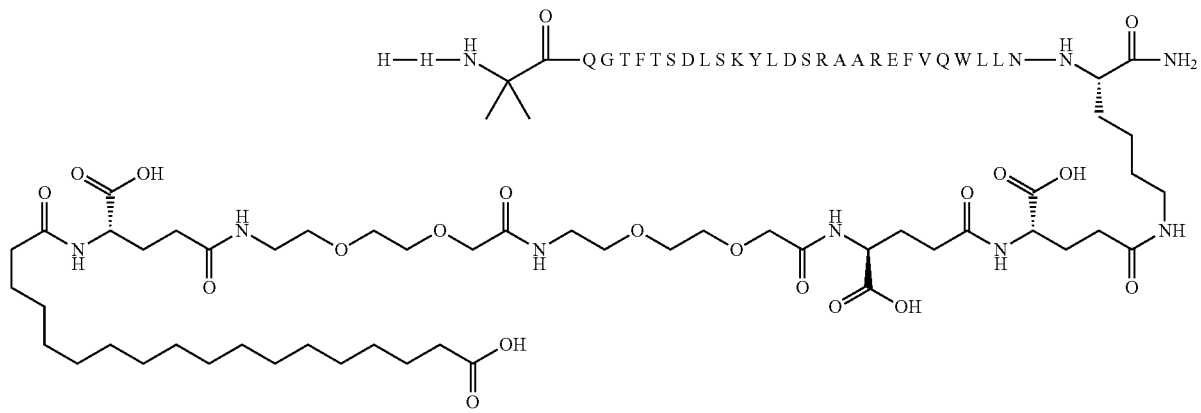

UPLC Method: 10_B4_1; Rt=8.6 min
UPLC Method: 04_A9_1; Rt=16.7 min
LC-MS Method: LCMS_4; Rt=2.3 min, m/3: 1458; m/4: 1093; m/5: 875

Example 10

$N^{\epsilon16}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Glu21,Leu27]-Glucagon amide

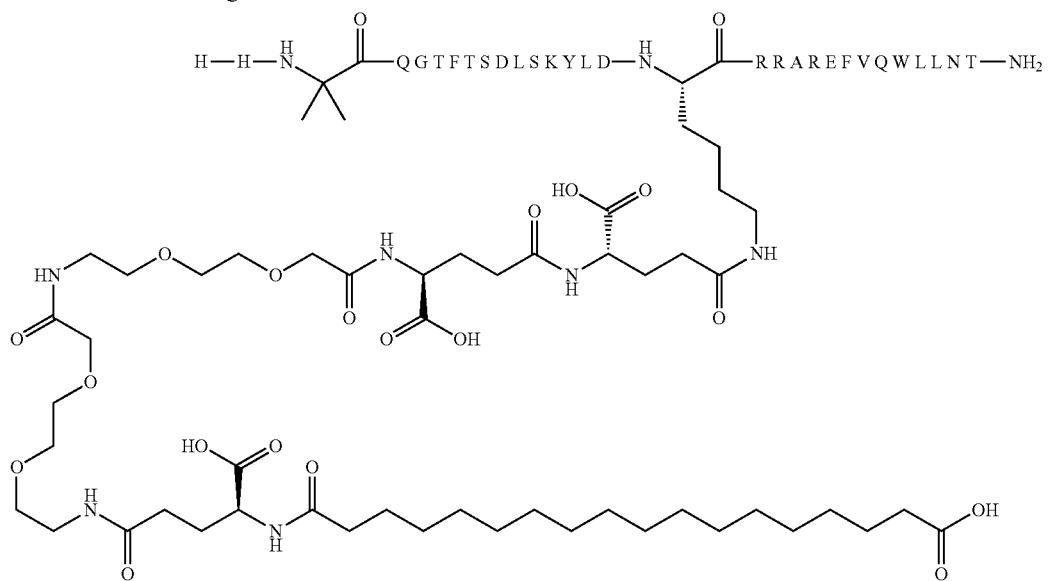

UPLC Method: 10_B4_1; Rt=8.0 min
UPLC Method: 04_A9_1; Rt=16.6 min
LC-MS Method: LCMS_4; Rt=2.2 min, m/3: 1491; m/4: 1118; m/5: 895

Example 11

$N^{\epsilon29}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Thr16,Lys20,Leu27,Ser28,Lys29]-Glucagon amide

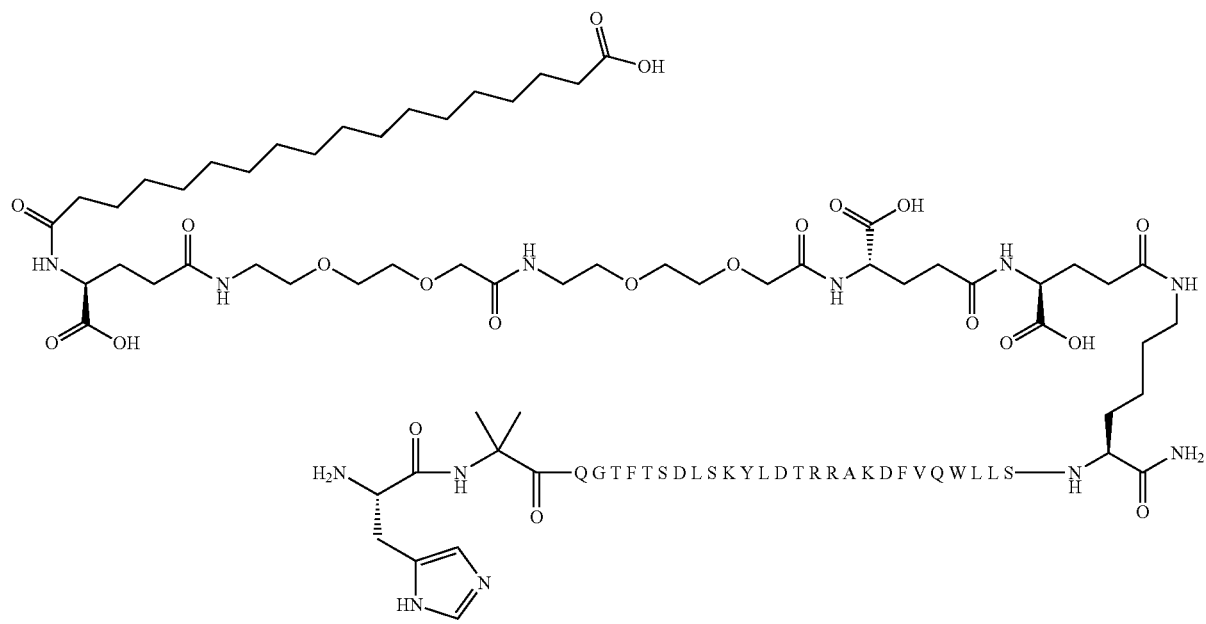

UPLC Method: 09_B2_1; Rt=12.5 min
LC-MS Method: LCMS_4; Rt=2.28 min; m/6: 734

Example 12

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys29]-Glucagon amide

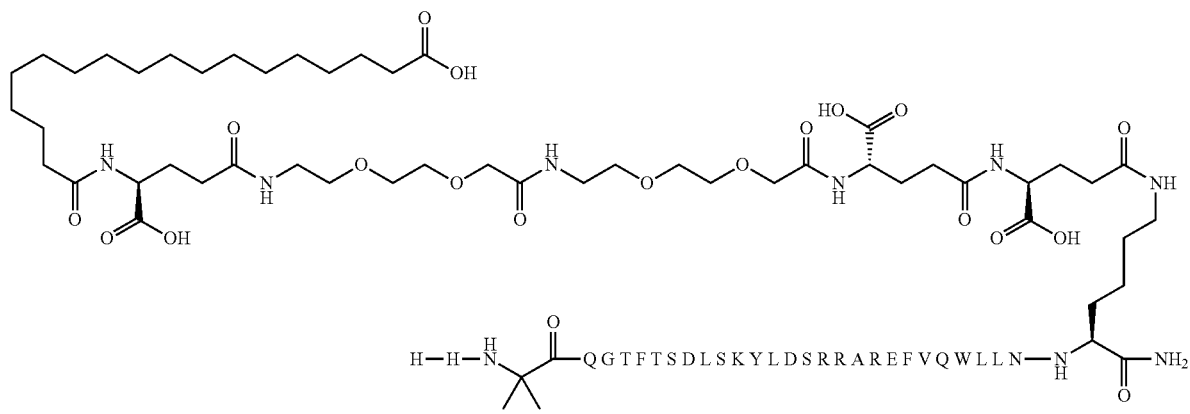

UPLC Method: 09_B4_1; Rt=8.0 min
UPLC Method: 04_A9_1; Rt=14.7 min
LC-MS Method: LCMS_4; Rt=2.2 min, m/3: 1486; m/4: 1115; m/5: 892

Example 13

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu16,Lys20,Leu27,Ser28,Lys29]-Glucagon amide

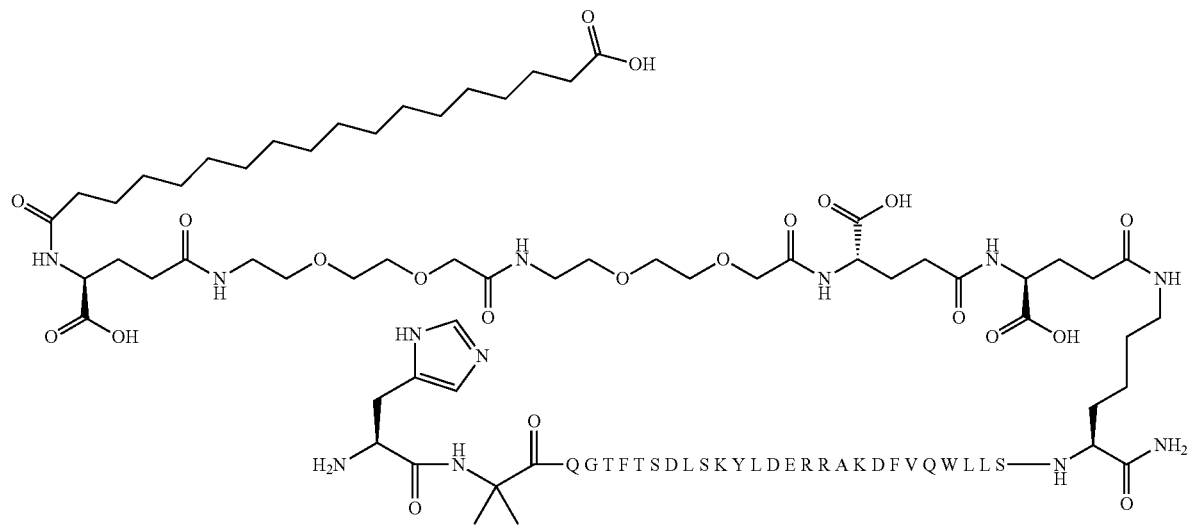

UPLC Method: 09_B2_1; Rt=12.4 min
LC-MS Method: LCMS_4; Rt=2.2 min; m/6: 739

Example 14

N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Glu20,Leu27,Ser28,Lys29]-Glucagon amide

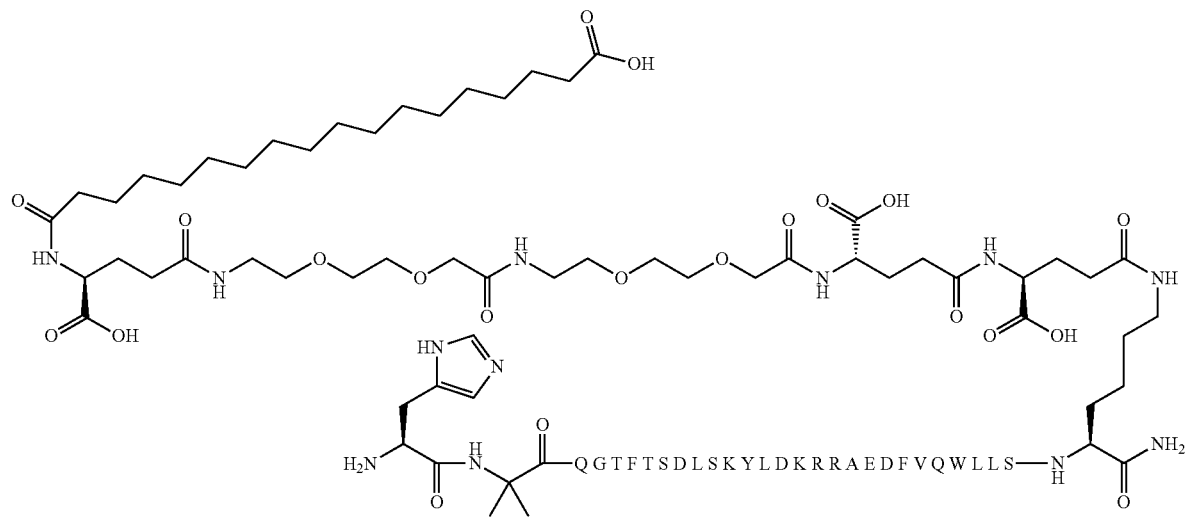

UPLC Method: 09_B2_1; Rt=12.5 min
UPLC Method: 04_A9_1; Rt=13.4 min
LC-MS Method: LCMS_4; Rt=2.3 min; m/3: 1108; m/4: 1006; m/5: 886

Example 15

N$^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Thr16,Arg24,Leu27,Ser28,Lys29]-Glucagonamide

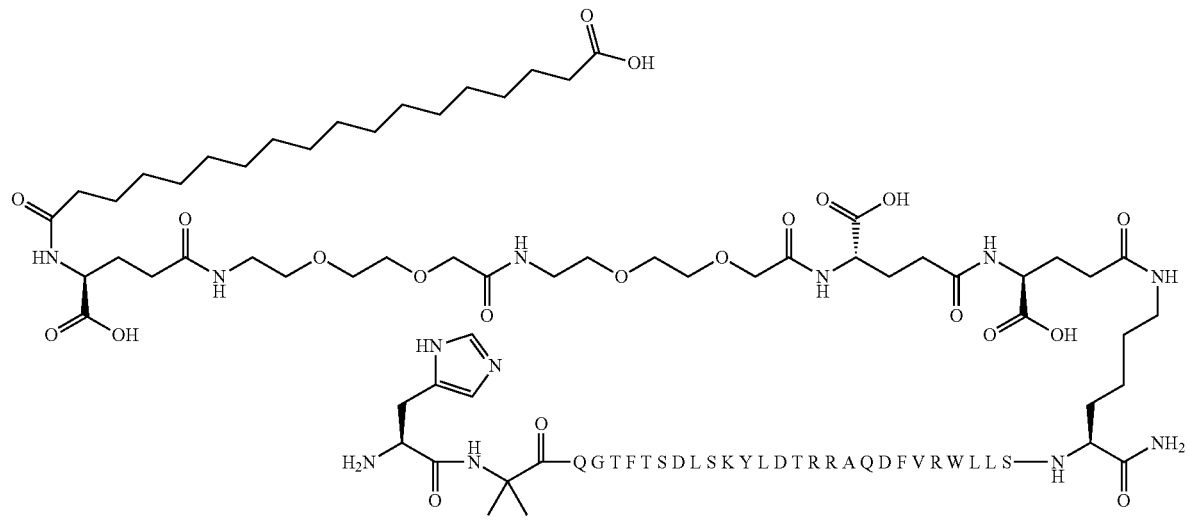

UPLC Method: 09_B2_1; Rt=12.4 min
UPLC Method: 04_A9_1; Rt=16.1 min
LC-MS Method: LCMS_4; Rt=2.3 min; m/3: 1477; m/4: 1108; m/5: 886

Example 16

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Glu16,Arg20,Leu27,Lys28]-Glucagon amide

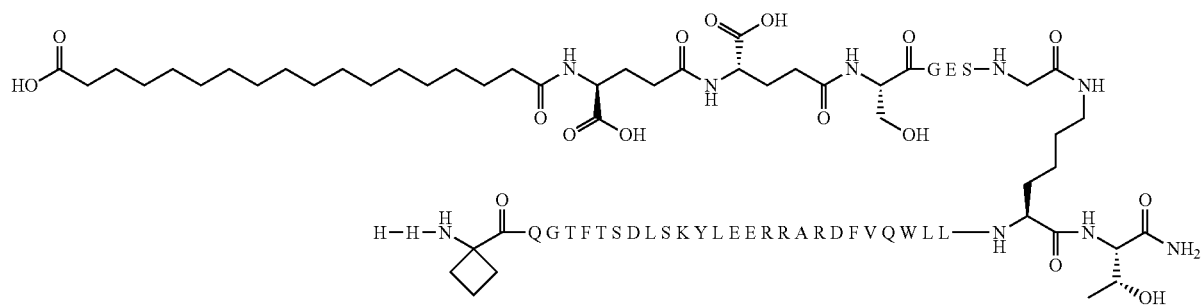

UPLC Method: UPLC02v01: Rt=7.9 min
LC-MS Method: LCMS01v01: Rt=2.1 min; m/3: 1499; m/4: 1124; m/5: 900

Example 17

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Lys17,Ala18,Arg20,Glu21,Ala24,Leu27]-Glucagon amide

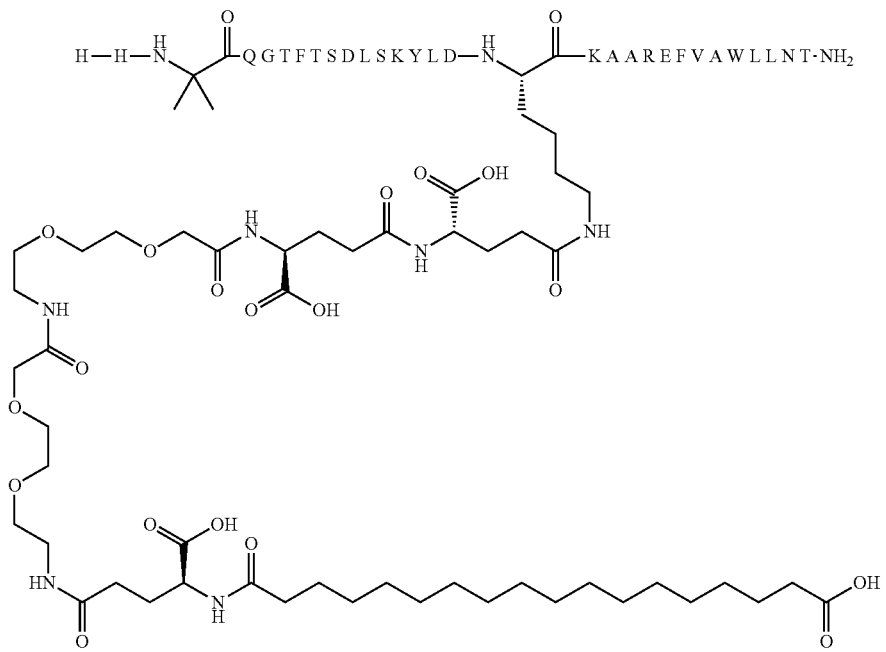

UPLC Method: 09_B4_1; Rt=8.5 min
UPLC Method: 04_A9_1; Rt=15.6 min
LC-MS Method: LCMS_4; Rt=2.3 min, m/3: 1433; m/4: 1075; m/5: 860

Example 18

$N^{\epsilon 29}$[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Lys16,Ala18,Arg20,Glu21,Ala24,Leu27]-Glucagon amide

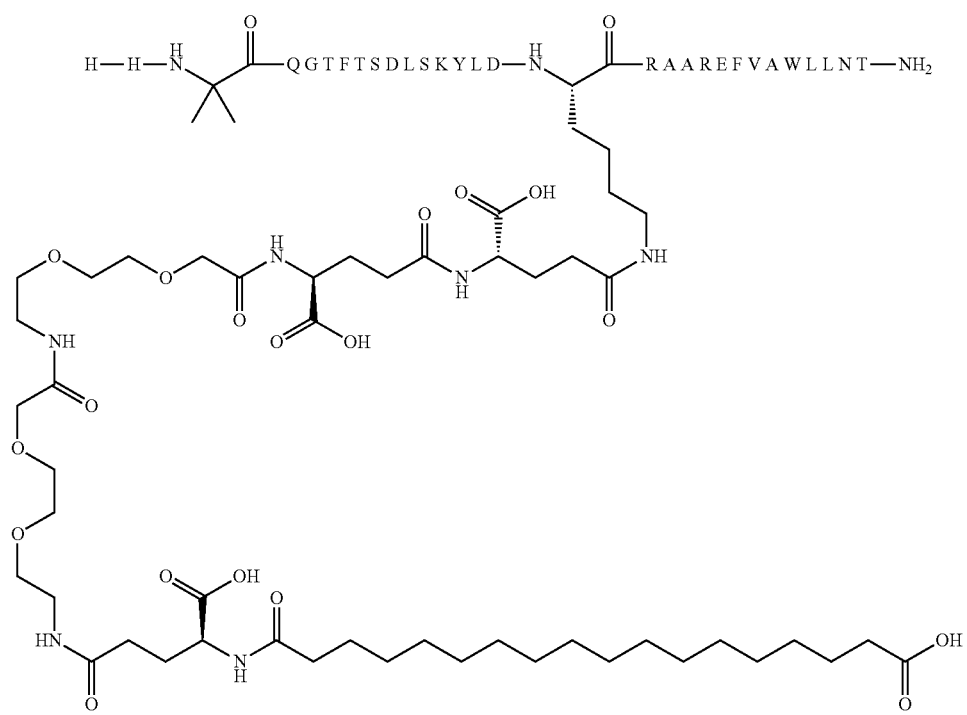

UPLC Method: 09_B4_1; Rt=8.4 min
UPLC Method: 04_A9_1; Rt=16.0 min
LC-MS Method: LCMS_4; Rt=2.3 min, m/3: 1443; m/4: 1082; m/5: 866

Example 19

$N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Arg20,Glu21,Ala24,Leu27]-Glucagon amide

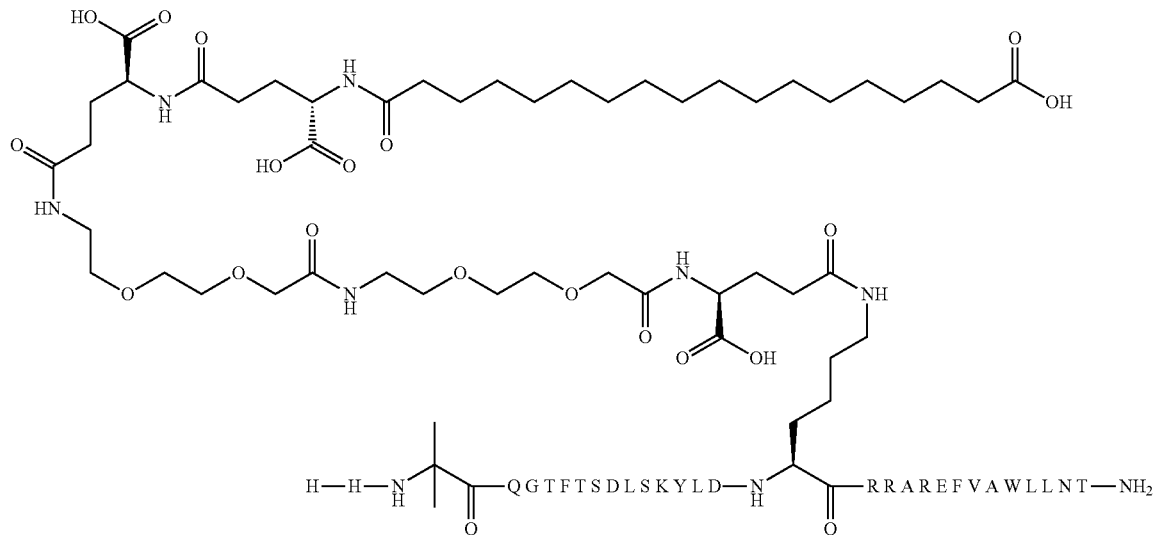

UPLC Method: UPLC01v01: Rt=12.2 min
LC-MS Method: LCMS01v01: Rt=1.9 min, m/3 1471; m/4 1103; m/5 882

Example 20

$N^{\epsilon 29}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys28]-Glucagon amide

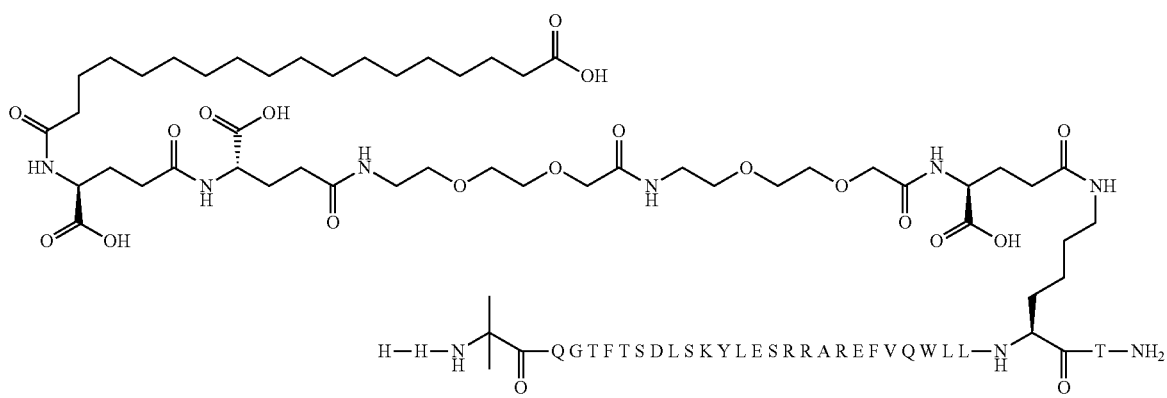

UPLC Method: UPLC01v01: Rt=12.3 min
LC-MS Method: LCMS01v01: Rt=1.8 min, m/3 1485; m/4 1114; m/5 891

Example 21

N^ε29-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys29]-Glucagon amide

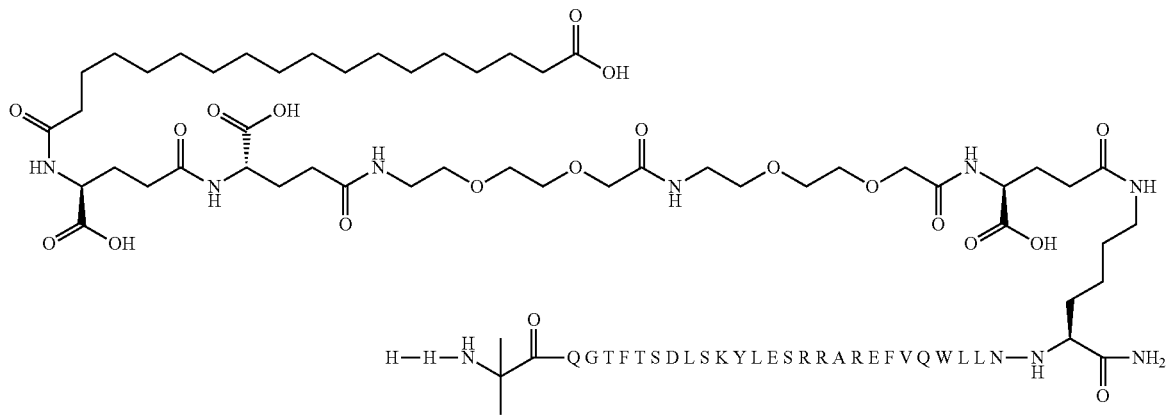

UPLC Method: UPLC01v01: Rt=12.1 min
LC-MS Method: Rt=1.8 min, m/3 1490; m/4 1117; m/5 894

Example 22

N^ε29-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Arg120,Glu21,Leu27,Lys28]-Glucagon amide

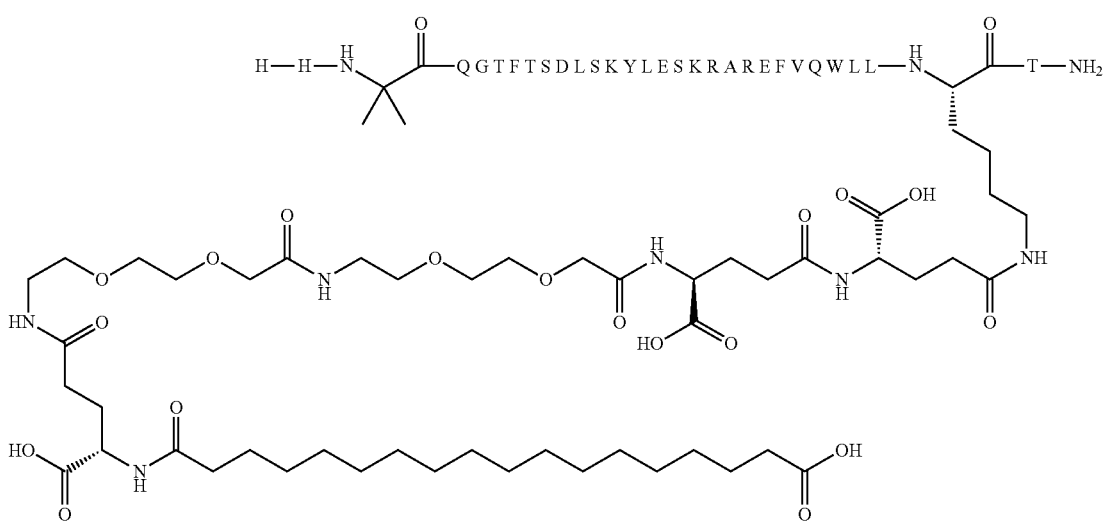

UPLC Method: 09_B2_1; Rt=12.5 min
UPLC Method: 04_A10_1; Rt=9.7 min
LC-MS Method: LCMS_4; Rt=2.6 min, m/3: 1476; m/4: 1107; m/5: 886

Example 23

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Glu15,Arg20,Glu21,Leu27,Lys28]-Glucagon amide

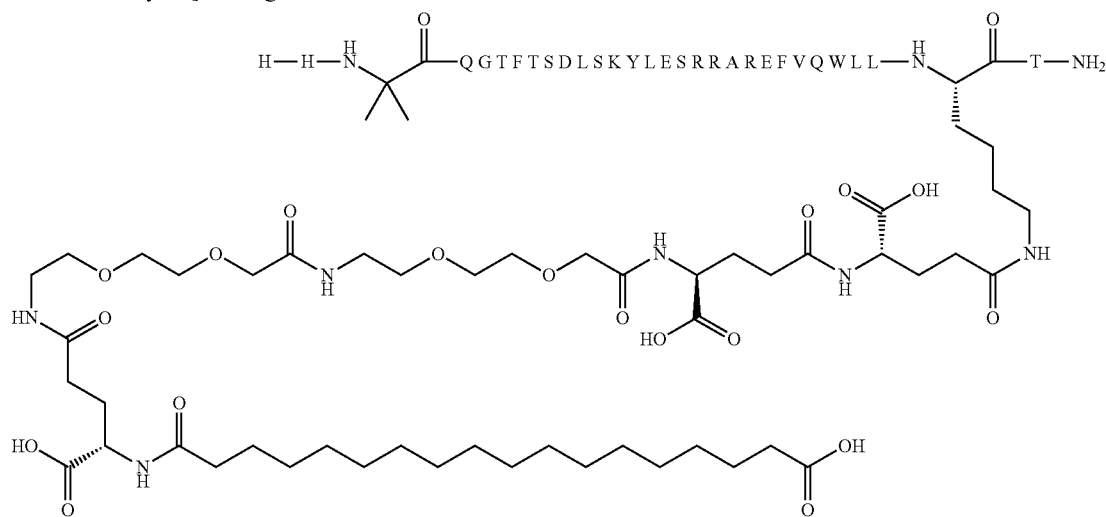

UPLC Method: 09_B2_1; Rt=12.5 min
UPLC Method: 04_A10_1; Rt=9.7 min
LC-MS Method: LCMS_4; Rt=2.6 min, m/3: 1486; m/4: 1114; m/5: 892

Example 24

N$^{\epsilon 28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Glu15,Lys17,Ala18,Arg20,Glu21,Leu27,Lys28]-Glucagon amide

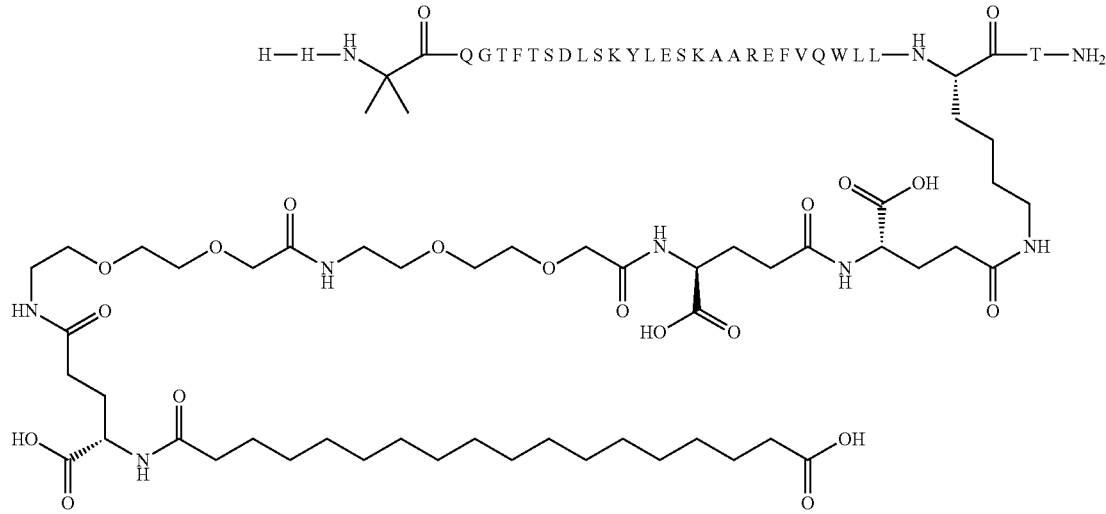

UPLC Method: 09_B2_1; Rt=13.4 min
UPLC Method: 04_A10_1; Rt=10.1 min
LC-MS Method: LCMS_4; Rt=2.8 min, m/3: 1448; m/4: 1086; m/5: 869

Example 25

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,Leu10,Glu15,Lys17,Arg20,Glu21,Leu27,Lys28]-Glucagon amide

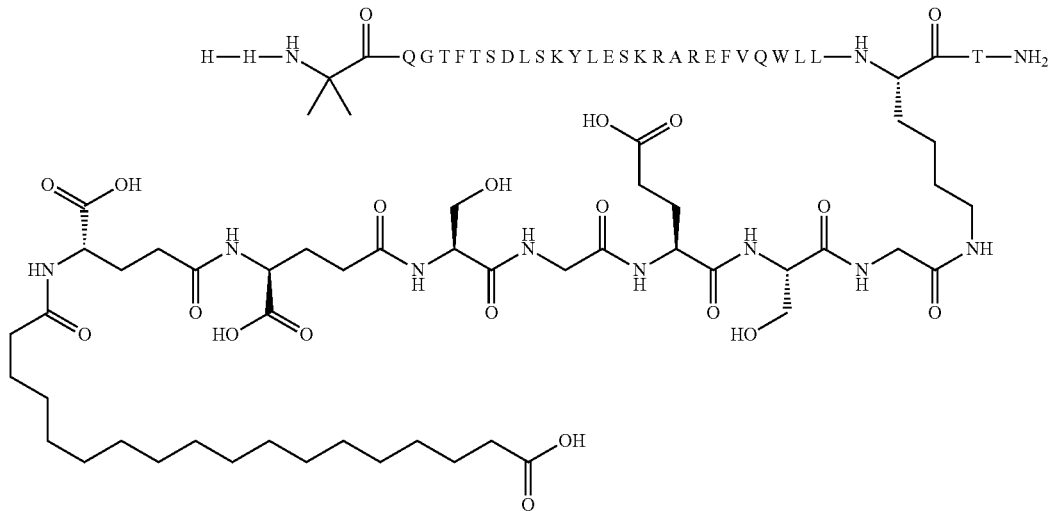

UPLC Method: 09_B2_1; Rt=12.6 min
UPLC Method: 04_A9_1; Rt=12.2 min
LC-MS Method: LCMS_4; Rt=1.7 min, m/3: 1475; m/4: 1107; m/5: 885

Example 26

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Leu16,Lys17,Arg20,Glu21,Leu27,Lys28]-Glucagon amide

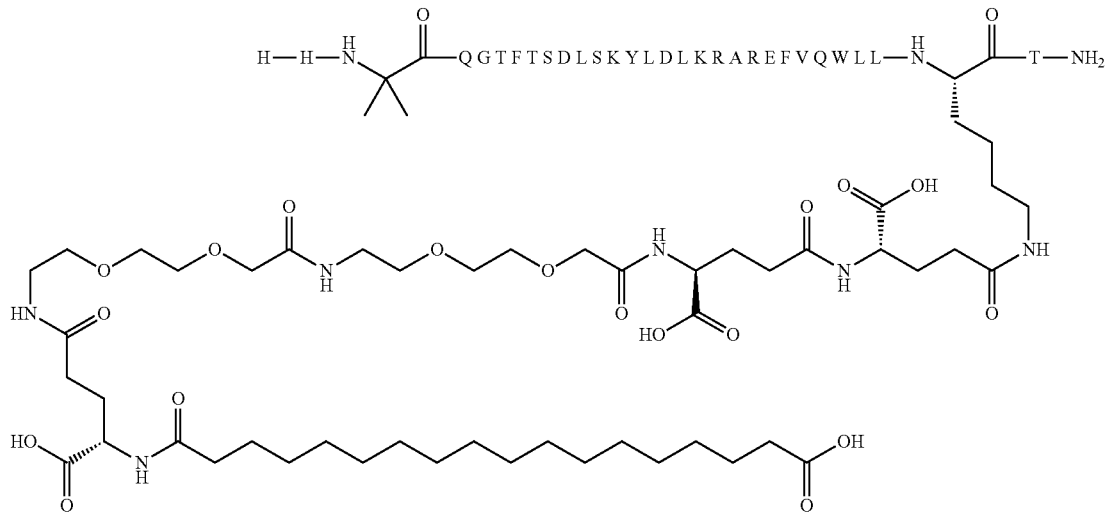

UPLC Method: 09_B2_1; Rt=13.3 min
UPLC Method: 04_A9_1; Rt=17.5 min
LC-MS Method: LCMS_4; Rt=1.8 min, m/3: 1481; m/4: 1111; m/5: 889

Example 27

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Lys17,Arg20,Glu21,Leu27,Lys28]-Glucagon amide

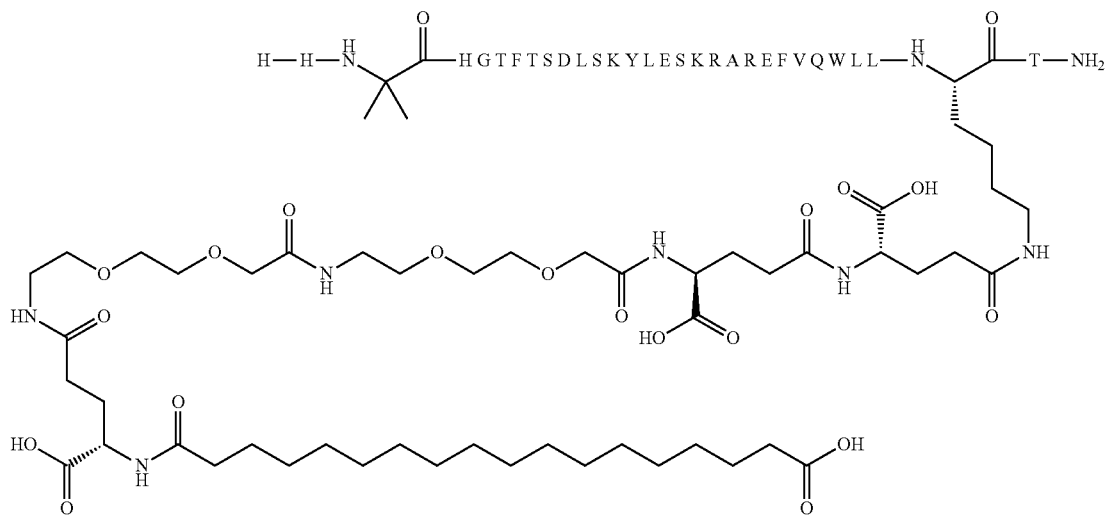

UPLC Method: 09_B2_1; Rt=12.6 min
UPLC Method: 04_A9_1; Rt=12.7 min
LC-MS Method: LCMS_4; Rt=1.7 min, m/3: 1479; m/4: 1110; m/5: 888

Example 28

$N^{\epsilon 16}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Glu21,Val27,Lys28,Gly29]-Glucagon amide

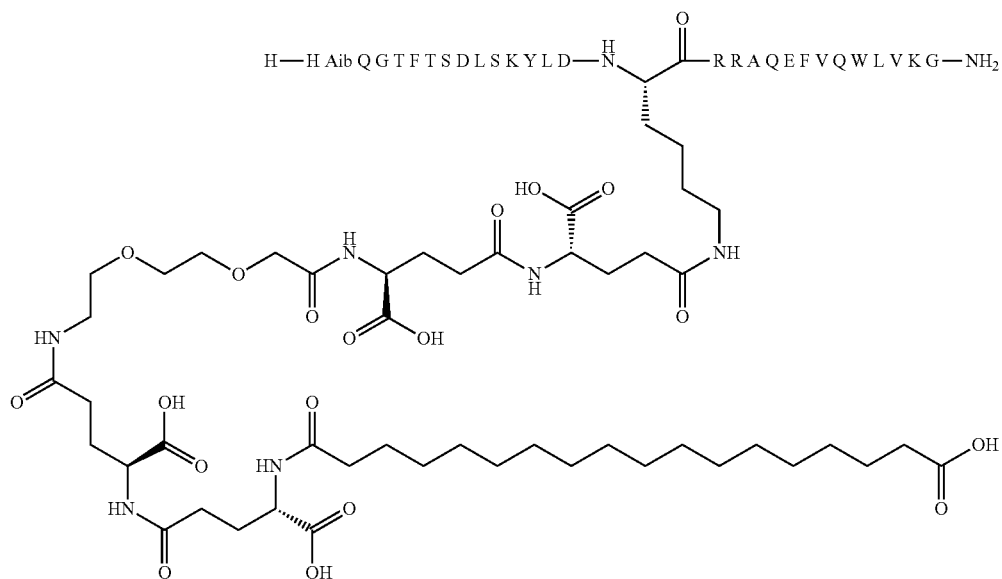

UPLC Method: UPLC02v01; Rt=7.7 min
LC-MS Method: LCMS13v01; Rt=2.1 min, m/3: 1461; m/4: 1096

Example 29

$N^{\epsilon 16}$-[(4S)-4-carboxy-4-[[(4S)-4-carboxy-4-[[2-[2-[2-[[(4S)-4-carboxy-4-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Lys16,Glu21,Leu27]-Glucagon amide

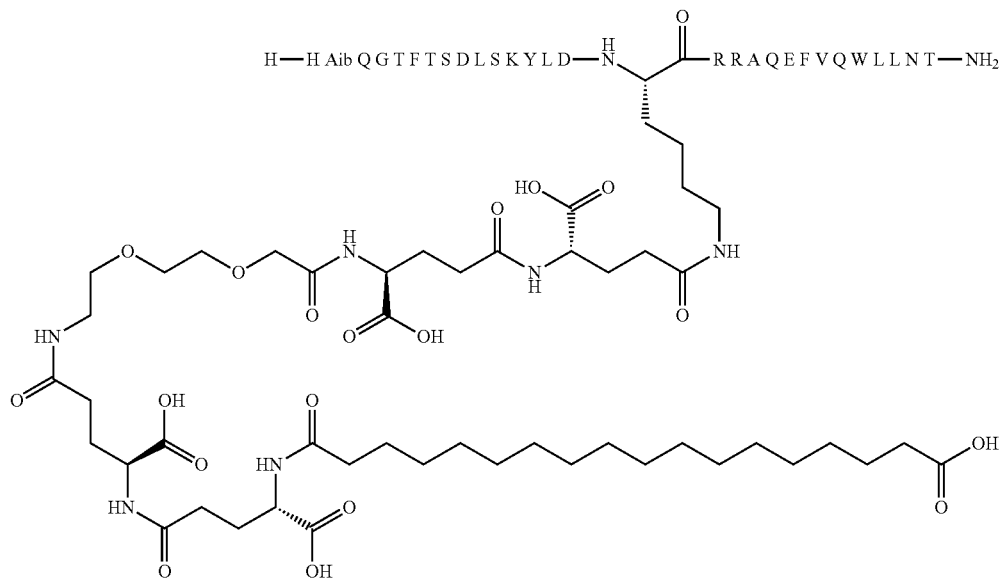

UPLC Method: UPLC02v01; Rt=8.1 min
LC-MS Method: LCMS13v01; Rt=2.2 min, m/3: 1476; m/4: 1107

Example 30

$N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Leu27,Lys28]-Glucagon amide

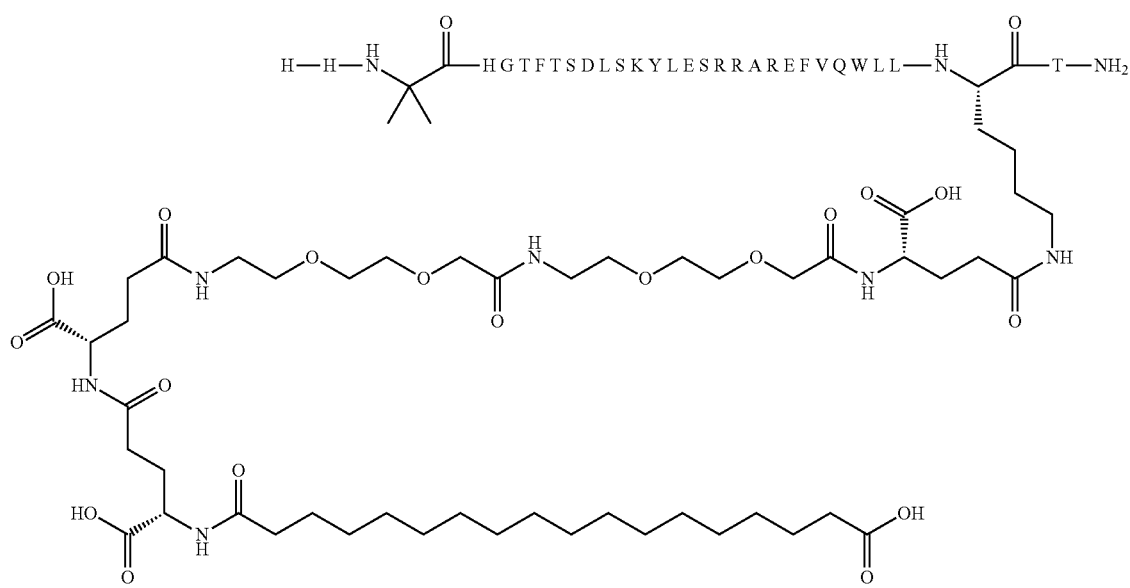

UPLC Method: 09_B2_1; Rt=12.1 min
UPLC Method: 04_A9_1; Rt=14.3 min
LC-MS Method: LCMS_4; Rt=2.1 min, m/3: 1489; m/4: 1117; m/5: 893

Example 31

$N^{\epsilon 28}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Arg20,Glu21,Ala24,Leu27,Lys28]-Glucagon amide

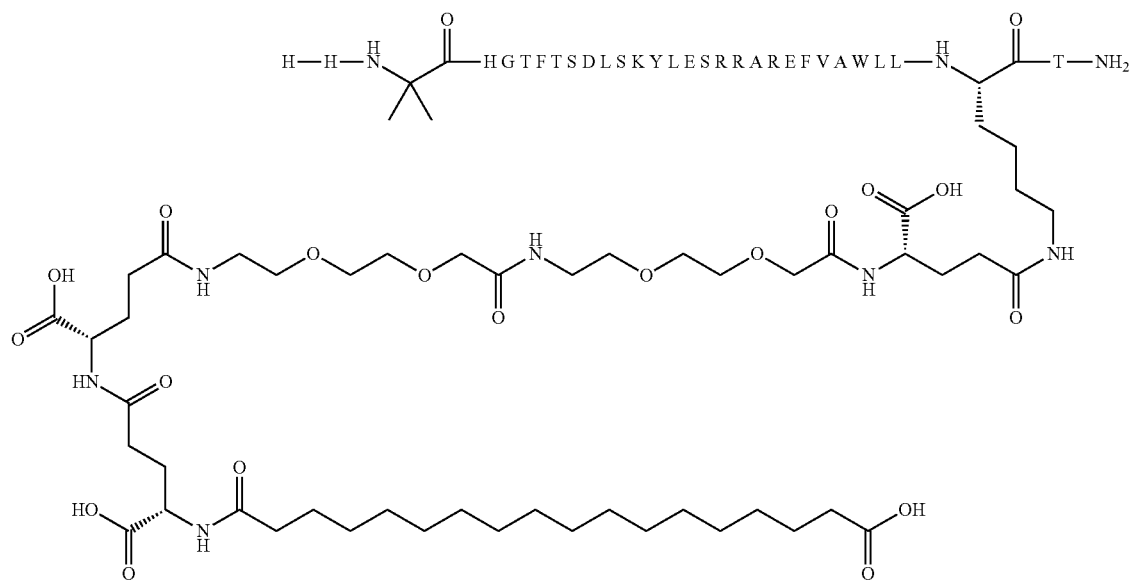

UPLC Method: 09_B2_1; Rt=12.2 min
UPLC Method: 04_A9_1; Rt=14.2 min
LC-MS Method: LCMS_4; Rt=2.2 min, m/4: 1102; m/5: 882

Example 32

$N^{\epsilon16}$-[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]-[Aib2,His3,Leu10,Glu15,Lys16,Arg20,Glu21,Ala24,Leu27,Ser28]-Glucagon amide

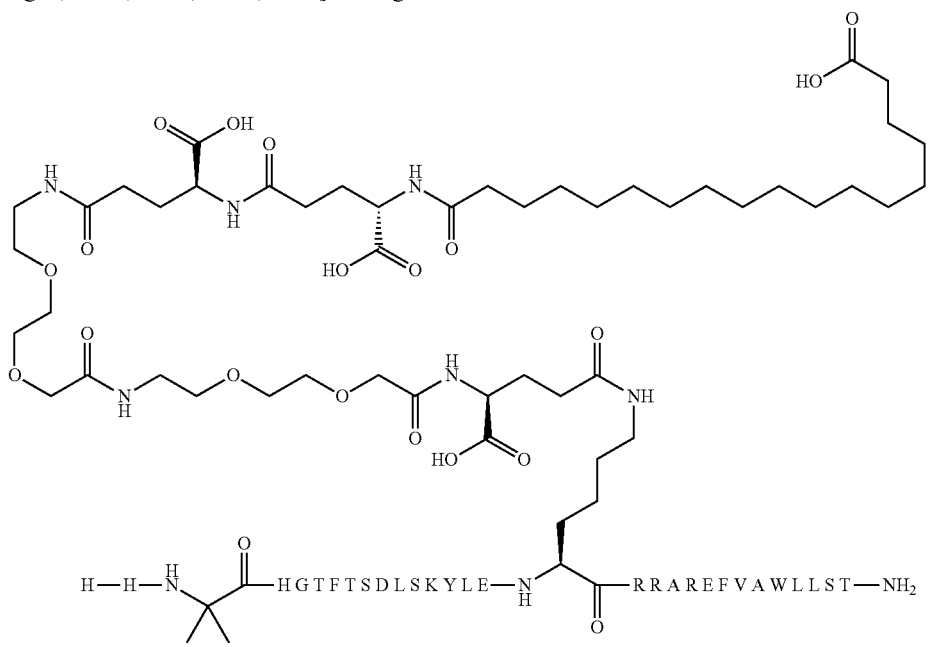

UPLC Method: 09_B2_1; Rt=12.1 min
UPLC Method: 04_A9_1; Rt=14.1 min
LC-MS Method: LCMS_4; Rt=2.1 min, m/4: 1102; m/5: 882

Example 33

$N^{\epsilon28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,His3,Leu10,Glu15,Arg20,Glu21,Leu27,Lys28]-Glucagon amide

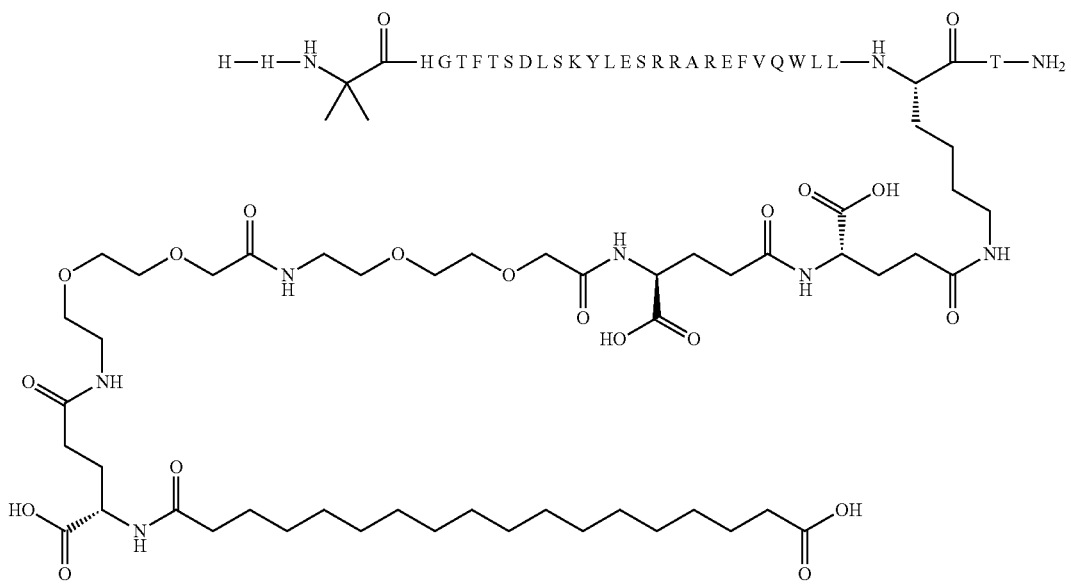

UPLC Method: 09_B2_1; Rt=12.2 min
UPLC Method: 04_A9_1; Rt=15.2 min
LC-MS Method: LCMS_4; Rt=2.0 min, m/3: 1489; m/4: 1117; m/5: 893

Example 34

$N^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,His3,Leu10,Glu15,Lys17,Arg20,Glu21,Leu27,Lys28]-Glucagon amide

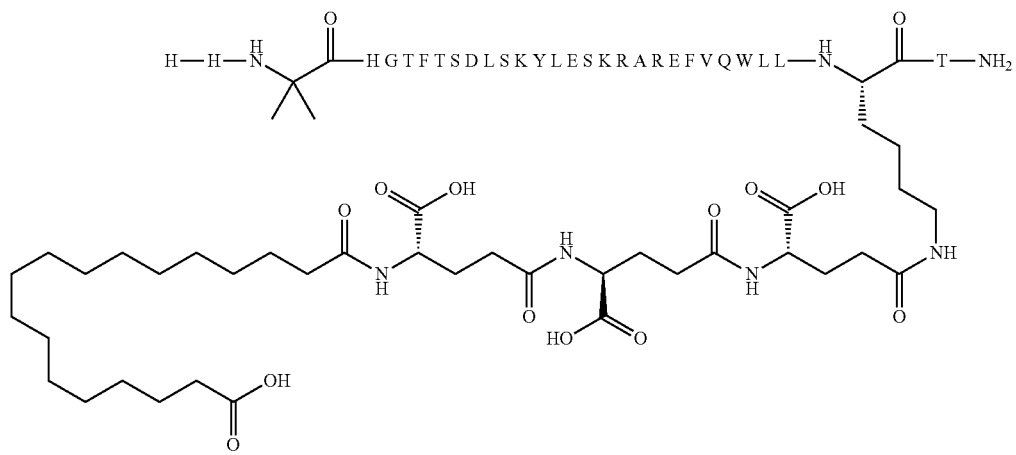

UPLC Method: 09_B2_1; Rt=12.2 min
UPLC Method: 04_A9_1; Rt=14.9 min
LC-MS Method: LCMS_4; Rt=2.0 min, m/3: 1383; m/4: 1037; m/5: 830

Example 35

$N^{\epsilon 28}$-[2-[[(2S)-2-[[(2S)-4-carboxy-2-[[2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,His3,Leu10,Glu15,Leu27,Lys28]-Glucagon amide

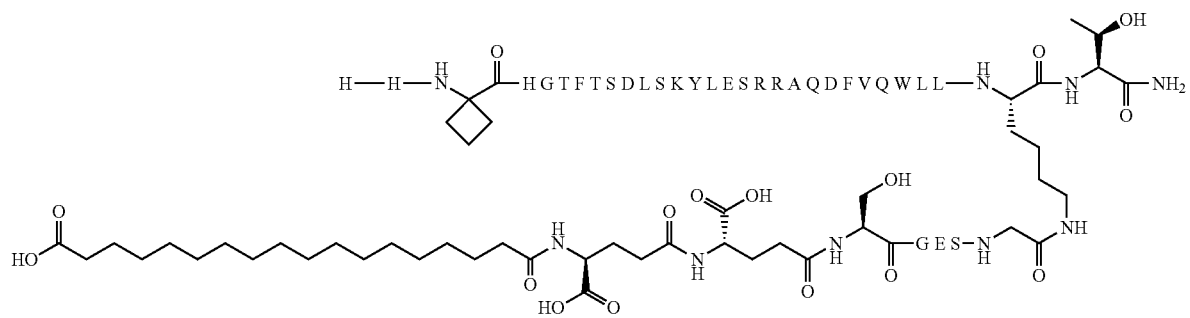

UPLC Method: UPLC02v01 Rt=8.14 min
LC-MS Method: LCMS01v01; Rt=2.1; m/3:1478; m/5: 1109; m/6:887

Example 36

N^ε28-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Glu15,Lys17,Arg120,Glu21,Leu27,Lys28]-Glucagon amide

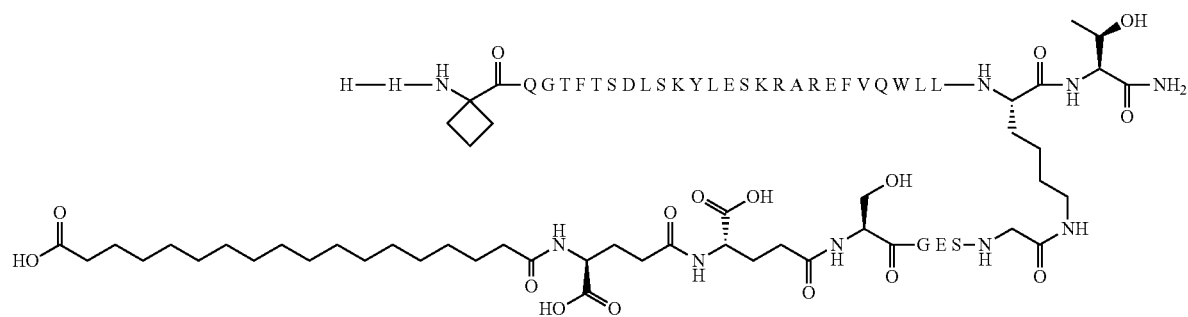

UPLC Method: UPLC02v01: Rt=7.9 min
LC-MS Method: LCMS01v01: Rt=2.1; m/3: 1480; m/4: 1110; m/5: 888

Example 37

N^ε28-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Aib2,His3,Leu10,Glu15,Arg120,Leu27,Lys28]-Glucagon amide

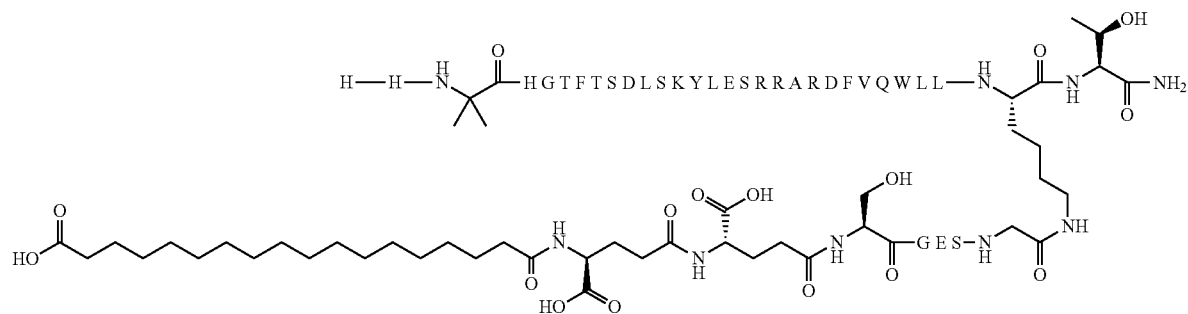

UPLC Method: UPLC02v01: Rt=7.8 min
LC-MS Method: LCMS01v01: Rt=2.1; m/3: 1484; m/4: 1113; m/5: 891

Example 38

$N^{\epsilon 29}$-[(4S)-4-carboxy-4-[[(4S)-4-carboxy-4-[[2-[2-[2-[[(4S)-4-carboxy-4-(17-carboxyheptadecanoy-lamino)butanoyl]amino]ethoxy]ethoxy]acetyl] amino]butanoyl]amino]butanoyl]-[Aib2,Leu10, Leu16,Arg20,Glu21,Leu27,Lys29]-Glucagon amide

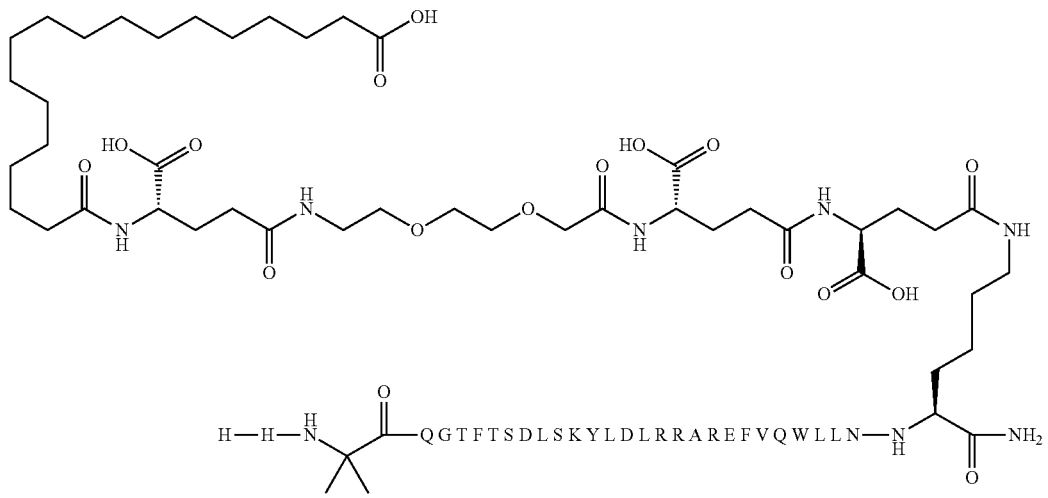

UPLC Method: 09_B2_1; Rt=12.8 min
UPLC Method: 04_A9_1; Rt=18.6 min
LC-MS Method: LCMS_4; Rt=2.9 min, m/3: 1446; m/4: 1084; m/5: 868

Example 39

$N^{\epsilon 29}$-[(4S)-4-carboxy-4-[[(4S)-4-carboxy-4-[[2-[2-[2-[[(4S)-4-carboxy-4-(17-carboxyheptadecanoy-lamino)butanoyl]amino]ethoxy]ethoxy]acetyl] amino]butanoyl]amino]butanoyl]-[Aib2,Leu10, Ala16,Arg20,Glu21,Leu27,Lys29]-Glucagon amide

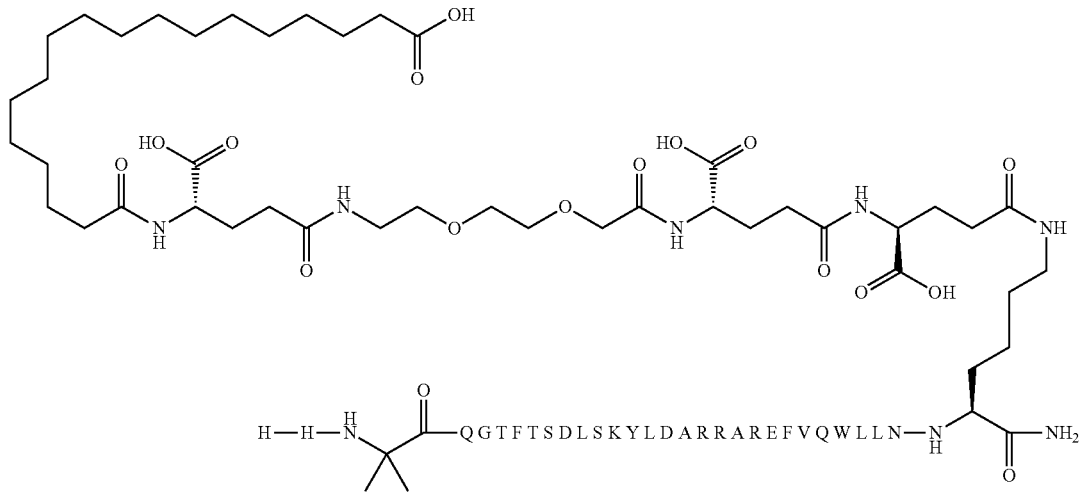

UPLC Method: 09_B2_1; Rt=12.3 min
UPLC Method: 04_A9_1; Rt=16.0 min
LC-MS Method: LCMS_4; Rt=2.8 min, m/3: 1432; m/4: 1074; m/5: 859

Example 40

N$^{\epsilon 29}$-[(4S)-4-carboxy-4-[[(4S)-4-carboxy-4-[[2-[2-[2-[[(4S)-4-carboxy-4-(17-carboxyheptadecanoy-lamino)butanoyl]amino]ethoxy]ethoxy]acetyl]amino]butanoyl]amino]butanoyl]-[Aib2,Leu10, Glu15,Arg20,Glu21,Leu27,Lys29]-Glucagon amide

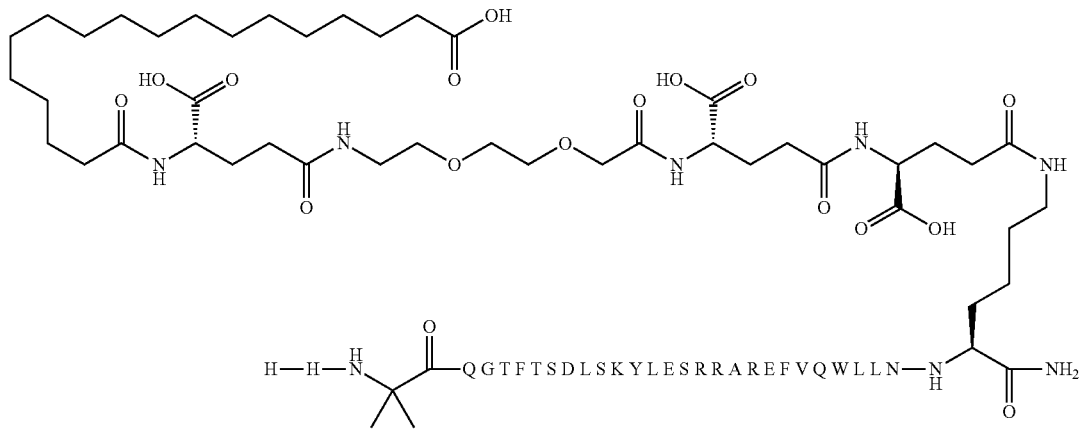

UPLC Method: 09_B2_1; Rt=12.2 min
UPLC Method: 04_A9_1; Rt=13.9 min
LC-MS Method: LCMS_4; Rt=2.7 min, m/3: 1442; m/4: 1081; m/5: 865

Example 41

N$^{\epsilon 29}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2, Leu10,Glu15,Arg20,Glu21,Leu27,Lys28]-Glucagon amide

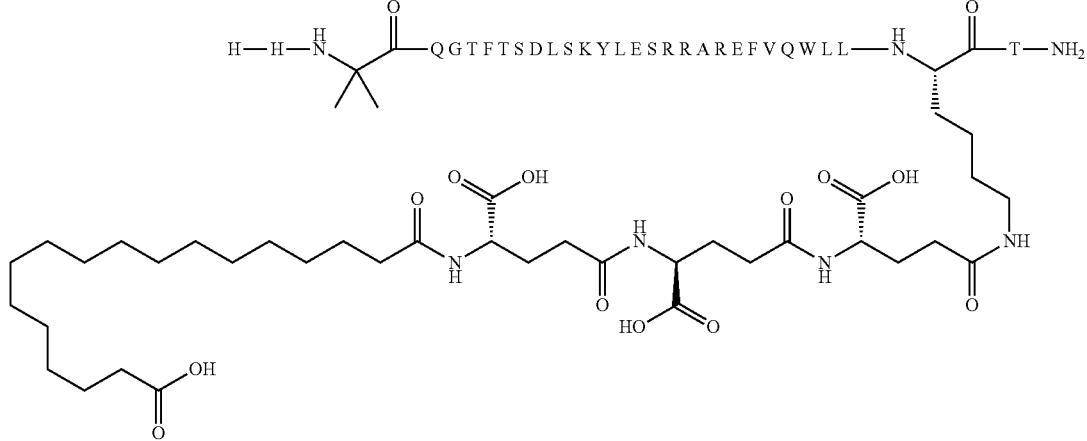

UPLC Method: 09_B2_1; Rt=12.3 min
UPLC Method: 04_A9_1; Rt=15.1 min
LC-MS Method: LCMS_4; Rt=2.3 min, m/3: 1389; m/4: 1042; m/5: 834

Example 42

N^ε28^-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Glu15,Arg20,Glu21,Leu27,Lys28]-Glucagon amide

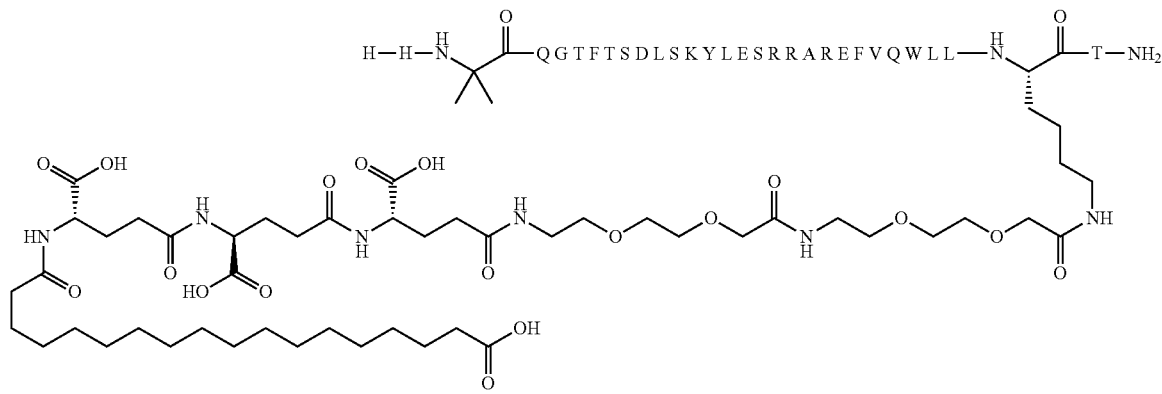

UPLC Method: 09_B2_1; Rt=12.2 min
UPLC Method: 04_A9_1; Rt=14.7 min
LC-MS Method: LCMS_4; Rt=2.3 min, m/3: 1486; m/4: 1114; m/5: 892

Example 43

N^ε28^-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Glu21,Leu27,Lys28]-Glucagon amide

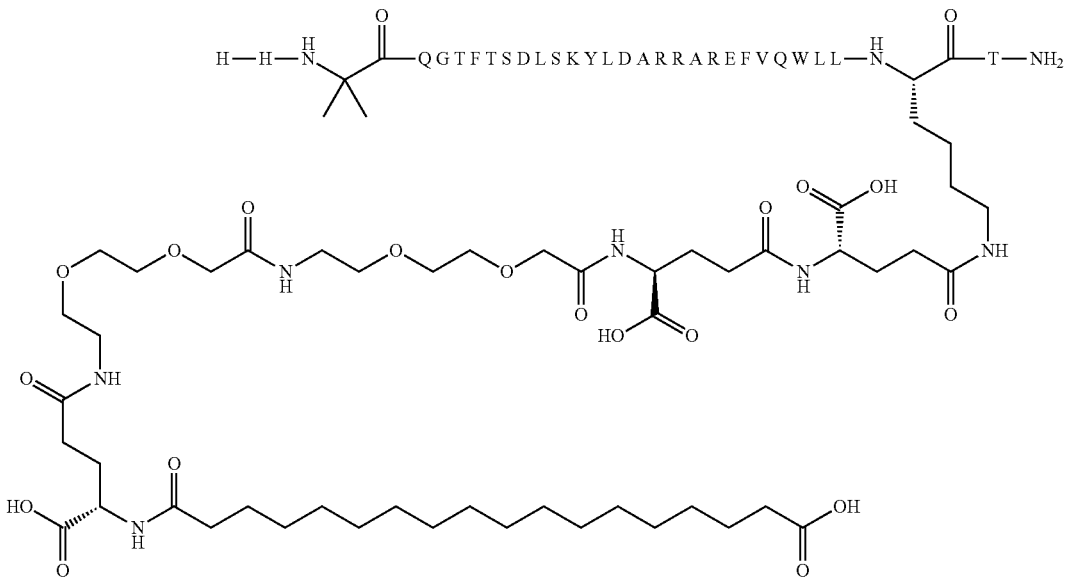

UPLC Method: 09_B2_1; Rt=12.4 min
UPLC Method: 04_A9_1; Rt=17.2 min
LC-MS Method: LCMS_4; Rt=2.4 min, m/3: 1476; m/4: 1107; m/5: 886

Example 44

N$^{\epsilon28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Acb2,Leu10,Glu15,Arg20,Glu21,Leu27,Lys28]-Glucagon amide

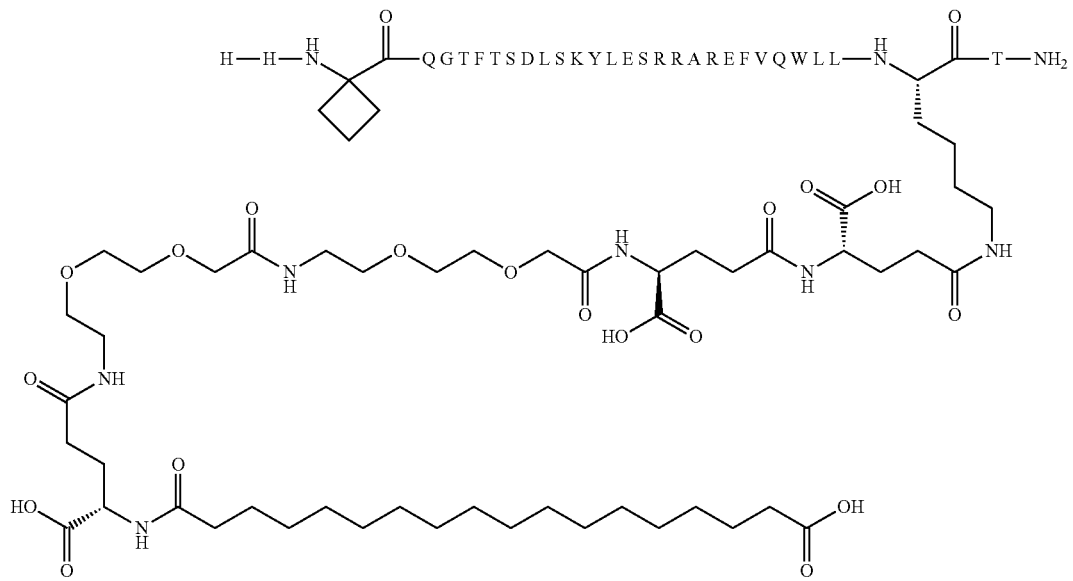

UPLC Method: 09_B2_1; Rt=12.3 min  
UPLC Method: 04_A9_1; Rt=15.2 min  
LC-MS Method: LCMS_4; Rt=2.3 min, m/3: 1490; m/4: 1117; m/5: 894

Example 45

N$^{\epsilon28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Leu27,Lys28]-Glucagon amide

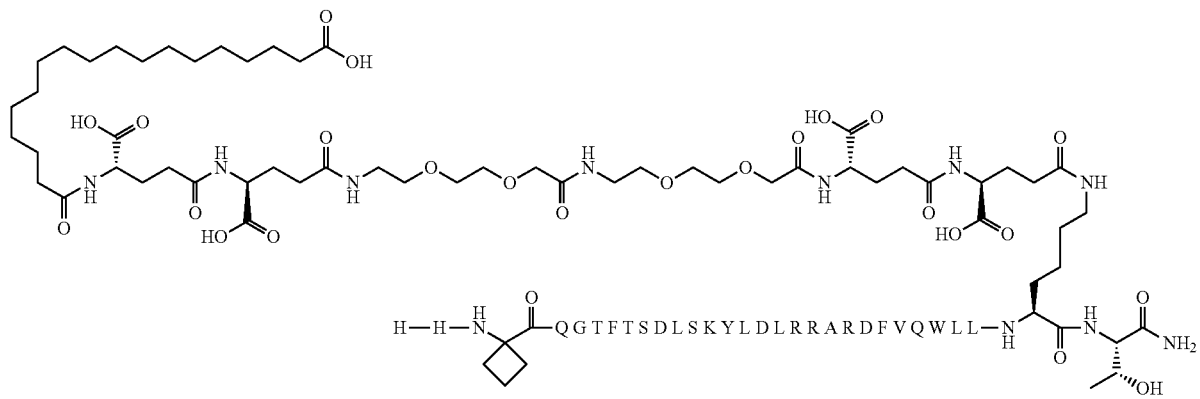

UPLC Method: UPLC02v01 Rt=8.4 min  
LC-MS Method: LCMS01v01; Rt=2.7 min; m/3:1532; m/5:1150; m/6:920

Example 46

N$^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Arg12,Leu16,Arg20,Leu27,Lys28]-Glucagon amide

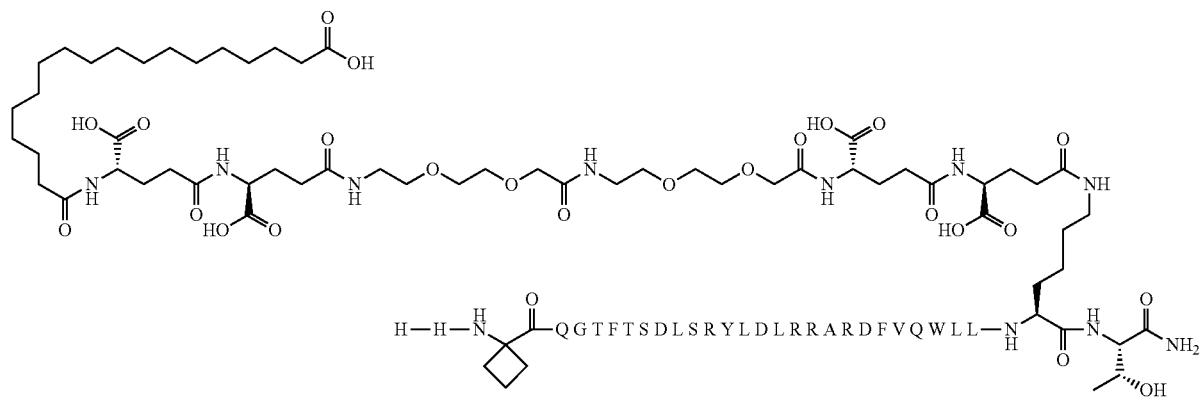

UPLC Method: UPLC02v01 Rt=8.4 min
LC-MS Method: LCMS01v01; Rt=2.7 min; m/3:1542; m/5:1157; m/6:925

Example 47

N$^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide

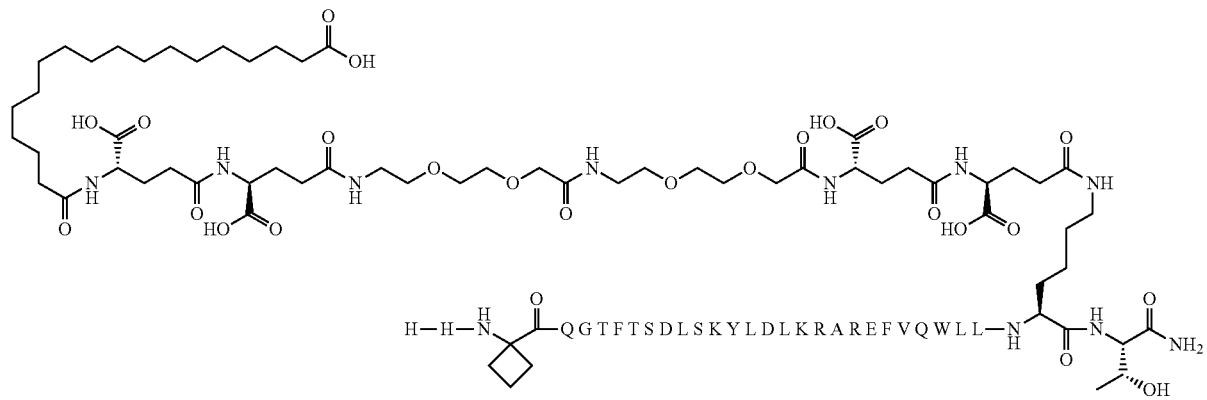

UPLC Method: UPLC02v01: Rt=8.4 min
LC-MS Method: LCMS01v01: Rt=2.7 min; m/3: 1528; m/4: 1146; m/5: 917

Example 48

N^ε28-[2-[[(2S)-2-[[(2S)-4-carboxy-2-[[2-[[(2S)-2-[[(4S)-4-carboxy-4-[[(4S)-4-carboxy-4-(17-carboxy-heptadecanoylamino)butanoyl]amino]butanoyl]amino]-3-hydroxypropanoyl]amino]acetyl]amino]butanoyl]amino]-3-hydroxypropanoyl]amino]acetyl]-[Acb2,Leu10,Leu16,Lys17,Arg120,Glu21,Leu27,Lys28]-Glucagon amide

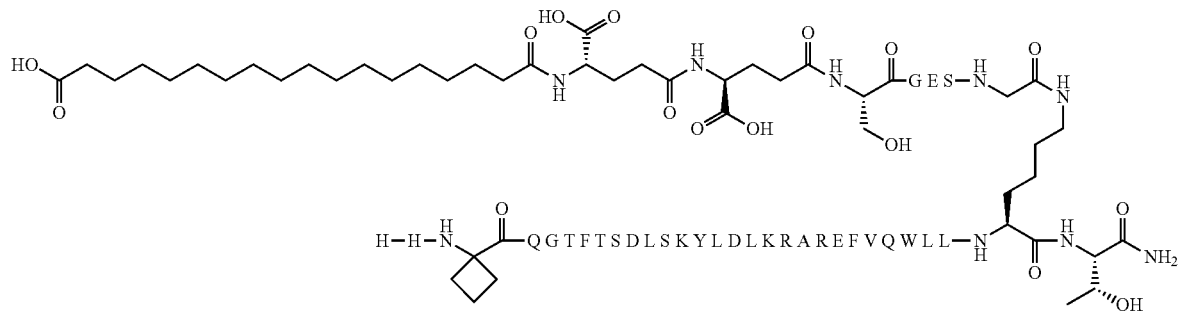

UPLC Method: UPLC02v01: Rt=8.3 min
LC-MS Method: LCMS01v01: Rt=2.1 min; m/3: 1484; m/4: 1113; m/5: 891

Example 49

N^ε28-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Arg20,Glu21,Leu27,Lys28]-Glucagon amide

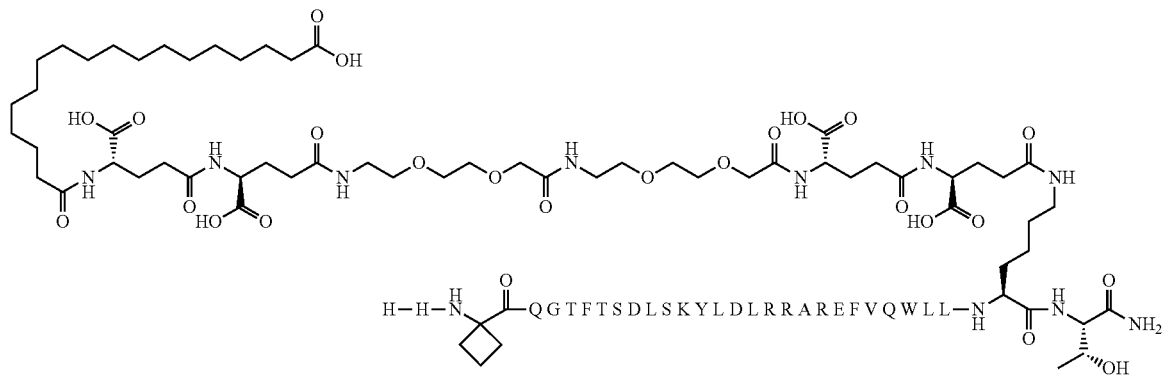

UPLC Method: 09_B2_1; Rt=12.4 min
UPLC Method: 04_A9_1; Rt=14.5 min
LC-MS Method: LCMS_4; Rt=2.4 min, m/3: 1485; m/4: 1114; m/5: 891

Example 50

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Acpr2,Leu10,Glu15,Arg20,Glu21,Leu27,Lys28]-Glucagon amide

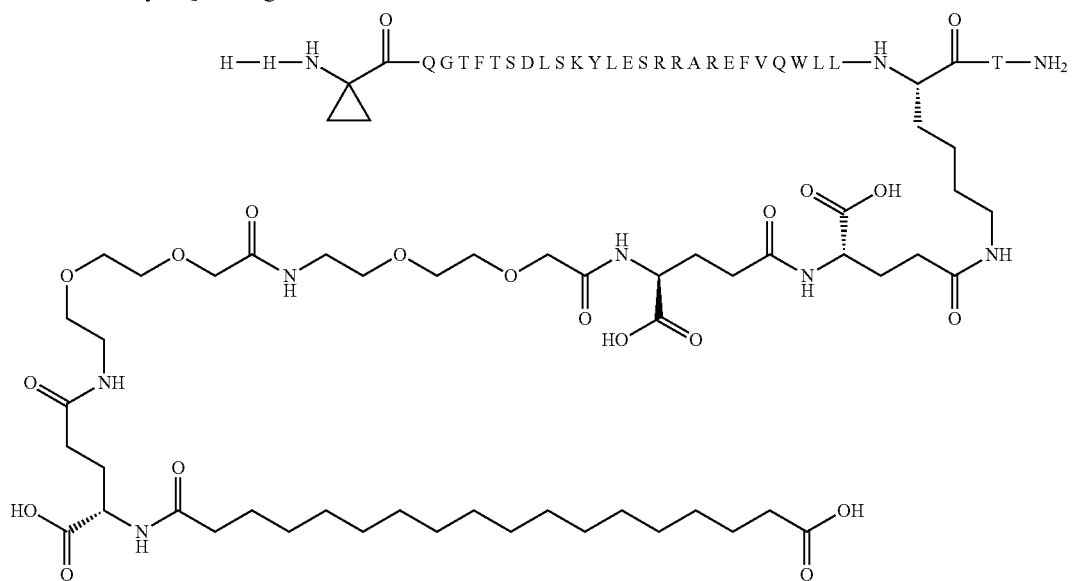

UPLC Method: 09_B2_1; Rt=12.4 min
UPLC Method: 04_A9_1; Rt=14.5 min
LC-MS Method: LCMS_4; Rt=2.4 min, m/3: 1485; m/4: 1114; m/5: 891

Example 51

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Aib16,Arg20,Glu21,Leu27,Lys28]-Glucagon amide

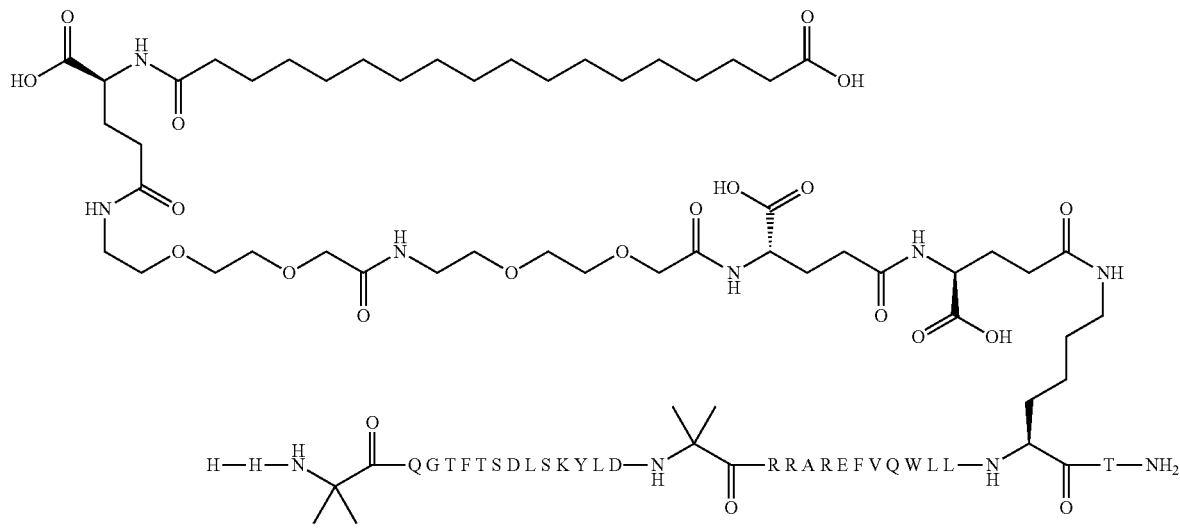

UPLC method: UPLC01v01: Rt=12.7 min
LC-MS method: LCMS01v01: Rt=2.7 min; m/3=1480; m/4=1110; m/5=888

Example 52

N$^{\epsilon 28}$(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]]amino]butanoyl]-[Aib2,Leu10,Glu15,Lys17,Arg20,Glu21,Leu27,Lys28]-Glucagon amide

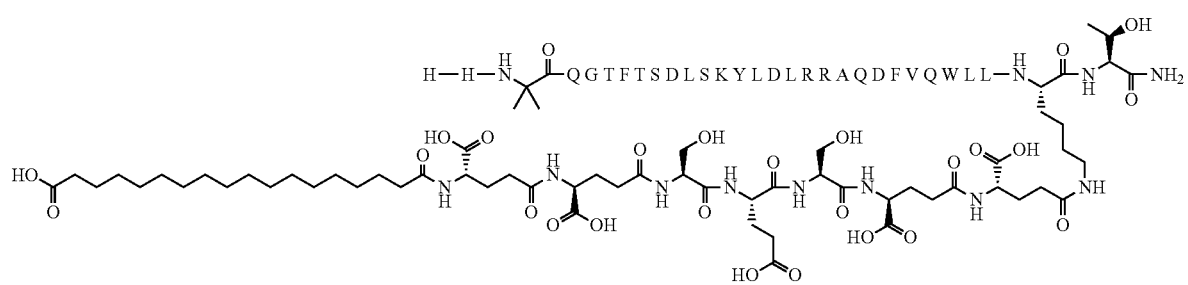

UPLC method: UPLC02v01: Rt=8.0 min
LC-MS method: LCMS01v01: Rt=2.6 min; m/1=4570; m/3=1524; m/4=1143; m/5=915

Example 53

N$^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]]amino]butanoyl]-[Aib2,Leu10,Leu16,Leu27,Lys28]-Glucagon amide

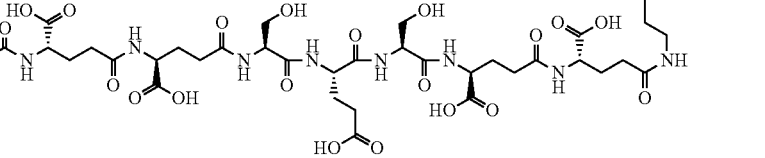

UPLC method: UPLC02v01: RT=8.5 min
LC-MS method: LCMS01v01: Rt=2.8 min; m/1=4569; m/3=1523; m/4=1143; m/5=915

Example 54

$N^{\epsilon 28}$-[(4S)-4-carboxy-4-[[(4S)-4-carboxy-4-[[(2S)-2-
[[(2S)-4-carboxy-2-[[(2S)-2-[[(4S)-4-carboxy-4-
[[(4S)-4-carboxy-4-(17-carboxyheptadecanoyl-
lamino)butanoyl]amino]butanoyl]amino]-3-
hydroxypropanoyl]amino]butanoyl]amino]-3-
hydroxypropanoyl]amino]butanoyl]]amino]
butanoyl]-[Aib2,Leu10,Glu15,Lys17,Arg20,Glu21,
Leu27,Lys28]-Glucagon amide

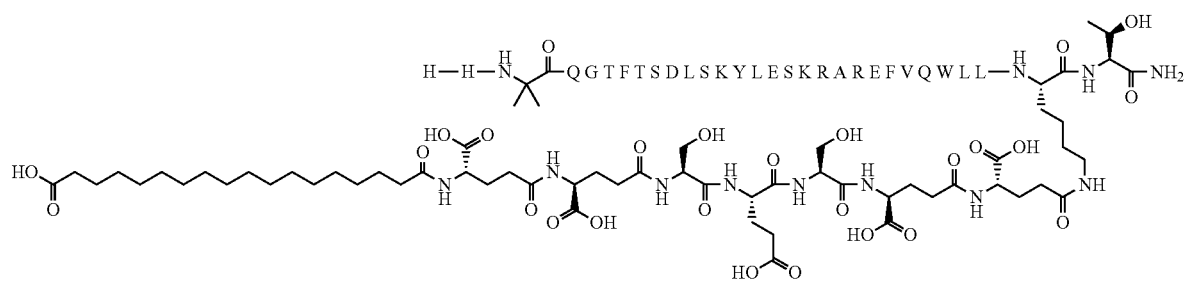

UPLC method: UPLC02v01: RT=8.0 min
LC-MS method: LCMS01v01: Rt=2.5 min; m/3=1524; m/4=1143; m/5=915; m/z=4571

Example 55

$N^{\epsilon 28}$-[2-[[(2S)-2-[[(2S)-4-carboxy-2-[[2-[[(2S)-2-
[[(4S)-4-carboxy-4-[[(4S)-4-carboxy-4-(17-carboxy-
heptadecanoylamino)butanoyl]amino]butanoyl]
amino]-3-hydroxypropanoyl]amino]butanoyl]
amino]-3-hydroxypropanoyl]amino]acetyl]-[Aib2,
Leu10,Leu16,Arg20,Leu27,Lys28]-Glucagon amide

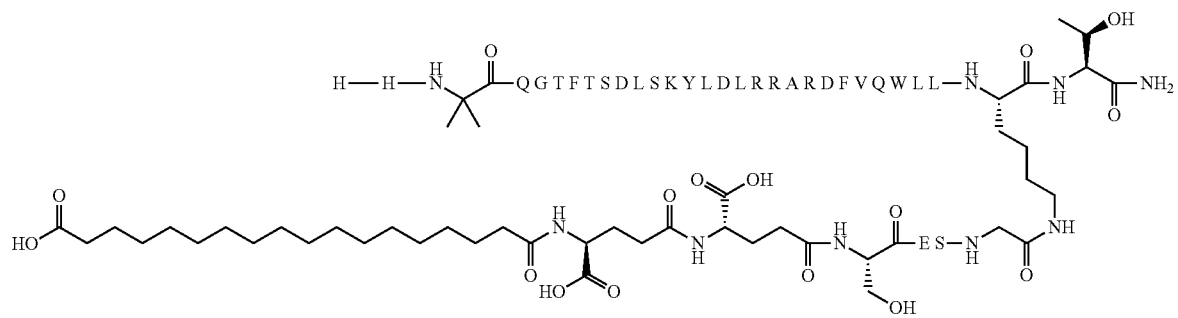

UPLC method: UPLC02v01: RT=8.4 min
LC-MS method: LCMS01v01: Rt=2.8 min; m/3=1466; m/4=1100; m/5=880; m/z=4395

Example 56

$N^{\epsilon 28}$-[(4S)-4-carboxy-4-[[(4S)-4-carboxy-4-[[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]butanoyl]amino]butanoyl]-[Aib2,Leu10,Arg20,Glu21,Leu27,Lys28]-Glucagon amide

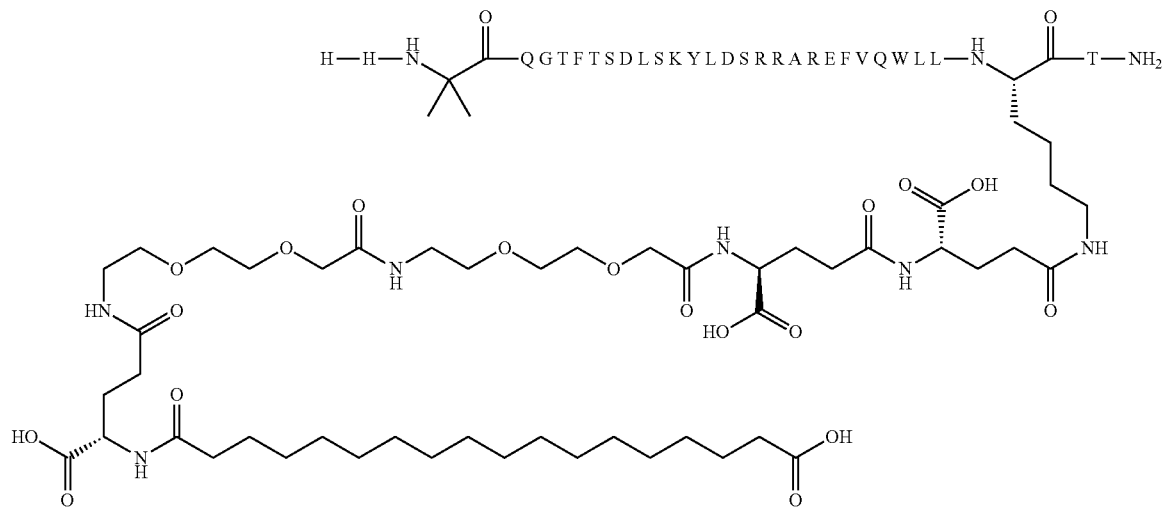

UPLC method: UPLC01v01: RT=12.386 min
LC-MS method: LCMS01v01: m/3=1481.4; m/4=1111.03; m/5=889.3

Example 57

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptade-canoylamino)butanoyl]amino]butanoyl]amino]bu-tanoyl]amino]ethoxy]ethoxy]acetyl]amino]ethoxy]ethoxy]acetyl]-[Aib2,Leu10,Glu15,Arg20,Leu27,Lys28]-Glucagon amide

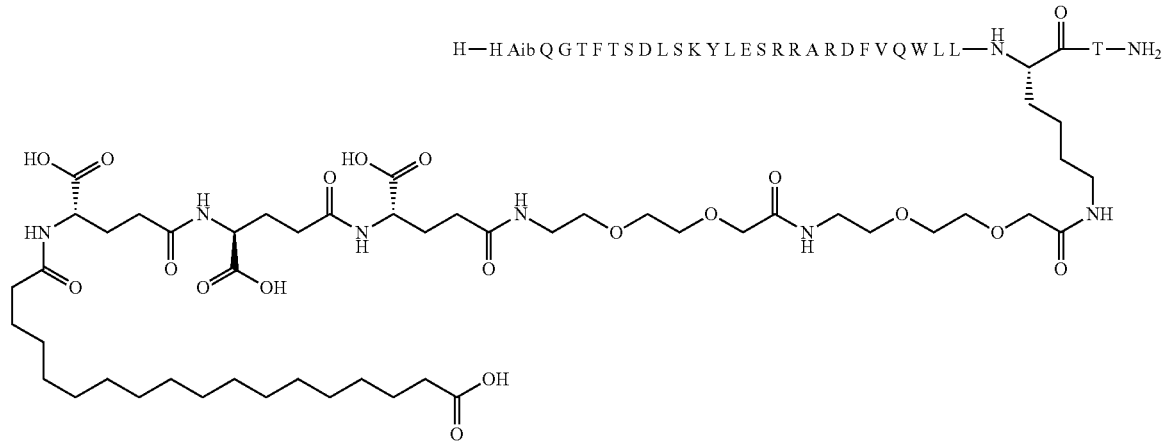

UPLC method: UPLC02v01: RT=8.0 min
LC-MS method: LCMS13v01: Rt=2.2 min; m/3=1480.8; m/4=1111.04

Example 58

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Ala16,Arg20,Leu27,Lys28]-Glucagon amide

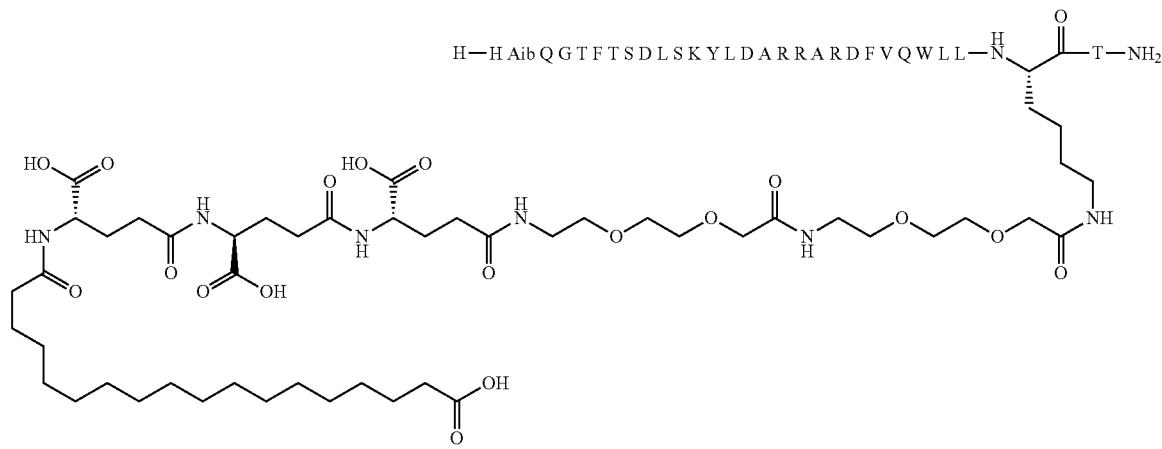

UPLC method: UPLC02v01: RT=8.7 min
LC-MS method: LCMS13v01: Rt=2.2 min; m/3=1471.05; m/4=1103.69

Example 59

$N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl][Acb2,Leu10,Arg12,Glu15,Arg20,Glu21,Leu27,Lys28]-Glucagon amide

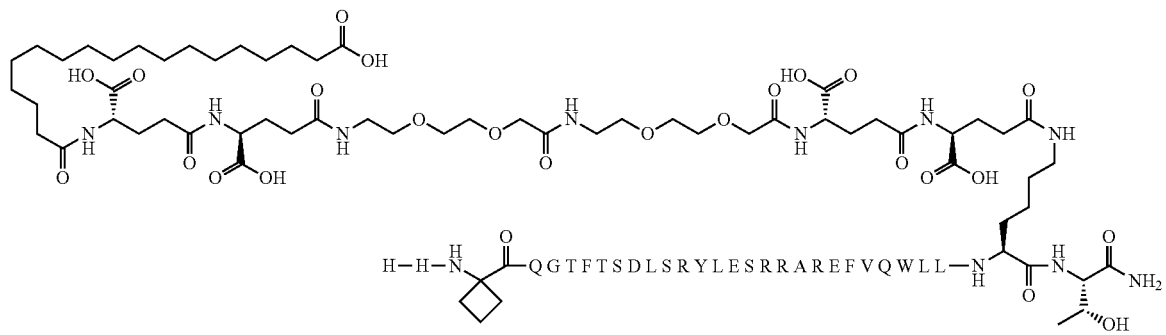

UPLC method: UPLC02v01: RT=8.0 min
LC-MS method: LCMS01v01: m/3=1542; m/4=1157; m/5=926; m/z=4626

Example 60

N$^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl][Aib2,Leu10,Glu15,Arg20,Glu21,Leu27,Lys28]-Glucagon amide

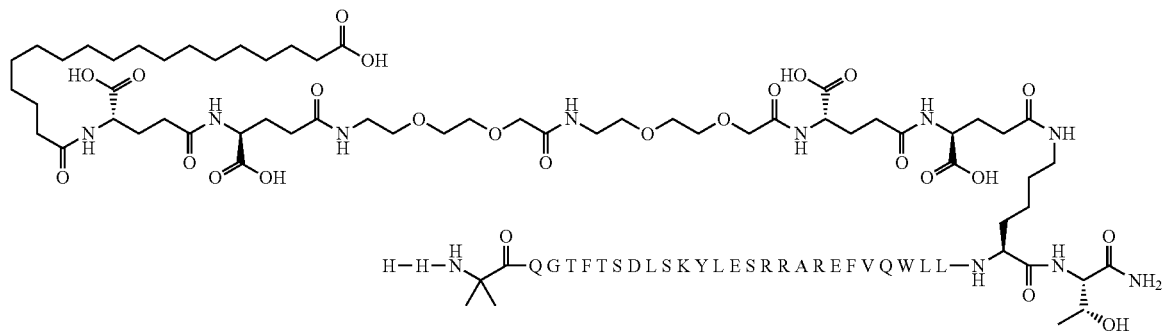

UPLC method: UPLC02v01: RT=7.9 min
LC-MS method: LCMS01v01: Rt=2.0 min; m/1=4587; m/3=1529; m/4=1147; m/5=918

Example 61

N$^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl][Acb2,Leu10,Glu15,Arg20,Glu21,Leu27,Lys28]-Glucagon amide

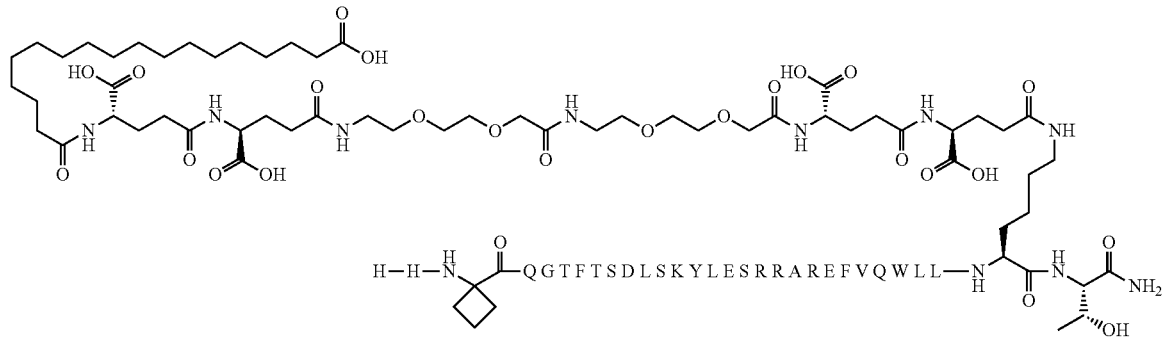

UPLC method: UPLC02v01: RT=8.2 min
LC-MS method: LCMS01v01: Rt=2.1 min; m/1=4598; m/4=1150; m/5=920

Example 62

$N^{\epsilon 28}$-[(4S)-4-carboxy-4-[[(4S)-4-carboxy-4-[[(4S)-4-carboxy-4-(17-carboxyheptadecanoylamino)butanoyl]amino]butanoyl]amino]butanoyl]-[Aib2,Leu10,Arg12,Ala16,Arg20,Leu27,Lys28]-Glucagon amide

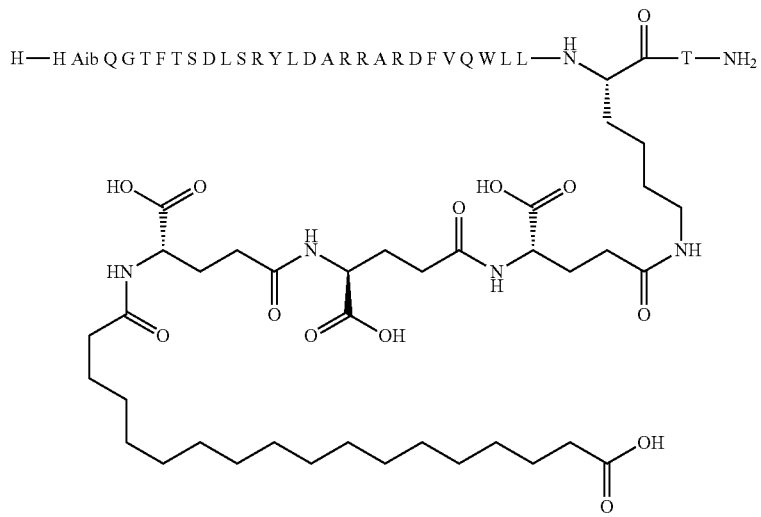

UPLC method: UPLC02v01: RT=8.2 min
LC-MS method: LCMS13v01: Rt=2.3 min; m/3=1384.04; m/4=1038.14

Example 63

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Acb2,Leu10,Glu15,Leu27,Lys28]-Glucagon amide

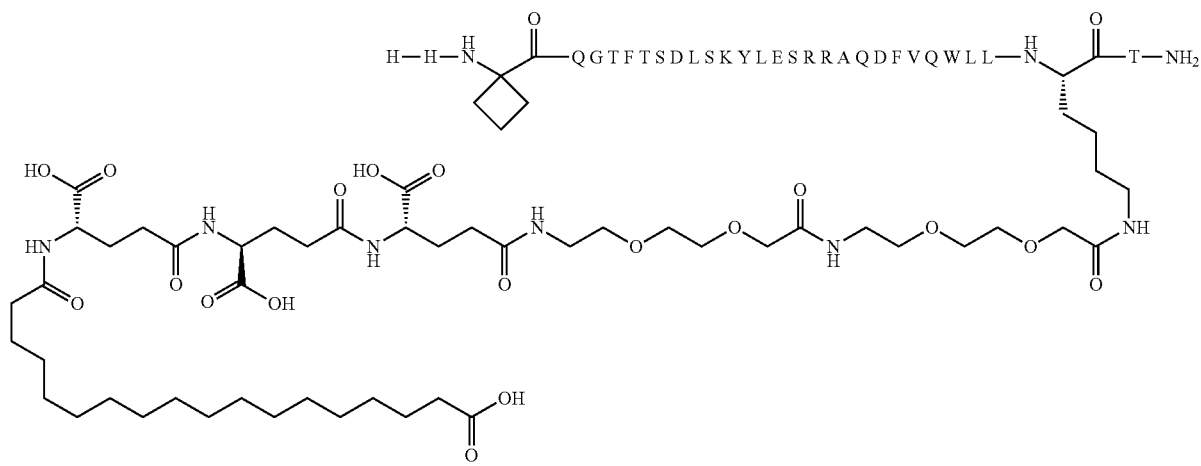

UPLC method: UPLC02v01: RT=8.3 min
LC-MS method: LCMS13v01: Rt=2.2 min; m/3=1476.15; m/4=1107.36

Example 64

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Leu10,Arg12,Ala16,Leu27, Lys28]-Glucagon amide

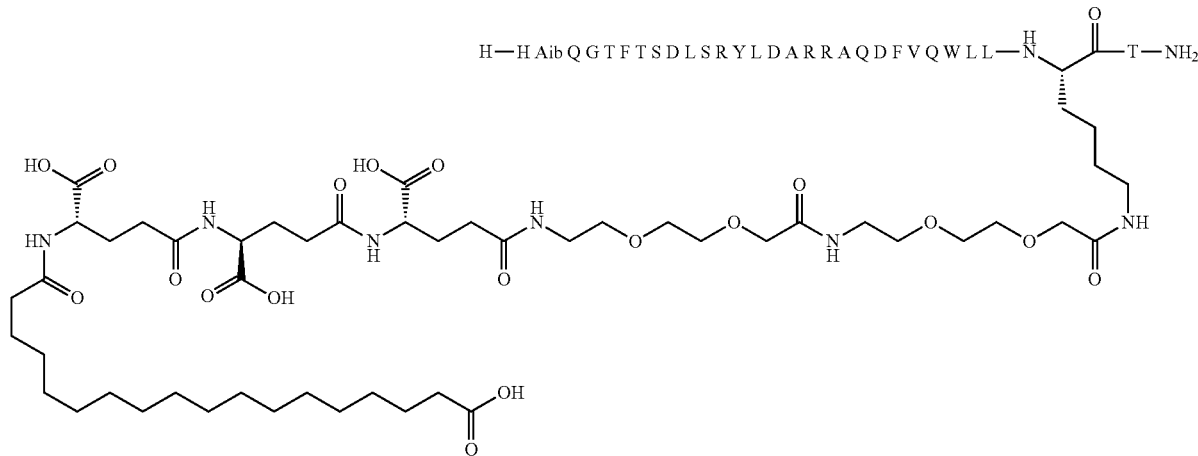

UPLC method: UPLC02v01: RT=8.3 min
LC-MS method: LCMS13v01: Rt=2.2 min; m/3=1471.27; m/4=1103.76

Example 65

$N^{\epsilon 28}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Leu27,Lys29]-Glucagon amide

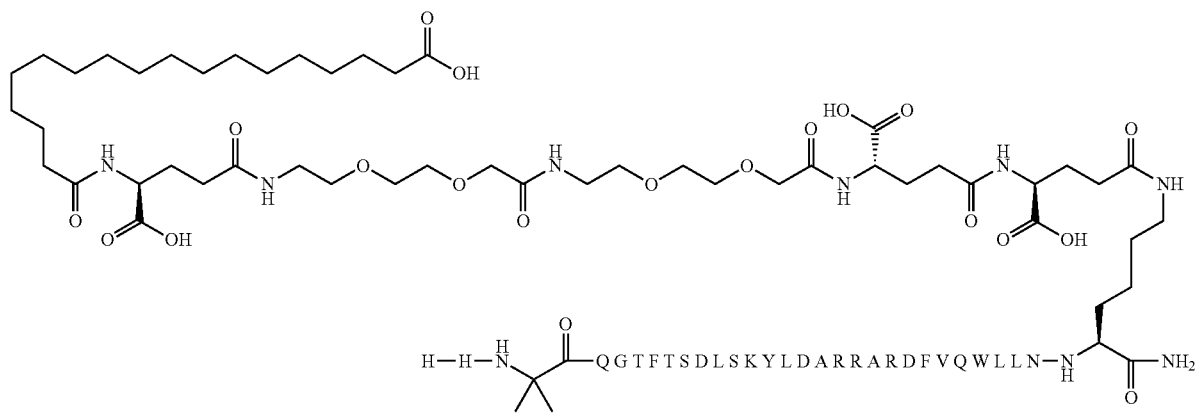

UPLC method: UPLC02v01: RT=8.1 min
LC-MS method: LCMS01v01: Rt=2.2 min; m/3=1476; m/4=1107; m/5=886

Example 66

$N^{\epsilon 29}$-[(4S)-4-carboxy-4-[[(4S)-4-carboxy-4-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]butanoyl]amino]butanoyl]-[Aib2,Leu10,Ala16,Arg20,Leu27,Ser28,Lys29]-Glucagon amide

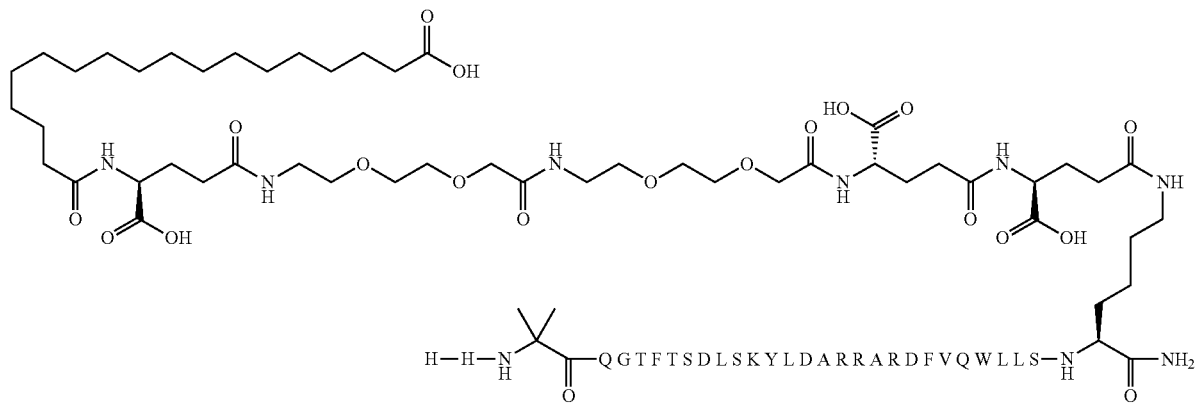

UPLC method: UPLC02v01: RT=8.2 min
LC-MS method: LCMS01v01: Rt=2.2 min; m/3=1467; m/4=1100; m/5=880

Example 67

$N^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Arg20,Glu21,Leu27,Lys28]-Glucagon amide

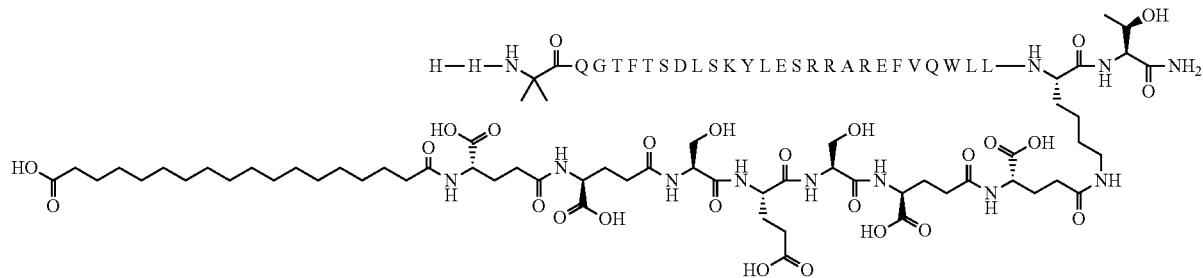

UPLC method: UPLC02v01: RT=8.0 min
LC-MS method: LCMS01v01: Rt=2.1 min; m/3=1533; m/4=1150; m/5=920

Example 68

N$^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Acb2,Leu10,Glu15,Lys17,Arg20,Glu21,Leu27,Lys28]-Glucagon amide

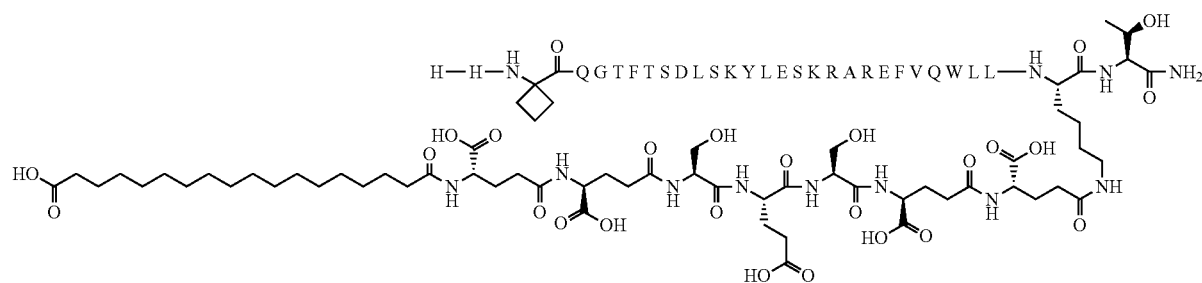

UPLC method: UPLC02v01: RT=7.9 min
LC-MS method: LCMS01v01: Rt=2.0 min; m/3=1528; m/4=1146; m/5=917

Example 69

N$^{\epsilon 28}$-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl]amino]butanoyl]amino]-3-hydroxypropanoyl]amino]butanoyl]amino]butanoyl]-[Aib2,Leu10,Glu15,Lys17,Arg20,Ser21,Leu27,Lys28]-Glucagon amide

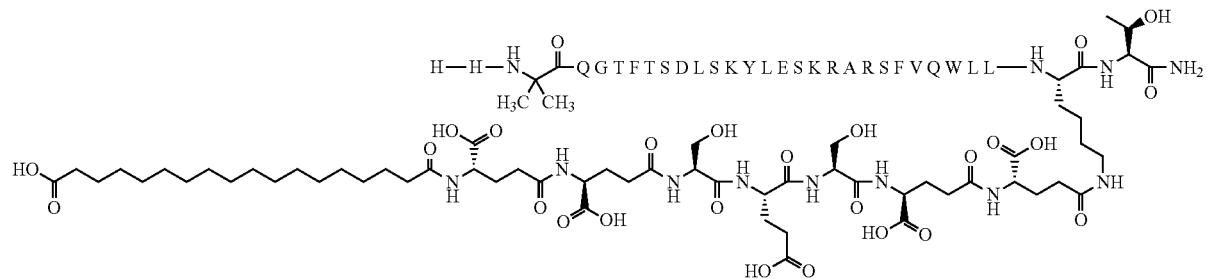

UPLC method: UPLC02v01: RT=8.1 min
LC-MS method: LCMS01v01: Rt=2.6 min; m/3=1133; m/4=906; m/5=756

Example 70

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Ala16,Leu27,Lys28]-Glucagon amide

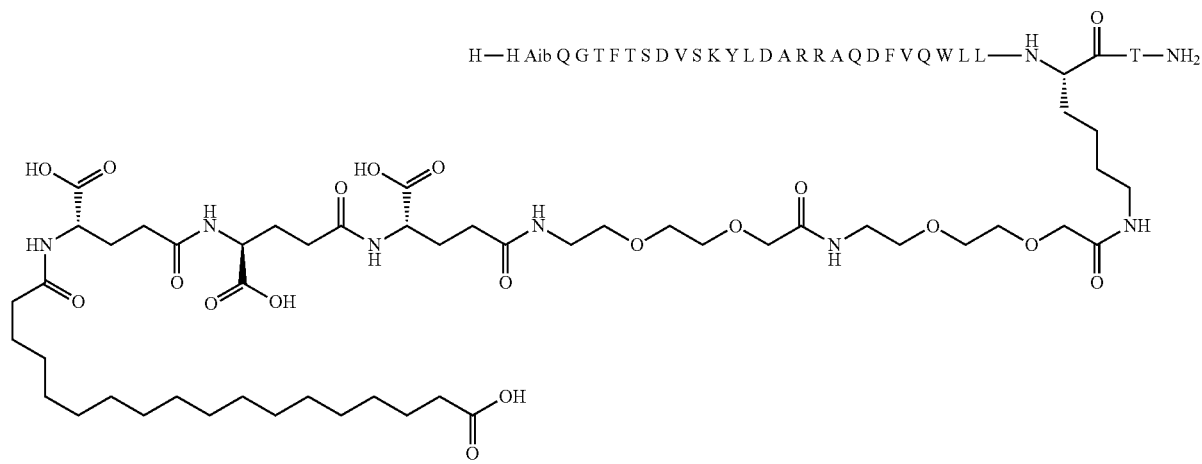

UPLC method: UPLC02v01: RT=8.4 min
LC-MS method: LCMS13v01: Rt=2.2 min; m/3=1457; m/4=1093; m/5=874

Example 71

N^ε28-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Leu16,Leu27,Lys28]-Glucagon amide

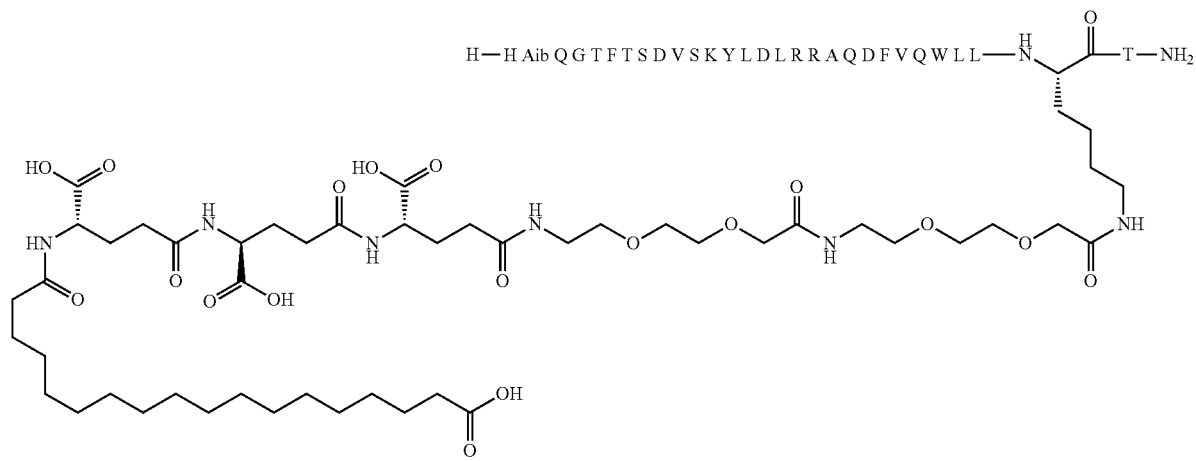

UPLC method: UPLC02v01: RT=8.5 min
LC-MS method: LCMS13v01: Rt=2.3 min; m/3=1471; m/4=1104

Example 72

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Arg12,Ala16,Leu27,Lys28]-Glucagon amide

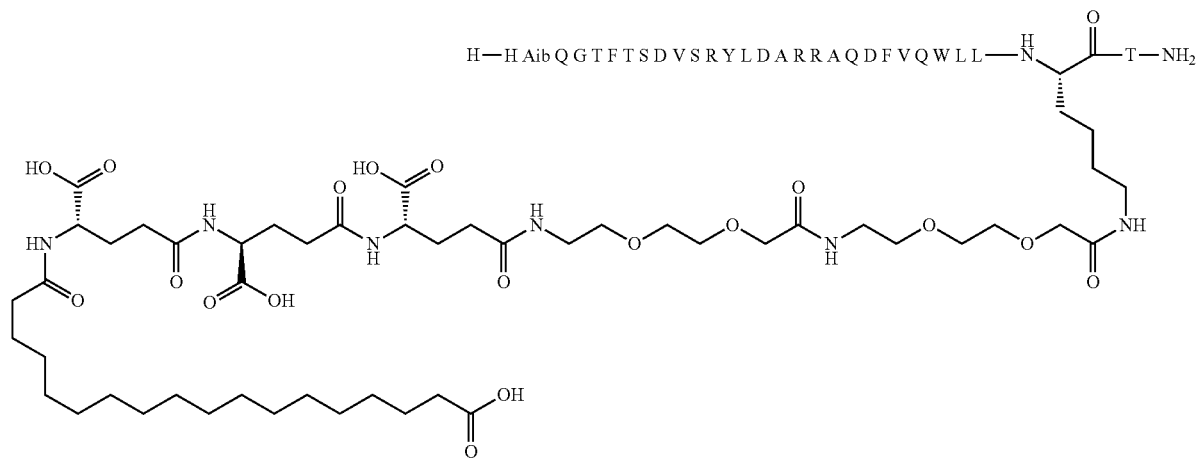

UPLC method: UPLC02v01: RT=8.4 min
LC-MS method: LCMS13v01: Rt=2.3 min; m/3=1467; m/4=1100

Example 73

$N^{\epsilon 28}$-[2-[2-[2-[[2-[2-[2-[[(4S)-4-carboxy-4-[[(4S)-4-carboxy-4-[[(4S)-4-carboxy-4-(17-carboxyheptadecanoylamino)butanoyl]amino]butanoyl]amino]butanoyl]amino]ethoxy]ethoxy]acetyl]amino]ethoxy]ethoxy]acetyl]-[Aib2,Val10,Arg12,Leu16,Leu27,Lys28]-Glucagon amide

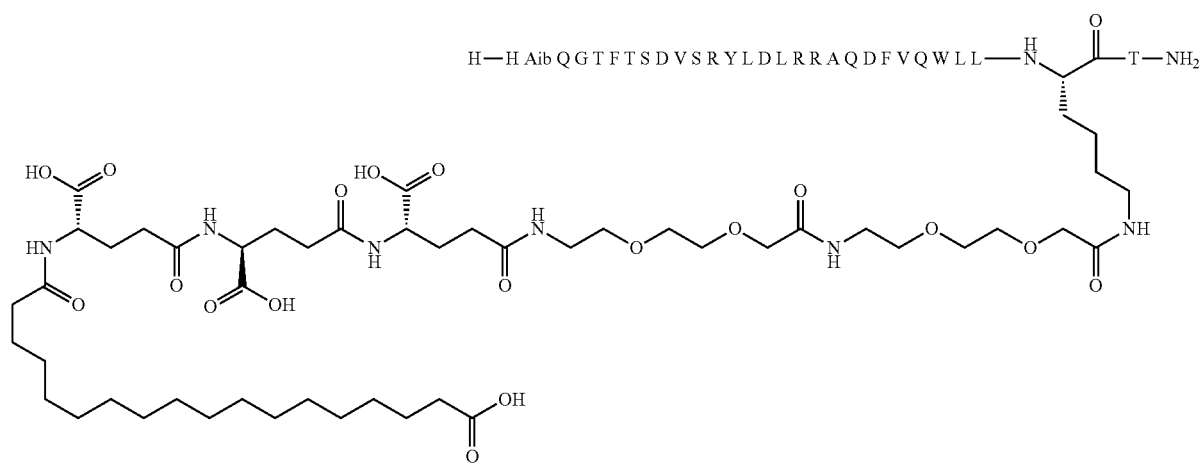

UPLC method: UPLC02v01: RT=8.5 min
LC-MS method: LCMS13v01: Rt=2.3 min; m/3=1481; m/4=1111

Example 74

GLP-1 and Glucagon Receptor Potency

The purpose of this example was to test the potency, of the glucagon derivatives of the invention, in vitro. The in vitro potency is the measure of human GLP-1 receptor or glucagon receptor activation, respectively, in a whole cell assay.

Principle

In vitro potency was determined by measuring the response of human GLP-1 or glucagon receptor, respectively, in a reporter gene assay. The assay was performed in a stably transfected BHK cell line that expresses either the human GLP-1 receptor or the human glucagon receptor and contains the DNA for the cAMP response element (CRE) coupled to a promoter and the gene for firefly luciferase (CRE luciferase). When the human GLP-1 or glucagon receptor, respectively, was activated it resulted in the production of cAMP, which in turn resulted in the luciferase protein being expressed. When assay incubation was completed, the luciferase substrate (luciferin) was added and the enzyme converted luciferin to oxyluciferin and produces bioluminescence. The luminescence was measured as the readout for the assay.

(a) GLP-1 Receptor Activation

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in DMEM medium with 10% FBS, 1× GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: PLURONIC® F-68 (nonionic surfactant) (10%) (Gibco 2404), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Assay Medium consisted of DMEM w/o phenol red, 10 mM Hepes, 1× GlutaMAX, 2% Ovalbumin and 0.2% PLURONIC® F-68 (nonionic surfactant).

Procedure

Cell stocks were thawed in a 37° C. water bath. Cells were washed three times in PBS. The cells were counted and adjusted to 5×10EE3 cells/50 µl (1×10EE5 cells/ml) in Assay Medium. A 50 µl aliquot of cells was transferred to each well in the assay plate.

Stocks of the test compounds and reference compounds were diluted to a concentration of 0.2 µM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% $CO_2$ incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). $EC_{50}$ values were calculated by the software and reported in pM. Data are shown in Table 6.

(b) Glucagon Receptor Activation

Cell Culture and Preparation

The cells used in this assay (clone pLJ6'-4-25) were BHK cells with BHK570 as a parent cell line expressing the CRE luciferase gene (clone BHK/KZ10-20-48) and were established by further transfection with the human glucagon receptor (clone pLJ6' in pHZ-1 vector).

The cells were cultured at 5% $CO_2$ in DMEM medium with 10% FBS, 1× GlutaMAX, 1 mg/ml G418, 240 nM MTX (methotrexate) and 1% pen/strep (penicillin/streptomycin). They were aliquoted and stored in liquid nitrogen. Before each assay, an aliquot was taken up and washed three times in PBS before being suspended at the desired concentration in assay medium. For 96-well plates the suspension was made to give a final concentration of 5×10EE3 cells/well.

Materials

The following chemicals were used in the assay: PLURONIC® F-68 (nonionic surfactant) (10%) (Gibco 2404), ovalbumin (Sigma A5503), DMEM w/o phenol red (Gibco 11880-028), 1 M Hepes (Gibco 15630), Glutamax 100× (Gibco 35050) and steadylite plus (PerkinElmer 6016757).

Assay Medium consisted of DMEM w/o phenol red, 10 mM Hepes, 1× GlutaMAX, 2% Ovalbumin and 0.2% PLURONIC® F-68 (nonionic surfactant).

Procedure

Cell stocks were thawed in a 37° C. water bath. Cells were washed three times in PBS. The cells were counted and adjusted to 5×10EE3 cells/50 µl (1×10EE5 cells/ml) in Assay Medium. A 50 µl aliquot of cells was transferred to each well in the assay plate.

Stocks of the test compounds and reference compounds were diluted to a concentration of 0.2 µM in Assay Medium. Compounds were diluted 10-fold to give the following concentrations: 2×10EE-6 M, 2×10EE-7 M, 2×10EE-8 M; 2×10EE-9 M, 2×10EE-10 M, 2×10EE-11 M, 2×10EE-12 M and 2×10EE-13 M. For each compound a blank assay medium control was also included.

A 50 µl aliquot of compound or blank was transferred from the dilution plate to the assay plate. Compounds were tested at the following final concentrations: 1×10EE-6 M, 1×10EE-7 M, 1×10EE-8 M; 1×10EE-9 M, 1×10EE-10 M, 1×10EE-11 M and 1×10EE-12 M and 1×10EE-13 M.

The assay plate was incubated for 3 h in a 5% $CO_2$ incubator at 37° C. The assay plate was removed from the incubator and allowed to stand at room temperature for 15 min. A 100 µl aliquot of steadylite plus reagent was added to each well of the assay plate (reagent is light sensitive). Each assay plate was covered with aluminum foil to protect it from light and shaken for 30 min at room temperature. Each assay plate was read in a Perkin Elmer TopCount NXT instrument.

Calculations

The data from the TopCount instrument was transferred to GraphPad Prism software. The software performed a non-linear regression (log(agonist) vs response-Variable slope (four parameter)). $EC_{50}$ values were calculated by the software and reported in pM. Data are shown in Table 6.

Example 75

GLP-1 and Glucagon Receptor Binding (a) GLP-1 Receptor Binding

The purpose of this assay was to test the in vitro receptor binding activity of the glucagon derivatives of the invention. The receptor binding is a measure of affinity of a compound for the human GLP-1 receptor.

Principle

The receptor binding of each compound to the human GLP-1 receptor was measured in a displacement binding assay. In this type of assay a labelled ligand (in this case 125I-GLP-1) is bound to the receptor. Each derivative was added in a series of concentrations to isolated membranes containing the human GLP-1 receptor and displacement of the labelled ligand was monitored. The receptor binding was reported as the concentration at which half of the labelled ligand was displaced from the receptor, the $IC_{50}$ value.

In order to test the binding of the derivatives to albumin, the assay may be performed in a very low concentration of serum albumin (max. 0.001% final assay concentration) as well as in the presence of a higher concentration of serum albumin (2.0% final assay concentration). An increase of the $IC_{50}$ value, in the presence of serum albumin indicates an affinity to serum albumin and represents a method to predict a protracted pharmacokinetic profile of the test substance in animal models.

Materials

The following chemicals were used in the assay: DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, $MgCl_2$ (Merck 1.05832.1000), TWEEN® 20 (nonionic surfactant) (Amresco 0850C335), SPA particles (wheat germ agglutinin (WGA) SPA beads, Perkin Elmer RPNQ0001), [125I]-GLP-1]-(7-36)NH2 (produced in-house), OptiPlate™-96 (Perkin Elmer).

Buffer 1 consisted of 20 mM Na-HEPES plus 10 mM EDTA and pH was adjusted to 7.4.

Buffer 2 consisted of 20 mM Na-HEPES plus 0.1 mM EDTA and pH was adjusted to 7.4.

Assay buffer consisted of 50 mM HEPES supplemented with 5 mM EGTA, 5 mM $MgCl_2$, 0.005% TWEEN® 20 (nonionic surfactant) and pH was adjusted to 7.4.

Cell Culture and Membrane Preparation

The cells used in this assay (clone FCW467-12A) were BHK cells with BHKTS13 as a parent cell line. The cells express the human GLP-1 receptor.

The cells were grown at 5% $CO_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX dispersing instrument for 20-30 sec in a suitable amount of buffer 1 (e.g. 10 ml). The homogenate was centrifuged for 15 min. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay, 50 μl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five μl were added to appropriate wells in the assay plate.
3. Cell membrane aliquots were thawed and diluted to their working concentration. Fifty μl were added to each well in the assay plate.
4. WGA SPA beads were suspended in assay buffer at 20 mg/ml. The suspension was diluted to 10 mg/ml in assay buffer just prior to addition to the assay plate. Fifty μl were added to each well in the assay plate.
5. The incubation was started by adding 25 μl of 480 pM solution of [125I]-GLP-1]-(7-36)$NH_2$ to each well of the assay plate. A 25 μl aliquot was reserved for measuring total counts/well.
6. The assay plate was incubated for 2 h at 30° C.
7. The assay plate was centrifuged for 10 min.
8. The assay plate was read in a Perkin Elmer TopCount NXT instrument.

Calculations

The data from the TopCount instrument were transferred to GraphPad Prism software. The software averaged the values for the replicates and performed a non-linear regression. $IC_{50}$ values were calculated by the software and reported in nM. Data are shown in Table 6.

(b) Glucagon Receptor Binding

The purpose of this assay was to test the in vitro receptor binding activity (i.e. affinity) of the glucagon derivatives of the invention. The receptor binding activity is a measure of affinity of a derivative for the human glucagon receptor.

Principle

The receptor binding of each compound to the human glucagon receptor was measured in a displacement binding assay. In this type of assay a labelled ligand (in this case 125I-glucagon) is bound to the receptor. Each derivative was added in a series of concentrations to isolated membranes containing the human glucagon receptor and displacement of the labelled ligand is monitored. The receptor binding was reported as the concentration at which half of the labelled ligand is displaced from the receptor, the $IC_{50}$ value.

In order to test the binding of the derivatives to albumin, the assay may be performed in a very low concentration of serum albumin (max. 0.001% final assay concentration) as well as in the presence of a higher concentration of serum albumin (0.2% final assay concentration). An increase of the $IC_{50}$ value, in the presence of serum albumin indicates an affinity to serum albumin and represents a method to predict a protracted pharmacokinetic profile of the test substance in animal models.

Materials

The following chemicals were used in the assay: DMEM w Glutamax (Gibco 61965-026), Pen/strep (Invitrogen 15140-122), G418 (Invitrogen 10131-027), Versene (Gibco 15040), 1 M Hepes (Gibco 15630), PBS (Invitrogen 14190-094), fetal calf serum (Invitrogen 16140-071), $MgCl_2$ (Merck 1.05832.1000), EDTA (Invitrogen 15575-038), CaCl$_2$ (Sigma, C5080), TWEEN® 20 (nonionic surfactant) (Amresco 0850C335), ovalbumin (Sigma A5503), SPA particles (wheat germ agglutinin (WGA) SPA beads, Perkin Elmer RPNQ0001), [125I]-glucagon (produced in-house), OptiPlate™-96 (Packard 6005290).

HME buffer consisted of 25 mM HEPES, 2 mM MgCl$_2$ and 1 mM EDTA, and pH was adjusted to 7.4. Assay buffer consisted of 50 mM HEPES supplemented with 5 mM MgCl$_2$, 1 mM CaCl$_2$, 0.02% TWEEN® 20 (nonionic surfactant) and 0.1% Ovalbumin, and pH was adjusted to 7.4.
Cell culture and membrane preparation.

The cells used in this assay (clone BHK hGCGR A3*25) were BHK cells stable transfected with an expression plasmid containing the cDNA encoding the human glucagon receptor.

The cells were grown at 5% CO$_2$ in DMEM, 10% fetal calf serum, 1% Pen/Strep (Penicillin/Streptomycin) and 1.0 mg/ml of the selection marker G418. To make a membrane preparation the cells were grown to approximately 80% confluence. The cells were washed twice in phosphate-buffered saline and harvested. The cells were pelleted using a brief centrifugation and the cell pellet was kept on ice. Lyse the cells by adding approx. 5 ml HME buffer, mix by pipetting and snap freeze in liquid nitrogen. Thaw quickly and add HME buffer to 10 ml. The cell pellet was homogenised with an ULTRA-THURRAX dispersing instrument for 20-30 sec. The homogenate was centrifuged at 20.000×G, 4° C. for 10 min. The pellet was re-suspended (homogenised) in 1-2 ml HME buffer. The protein concentration was determined. The membranes were aliquoted and snap-frozen in liquid nitrogen and stored at minus 80° C.
Procedure 1. For the receptor binding assay, 50 µl of the assay buffer was added to each well of an assay plate.
2. Test compounds were serially diluted to give the following concentrations: 8×10EE-7 M, 8×10EE-8 M, 8×10EE-9 M, 8×10EE-10 M, 8×10EE-11 M, 8×10EE-12 M and 8×10EE-13 M. Twenty-five µl were added to appropriate wells in the assay plate.
3. Cell membrane aliquots were thawed and diluted to their working concentration. Fifty µl were added to each well in the assay plate.
4. WGA SPA beads were suspended in assay buffer at 20 mg/ml. The suspension was diluted to 10 mg/ml in assay buffer just prior to addition to the assay plate. Fifty µl were added to each well in the assay plate.
5. The incubation was started by adding 25 µl of 480 pM solution of [125I]-glucagon to each well of the assay plate. A 25 µl aliquot was reserved for measuring total counts/well.
6. The assay plate was incubated for 2 h at 25° C.
7. The assay plate was centrifuged for 10 min at 1500 rpm.
8. The assay plate was read in a Perkin Elmer TopCount NXT instrument.
Calculations The data from the TopCount instrument were transferred to GraphPad Prism software. The software averaged the values for the replicates and performed a non-linear regression. IC$_{50}$ values were calculated by the software and reported in nM. Data are shown in Table 6.

Example 76

Thioflavin T (ThT) Fibrillation Assay for the Assessment of Physical Stability of Peptide Formulations The purpose of this assay was to assess the physical stability of the glucagon derivatives of the invention in aqueous solutions.

Low physical stability of a peptide may lead to amyloid fibril formation, which is observed as well-ordered, thread-like macromolecular structures in the sample, which eventually may lead to gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al; Anal. Biochem. 1989 177 244-249; LeVine; Methods. Enzymol. 1999 309 274-284].

The time course for fibril formation can be described by a sigmoidal curve with the following expression [Nielsen et al; Biochemistry 2001 40 6036-6046]:

$$F = f_i + m_i t + \frac{f_f + m_f t}{1 + e^{-[(t-t_0)/\tau]}} \qquad \text{Eq. (1)}$$

Here, as depicted in FIG. 1, F is the ThT fluorescence at the time t. The constant $t_0$ is the time needed to reach 50% of maximum fluorescence. The two important parameters describing fibril formation are the lag-time calculated by $t_0-2\tau$ and the apparent rate constant kapp 1/τ.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Samples were prepared freshly before each assay. Each sample composition is described in the legends. The pH of the sample was adjusted to the desired value using appropriate amounts of concentrated NaOH and HCl. Thioflavin T was added to the samples from a stock solution in H$_2$O to a final concentration of 1 µM.

Sample aliquots of 200 µl (250 µM of the glucagon derivative/analogue in 10 mM HEPES buffer, pH 7.5) were placed in a 96 well microtiter plate (Packard OptiPlate™-96, white polystyrene). Usually, four or eight replica of each sample (corresponding to one test condition) were placed in one column of wells. The plate was sealed with Scotch Pad (Qiagen).

Incubation at given temperature, shaking and measurement of the ThT fluorescence emission were done in a Fluoroskan Ascent FL fluorescence plate reader (Thermo Labsystems). The temperature was set to 37° C. and the plate was incubated with orbital shaking adjusted to 960 rpm with an amplitude of 1 mm. Fluorescence measurement was done using excitation through a 444 nm filter and measurement of emission through a 485 nm filter.

Each run was initiated by incubating the plate at the assay temperature for 10 min. The plate was measured every 20 minutes for a desired period of time. Between each measurement, the plate was shaken and heated as described.

After completion of the ThT assay the four or eight replica of each sample was pooled and centrifuged at 20000 rpm for 30 minutes at 18° C. The supernatant was filtered through a 0.22 µm filter and an aliquot was transferred to a HPLC vial.

The concentration of peptide in the initial sample and in the filtered supernatant was determined by reverse phase HPLC using an appropriate standard as reference. The percentage fraction the concentration of the filtered sample constituted of the initial sample concentration was reported as the recovery.

The measurement points were saved in Microsoft Excel format for further processing and curve drawing and fitting was performed using GraphPad Prism. The background emission from ThT in the absence of fibrils was negligible. The data points were typically a mean of four or eight samples.

The data set may be fitted to Eq. (1). However, the lag time before fibrillation may be assessed by visual inspection of the curve identifying the time point at which ThT fluorescence increases significantly above the background level. The data, as shown in Table 6, strongly confirmed the improved physical stability of the compounds of this invention.

Example 77

In Vivo Test in Diet-Induced Obese (DIO)-Mice

The purpose of this experiment was to investigate effect of the glucagon-GLP-1R co-agonists from Example 8 and Example 12 on body weight and blood glucose in vivo in DIO mice. Liraglutide (a human GLP-1 analogue marketed by Novo Nordisk A/S under the brand name Victoza™) was included for comparison.

Male c57bl/6J mice obtained from Jackson Lab (USA) were fed a high fat diet (Research Diets D12451, 45% kcal fat) to obtain approximately 50% overweight compared to age-matched lean control mice. The DIO mice are characterized by normoglycemia, insulin resistance and obesity. DIO mice with a body weight of approximately 40 g were allocated to groups of 8 animals to obtain comparable body weight and body fat proportion between groups.

The co-agonists, i.e. the glucagon derivatives, were dissolved in 50 mM $Na_2HPO_4$, 145 mM NaCl og 0.05% TWEEN® 80 (nonionic surfactant), pH 7.4, while liraglutide was diluted from 6 mg/ml Victoza™ pens in DPBS buffer (Invitrogen) containing 0.5% rat serum albumin. Vehicle treated animals received 50 mM $Na_2HPO_4$, 145 mM NaCl og 0.05% TWEEN® 80 (nonionic surfactant), pH 7.4. Compounds and vehicle were dosed (1 ml/kg) for 5 weeks s.c. once daily just prior to lights out. For the first half of the study co-agonists were administered at a dose of 5 nmol/kg and for the second half of the study co-agonists were administered at a dose of 10 nmol/kg. For comparison, liraglutide at a dose of 100 nmol/kg, likewise dosed s.c. once daily, was included. Body weight was monitored before dosing, daily during the dosing period. Non-fasted blood glucose was measured on the day of initiation of dosing and weekly during the dosing period, prior to dosing. Blood for measurement of blood glucose was taken from the tail tip capillary and blood glucose was measured using a glucose analyzer (Biosen 5040) based on the glucose oxidase method.

The body weight reduction/body weight at the end of the 5 week treatment period and area under the blood glucose curve during the five week treatment period are given in the tables below.

TABLE 1

Normalized body weight after 5 weeks of treatment

| Compound | Percent BW of baseline at week 5 (mean ± SD) | Body weight |
|---|---|---|
| Vehicle | 103% ± 2% | 42 g ± 4 g |
| Liraglutide | 87% ± 4% | 36 g ± 5 g* |
| Example 8 | 88% ± 8% | 36 g ± 5 g* |
| Example 12 | 75% ± 8% | 31 g ± 2 g** |

*$p < 0.05$;
**$p < 0.001$ vs vehicle, One-way ANOVA, Bonferoni post-hoc test

TABLE 2

Area under the blood glucose curve measured during the 5-week treatment period

| Compound | AUC $BG_{(week\ 1\text{-}5)}$ (mean ± SD) |
|---|---|
| Vehicle | 243 mM * day ± 16 mM * day |
| Liraglutide | 208 mM * day ± 10 mM * day*** |
| Example 8 | 187 mM * day ± 11 mM * day*** |
| Example 12 | 206 mM * day ± 16 mM * day*** |

***$p < 0.001$ vs vehicle, One-way ANOVA, Bonferoni post-hoc test

The results in Tables 1 and 2 show that the glucagon-GLP-1R co-agonist derivatives of the invention are biologically active in vivo, with effective lowering of body weight, which for the compound from Example 12 tends to be superior to liraglutide alone, while blood glucose remains improved as compared to vehicle treated animals and on par with liraglutide treated animals.

Example 78

Pharmacokinetic Profile in Mice

The purpose of this assay was to assess the pharmocokinetic profiles of the glucagon derivatives of the invention in mice.

The pharmacokinetic profile of glucagon-GLP1 co-agonists was tested in normal male c57/BL6 mice (approximately body weight: 30 grams), in a sparse sampling design with for example 3 mice represented at each time point (for example: t=0.25, 0.5, 1, 3, 6, 10, 24, 30 and 48 hours). The compound was dosed as a single subcutaneous dose of 10 nmol/kg at t=0.

The plasma levels of the glucagon-GLP1 co-agonist compounds were determined using an ELISA/LOCI assay (see Example 80 herein). Pharmacokinetic calculations such as half-life ($T_{1/2}$) maximum concentration ($C_{max}$) and time for maximum concentration ($T_{max}$) of the compounds were determined using the PC based software, Phoenix (WinNonLin version 6.3 from Pharsight, Certara).

The results strongly confirmed the protracted effect of the glucagon-GLP1 co-agonists of this invention.

TABLE 3

Mean half-life ($T_{1/2}$), maximum concentration ($C_{max}$) and time for maximum concentration ($T_{max}$)

| Compound | $T_{1/2}$ (hours) | $C_{max}$ (pM) | $T_{max}$ (hours) |
|---|---|---|---|
| Example 8 | 23 | 45,000 | 3 |
| Example 12 | 14 | 24,400 | 3 |

Example 79

Chemical Stability Assessment

The purpose of this assay was to assess the chemical stability of the glucagon derivatives of the invention in aqueous solutions.

Chemical stability of glucagon derivatives or analogues was investigated by RP-UPLC separation and UV detection. Lyophilized samples were dissolved in a 8 mM Phosphate buffer pH 8.6, followed by adjustment to pH 7.3. using HCl to a final concentration of 333 μM. Samples were incubated for 14 days at 5° C. and 37° C. followed by RP-UPLC analysis. Purity was defined as the area percentage of the main peak in relation to the total area of all integrated peaks in each chromatogram. Purity loss after 14 days at 37° C. was determined as the difference in purity between the samples incubated at 5° C. and 37° C., divided by the purity of the sample after incubation for 14 days at 5° C.

RP-UPLC analysis was performed using a Waters BEH130 2.1 mm×150 mm, 1.7 μm column operated at 50° C. and a flow rate of 0.4 mL/min using a mobile phase system consisting of A: 0.05% TFA in MQ-water B: 0.05% TFA in Acetonitrile. UV-detection was performed at 215 nm. The typical gradient profile used for most of the samples is shown below.

TABLE 4

Typical gradient profile used for RP-UPLC analysis

| Time (min) | % B |
| --- | --- |
| Injection | 20 |
| 30 | 60 |
| 31 | 99 |
| 37 | 99 |
| 39 | 20 |
| 40 | 20 |
| 45 | 20 |

For some individual derivatives or analogues eluting at substantially different retention times compared with the majority of derivatives or analogues, some adjustments to the gradient profile were made to better enable purity assessment comparison across samples. The data confirmed the improved chemical stability of the glucagon derivatives of this invention.

TABLE 5

Chemical stability of GLP-1/plucaponreceptor co-agonists
Data shown are purity loss after 14 days at 37° C. in percent (%)

| Compound | Purity loss; 14 days at 37° C. |
| --- | --- |
| Example 8 | 9 |
| Example 12 | 8 |
| Example 16 | 3 |
| Example 22 | 1 |
| Example 23 | 2 |
| Example 25 | 1 |
| Example 26 | 2 |
| Example 27 | 5 |
| Example 34 | 5 |
| Example 36 | 2 |
| Example 38 | 2 |
| Example 39 | 3 |
| Example 40 | 2 |
| Example 41 | 1 |
| Example 42 | 3 |

TABLE 5-continued

Chemical stability of GLP-1/plucaponreceptor co-agonists
Data shown are purity loss after 14 days at 37° C. in percent (%)

| Compound | Purity loss; 14 days at 37° C. |
| --- | --- |
| Example 43 | 2 |
| Example 44 | 2 |
| Example 45 | 3 |
| Example 46 | 1 |
| Example 47 | 3 |
| Example 48 | 2 |
| Example 49 | 2 |
| Example 51 | 3 |
| Example 54 | 1 |
| Example 55 | 2 |
| Example 57 | 1 |
| Example 58 | 2 |
| Example 60 | 4 |
| Example 56 | 4 |
| Example 62 | 2 |
| Example 63 | 1 |
| Example 65 | 3 |
| Example 66 | 2 |
| Example 68 | 3 |
| Example 67 | 4 |
| Example 69 | 2 |
| Example 70 | 2 |

Example 80

ELISA/LOCI Assay for Determination of Peptides in Blood Plasma

The purpose of this assay was to determine the content of GLP-1/glucagon receptor co-agonists in blood plasma.

Samples were analysed for peptide levels using Luminescence Oxygen Channeling Immunoassay (LOCI). The donor beads were coated with streptavidin. Acceptor beads are conjugated with a monoclonal antibody specific to gGlu in the linker (NN454-1F31) while the second monoclonal antibody (1F120) specific for glucagon was biotinylated. Three reactants were combined with the analyte and formed a two-sited immuno-complex. Illumination of the complex released singlet oxygen atoms from the donor beads. They were channeled into the acceptor beads and triggered chemi-luminescence which was measured in the EnVision plate reader. The amount of emitted light is proportional to the concentration of peptide.

One μL sample/calibrator/control was applied to the wells of 384-well LOCI plates followed by a 15 μL mixture of the antibody-coated acceptor beads (0.5 μg/well) and the biotinylated antibody. The plates were incubated over night at 21-22° C. Following incubation, 30 μL of the streptavidin-coated donor-beads (2 μg/well) was added to each well and incubated for 30 minutes at 21-22° C. The plates were read in an Envision plate reader at 21-22° C. with a filter having a bandwidth of 520-645 nm after excitation by a 680 nm laser. The total measurement time per well was 210 ms including a 70 ms excitation time.

The following table shows data of the glucagon derivatives of the invention obtained as described in the examples above.

TABLE 6

EC$_{50}$ (Assay described in Example 74 herein) and IC$_{50}$ (Assay described in Example 75 herein) values for GLP-1/glucagon receptor co-agonists and physical stability data (Assay described in Example 76 herein)

| Compound of Example No | EC$_{50}$ GLP-1R [pM] | EC$_{50}$ GlucR [pM] | IC$_{50}$ GLP-1R [nM] | IC$_{50}$ GlucR [nM] | THT assay Lag time (Ex. 76) | THT assay Recovery (Ex. 76) |
|---|---|---|---|---|---|---|
| 1 | 8.0 | 54.0 | | | 45.0 | 100.0 |
| 2 | 44.0 | 97.0 | | | 7.0 | 2.0 |
| 3 | 6.0 | 60.0 | | | 45.0 | 100.0 |
| 4 | 4.0 | 16.0 | | | 45.0 | 100.0 |
| 5 | 5.0 | 109.0 | | | 45.0 | 100.0 |
| 6 | 20.0 | 1210.0 | | | 45.0 | 100.0 |
| 7 | | | 2.4 | 1.1 | 45.0 | 100.0 |
| 8 | 29.6 | 1128.1 | 1.1 | 6.7 | 45.0 | 98.0 |
| 9 | 3.2 | 698.9 | .2 | 380.8 | 8.0 | 45.0 |
| 10 | 9.2 | 42.3 | .5 | 1.2 | 7.0 | 11.0 |
| 11 | 15.0 | 672.0 | | | | |
| 12 | 14.7 | 104.0 | .5 | 7.0 | 45.0 | 100.0 |
| 13 | 6.0 | 1430.0 | | | | |
| 14 | 28.0 | 599.0 | | | | |
| 15 | 20.0 | 190.0 | | | | |
| 16 | 5.8 | 113.1 | .2 | 3.9 | 45.0 | 100.0 |
| 17 | | | .2 | 53.0 | 45.0 | 92.6 |
| 18 | 2.3 | 220.3 | .1 | 11.0 | 45.0 | 103.3 |
| 19 | 4.7 | 39.9 | .9 | 8.5 | 6.7 | 5.0 |
| 20 | 4.4 | 62.4 | .4 | 6.7 | 6.0 | 5.0 |
| 21 | 2.7 | 240.3 | .3 | 51.0 | 18.0 | 33.0 |
| 22 | 11.8 | 87.1 | .2 | 7.1 | 45.0 | 100.0 |
| 23 | 22.1 | 77.3 | .3 | 6.4 | 45.0 | 104.0 |
| 24 | 11.9 | 506.3 | .2 | 61.0 | 28.0 | 105.0 |
| 25 | 5.7 | 44.7 | .2 | 5.1 | 45.0 | 104.0 |
| 26 | 9.0 | 8.7 | .5 | 4.0 | 45.0 | 100.0 |
| 27 | 4.1 | 1.7 | .9 | .7 | 42.0 | 98.0 |
| 28 | 29.5 | 1328.0 | 1.6 | 148.0 | | |
| 39 | 26.6 | 58.8 | 1.4 | 5.9 | 33.0 | 77.0 |
| 30 | 35.7 | 4.8 | 1.4 | .5 | 45.0 | 100 |
| 31 | 19.5 | 2.9 | 1.5 | .8 | 45.0 | 100 |
| 32 | 32.7 | 6.8 | 3.9 | 1.9 | 45.0 | 100 |
| 33 | 14.6 | 3.6 | .6 | 2.0 | 45 | 100 |
| 34 | 14.7 | 2.9 | .2 | .2 | 45 | 100 |
| 35 | 3.0 | 1.0 | 2.6 | .7 | 45 | 119 |
| 36 | 2.0 | 4.0 | .2 | .6 | 45 | 131 |
| 37 | 4.0 | 2.0 | .2 | .1 | 45 | 50 |
| 38 | 13.0 | 24.0 | 1.2 | 29.4 | 45 | 99 |
| 39 | 4.0 | 12.0 | .3 | 5.6 | 45 | 98 |
| 40 | 4.0 | 136.0 | .4 | 37.7 | 40 | 96 |
| 41 | 7.0 | 29.0 | .3 | 1.2 | 45 | 100 |
| 42 | 3.0 | 32.0 | .3 | 38.2 | 45 | 100 |
| 43 | 5.0 | 2.0 | .3 | 5.6 | 45 | 105 |
| 44 | 3.0 | 10.0 | .3 | 7.2 | 45 | 105 |
| 45 | 18.0 | 6.0 | .4 | 4.5 | 45 | 105 |
| 46 | 21.0 | 16.0 | 1.1 | 8.5 | 45 | 105 |
| 47 | 17.0 | 5.0 | .2 | 1.5 | 45 | 105 |
| 48 | 44.0 | 8.0 | .2 | 3.1 | 45 | 105 |
| 49 | 17.0 | 4.0 | .4 | 1.7 | 45 | 104 |
| 50 | 11.0 | 280.0 | 2.2 | 26.2 | 28 | 80 |
| 51 | 6.0 | 4.0 | .7 | 1.4 | 45 | 104 |
| 52 | 4.0 | 16.0 | .2 | | 45 | 88 |
| 53 | 11.0 | 7.0 | 1.9 | | 45 | 100 |
| 54 | 2.7 | 12.7 | .2 | 1.7 | 45 | 100 |
| 55 | 27.0 | 30.5 | 1.1 | 18.4 | 45 | 100 |
| 56 | 5.3 | 6.3 | .3 | 2.1 | 45 | 100 |
| 57 | 3.0 | 129.0 | .2 | 19.0 | 45 | 100 |
| 58 | 4.3 | 11.3 | .2 | 2.6 | 45 | 100 |
| 59 | 4.0 | 17.0 | .2 | 1.4 | 12 | 9 |
| 60 | 6.0 | 54.0 | .2 | 4.0 | 45 | 100 |
| 61 | 6.0 | 11.0 | .3 | 1.8 | 20 | 27 |
| 62 | 8.0 | 10.0 | .2 | 3.9 | 45 | 100 |
| 63 | 7.0 | 24.0 | .8 | 7.7 | 45 | 100 |
| 64 | 3.0 | 20.0 | .9 | 5.5 | 19 | 27 |
| 65 | 6.0 | 44.0 | .5 | 17.0 | 45 | 100 |
| 66 | 5.0 | 47.0 | .6 | 10.4 | 45 | 104 |
| 67 | 4.0 | 10.0 | .3 | 1.5 | 45 | 100 |
| 68 | 7.0 | 5.0 | .3 | .6 | 45 | 100 |
| 69 | 7.0 | 68.0 | 0.2 | 9.5 | 45 | 105 |
| 70 | 1.5 | 30.0 | 0.2 | 3.2 | 45 | 106 |
| 71 | 4.0 | 17.0 | 0.7 | 5.7 | 45 | 100 |
| 72 | 3.0 | 57.0 | 0.5 | 11.3 | 31 | 98 |
| 73 | 5.0 | 49.0 | 1.5 | 16.2 | 22 | 88 |

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A pharmaceutical composition comprising a glucagon derivative as the only active compound, wherein the glucagon derivative is $N^{\epsilon 28}$-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide:

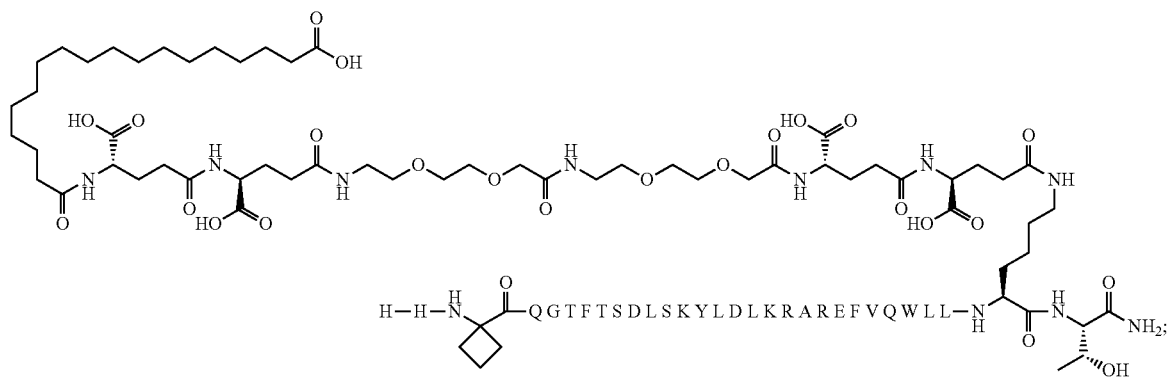

N^{ε28}-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl] amino]butanoyl] amino]-3-hydroxypropanoyl] amino]butanoyl]amino]butanoyl]-[Aib2,Leu10,Glu15,Lys17,Arg20,Glu21,Leu27,Lys28]-Glucagon amide:

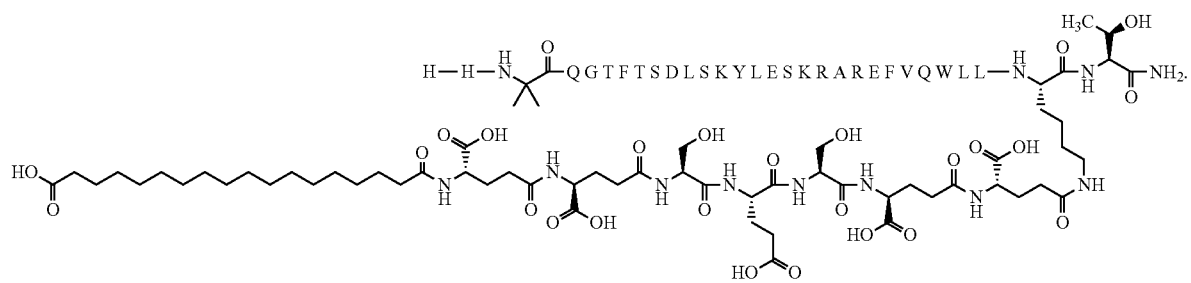

2. The pharmaceutical composition according to claim 1, wherein the glucagon derivative is:
N^{ε28}-[(4S)-4-carboxy-4-[[(4S)-4-carboxy-4-[[2-[2-[2-[[2-[2-[2-[[(4S)-4-carboxy-4-[[(4S)-4-carboxy-4-(17-carboxyheptadecanoylamino)butanoyl]amino]butanoyl]amino]ethoxy]ethoxy]acetyl]amino]ethoxy]ethoxy]acetyl]amino]butanoyl]amino]butanoyl]-[Acb2,Leu10,Leu16,Lys17,Arg20,Glu21,Leu27,Lys28]-Glucagon amide:

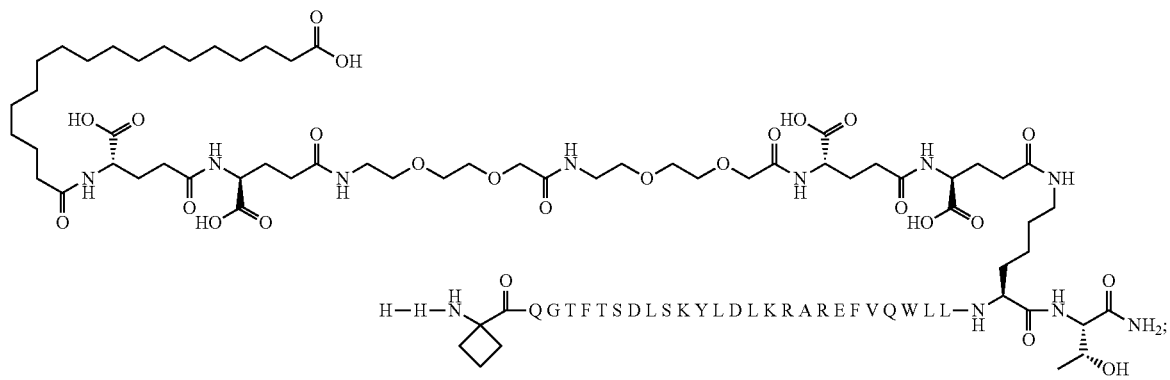

3. The pharmaceutical composition according to claim 1, wherein the glucagon derivative is:
N^{ε28}-[(4S)-4-carboxy-4-[[(4S)-4-carboxy-4-[[(2S)-2-[[(2S)-4-carboxy-2-[[(2S)-2-[[(4S)-4-carboxy-4-[[(4S)-4-carboxy-4-(17-carboxyheptadecanoylamino)butanoyl]amino]butanoyl]amino]-3-hydroxypropanoyl] amino]butanoyl]amino]-3-hydroxypropanoyl]amino]butanoyl]amino]butanoyl]-[Aib2,Leu10,Glu15,Lys17,Arg20,Glu21,Leu27,Lys28]-Glucagon amide:

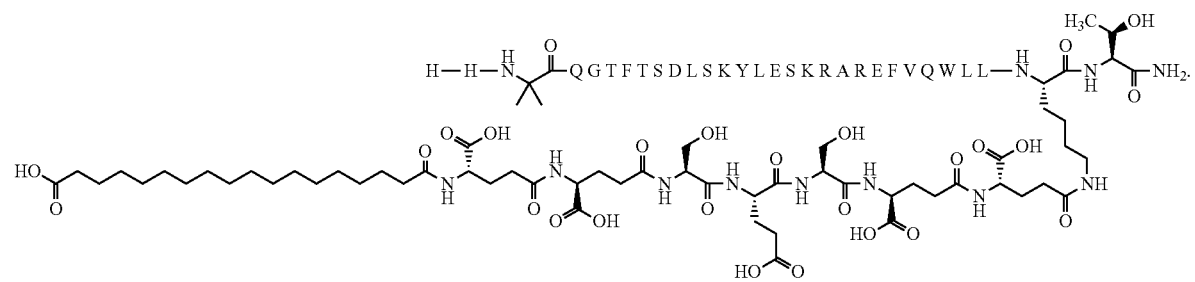
* * * * *